US005536443A

United States Patent [19]

Takatsu et al.

[11] Patent Number: 5,536,443

[45] Date of Patent: Jul. 16, 1996

[54] CYCLIC HYDROCARBON DERIVATIVE AND LIQUID CRYSTAL COMPOSITION CONTAINING THE SAME

[75] Inventors: Haruyoshi Takatsu, Tokyo; Sadao Takehara, Chiba; Kiyohumi Takeuchi, Tokyo; Masashi Osawa, Saitama; Shinji Ogawa, Saitama; Norie Ishida, Saitama, all of Japan

[73] Assignee: Dainippon Ink & Chemicals, Inc., Tokyo, Japan

[21] Appl. No.: 429,485

[22] Filed: Apr. 25, 1995

Related U.S. Application Data

[62] Division of Ser. No. 278,260, Jul. 21, 1994, Pat. No. 5,474,707.

[30] Foreign Application Priority Data

Jul. 23, 1993 [JP] Japan .................................. 5-182734

[51] Int. Cl.$^6$ .............................. G02F 1/13; C09K 19/30

[52] U.S. Cl. ............... 252/299.63; 359/103; 252/299.01

[58] Field of Search ......................... 252/299.63, 299.01; 359/103

[56] References Cited

U.S. PATENT DOCUMENTS

| | | | |
|---|---|---|---|
| 4,405,488 | 9/1983 | Sugimori et al. | 252/299.63 |
| 4,917,819 | 4/1990 | Goto et al. | 252/299.63 |
| 5,032,313 | 7/1991 | Goto et al. | 252/299.63 |

OTHER PUBLICATIONS

Gray et al., "The Transition Temperature of Some Deuteriated Liquid Crystals", *Mol. Cryst. Liq. Cryst.*, 41, pp. 75–79 (1977).

Gray et al., "The Synthesis of Deuteriated 4–n–Alkyl–4'–Cyanobiphenyls", *Mol. Cryst. Liq. Cryst.*, 48, pp. 233–242 (1978).

Neubert, "Synthesis of Some Deuterated Aromatic Mesomorphic Compounds Used in Broad–Line $^2$H–NMR Studies", *Mol. Cryst. Liq. Cryst.*, 129, pp. 327–374 (1985).

Zimmermann, "Specifically Deuteriated Intermediates for the Synthesis of Liquid Crystals and Liquid–Crystalline Polymers", *Liquid Crystals*, 4, pp. 591–618 (1989).

Ossowska–Chrusciel et al., "Synthesis and Mesomorphic Properties of Deuteriated 4,4'–di–n–alkyloxyazoxybenzenes–$d_{2(2n+1)}$". *Liquid Crystals*, 8, pp. 183–191 (1990).

Demus et al., *Flüssige Kristalle in Tabellen*, Nos. 387–398 and 2648–2652, pp. 58, 59, 168, 169 and 340–347 (1974).

Demus et al., *Flüssige Kristalle in Tabellen II*, Nos. 8944 and 10656, pp. 216, 217, 304, 305, 456, 457, 460 and 461 (1984).

R. Y. Dong et al, *Liquid Crystals*, 5, No. 3, pp. 1019–1031 (1989).

F. A. L. Anet et al, *Tetrahedron Letters*, No. 9, pp. 741–744 (1969).

G. Eadon et al, *J. Org. Chem.*, 41, No. 1, pp. 171–173 (1976).

J. P. Begue et al, *Tetrahedron*, 34, pp. 2095–2103 (1978).

*Primary Examiner*—Cynthia Harris Kelly
*Attorney, Agent, or Firm*—Armstrong, Westerman, Hattori, McLeland & Naughton

[57] ABSTRACT

A liquid crystal display comprising a compound of the formula (I)

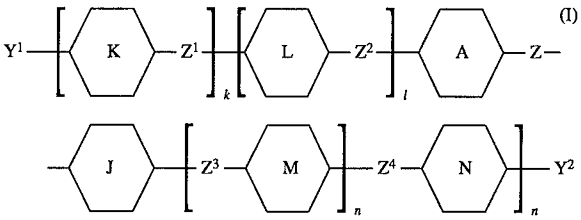

wherein each of $Y^1$ and $Y^2$ is independently F, Cl, CN, OCN, SCN, $OCF_3$, $OCF_2H$, $OCF_2CF_3$, $CF_3$, R, —OR, —COOR or —OCOR, wherein R is alkyl, alkenyl or alkoxyalkyl, provided that at least one of $Y^1$ and $Y^2$ is R, —OR, —COOR or —OCOR; each of Z, $Z^1$, $Z^2$, $Z^3$ and $Z^4$ is independently a single bond. $CH_2CH_2$—, —CH=CH—, —C≡C—, —COO—, —OCO—, —$CH_2O$—, $OCH_2$—, —$(CH_2)_4$—, —$(CH_2)_3$—O— or —O—$(CH_2)_3$—: ring A is a group of formula (II):

(II)

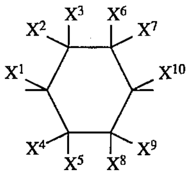

wherein each of $X^1$, $X^2$, $X^3$, $X^4$, $X^5$, $X^6$, $X^7$, $X^8$, $X^9$, and $X^{10}$ is independently H or D, provided that at least one of them is D; each of rings K, L, J, M and N is independently trans-1,4-cyclohexylene, 1,4-cyclohexenylene, substituted trans-1,4-cyclohexylene, 1,4-phenylene, substituted 1,4-phenylene, 1,3-dioxane-2,6-diyl, pyrimidine-2,5-diyl, pyridine-2,5-diyl, pyrazine-2,5-diyl or a group of formula (III):

(III)

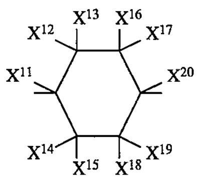

wherein each of $X^{11}$, $X^{12}$, $X^{13}$, $X^{14}$, $X^{15}$, $X^{16}$, $X^{17}$, $X^{18}$, $X^{19}$, and $X^{20}$ is independently H or D, provided that at least one of them is D; in which the ring of formula (III) may be the same as or different from ring A; and k, l, m, and n each independently is 0 or 1, provided that the sum of k, l, m, and n is 0, 1 or 2. The compound is useful as an electro-optic liquid crystal display material.

9 Claims, No Drawings

CYCLIC HYDROCARBON DERIVATIVE AND LIQUID CRYSTAL COMPOSITION CONTAINING THE SAME

This is a division of application Ser. No. 08/278,260 filed Jul. 21, 1994, U.S. Pat. No. 5,474,707.

FIELD OF THE INVENTION

This invention relates to a deuterated cyclohexane derivative which is a novel liquid crystal compound useful as an electro-optic liquid crystal display material and to a liquid crystal composition containing the same. More particularly, it relates to a liquid crystal composition which is not crystallized in low temperatures and yet are not inferior to generally used liquid crystal compositions in electro-optic characteristics, such as nematic-isotropic phase transition temperature, threshold voltage, refractive index anisotropy, dielectric constant anisotropy, a response time, and voltage holding ratio. This invention also relates to a liquid crystal display using the liquid crystal composition, which is capable of making a display in a stable manner without suffering from crystallization and exhibits excellent electro-optical characteristics.

BACKGROUND OF THE INVENTION

Liquid crystal displays have found broad applications to watches, calculators, measuring instruments, automobile control panels, word processors, pocket computers, printers, computers, and TV sets. Liquid crystal display systems include a twisted nematic (TN) mode, a supertwisted nematic (STN) mode, a dynamic scattering (DS) mode, a guest-host (GH) mode, and a ferroelectric liquid crystal (FLC) mode. The liquid crystal display driving system has started with a static driving system, developed into a multiplex driving system, and recently further developed from a simple matrix system into an active matrix system.

Liquid crystal materials to be used in these displays are required to satisfy various characteristics in accordance with the display system or driving system. In particular, (1) to show a liquid crystal phase in a low-to-high broad temperature range to be driven in a broad temperature range, (2) to have a low threshold voltage to be driven at a low voltage, and (3) to have a low viscosity and a short response time are important characteristics common to all liquid crystal materials irrespective of the display system or driving system.

For the time being, a liquid crystal compound satisfying all the requirements (1to (3) by itself is not available, and a plurality of liquid crystal compounds must be mixed to provide a liquid crystal composition which will exhibit desired characteristics.

Among a wide variety of liquid crystal compounds heretofore developed, those having a cyclohexane skeleton have been used comparatively widely because they satisfy the requirements (1) to (3) comparatively.

Liquid crystal compounds having a cyclohexane skeleton area characterized by their low viscosity as compared with those having other cyclic structures. However, they are not deemed to be pronouncedly superior to those having other structures as for low-temperature characteristics.

In order to decrease the melting point of a liquid crystal material, it is effective to mix an increased number of compounds. For example, it has been a practice to mix a plurality of such analogues as have the same basic skeleton, composed of rings and a linking group(s), but different numbers of carbon atoms at the terminal group. Nevertheless, it is extremely difficult to reduce the melting point of a liquid crystal material so as to prevent crystallization in a low temperature region even by the above-described method.

It has therefore been demanded to develop a liquid crystal compound which has a cyclohexane skeleton and thereby has a relatively low viscosity, which has a reduced melting point or is hardly crystallized in a low temperature region without adversely affecting other characteristics, and which has improved co-solubility with other liquid crystal compounds.

Various liquid crystal compounds having different liquid crystal phase temperature ranges have been mixed in order to obtain a liquid crystal material satisfying the requirement (1). For example, where it is desired to increase a nematic-isotropic phase transition temperature (hereinafter referred to as $T_{N-I}$ point), a liquid crystal compound having a high $T_{N-I}$ point could be added in an increased proportion. However, because such a compound also has a high lower limit for the nematic phase (hereinafter referred to a $T_{C-N}$ point), the resulting liquid crystal composition necessarily has an increased $T_{C-N}$ point. As a result, the liquid crystal composition often suffers from crystallization, resulting in a failure of practical use.

Hence, a practically useful liquid crystal composition showing a nematic phase over a low-to-high broad temperature range has generally been prepared by mixing 10 to 20 kinds of liquid crystal compounds selected by experience so as to contain a compound having a low melting point, a compound showing a nematic phase at about room temperature, and a compound having a high $T_{N-I}$ point. On actually making a choice of liquid crystal compounds, consideration should be given to not only broadening of an operating temperature range but optimization of electro-optic characteristics and viscosity according to the end use. That is, the liquid crystal compounds to be combined together to provide a liquid crystal composition should satisfy various requirements, inclusive of compatibility among themselves, to some extent. Therefore, although a large number of liquid crystal compounds are available, the choice of compounds usable for preparation of a practically useful liquid crystal composition is considerably limited.

For instance, liquid crystal compositions for active matrix driving system, such as TFT or MIM, which are now getting predominant among various liquid crystal displays, are demanded to satisfy not only the above-described requirements (1) to (3) but a fourth requirement for a high voltage halding ratio. Should the liquid crystal composition have a low voltage holding ratio, a so-called flicker phenomenon would take place, in which the luminance of pixels that should have been driven flickers.

In general, in order that a liquid crystal composition may have a high voltage holding ratio, it must be chemically stable against heat or light applied in a device and have a high specific resistivity. As a result of investigations in pursuit of liquid crystal compounds meeting these demands, known compounds having an ester group, a cyano group, a pyrimidine ring or a dioxane ring, which have been employed for TN and STN displays, turned out to be unsuitable for an active matrix driving system because they reduce the voltage holding ratio.

Further, in the active matrix driving system, since the display system is the same as a conventional TN mode, the liquid crystal composition to be used must have positive dielectric anisotropy ($\Delta\epsilon$) as a whole. However, among conventionally employed liquid crystal compounds having positive dielectric anisotropy (hereinafter referred to as p-type liquid crystal compounds), even those having a relatively high $\Delta\epsilon$ similarly reduce the voltage halding ratio. That is, the compounds shown below were revealed to be unsuited to active matrix driving.

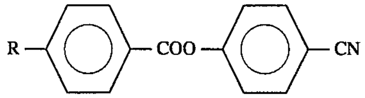

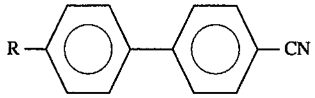

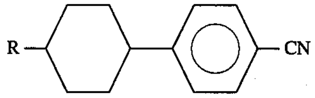

wherein R represents an alkyl group.

In order to adjust the $\Delta\epsilon$ of a liquid crystal composition for active matrix driving to a proper positive value, p-type liquid crystal compounds having a fluorine atom or a chlorine atom as a functional group have been used for the present time. Examples of such compounds are shown below.

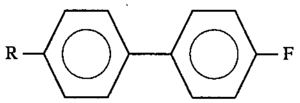

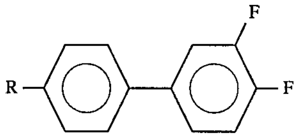

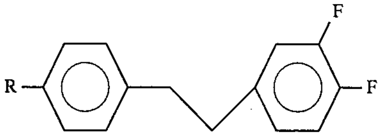

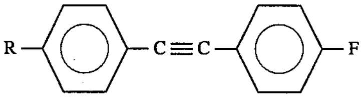

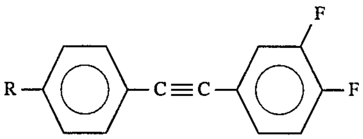

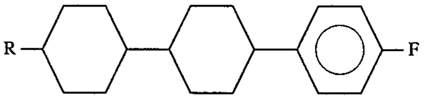

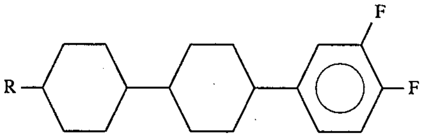

-continued

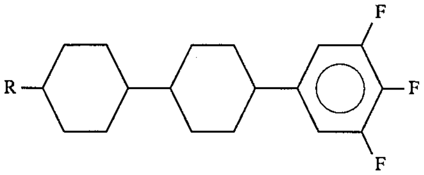

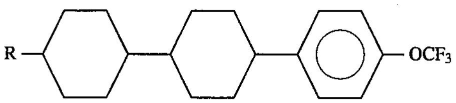

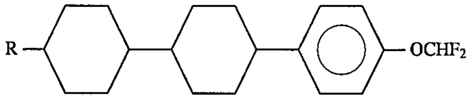

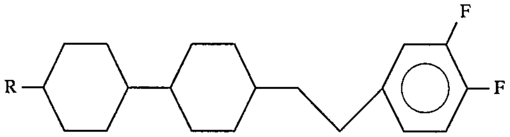

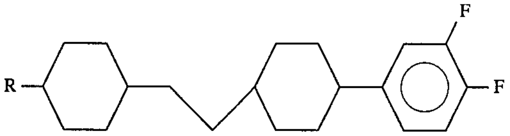

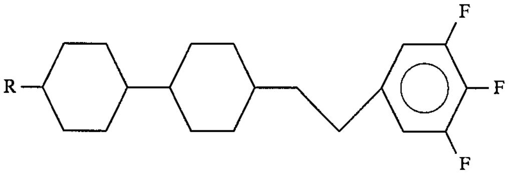

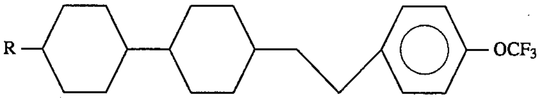

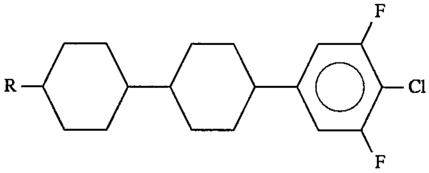

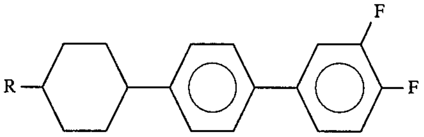

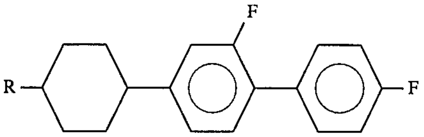

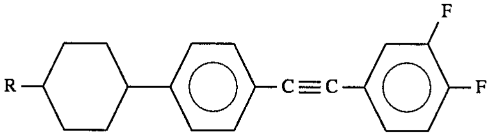

-continued

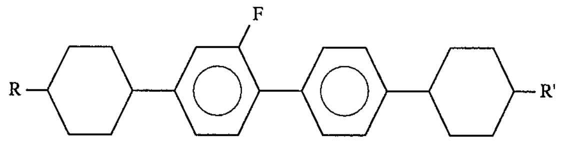

wherein R and R' each independently represent an alkyl group, an alkenyl group or an alkoxylalkyl group.

However, although it is possible to achieve electro-optic characteristics necessary for active matrix driving by using these compounds, it is very difficult to prepare a liquid crystal composition having a sufficiently low $T_{C-N}$ point because many of liquid crystal compounds useful for active matrix driving have a relatively high $T_{N-I}$ point.

In order to solve this problem, it has been proposed to reduce the $T_{C-N}$ point of a liquid crystal composition by adding a plurality of such analogous compounds as have the same skeleton but with the number of carbon atoms at the terminal alkyl group varied from 2 to 7, which are selected from the above-mentioned fluorine-containing p-type liquid crystal compounds. However, this approach does not accomplish reduction in $T_{C-N}$ point to a considerable degree. Moreover, the viscosity of the compound tends to increase as the number of carbon atoms of the terminal alkyl group increases, resulting in deterioration of the response characteristics, the requirement (3).

Thus, a liquid crystal composition for active matrix driving which fulfills all the characteristics (1) to (4) has not yet been developed. Under these circumstances, the characteristics (2), (3) and (4) take precedence over the characteristic (1), we cannot help using liquid crystal composition for active matrix driving. As for the characteristic (1), we cannot help using liquid crystal compounds whose $T_{C-N}$ point is not sufficiently low. As an expected result, the currently available liquid crystal compositions are often crystallized in low temperatures.

The liquid crystal compositions used in STN liquid crystal displays are demanded to meet the requirements (1) to (3) and, in addition, (5) to have a high elastic constant ratio ($K_{33}/K_{11}$) for achieving high contrast. The characteristic (2) (to have a low threshold voltage) is also important for the liquid crystal compositions for STN displays widespread in general-purpose equipment, such as laptop computers.

For reduction of the threshold voltage of a liquid crystal composition, it is effective to increase the dielectric anisotropy $\Delta\epsilon$ or to reduce the elastic constant K according to the following formula:

$$Vth = k\sqrt{K/\Delta\epsilon}$$

wherein $V_{th}$ represents a threshold voltage; k represents a proportionality factor; K represents an elastic constant; and $\Delta\epsilon$ represents a dielectric anisotropy.

Liquid crystal compounds having a very large $\Delta\epsilon$ include, for example, those represented by formula:

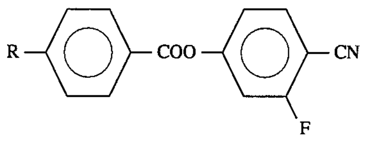

wherein R represents an alkyl group. Use of a large quantity of such a compound with too large a $\Delta\epsilon$ is liable to raise such problems as an increase in electrical current. This deteriorates reliability on actual use as a liquid crystal display.

A liquid crystal composition having a small elastic constant can be prepared by mixing a mother liquid crystal material comprising a p-type liquid crystal compound, a tricyclic liquid crystal compound of three ring system having a high $T_{N-I}$ point, a relatively small elastic constant, and a negative $\Delta\epsilon$ (hereinafter referred to as an n-type liquid crystal compound) or a tricyclic p-type liquid crystal compound.

p-Type liquid crystal compounds having a high elastic constant ratio $K_{33}/K_{11}$ include, for example, compounds represented by formula:

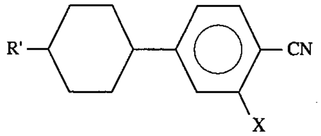

wherein R' represents an alkyl group, an alkenyl group or an alkoxylalkyl group; and X represents a hydrogen atom or a fluorine atom.

In an attempt to satisfy the threshold voltage characteristics and the contrast characteristics in STN displays, a mixture comprising the above-mentioned p-type liquid crystal compound and the tricyclic p- or n-type liquid crystal compound tends to be crystallized in a low temperature. Hence, similarly to the case of the active matrix driving system, it has been a practice to add several kinds of analogues having the same skeleton with different carbon atom numbers in the moiety R' or, in cases where R' is an alkenyl group, to add several kinds of analogues in which the position of the double bond differs, to thereby prepare a liquid crystal composition with a reduced $T_{C-N}$ point.

However, the elastic constant ratio $K_{33}/K_{11}$ of such analogous compounds largely differs with a difference in the carbon atom number or a difference in the double bond position. As a result, cases are often met with, in which the resulting liquid crystal composition has a reduced elastic constant ratio $K_{33}/K_{11}$ and thereby reduced contrast. Where the method of adding analogues is followed, there is a limit of possible reduction of $T_{C-N}$ point, the viscosity increases, and the response time is slow. It would be very difficult to design the composition of a liquid crystal composition while taking these problems into consideration.

Under the present situation, liquid crystal compositions for an STN mode which have a low threshold voltage of about 1.2 V have been prepared. However, not having a sufficiently high elastic constant ratio $K_{33}/K_{11}$ as mentioned above, these compositions have failed to provide STN liquid crystal displays having low-voltage driving properties and high contrast.

As hereinabove discussed, a liquid crystal composition satisfying the requirement (1) (to have a broad temperature range for the liquid crystal phase) should have a low $T_{C-N}$ point. Since not a few materials actually undergo crystallization even at a temperature higher than their $T_{C-N}$ point, a highly reliable liquid crystal display should use a liquid crystal composition which is not crystallized even in a low temperature region so as to eliminate display defects due to changes in environmental temperature all over the display area.

A liquid crystal composition consisting of a plurality of liquid crystal single substances often shows a supercooling phenomenon. Therefore, a $T_{C-N}$ point of a liquid crystal composition is measured by once cooling to a low temperature sufficient for solidification or transition into a glassy state with liquid nitrogen, etc. (for example, to −70° C.)

thereby to crystallize, then gradually increasing the temperature, and, during the temperature rise, measuring a transition temperature from the solid to a nematic phase.

However, in the case of a practical liquid crystal composition comprising 10 to 20 kinds of components, because it is not an eutectic mixture, cases not infrequency occur in which the composition crystallizes even if it is preserved at a temperature higher than the lower limit of the nematic phase as measured by the above-mentioned method. The possible temperature range for driving is virtually narrower than the measured temperature range. It is not a rare case that a liquid crystal composition having a $T_{C\text{-}N}$ point of −70° C. is crystallized at room temperature. While liquid crystal displays installed on automobiles or aircraft are demanded to stably exhibit a nematic phase in a temperature widely ranging from −40° to 110° C., a liquid crystal composition which is not crystallized even in storage at −55° C. has not yet been developed. Some of the liquid crystal compositions practically used in displays installed on automobiles is crystallized in about 1 week in storage at, e.g., −25° C.

It should now be understood that a liquid crystal composition, even having a very low $T_{C\text{-}N}$ point, is not always prevented from crystallization at a temperature above the $T_{C\text{-}N}$ point. Accordingly, what is demanded for a liquid crystal composition that satisfies the requirement (1) to show high reliability is not a low $T_{C\text{-}N}$ point but non-crystallization in a low temperature range.

As discussed above, a liquid crystal composition is prepared by mixing various liquid crystal compounds selected so as to agree with a particular display system or a particular driving system but there are limits of improvements of characteristics that can be achieved only with the liquid crystal compounds currently employed. In particular, many of general-purpose liquid crystal compositions are designed with weight on satisfaction of electro-optic characteristics. On reviewing these general-purpose liquid crystal compositions, particularly those for an active matrix driving system, such as TFT or MIM, and those for STN liquid crystal displays, there are few materials that have a broad temperature range for the liquid crystal phase, are not crystallized in lower temperatures, and are thereby highly reliable.

The general-purpose liquid crystals substantially satisfying the requirements (2) to (5) are regarded as highly reliable and practical liquid crystal materials provided that they are not crystallized for a period of about 1 month even in storage in a relatively low temperature, which varies depending on the end use, though.

However, the temperature of the environment in which the liquid crystal display containing such a reliable liquid crystal composition operates is naturally limited.

For the above-described reasons, there has not yet been obtained such a liquid crystal composition that is not crystallized in a lower temperature and therefore has high reliability while sufficiently satisfying electro-optic characteristics demanded in carrying out various display systems or driving systems.

SUMMARY OF THE INVENTION

An object of the present invention is to provide a novel liquid crystal compound having a cyclohexane skeleton, which, when mixed with other liquid crystal compounds to prepare a liquid crystal composition, reduces the viscosity of the liquid crystal composition, does not narrow the temperature range for the liquid crystal phase of the composition, and undergoes neither crystallization nor phase separation even in a low temperature region.

Another object of the present invention is to provide a liquid crystal composition comprising the above-mentioned liquid crystal compound, which does not suffer from crystallization in a low temperature region while exhibiting excellent electro-optic characteristics, i.e., a threshold voltage, a contrast, and response properties.

A further object of the present invention is to provide a liquid crystal display using the above-mentioned liquid crystal composition, particularly a liquid crystal display for an active matrix driving system or for a TN or STN display system which does not suffer from display defects all over the display area even in a low temperature region.

In order to accomplish the above objects, the present invention provides a compound having a deuterated cyclohexane ring, represented by formula (I):

(I)

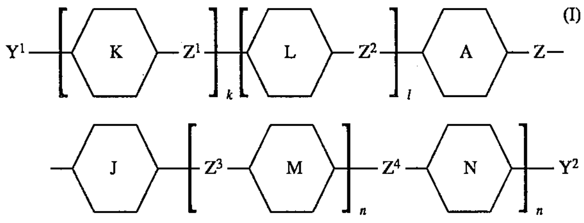

wherein $Y^1$ and $Y^2$ each independently represent a fluorine atom, a chlorine atom, a cyano group, a cyanato group (OCN), a thiocyanate group (SCN), a trifluoromethoxy group ($OCF_3$), a difluoromethoxy group ($OCF_2H$), a 2,2,2-trifluoroethoxy group ($OCH_2CF_3$), a trifluoromethyl group $(CF)_3$, R, —OR, —COOR or —OCOR, wherein R represents an alkyl group having from 1 to 20 carbon atoms, an alkenyl group having from 2 to 20 carbon atoms or an alkoxylalkyl group having from 2 to 20 carbon atoms, provided that at least one of $Y^1$ and $Y^2$ represents R, —OR, —COOR or —OCOR; Z, $Z^1$, $Z^2$, $Z^3$, and $Z^4$ each independently represent a single bond, $—CH_2CH_2—$, —CH═CH—, —C≡C—, —COO—, —OCO—, $—CH_2O—$, $—OCH_2—$, $—(CH_2)_4—$, $—(CH_2)_3—O—$ or $—O—(CH_2)_3—$; ring A represents a group of formula (II):

(II)

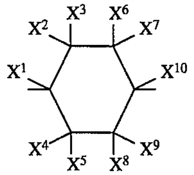

wherein $X^1$, $X^2$, $X^3$, $X^4$, $X^5$, $X^6$, $X^7$, $X^8$, $X^9$, and $X^{10}$ each independently represent a hydrogen atom (H) or a deuterium atom (D), provided that at least one of them represents a deuterium atom (D); rings K L,, J, M and N each independently represent a trans-1,4-cyclohexylene group, a 1,4-cyclohexenylene group, a trans-1,4-cyclohexylene group substituted with 1 to 4 substituents selected from a fluorine atom, a chlorine atom, a cyano group and a methyl group, a 1,3-dioxane-2,6-diyl group, a pyrimidine-2,5-diyl group, a pyridine-2,5-diyl group, a pyrazine-2,5-diyl group or a group of formula (III):

(III)

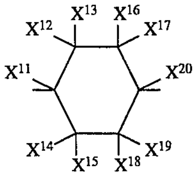

wherein $X^{11}$, $X^{12}$, $X^{13}$, $X^{14}$, $X^{15}$, $X^{16}$, $X^{17}$, $X^{18}$, $X^{19}$, and $X^{20}$ each independently represent a hydrogen atom (H) or a deuterium atom (D), provided that at least one of them represents a deuterium atom (D); in which the ring of formula (III) may be the same or different with ring A; and k, l, m, and n each independently represent 0 or 1, provided that the sum of k, l, m, and n is 0, 1 or 2.

DETAILED DESCRIPTION OF THE INVENTION

As defined above, the substituents as $X^1$ to $X^{10}$ or $X^{11}$ to $X^{20}$ in the deuterated cyclohexane ring represented by formula (II) or (III) each independently represent a hydrogen atom (H) or a deuterium atom (D), with at least one of $X^1$ to $X^{10}$ and at least one of $X^{11}$ to $X^{20}$ being a deuterium atom (D). Therefore, even with the cyclic structures other than ring A, the linking groups, and the terminal groups being fixed, formula (I) includes a great number of compounds with variations in position of the deuterium atom (D) and number of the substituents on ring A.

It is not an unknown technique to substitute a hydrogen atom (H) of a liquid crystal compound with a deuterium atom (D), as having been reported in the following publications:

1) H. Gasporoux, et al., *Ann. Rev. Phys. Chem.*, Vol. 27, p. 175 (1976),
2) G. W. Gray, et al., *Mol. Cryst. Liq. Cryst.*, Vol. 41, p. 75 (1977),
3) A. J. Leadbetter, et al., *J. Phys.*, [Paris] coll C3, Vol. 40, p. 125 (1979),
4) A. Kolbe, et al., *Z. Naturforsch.*, Vol. 23a, p. 1237 (1968),
5) J. D. Rowell, et al., *J. Chem. Phys.*, Vol. 43, p. 3442 (1965),
6) W. D. Philips, et al., *J. Chem. Phys.*, Vol. 41, p. 2551 (1964),
7) A. F. Martins, et al., *Mol. Cryst. Liq. Cryst.*, Vol. 14, p. 85 (1971), and
8) E. T. Samulski, et al., *Phys. Rev. Lett.*, Vol. 29, p. 340 (1972).

Literature (1) reports substitution of the hydrogen atom (H) of the carboxyl group of a 4-alkoxybenoic acid with a deuterium atom (D). All the literature other than (1) relates to substitution of the hydrogen atom (H) in the terminal group or the hydrogen atom (H) bonded to a benzene ring with a deuterium atom (D). No cases has been reported in which a hydrogen atom (H) bonded to a cyclohexane ring is substituted with a deuterium atom (D) as in the compound of formula (I) of the present invention.

Choices and combinations of rings A, J, K, L, M and N, Z, $Z^1$, $Z^2$, $Z^3$, $Z^4$, $Y^1$, $Y^2$, k, l, m, and n lead to creation of a large number of compound. Any of these compounds could exhibit the above-mentioned favorable properties on account of the cyclohexane ring substituted with a deuterium atom (D).

Preferred of the compounds represented by the formula (I) are bicyclic compounds, tricyclic compounds, and tetracyclic compounds represented by formulae (I-1) to (I-6) hereinafter shown.

The preferred bicyclic compounds are represented by formula (I-1):

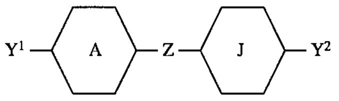

(I-1)

wherein $Y^1$, $Y^2$, Z and rings A and J are as defined above in formula (I).

More specifically, bicyclic compounds represented by formula (I-1') are preferred:

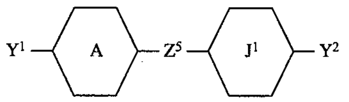

(I-1')

wherein ring A, $Y^1$, and $Y^2$ are as defined above; ring $J^1$ represents a trans-1,4-cyclohexylene group, a 1,4-cyclohexenylene group, a 1,4-phenylene group, a 1,4-phenylene group substituted with one or two fluorine atoms, or the group represented by formula (III) described above; and $Z^5$ represents a single bond, $—CH_2CH_2—$, $—(CH_2)_4—$ or $—COO—$.

More preferred of the compounds (I-1') are those represented by the following formulae (I-1'a), (I-1'b) and (I-1'c):

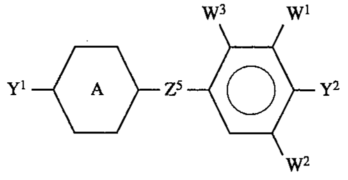

(I-1'a)

wherein ring A, $Y^1$, $Y^2$, and $Z^5$ are as defined above; and $W^1$, $W^2$, and $W^3$ each independently represent a hydrogen atom or a fluorine atom.

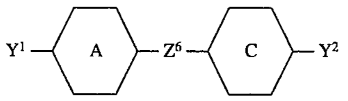

(I-1'b)

wherein ring A, $Y^1$, and $Y^2$ are as defined above; ring C represents

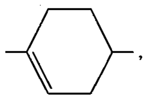 , 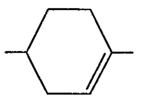

and $Z^6$ represents a single bond or $—CH_2CH_2—$.

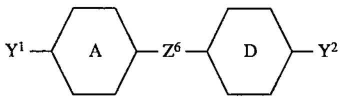

(I-1'c)

wherein ring A, $Y^1$, $Y^2$, and $Z^6$ are as defined above; and ring D represents a trans-1,4-cyclohexylene group or the group of formula (III) described above.

The most preferred of them are those represented by formulae (I-1'a'), (I-1'b'), and (I-1'c'):

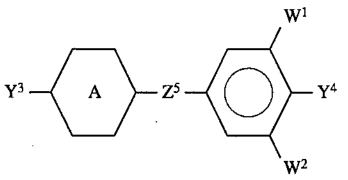

(I-1'a')

wherein ring A, $Z^5$, $W^1$, and $W^2$ are as defined above; $Y^3$ represents an alkyl group having from 1 to 20 carbon atoms or an alkenyl group having from 2 to 20 carbon atoms; and $Y^4$ represents a fluorine atom, a cyano group, a cyanato group (OCN), a trifluoromethoxy group ($OCF_3$), an alkyl group having from 1 to 20 carbon atoms, an alkenyl group having from 2 to 20 carbon atoms, an alkoxyl group having from 1 to 20 carbon atoms an alkenyloxy group having from 3 to 20 carbon atoms, or an alkoxyalkyl group having from 2 to 20 carbon atoms.

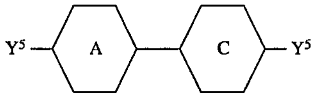

(I-1'b')

wherein ring A and ring C are as defined above; and the two $Y^5$'s each independently represent an alkyl group having from 1 to 20 carbon atoms.

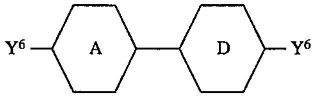

(I-1'c')

wherein ring A and ring D are as defined above; and the two $Y^6$'s each independently represent an alkyl group having from 1 to 20 carbon atoms, an alkenyl group having from 2 to 20 carbon atoms, an alkoxyl group having from 1 to 20 carbon atoms, or an alkoxylalkyl group having from 2 to 20 carbon atoms.

Specific examples of the compounds of formula (I-1'a') are shown below.

In the followings, the numerical values in the brackets shown by [] are the phase transition temperatures of the compounds, in which C represents a crystal phase, Sm a smectic phase, $S_A$ a smectic A phase, $S_B$ a smectic B phase, N a nematic phase, and I an isotropic liquid phase, the parentheses shown by () represent the monotropic phases, and # indicates that the melting point is not clear due to non-crystallization. For example, "C 44 N" means that the phase transition temperature from the crystal phase to the nematic phase is 44° C.

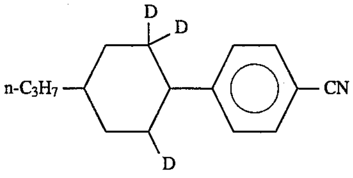

[C 42 N 46 I]

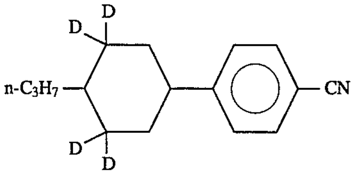

[C 39 N 45 I]

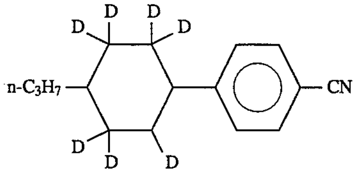

[C 40 N 44 I]

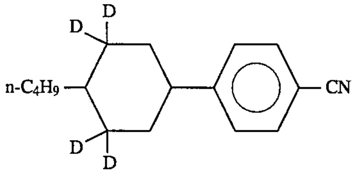

[C 40 (N 39.5) I]

-continued

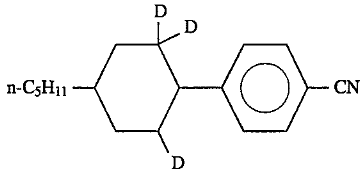

[C 27 N 53 I]

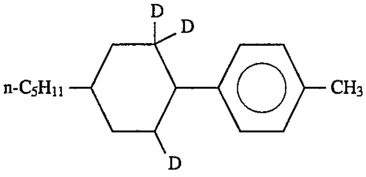

[C 18 (N -4) I]

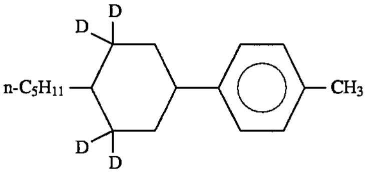

[C 15 (N -3) I]

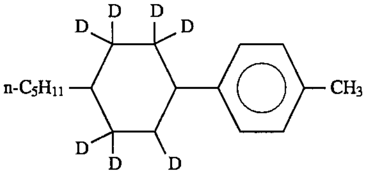

[C 16 (N -4) I]

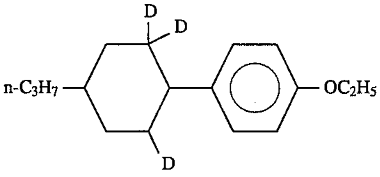

[C 37 (N 35) I]

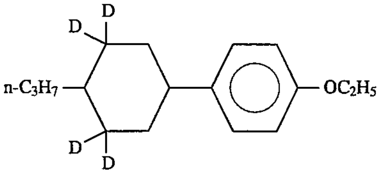

[C 38 (N 34) I]

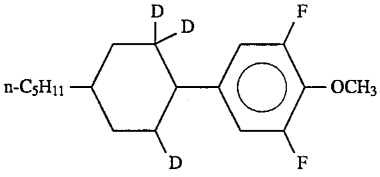

[C 42 (Sm 14) I]

-continued
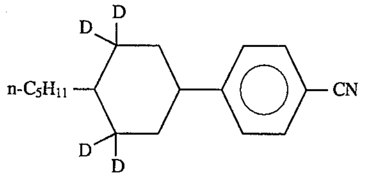
[C 26 N 52 I]
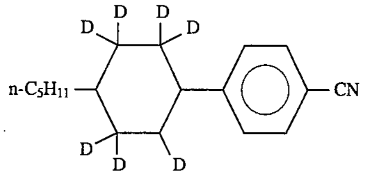
[C 29 N 54.5 I]
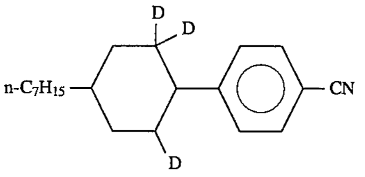
[C 27 N 55 I]
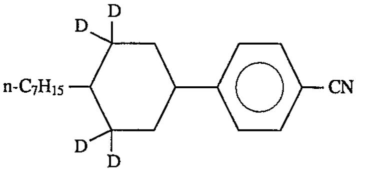
[C 26 N 55 I]
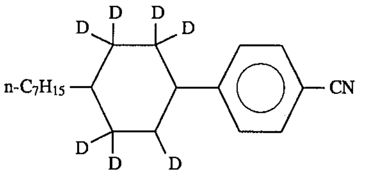
[C 25 N 54 I]
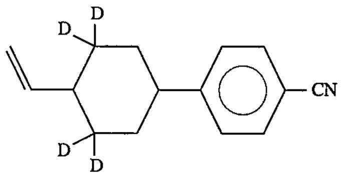
[C 51 (N 28) I]
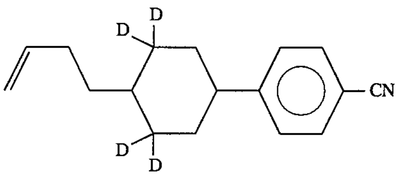
-continued
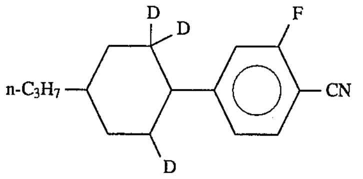
[C 8 N 4 I]
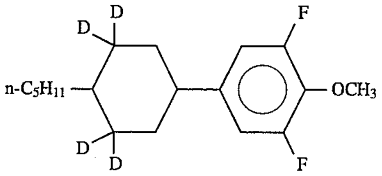
[C 44 (Sm 15) I]
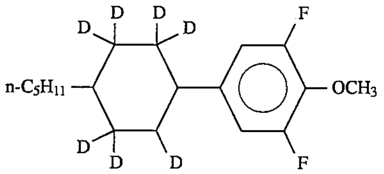
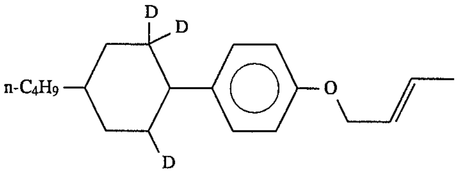
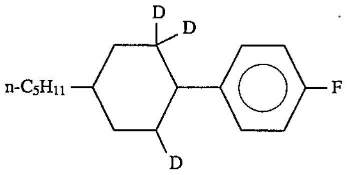
[C 27 (N -28) I]
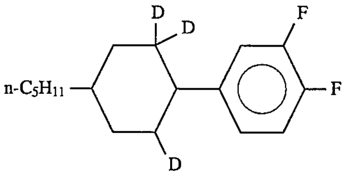
[C -5 (N -30) I]
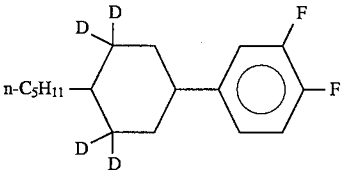
[C -5 (N -30) I]
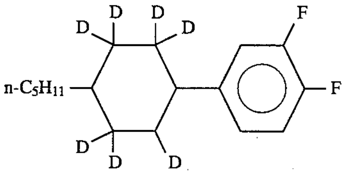

-continued
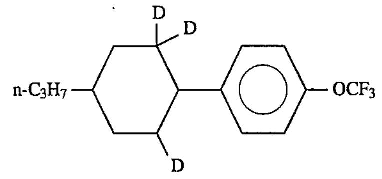
[C 7 I]
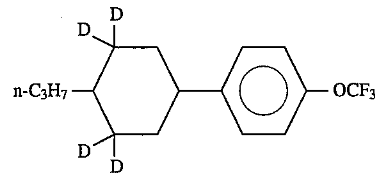
[C 5 I]
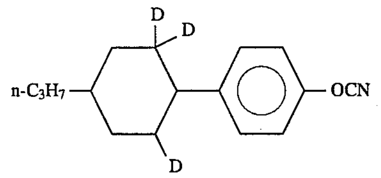
[C 14 (N -32) I]
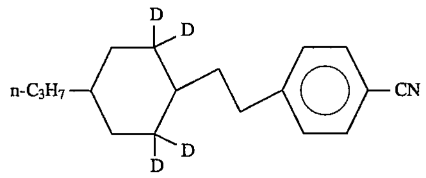
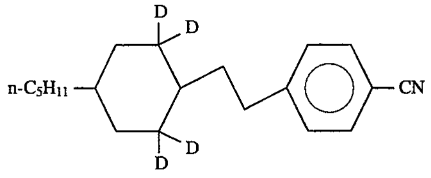
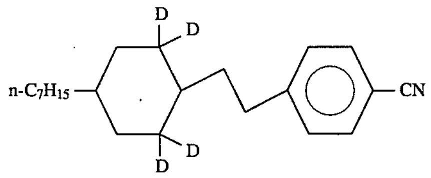
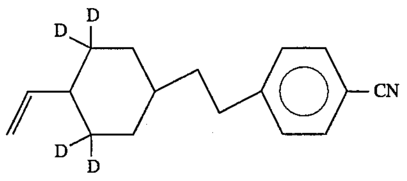
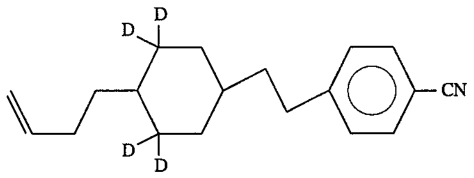
-continued
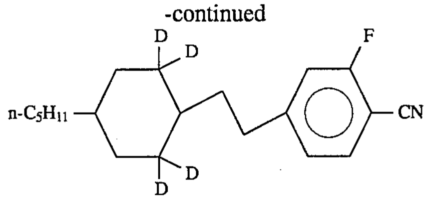
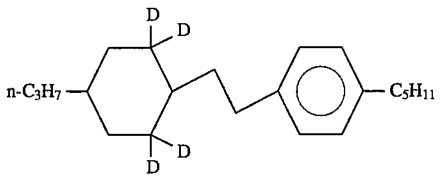
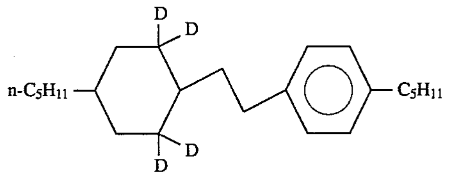
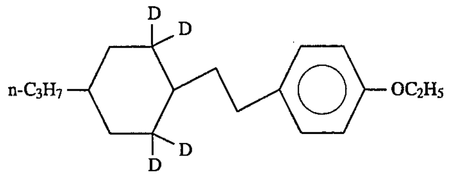
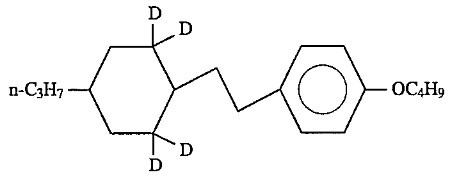
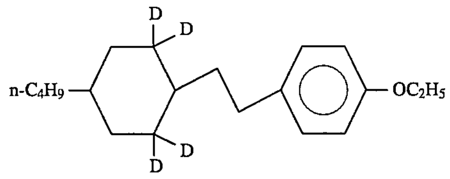
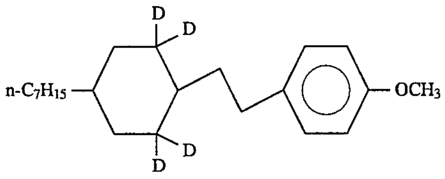
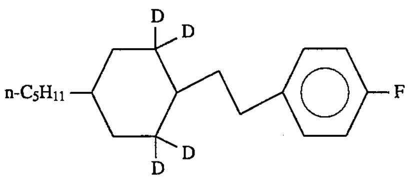
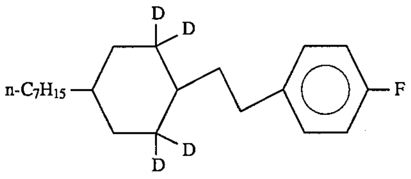

-continued
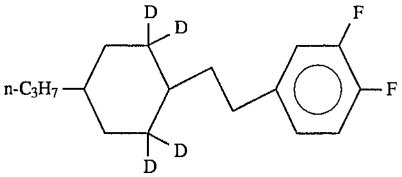
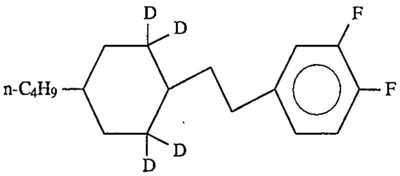
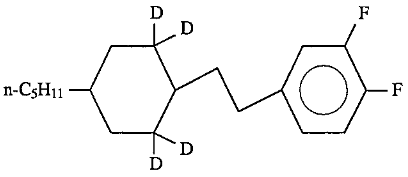
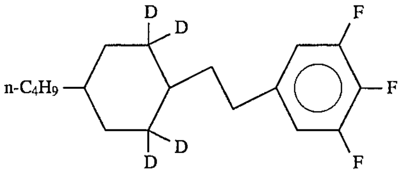
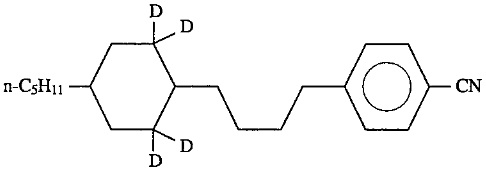
[C 49 (N 38) I]
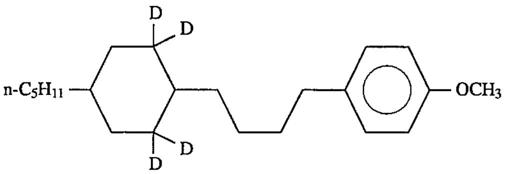
[C 25 ($S_B$ 15) I]
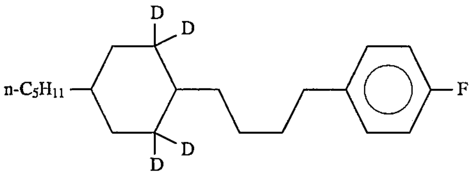
[C 10 I]
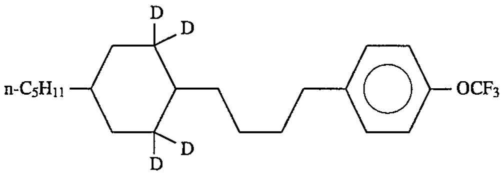
[C 16 I]
-continued
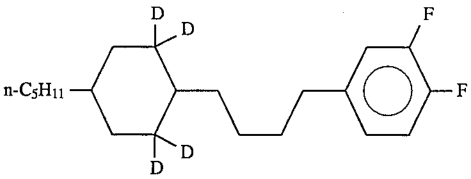
[oily matter]
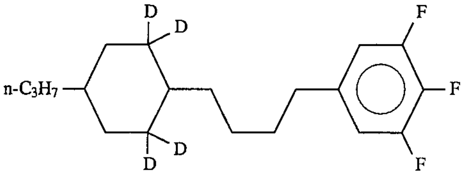
[C 15 I]
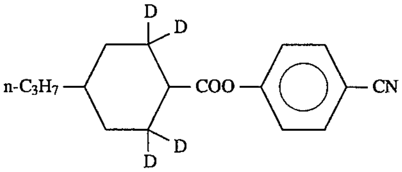
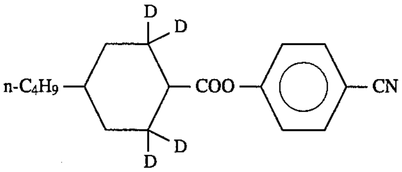
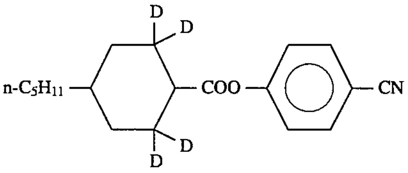
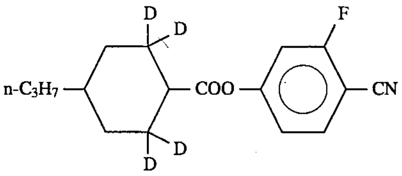
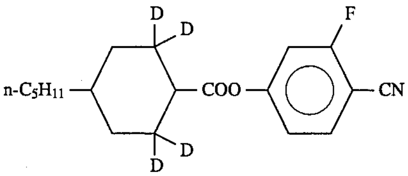
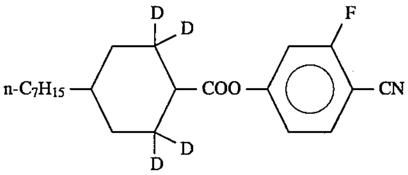
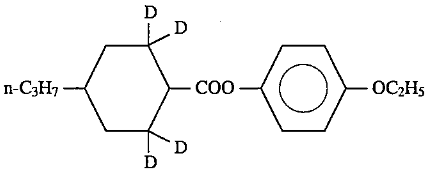

-continued
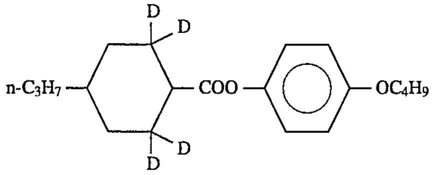
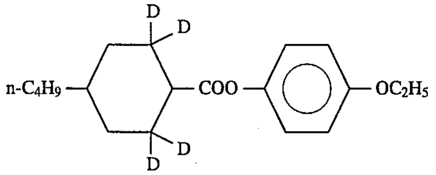
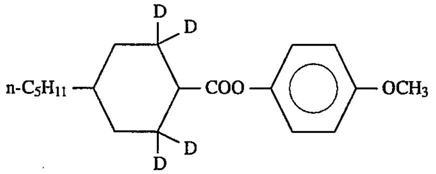
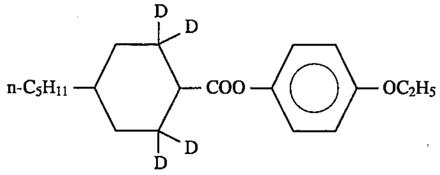
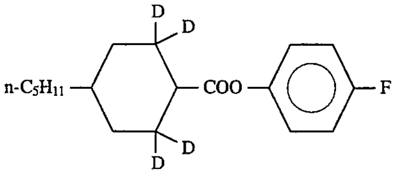
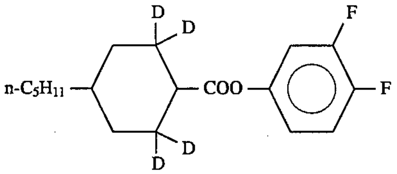
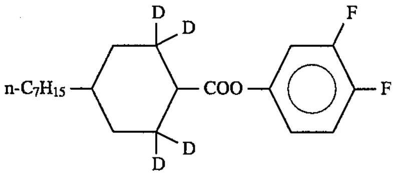
Specific examples of the compounds represented by formula (I-1'b') are shown below.
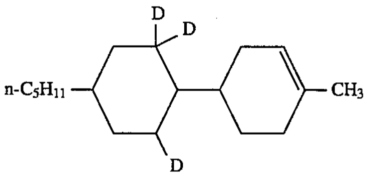
-continued
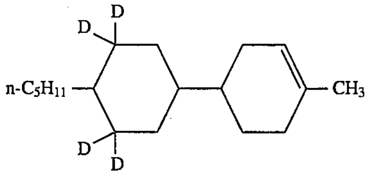
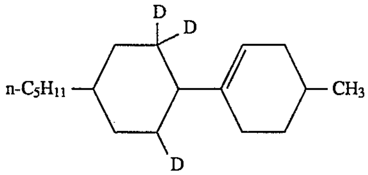
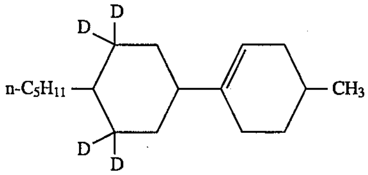
Specific examples of the compounds represented by formula (I-1'c') are shown below.
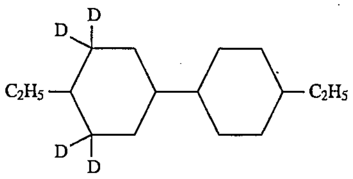
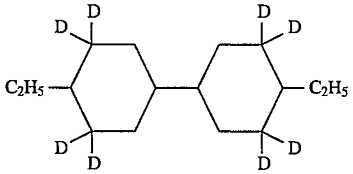
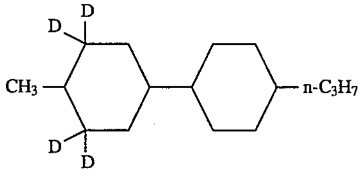
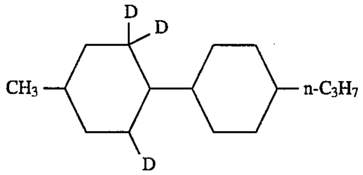
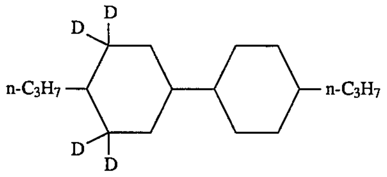

-continued
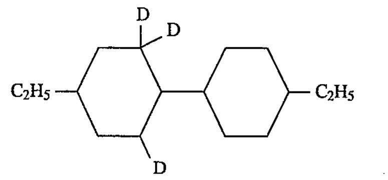
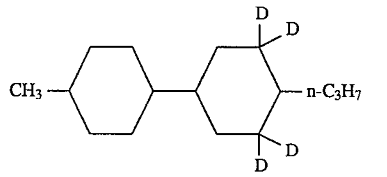
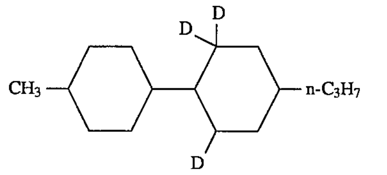
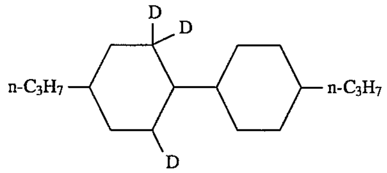
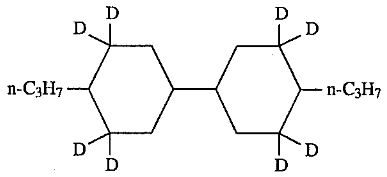
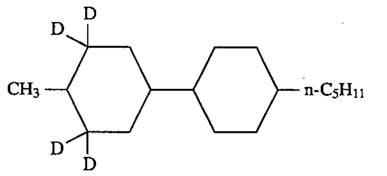
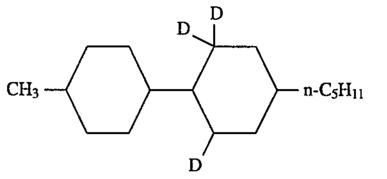
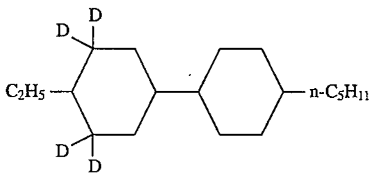
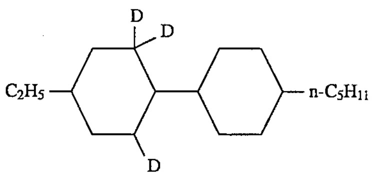
-continued
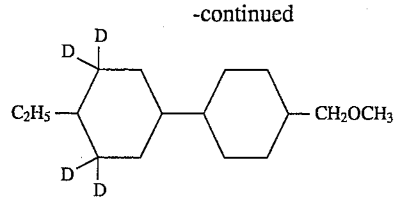
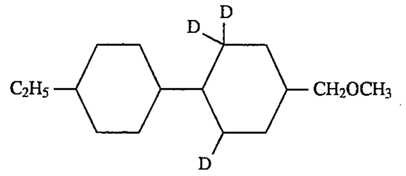
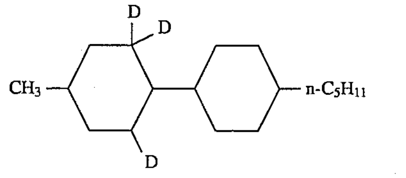
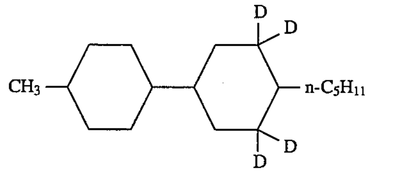
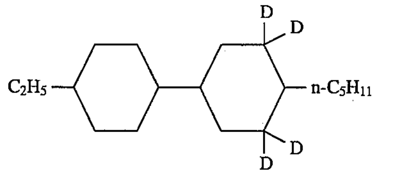
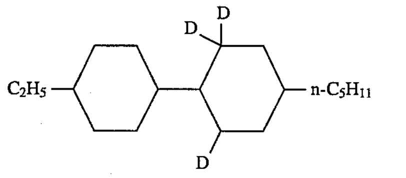
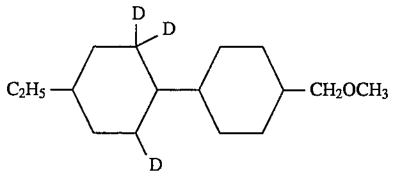
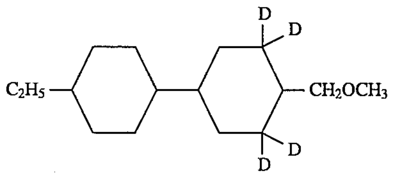
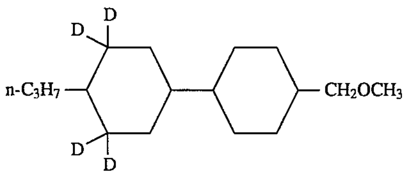

-continued

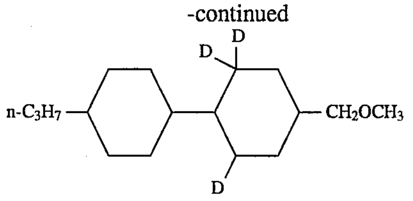

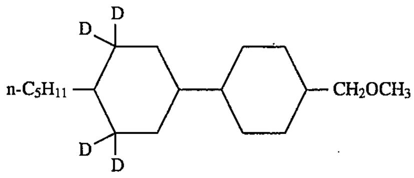

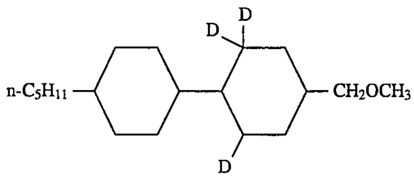

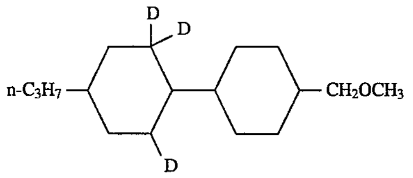

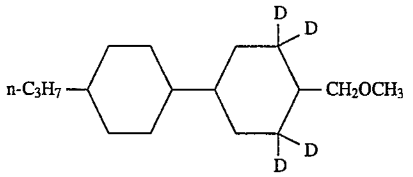

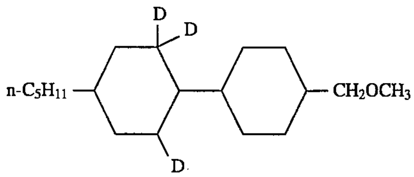

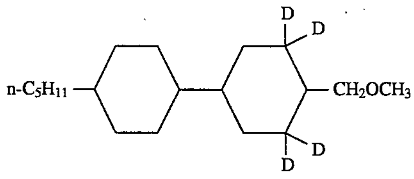

The preferred tricyclic compounds include those represented by formulae (I-2) and (I-3):

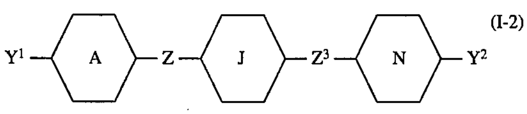

(I-2)

wherein $Y^1$, $Y^2$, Z, $Z^3$, and rings A, J and M are as defined above in formula (I).

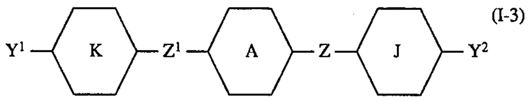

(I-3)

wherein $Y^1$, $Y^2$, Z, $Z^1$, and rings A, K and J are as defined above in formula (I).

More specifically, tricyclic compounds represented by formulae (I-2') and (I-3') are preferred:

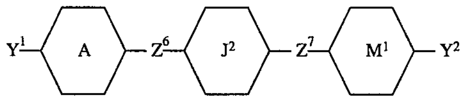

(I-2')

wherein rings A, $Z^6$, $Y^1$, and $Y^2$ are as defined above; ring $J^2$ represents a trans-1,4-cyclohexylene group, a 1,4-cyclohexenylene group, a 1,4-phenylene group, a 1,4-phenylene group substituted with one or two substituents selected from a fluorine atom and a methyl group, or the group of formula (III); ring $M^1$ represents a 1,4-phenylene group or a 1,4-phenylene group substituted with a fluorine atom or a methyl group; and $Z^7$ represents a single bond, $-CH_2CH_2-$, $-C\equiv C-$ or $-(CH_2)_4$.

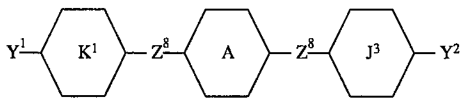

(I-3')

wherein ring A, $Y^1$and $Y^2$ are as defined above; ring $K^1$ represents a trans-1,4-cyclohexylene group or a 1,4-cyclohexenylene group; the two $Z^8$'s each independently represent a single bond, $-CH_2CH_2-$ or $-(CH_2)_4-$; and $J^3$ represents a 1,4-phenylene group or a 1,4-phenylene group substituted with one or two fluorine atoms.

More preferred of these tricyclic compounds are those represented by formulae (I-2'a) to (I-2'f), (I-3'a), and (I-3'b):

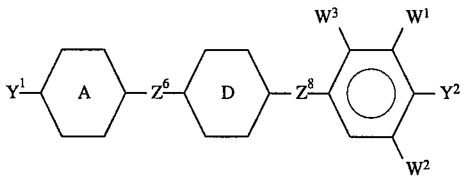

(I-2'a)

wherein ring A, ring D, $Z^6$, $W^1$, $W^2$, $W^3$, $Y^1$, and $Y^2$ are as defined above, and $Z^8$ represents a single bond, $-CH_2CH_2-$ or $-(CH_2)_4-$.

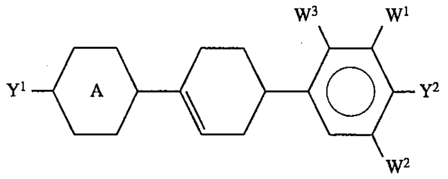

(I-2'b)

wherein ring A, $W^1$, $W^2$, $W^3$, $Y^1$, and $Y^2$ are as defined above.

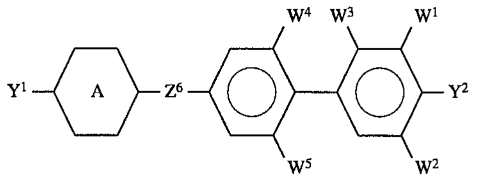

(I-2'c)

wherein ring A, $Z^6$, $W^1$, $W^2$, $W^3$, $Y^1$, and $Y^2$ are as defined above; and $W^4$ and $W^5$ each independently represent a hydrogen atom or a fluorine atom.

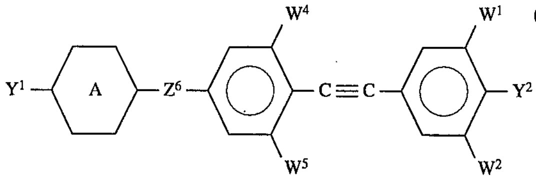
(I-2'd)

wherein ring A, $Z^6$, $W^1$,$W^2$, $W^4$, $W^5$, $Y^1$, and $Y^2$ are as defined above.

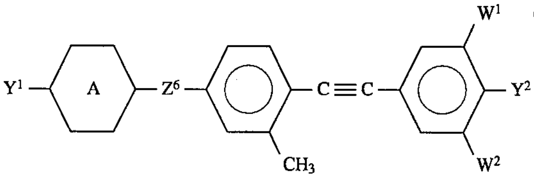
(I-2'e)

wherein ring A, $Z^6$, $W^1$, $W^2$, $Y^1$, and $Y^2$ are as defined above.

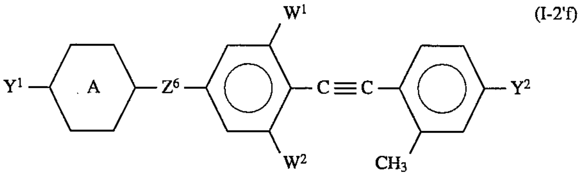
(I-2'f)

wherein ring A, $Z^6$, $W^1$, $W^2$, $Y^1$, and $Y^2$ are as defined above.

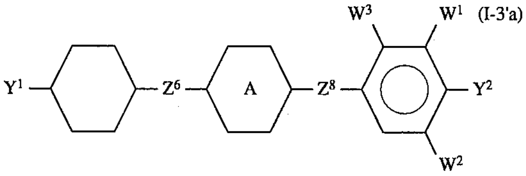
(I-3'a)

wherein ring A, $Z^6$, $Z^8$, $W^1$, $W^2$, $W^3$, $Y^1$, and $Y^2$ are as defined above.

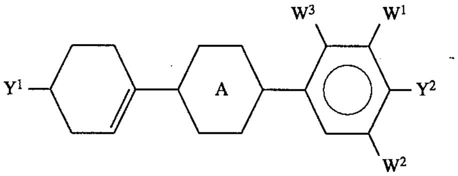
(I-3'b)

wherein ring A, $W^1$, $W^2$, $W^3$, $Y^1$, and $Y^2$ are as defined above.

Still more preferred of these tricyclic compounds are those represented by formulae (I-2'a') and (I-2'b'):

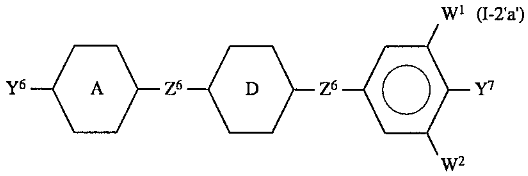
(I-2'a')

wherein ring A, ring D, $Z^6$, $Y^6$, $W^1$, and $W^2$ are as defined above; and $Y^7$ represents a fluorine atom, a chlorine atom, a cyano group, a difluoromethoxy group ($OCF_2H$), a 2,2,2-trifluoroethoxy group ($OCH_2CF_3$), a trifluoromethoxy group ($OCF_3$), an alkyl group having from 1 to 20 carbon toms, an alkenyl group having from 2 to 20 carbon atoms, an alkoxyl group having from 1 to 20 carbon atoms or an alkoxylalkyl group having from 2 to 20 carbon atoms.

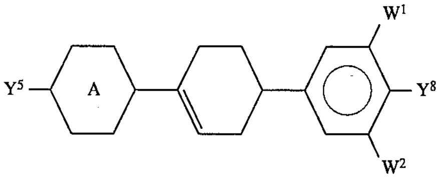
(I-2'b')

wherein ring A, $Y^5$, $W^1$, and $W^2$ are as defined above; and $Y^8$ represents a fluorine atom, an alkyl group having from 1 to 20 carbon atoms or an alkoxyl group having from 1 to 20 carbon atoms.

The same preference as described above for the compounds of formulae (I-2'a') and (I-2'b') also applies to the compounds of formulae (I-2'c), (I-2'd), (I-2'e) and (I-2'f).

Specific examples of the compounds of formula (I-2'a') are shown below.

In the following, the numerical values in the brackets shown by [] are the phase transition temperatures of the compounds, in which C represents a crystal phase, Sm a smectic phase, $S_A$ a smectic A phase, $S_B$ a smectic B phase, N a nematic phase, and I an isotropic liquid phase, the parentheses shown by () represent the monotropic phases, and # indicates that the melting point is not clear due to non-crystallization. For example, "C 44 N" means that the phase transition temperature from the crystal phase to the nematic phase is 44° C.

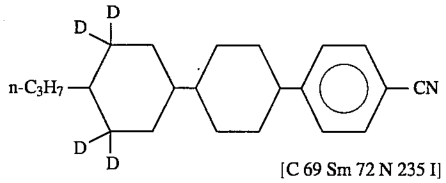
[C 69 Sm 72 N 235 I]

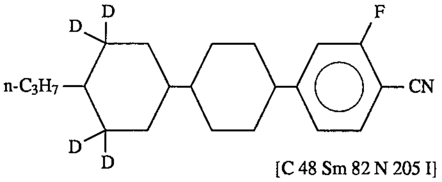
[C 48 Sm 82 N 205 I]

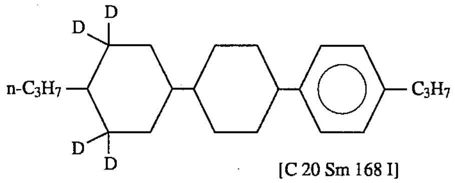
[C 20 Sm 168 I]

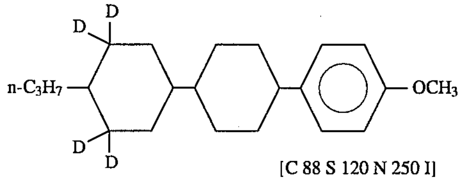
[C 88 S 120 N 250 I]

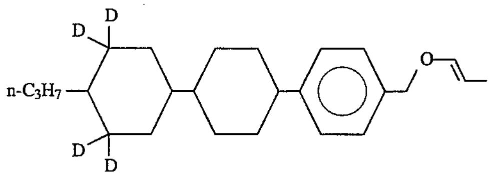

-continued
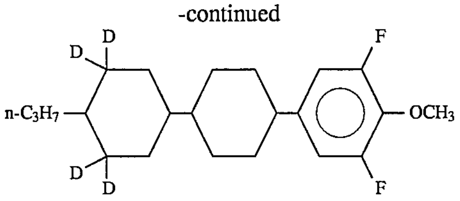
[C 33 N 147 I]
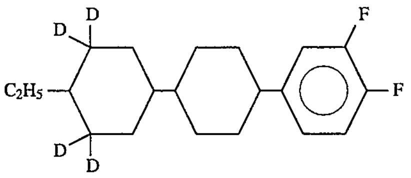
[C 50 N 84.5 I]
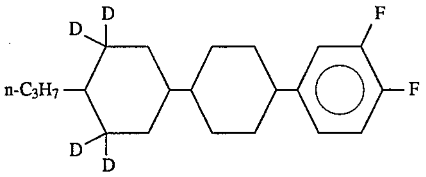
[C 40 N 122 I]
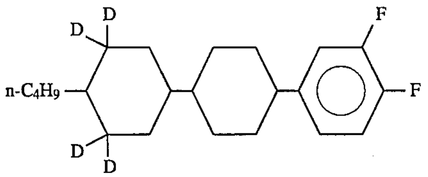
[C 43 N 118.5 I]
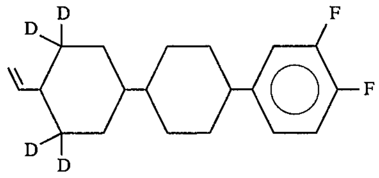
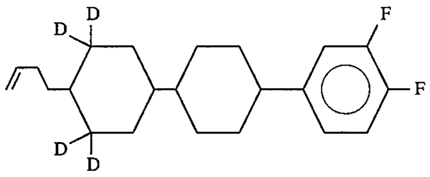
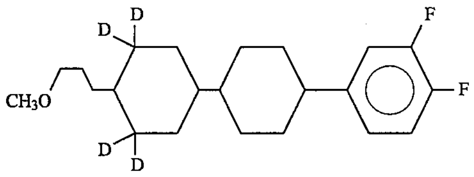
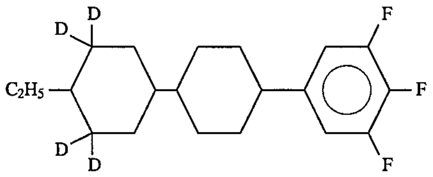
[C 60 (N 39) I]
-continued
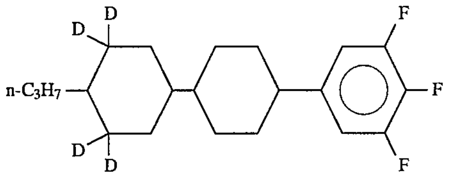
[C 60 N 90.5 I]
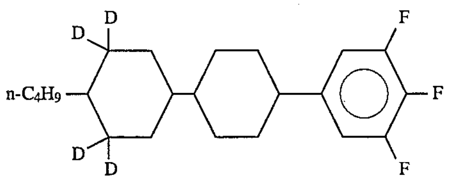
[C 67 N 88 I]
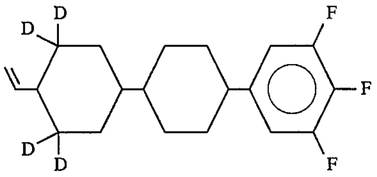
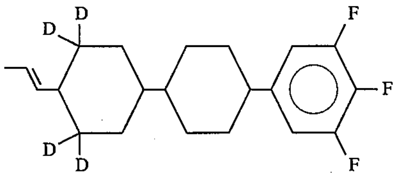
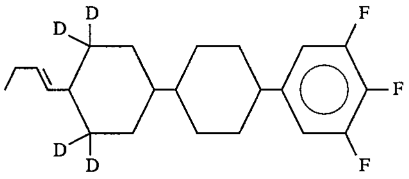
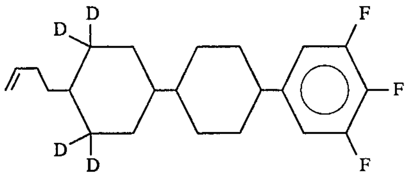
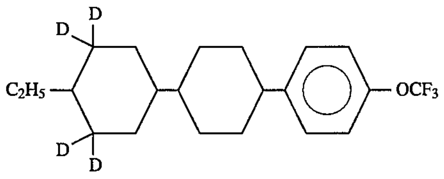
[Sm 72 N 117 I]
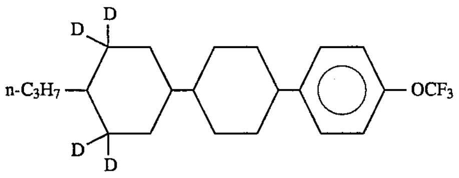
[C 43 Sm 70 N 155 I]

-continued
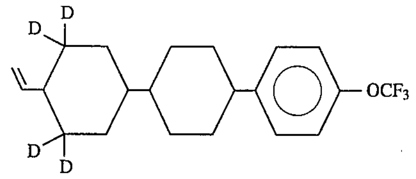
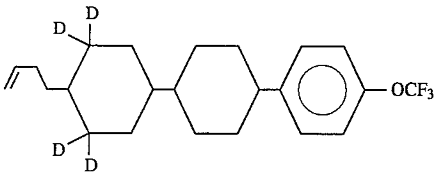
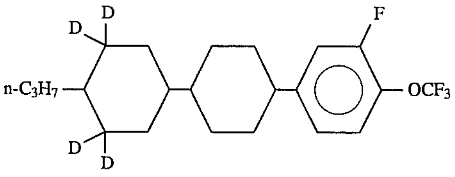
[C 33 N 123 I]
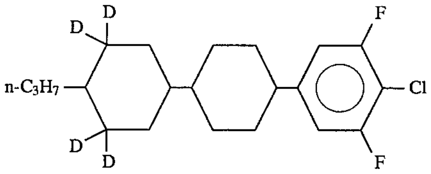
[C 74 N 141 I]
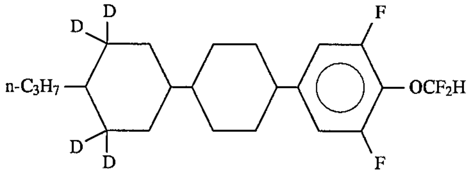
[C 57 N 125 I]
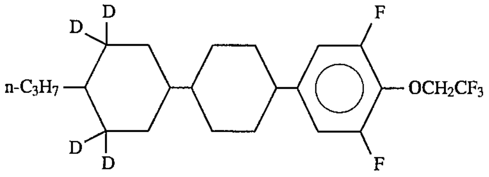
[C 35 N 148 I]
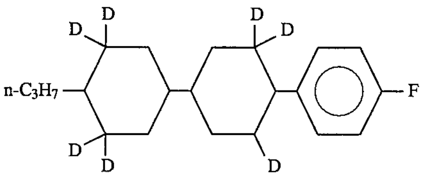
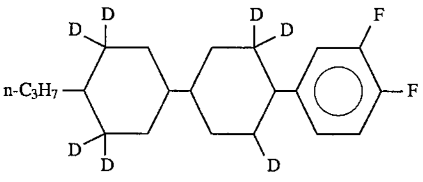
-continued
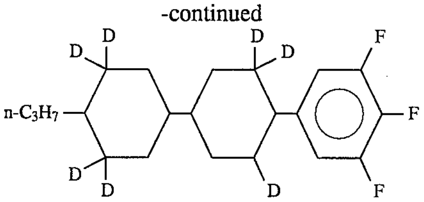
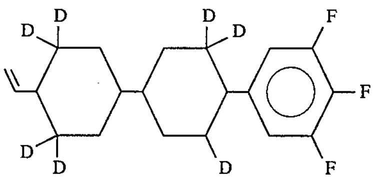
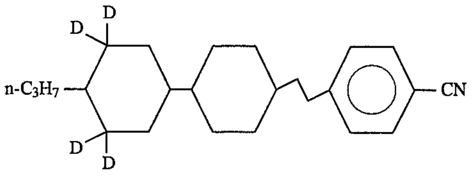
[C 68 N 239 I]
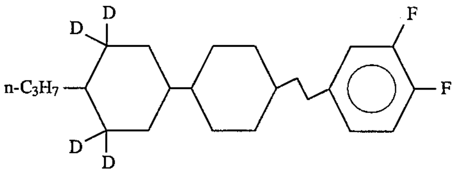
[Sm 47 N 117 I]
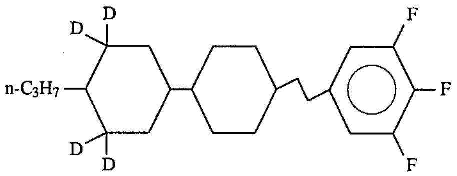
[C 40 N 98 I]
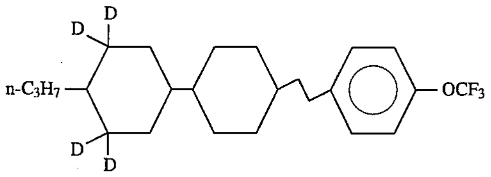
[Sm 74.5 N 134 I]
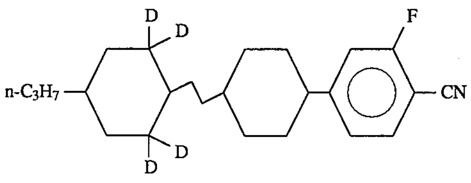
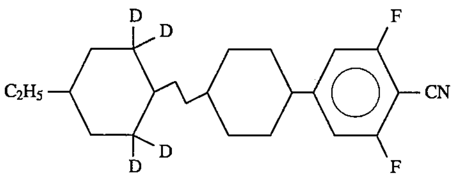

-continued
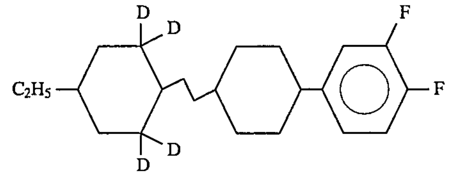
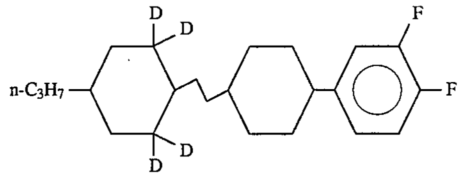
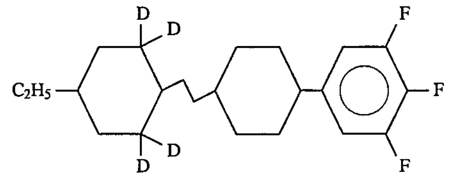
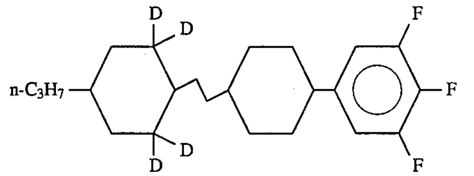
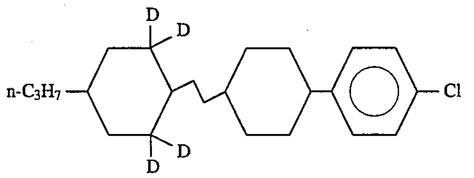
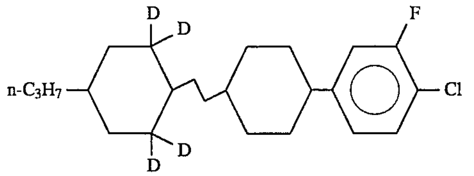
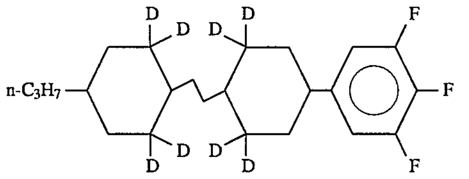
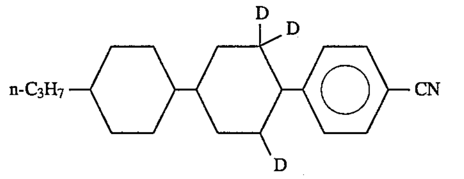
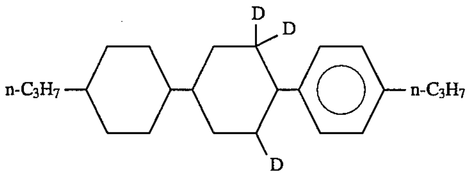
-continued
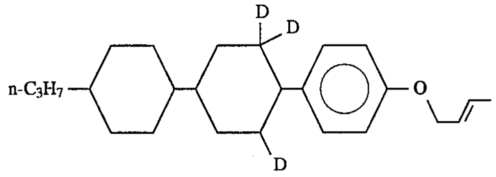
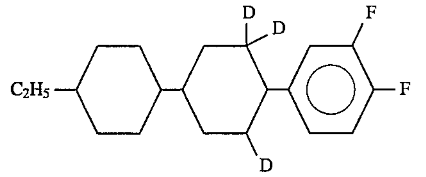
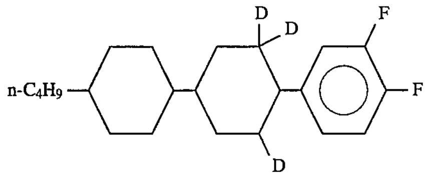
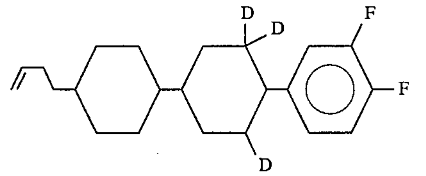
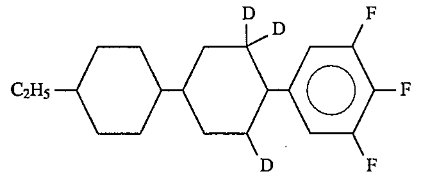
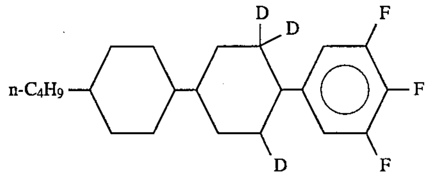
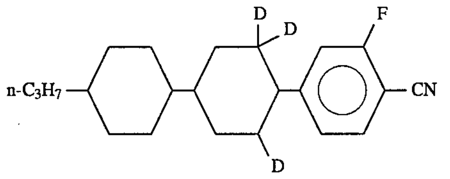
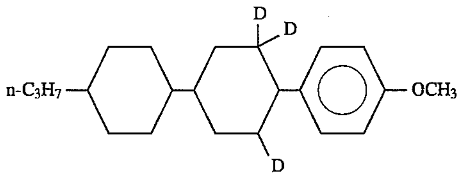
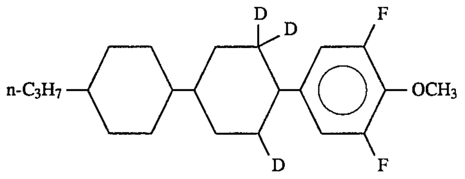

-continued
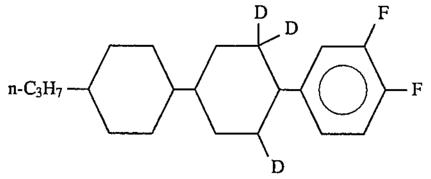
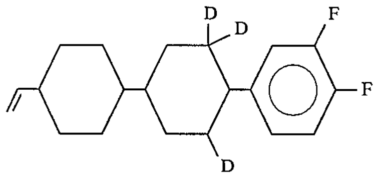
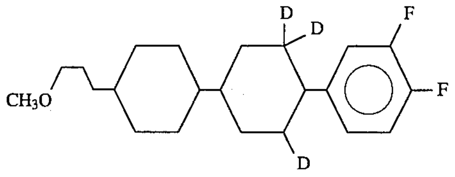
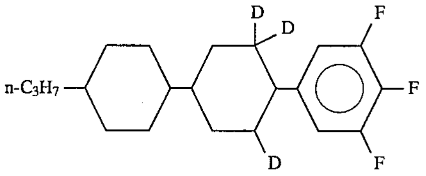
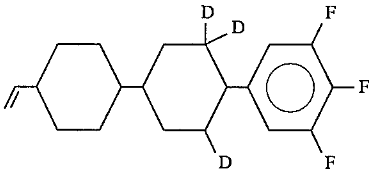
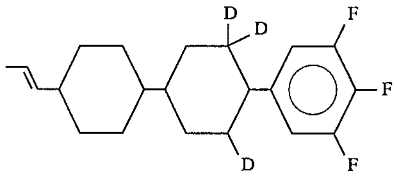
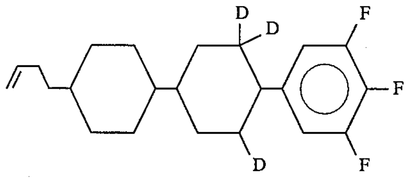
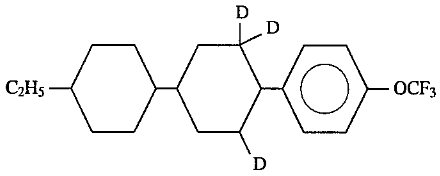
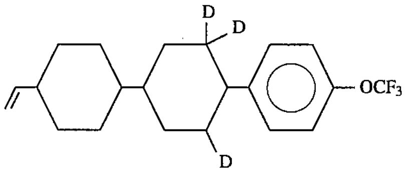
-continued
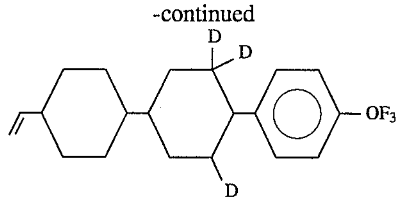
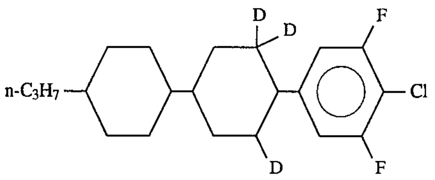
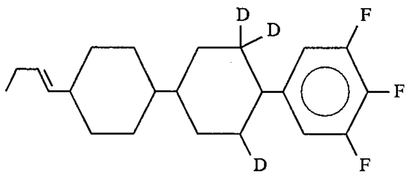
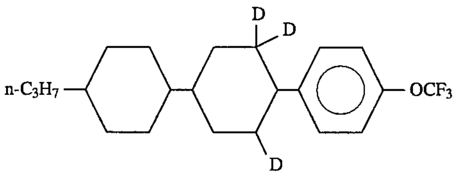
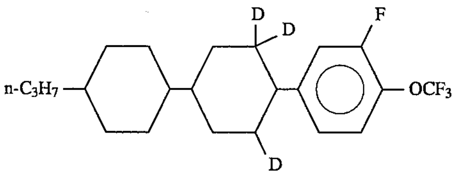
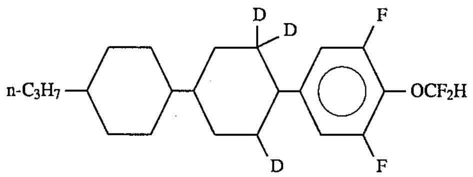
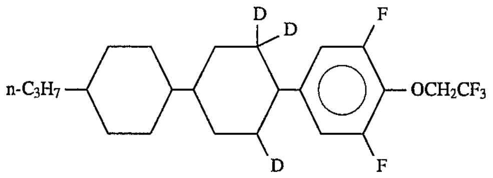
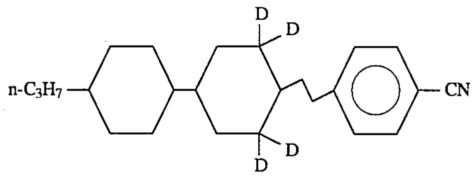
[C 68 N 240.5 I]
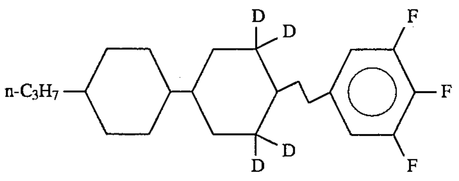
[C 40.5 N 98 I]

-continued
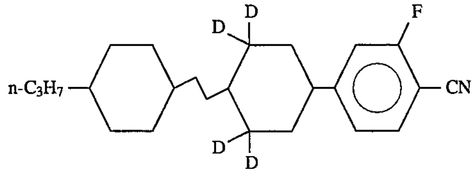
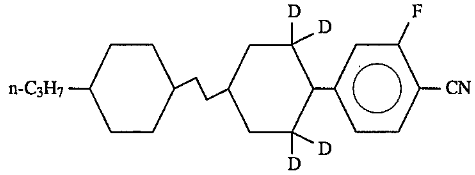
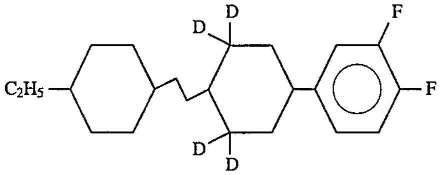
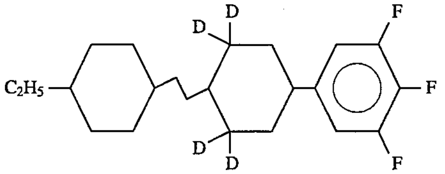
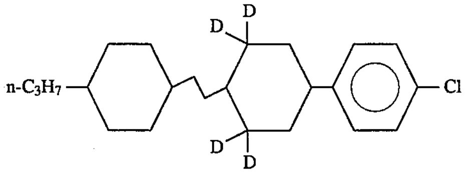
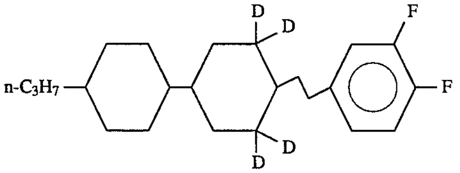
[#Sm 49 N 117.5 I]
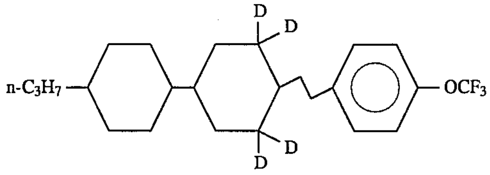
[#Sm 75 N 135 I]
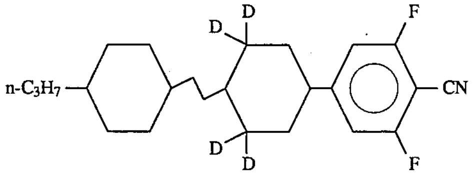
-continued
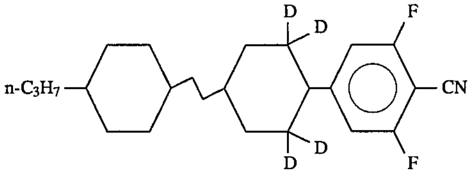
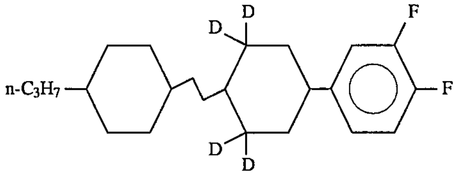
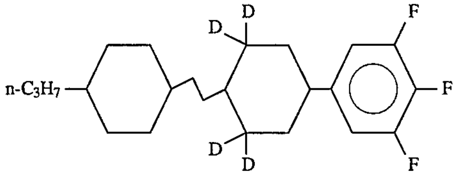
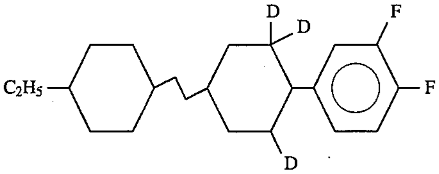
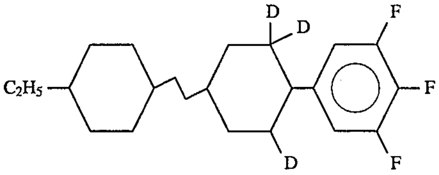
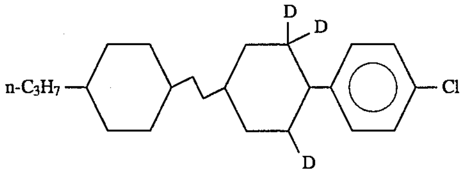
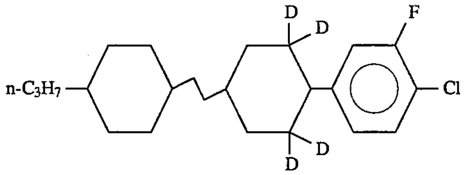
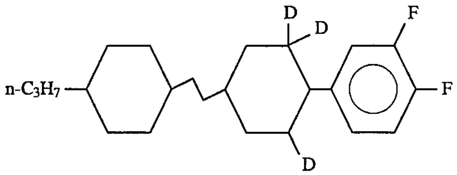
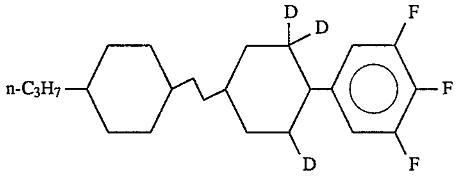

-continued
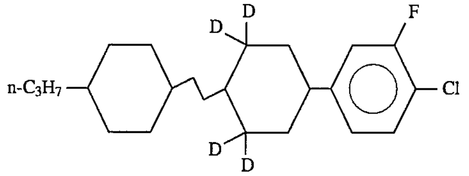
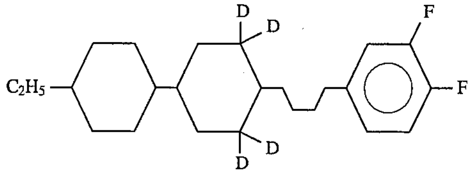
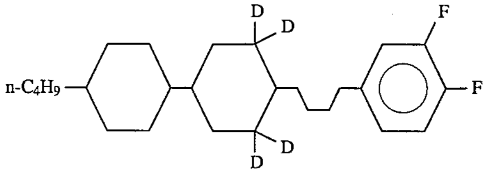
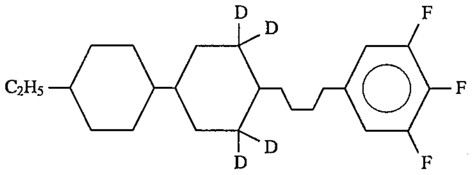
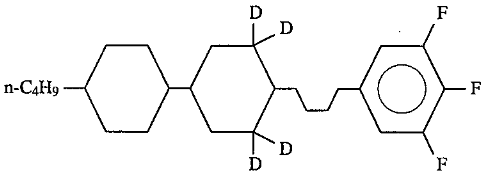
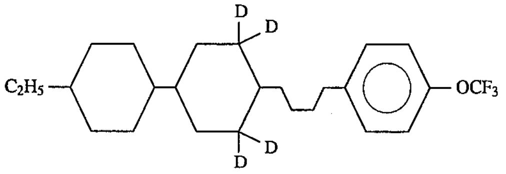
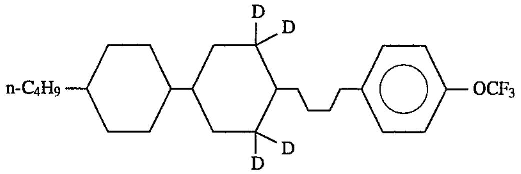
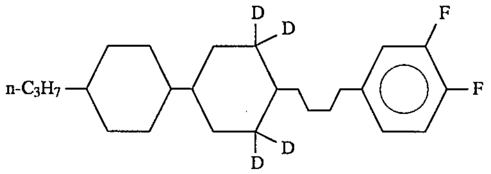
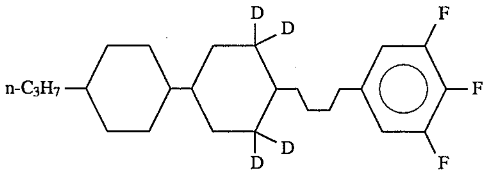
-continued
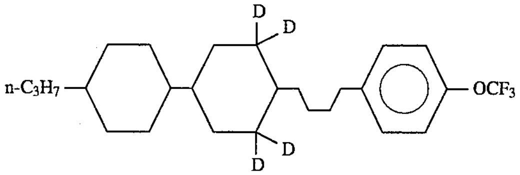
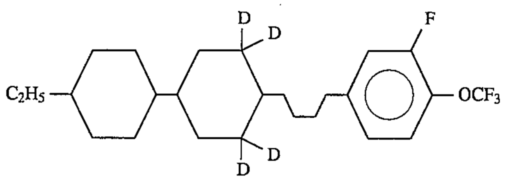
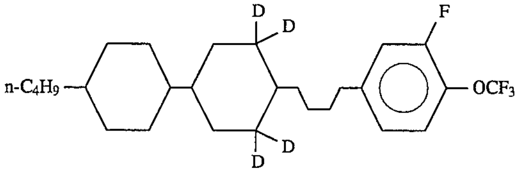
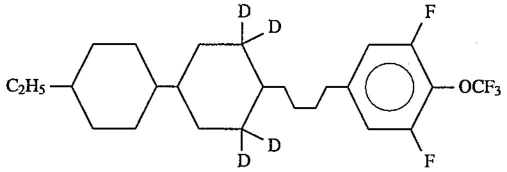
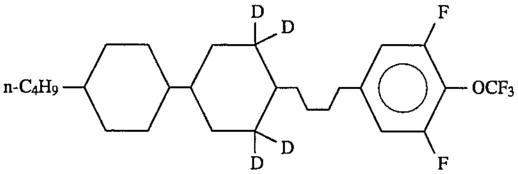
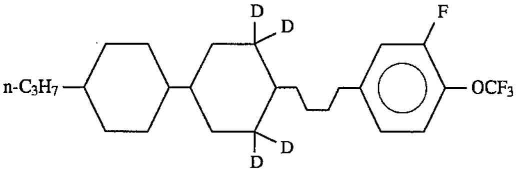
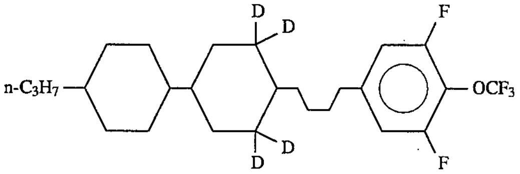
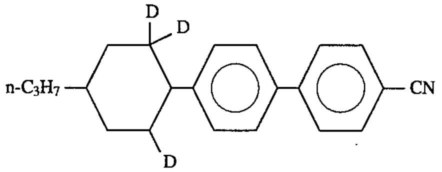
[C 88 N 218 I]
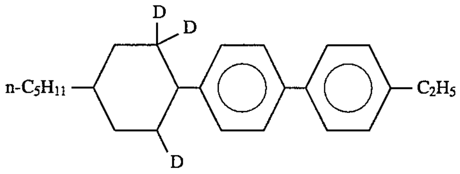
[C 25 Sm 137 N 160 I]

-continued
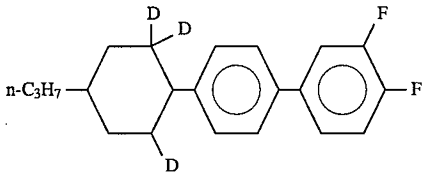
[C 62 N 96.5 I]
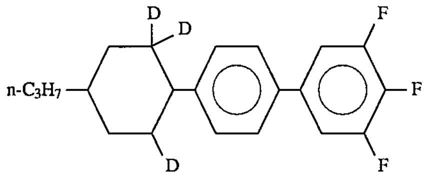
[C 35.5 N 34 I]
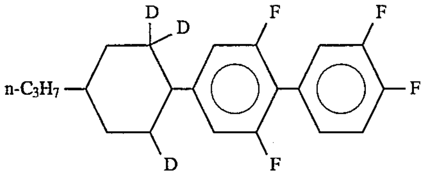
[C 72 I]
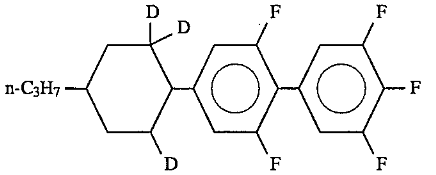
[C 121 I]
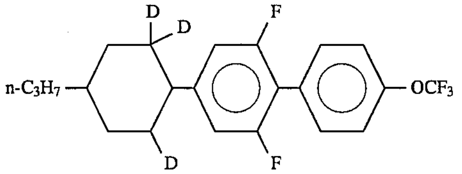
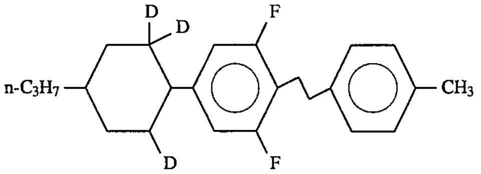
[C 75 (N) I]
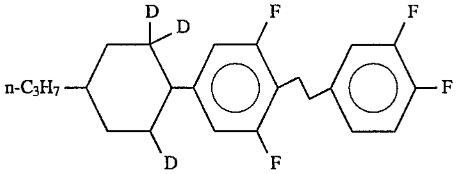
[C 67 I]
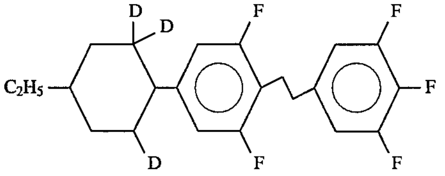
[C 95 I]
-continued
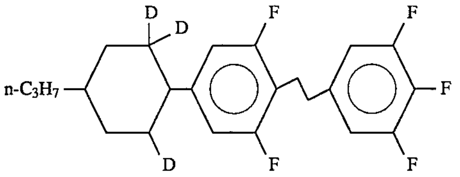
[C 77 I]
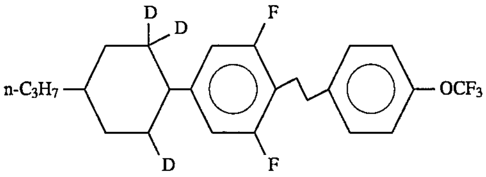
[C 42.5 I]
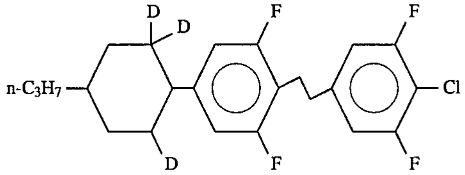
[C 87 I]
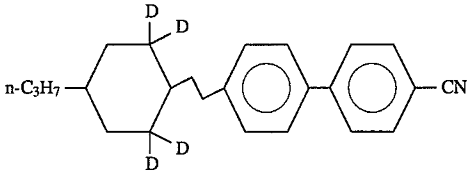
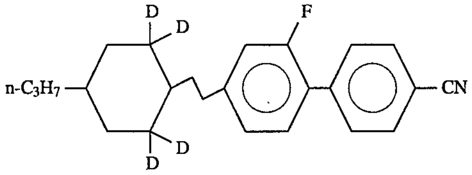
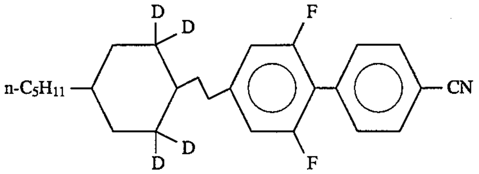
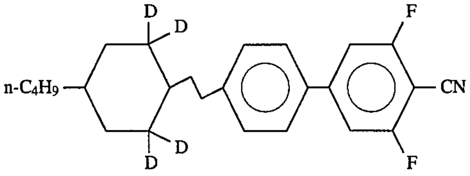
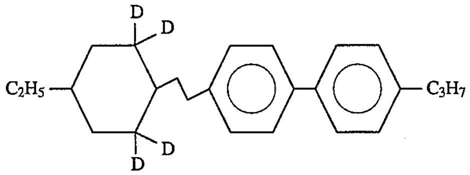

-continued
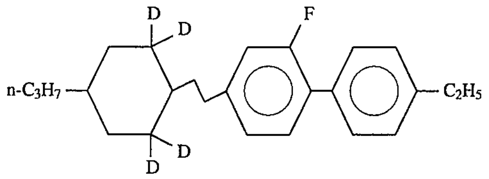
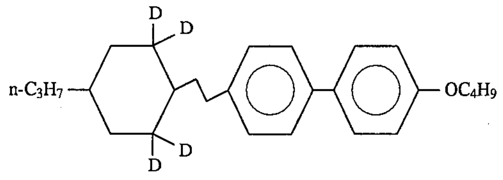
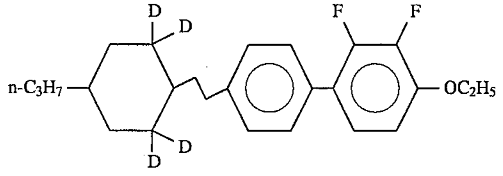
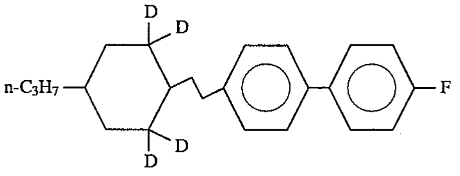
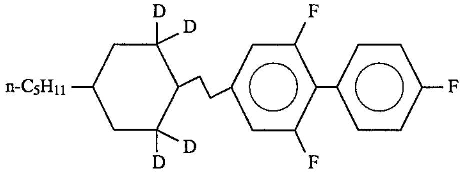
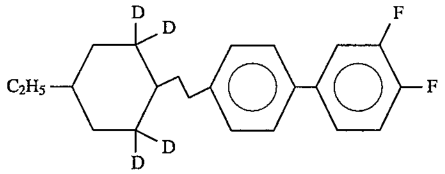
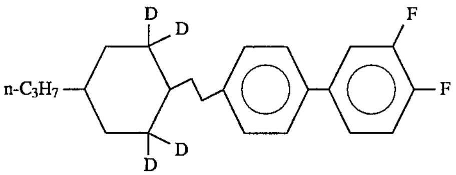
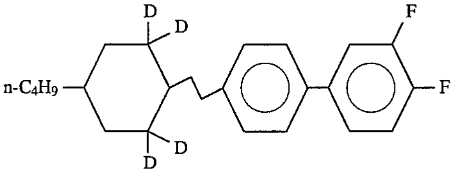
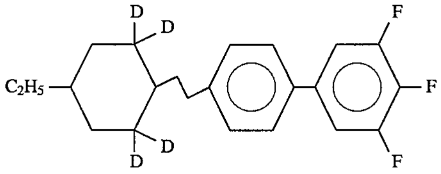
-continued
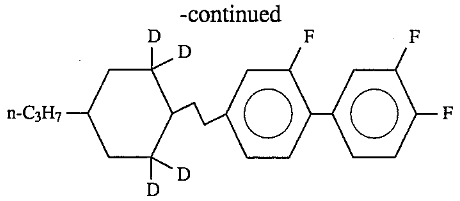
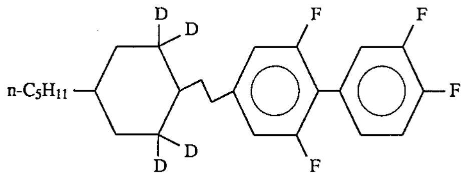
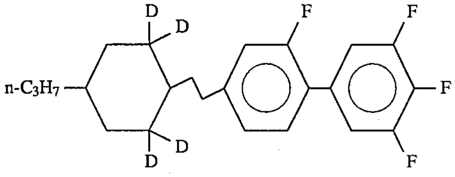
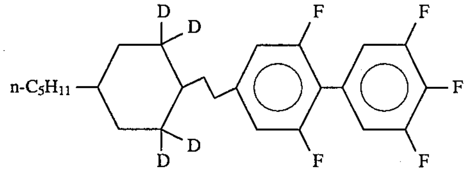
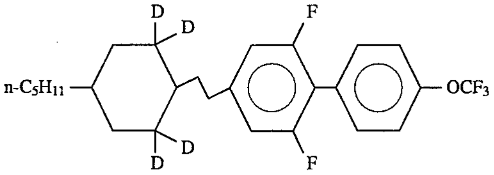
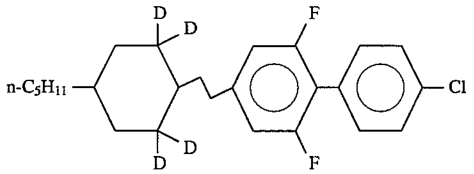
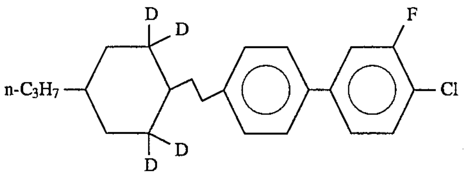
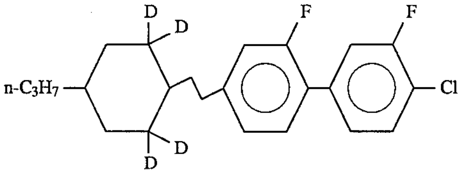
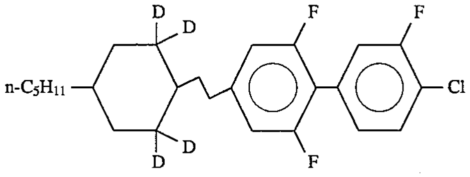

-continued
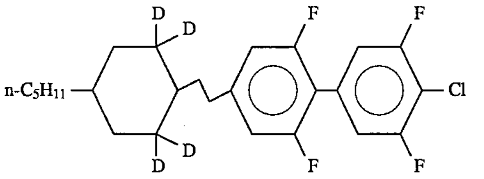
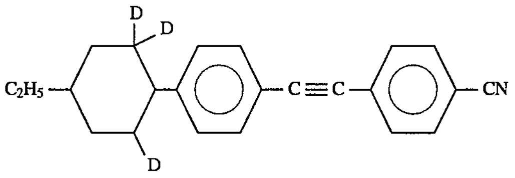
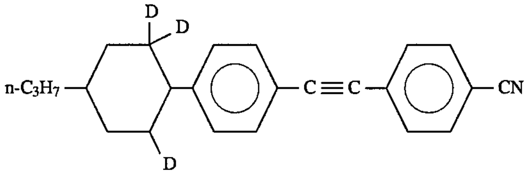
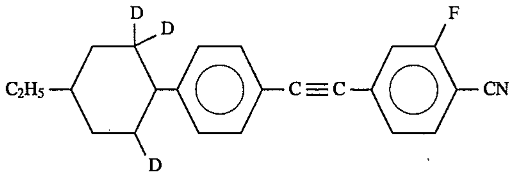
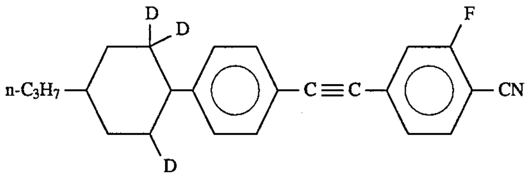
[C 130 N 220 I]
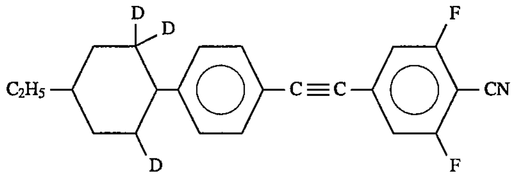
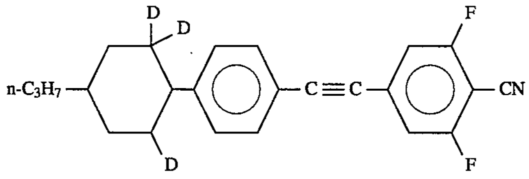
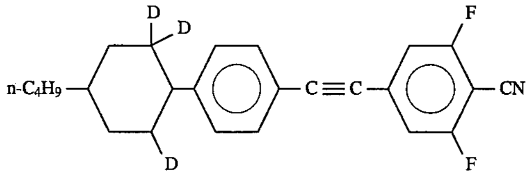
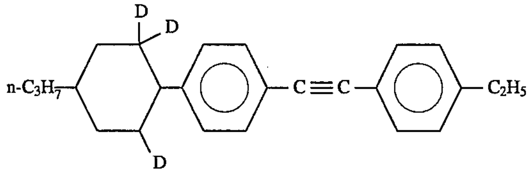
-continued
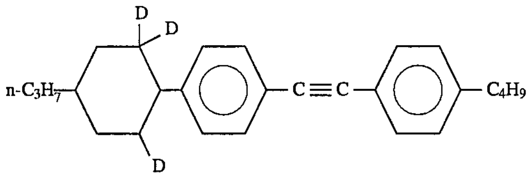
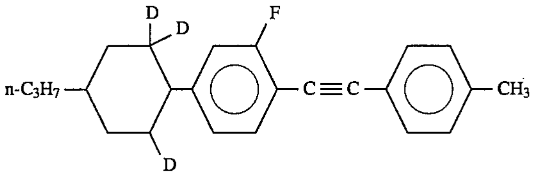
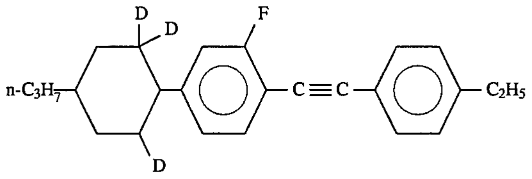
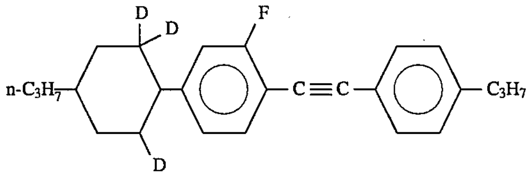
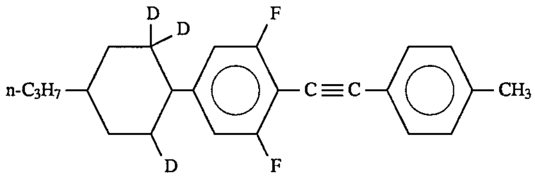
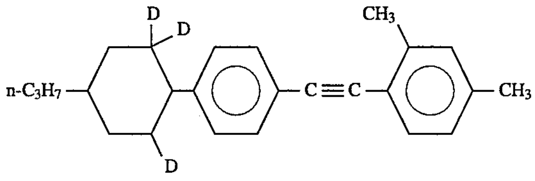
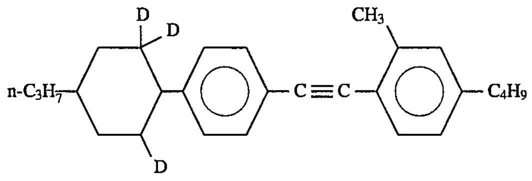
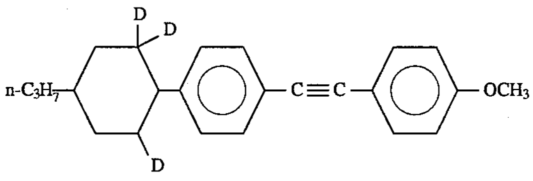
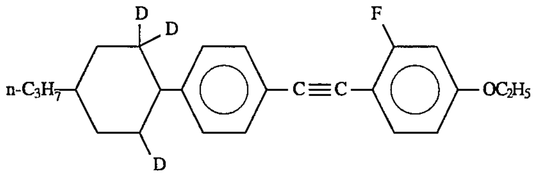

-continued
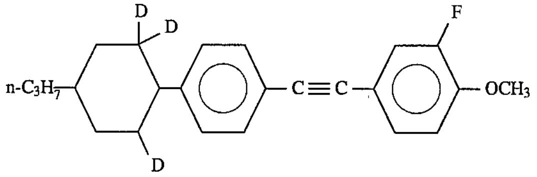
[C 103 N 202 I]
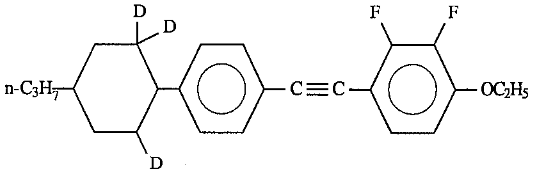
[C 80 N 227 I]
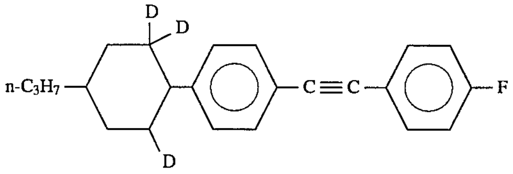
[C 85 N 187 I]
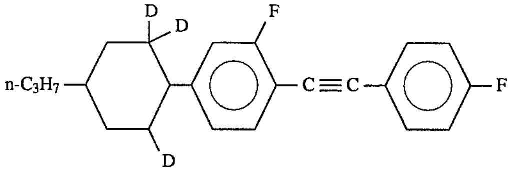
[C 75 N 103 I]
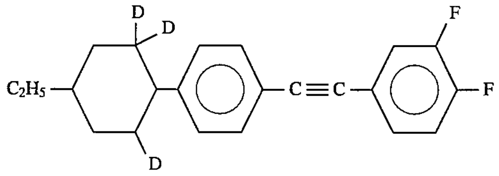
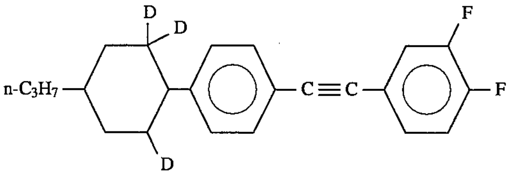
[C 82 N 147 I]
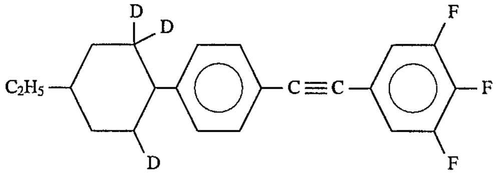
[C 85 N 90 I]
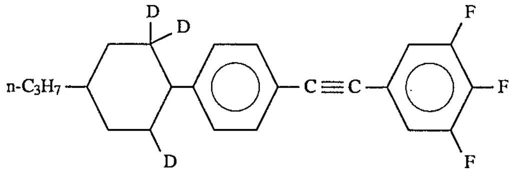
[C 74 N 96 I]
-continued
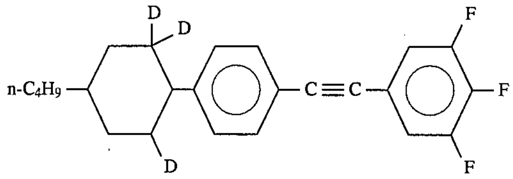
[C 58 N 92 I]
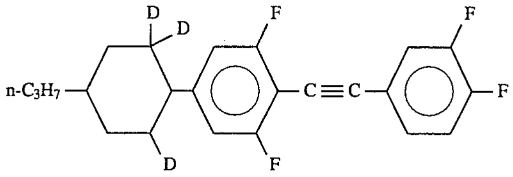
[C 72 N 123 I]
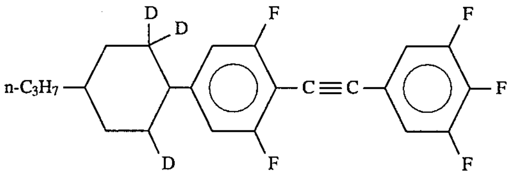
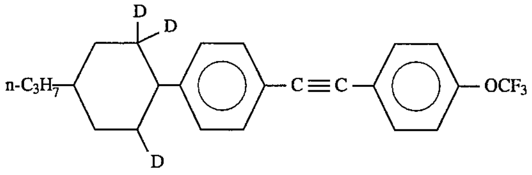
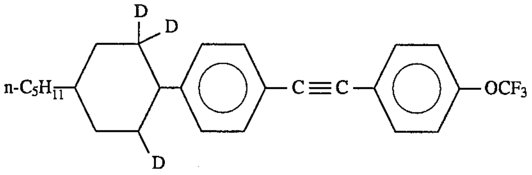
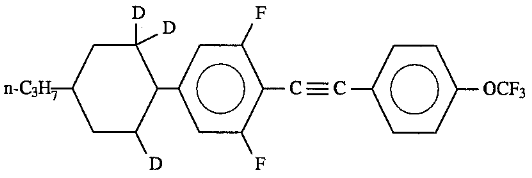
[C 55 $S_A$ 86.5 N 167 I]
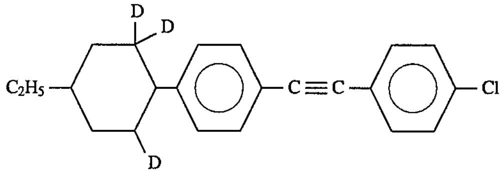
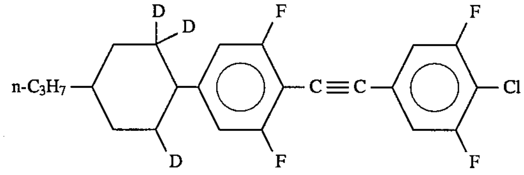
[C 94 N 143 I]

-continued

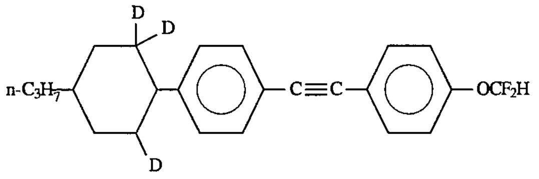

The preferred tetracyclic compounds of formula (I) include those represented by formula (I-4), (I-5) and (I-6):

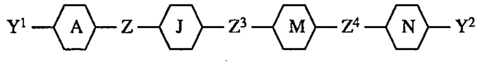
(I-4)

wherein $Y^1$, $Y^2$, Z, $Z^3$, $Z^4$, and rings A, J, M and N are as defined above in formula (I).

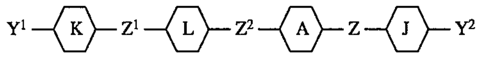
(I-5)

wherein $Y^1$, $Y^2$, Z, $Z^1$, $Z^2$, and rings A, K, L and J are as defined above in formula (I).

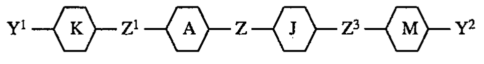
(I-6)

wherein $Y^1$, $Y^2$, Z, $Z^1$, $Z^3$, and rings A, K, J and M are as defined above in formula (I).

More specifically, the preferred tetracyclic compounds include those represented by formula (I-4'), (I-5'), and (I-6'):

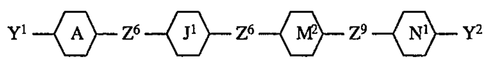
(I-4')

wherein ring A, ring $J^1$, $Z^6$, $Y^1$, and $Y^2$ are as defined above in which the two $Z^6$'s are independent to each other; ring $M^2$ and ring N each independently represent a trans-1,4-cyclohexylene group, a 1,4-phenylene group, a 1,4-phenylene group substituted with a fluorine atom, or the group of formula (I[I); and $Z^9$ represents a single bond, $-CH_2CH_2-$ or $-C\equiv C-$.

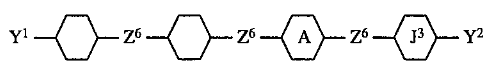
(I-5')

wherein ring A, ring $J^3$, $Z^6$, $Y^1$, and $Y^2$ are as defined above, in which the three $Z^6$'s are independent to each other.

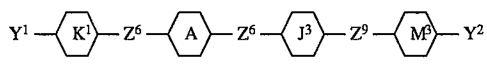
(I-6')

wherein ring A, ring $K^1$, ring $J^3$, $Z^6$, $Z^9$, $Y^1$, and $Y^2$ are as defined above, in which the two $Z^6$'s are independent to each other; and ring $M^3$ represents a 1,4-phenylene group or a 1,4-phenylene group substituted with a fluorine atom.

More preferred of these tetracyclic compounds are those represented by formulae (I-4'a) to (I-4'f), (I-5'a), and (I-6'a) to (I-6'c):

(I-4'a)
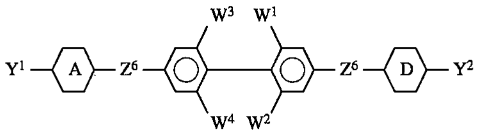

wherein ring A, ring D, $Z^6$, $W^1$, $W^2$, $W^3$, $W^4$, $Y^1$, and $Y^2$ are as defined above, in which the two $Z^6$'s are independent to each other.

(I-4'b)
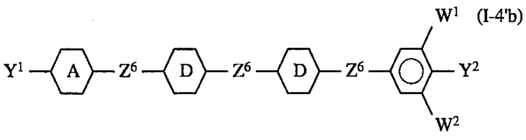

wherein ring A, ring D, $Z^6$, $W^1$, $W^2$, $Y^1$, and $Y^2$ are as defined above, in which the two D rings are independent to each other, and the three $Z^6$'s are independent to each other.

(I-4'c)
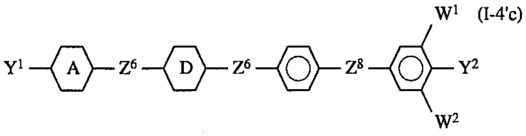

wherein ring A, ring D, $Z^6$, $Z^8$, $W^1$, $W^2$, $Y^1$, and $Y^2$ are as defined above, in which the two $Z^6$'s are independent to each other.

(I-4'd)
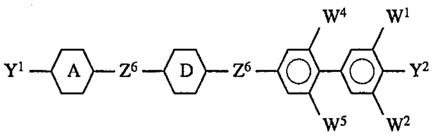

wherein ring A, ring D, $Z^6$, $W^1$, $W^2$, $W^4$, $W^5$, $Y^1$, and $Y^2$ are as defined above, in which the two $Z^6$'s are independent to each other.

(I-4'e)
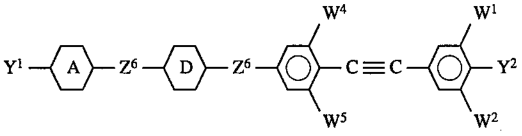

wherein ring A, ring D, $Z^6$, $W^1$, $W^2$, $W^4$, $W^5$, $Y^1$, and $Y^2$ are as defined above, in which the two $Z^6$'s are independent to each other.

(I-4'f)
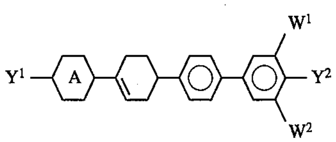

wherein ring A, $W^1$, $W^2$, $Y^1$, and $Y^2$ are as defined above.

(I-5'a)
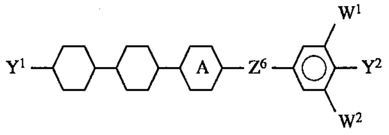

wherein ring A, $Z^6$, $W^1$, $W^2$, $Y^1$, and $Y^2$ are as defined above.

(I-6'a)
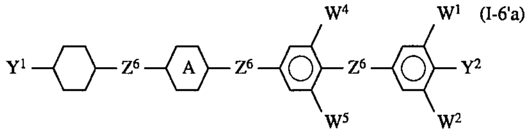

wherein ring A, $Z^6$, $W^1$, $W^2$, $W^4$, $W^5$, $Y^1$, and $Y^2$ are as defined above, in which the two $Z^6$'s are independent to each other.

(I-6'b)
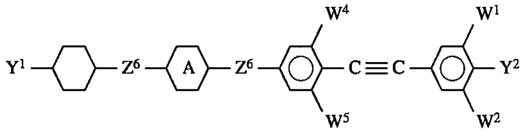

wherein ring A, $Z^6$, $W^1$, $W^2$, $W^4$, $W^5$, $Y^1$, and $Y^2$ are as defined above, in which the two $Z^6$'s are independent to each other.

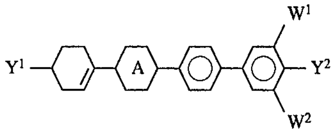

(I-6'c)

wherein ring A, $W^1$, $W^2$, $Y^1$, and $Y^2$ are as defined above.

Specific examples of the compounds represented by formulae (I-4'), (I-5') and (I-6') are shown below.

In the followings, the numerical values in the brackets shown by [] are the phase transition temperatures of the compounds, in which C represents a crystal phase, Sm a smectic phase, $S_A$ a smectic A phase, $S_B$ a smectic B phase, N a nematic phase, and I an isotropic liquid phase, the parentheses shown by () represent the monotropic phases, and # indicates that the melting point is not clear due to non-crystallization. For example, "C 44 N" means that the phase transition temperature from the crystal phase to the nematic phase is 44° C.

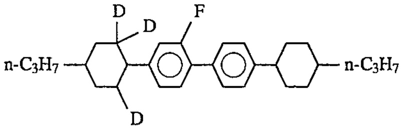

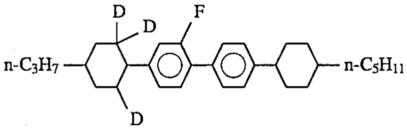

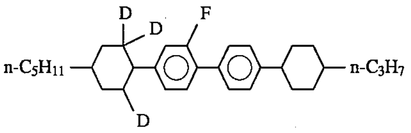

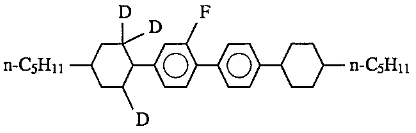

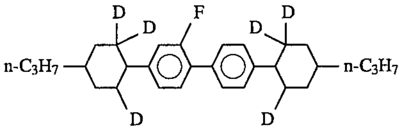

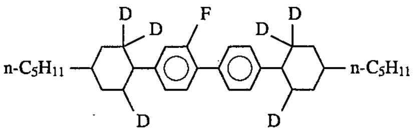

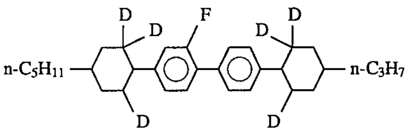

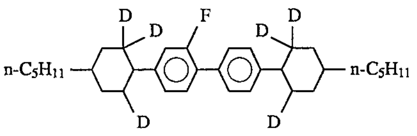

-continued

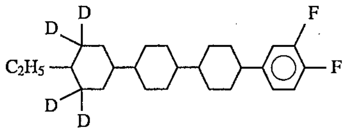

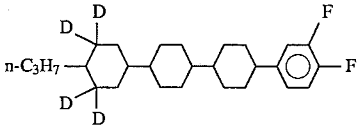

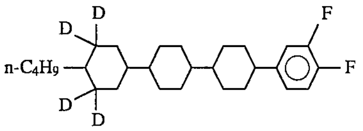

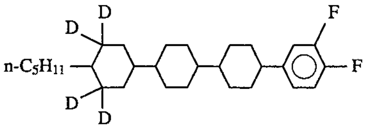

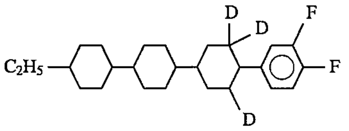

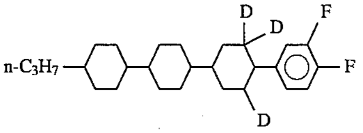

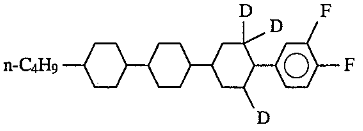

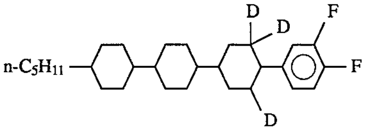

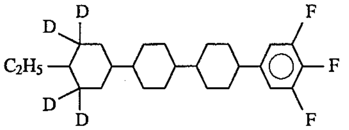

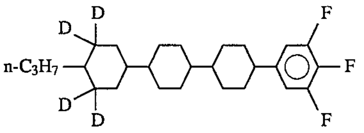

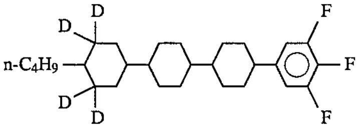

-continued
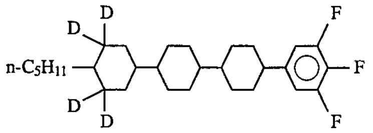
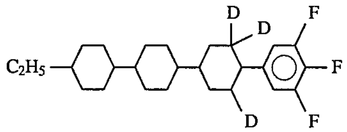
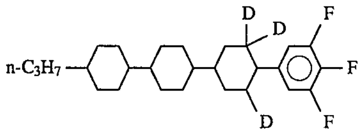
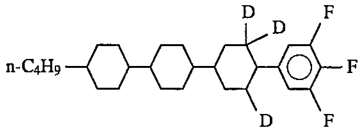
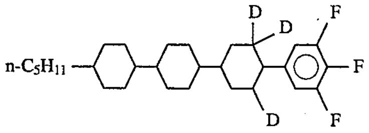
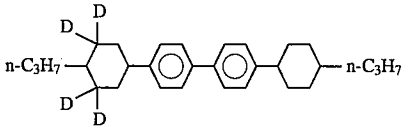
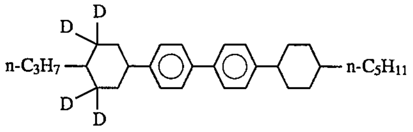
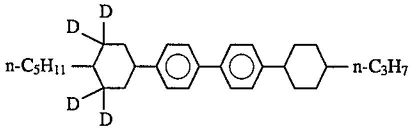
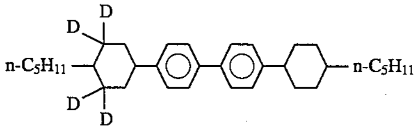
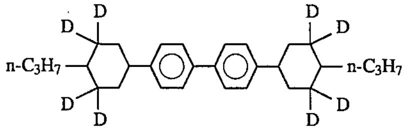
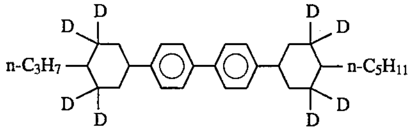
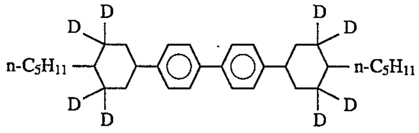
-continued
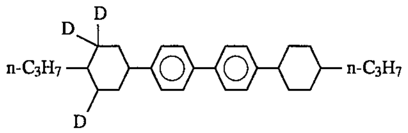
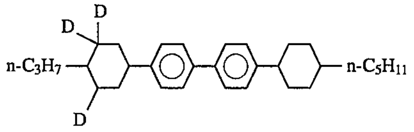
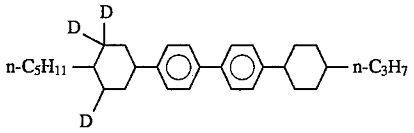
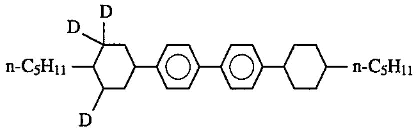
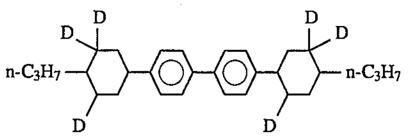
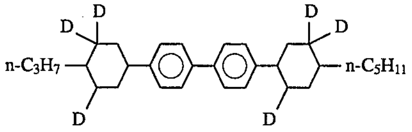
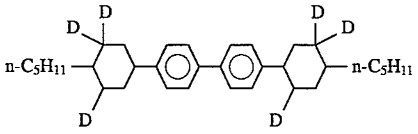
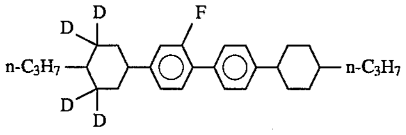
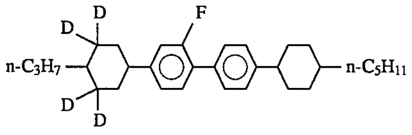
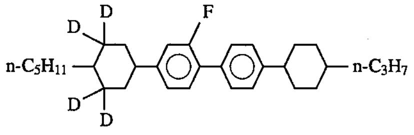
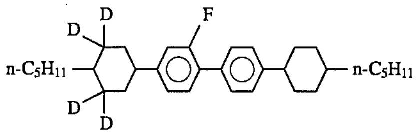

-continued
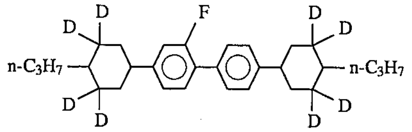
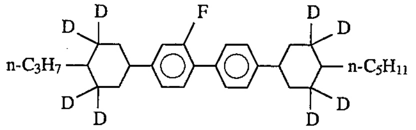
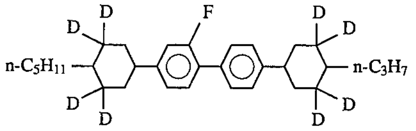
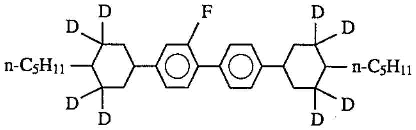
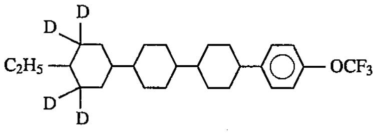
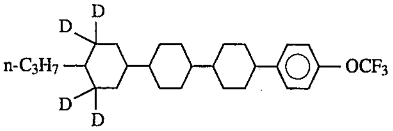
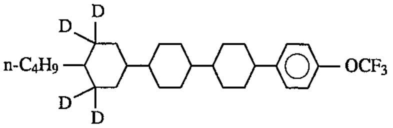
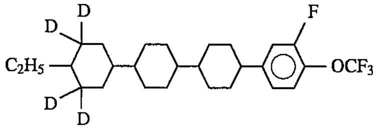
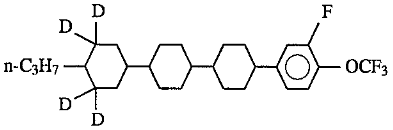
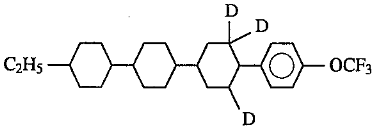
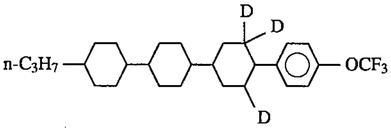
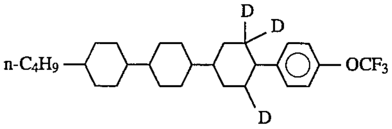
-continued
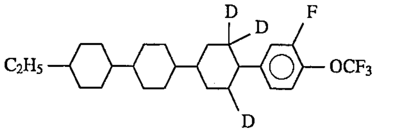
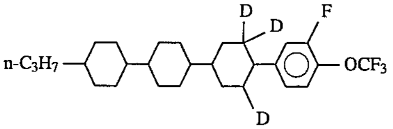
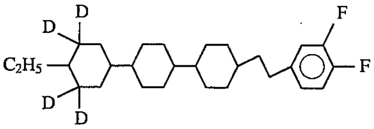
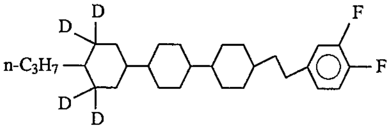
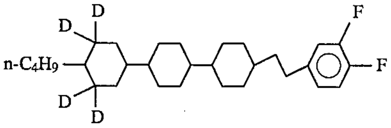
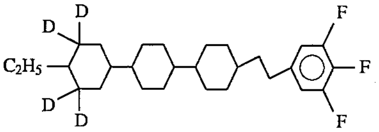
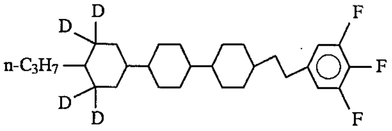
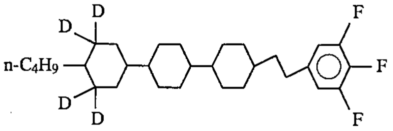
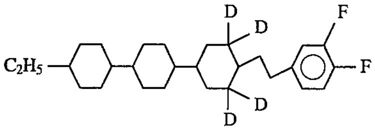
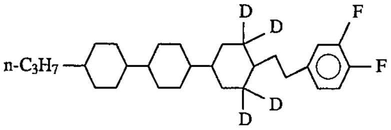
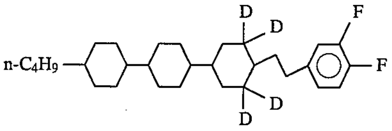

-continued
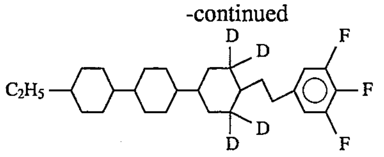
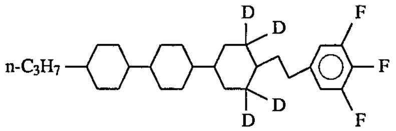
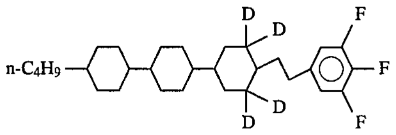
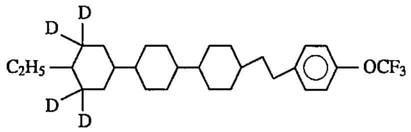
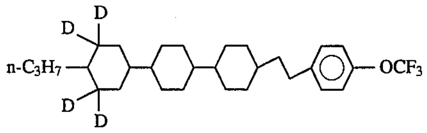
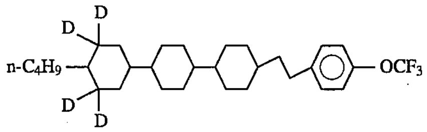
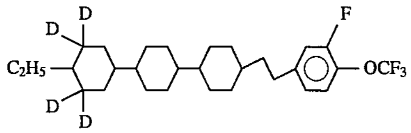
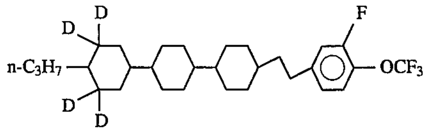
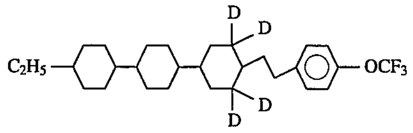
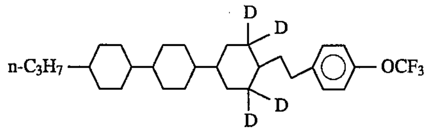
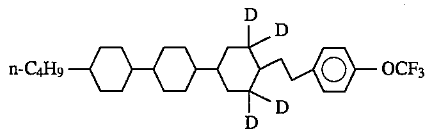
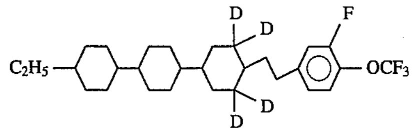
-continued
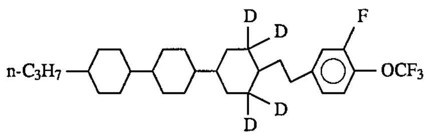
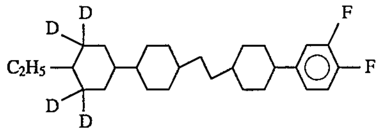
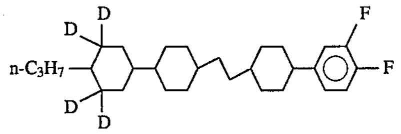
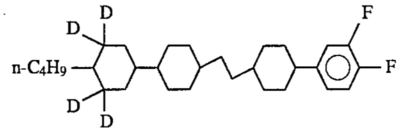
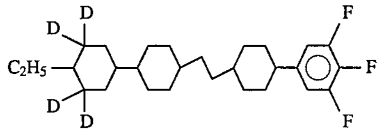
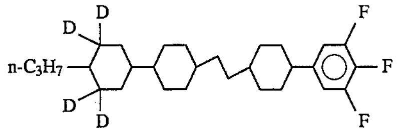
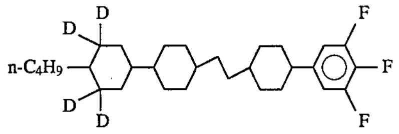
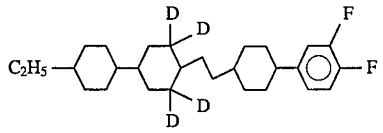
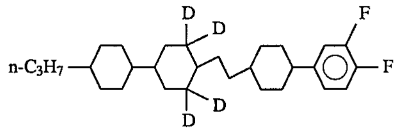
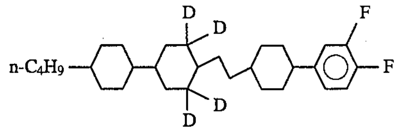
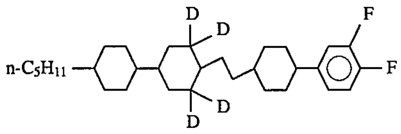

-continued
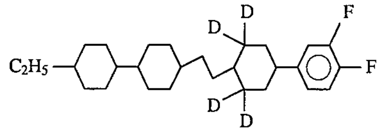
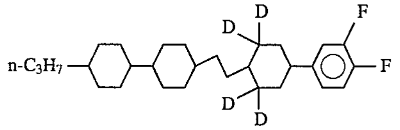
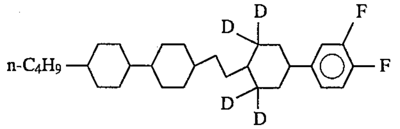
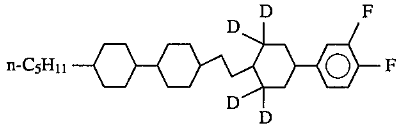
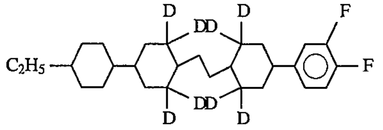
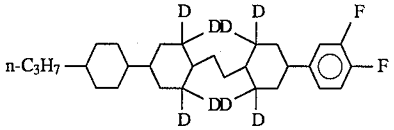
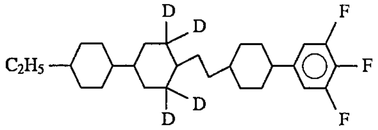
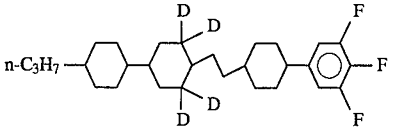
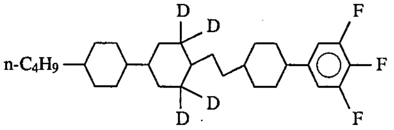
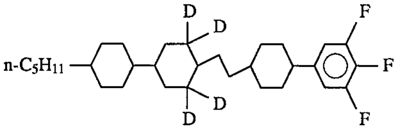
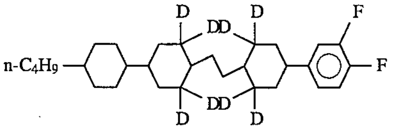
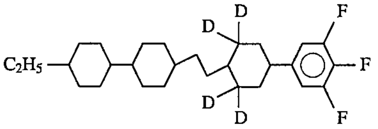
-continued
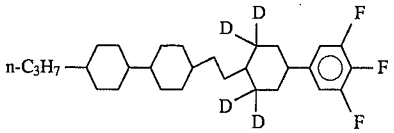
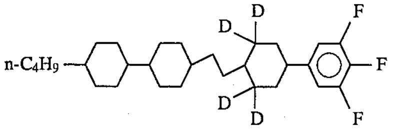
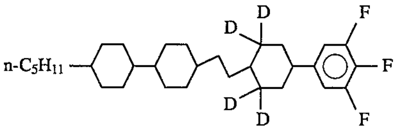
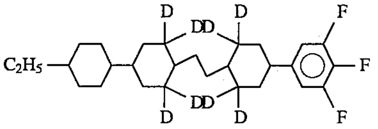
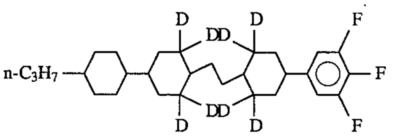
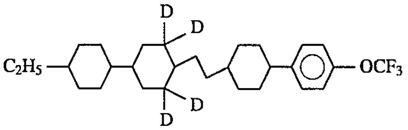
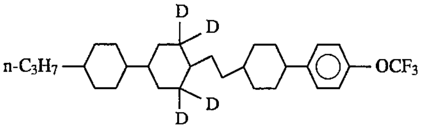
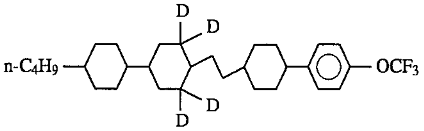
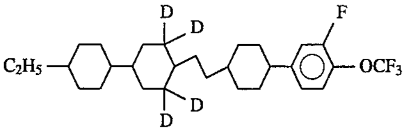
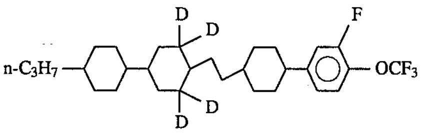
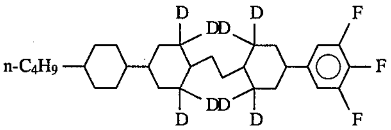

-continued
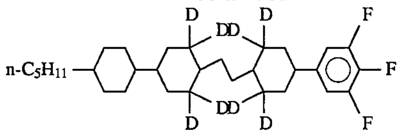
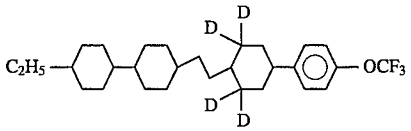
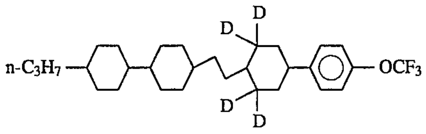
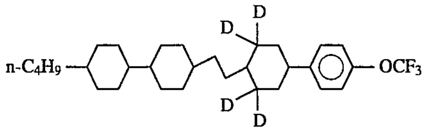
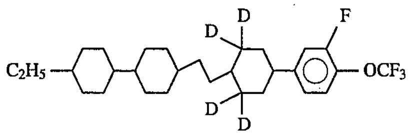
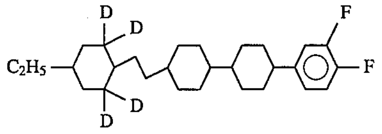
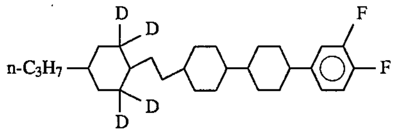
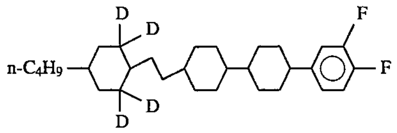
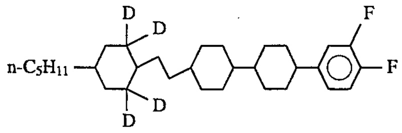
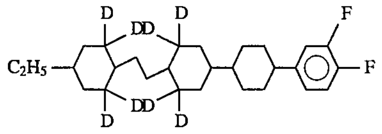
[C 115 $S_B$ 130 N 230 I]
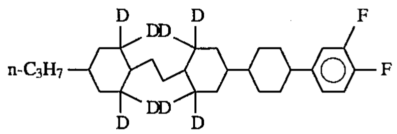
[C 125 $S_B$ 144 N 249 I]
-continued
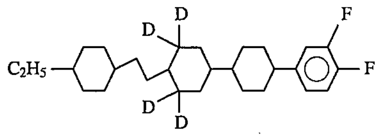
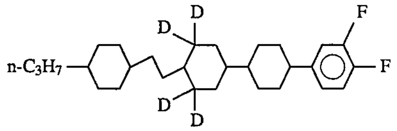
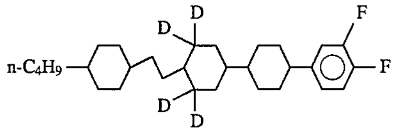
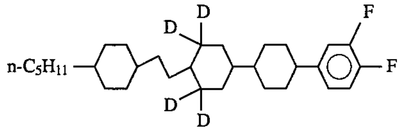
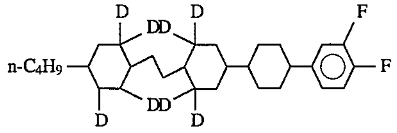
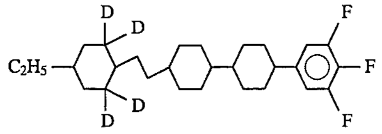
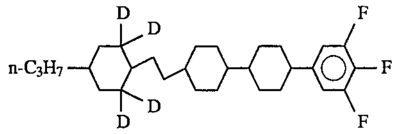
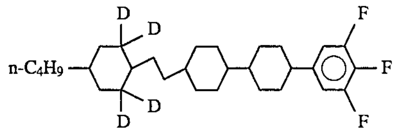
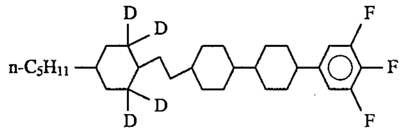
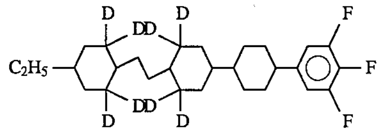
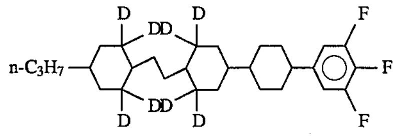
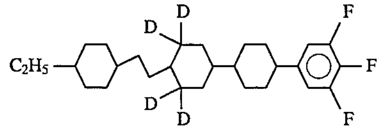

-continued
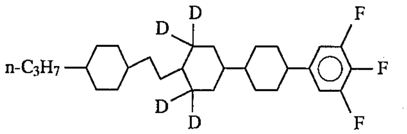
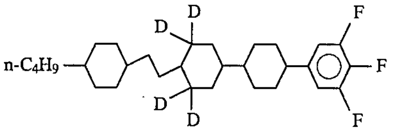
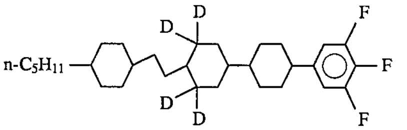
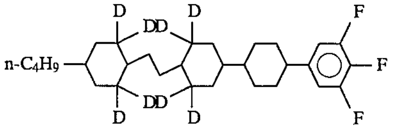
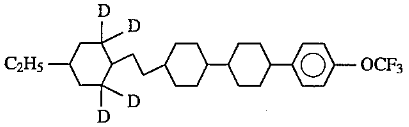
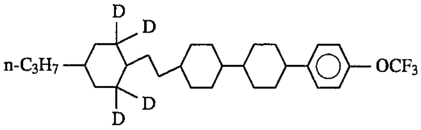
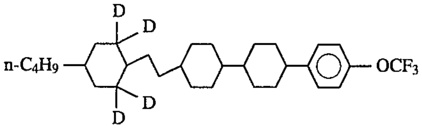
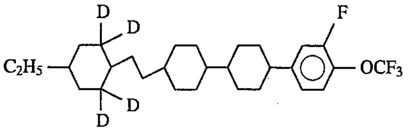
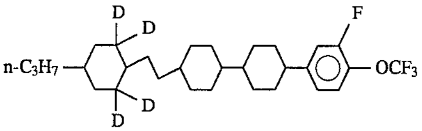
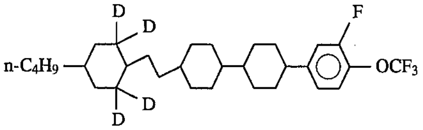
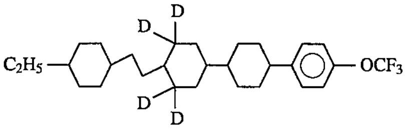
-continued
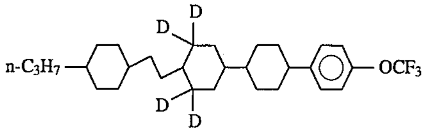
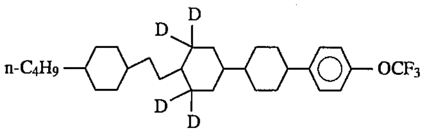
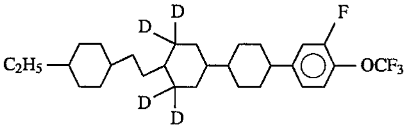
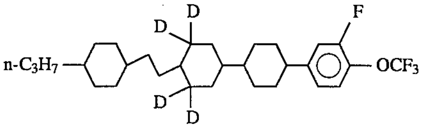
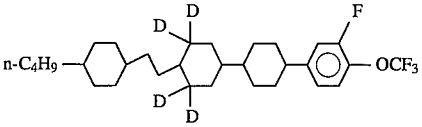
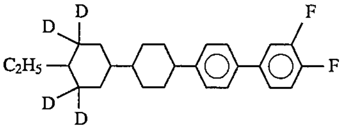
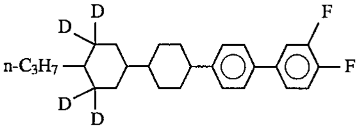
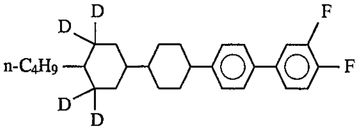
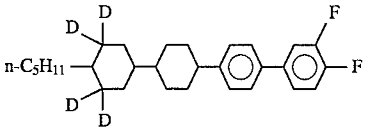
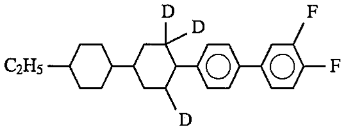
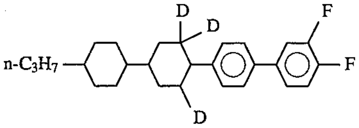
[C 88 (S 82) N 290 I]

-continued
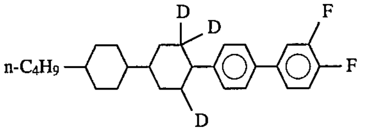
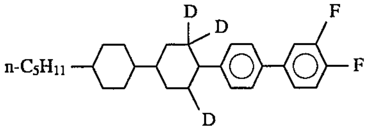
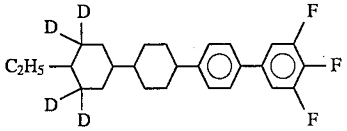
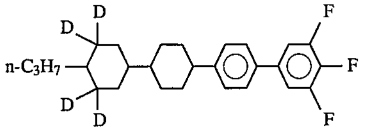
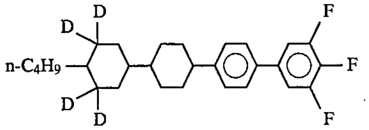
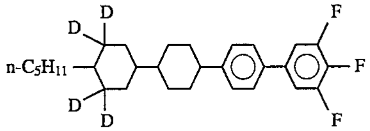
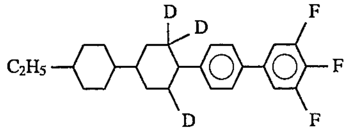
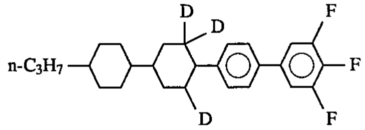
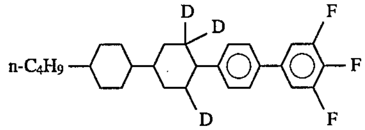
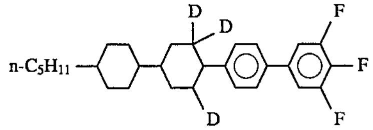
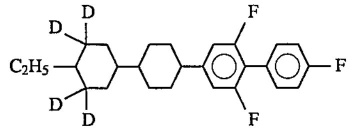
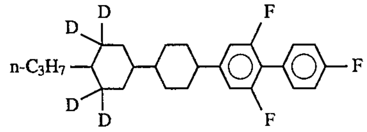
-continued
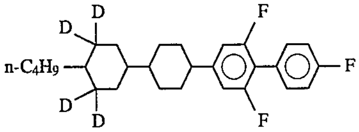
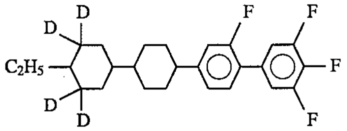
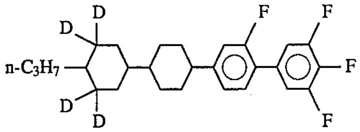
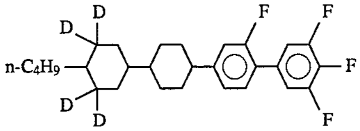
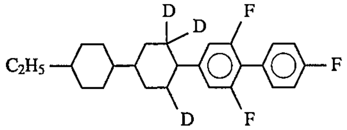
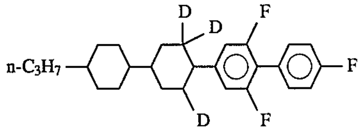
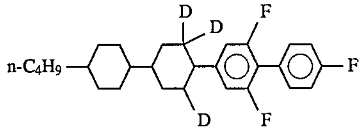
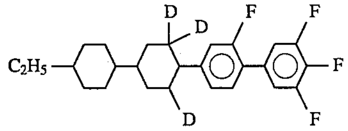
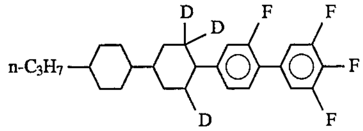
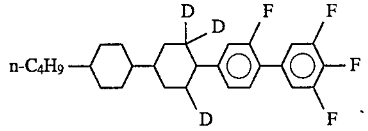
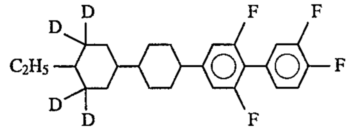

-continued
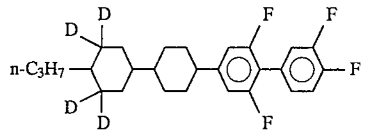
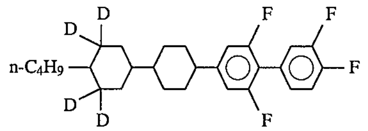
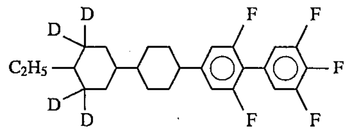
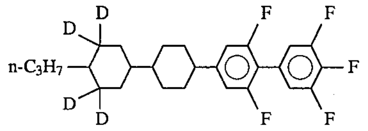
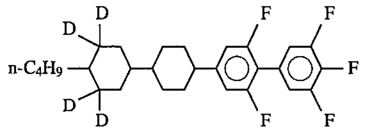
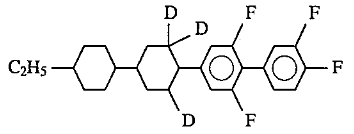
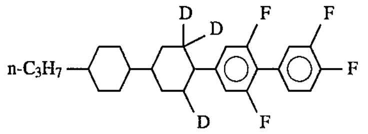
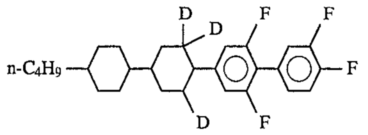
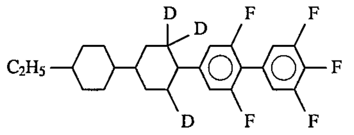
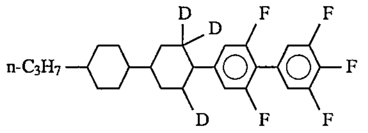
[C 149 N 232.5 I]
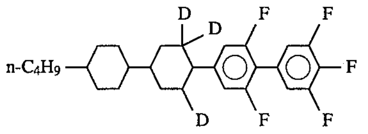
-continued
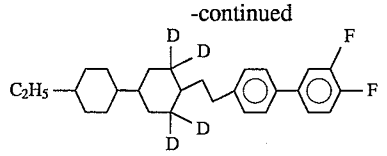
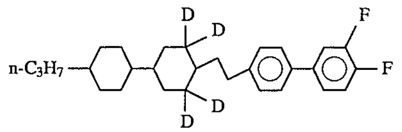
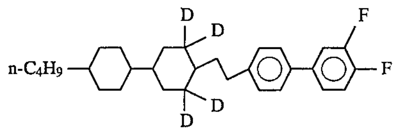
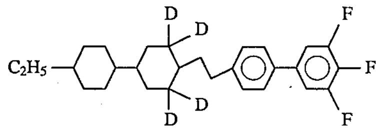
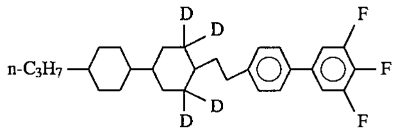
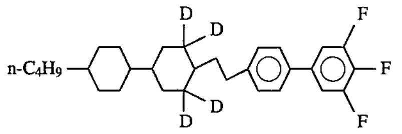
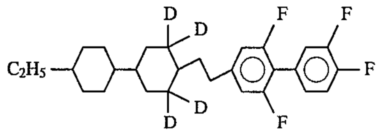
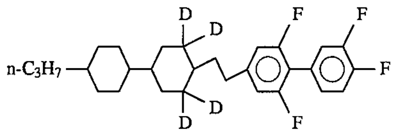
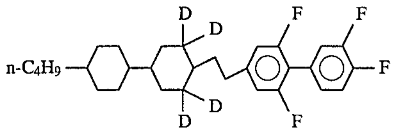
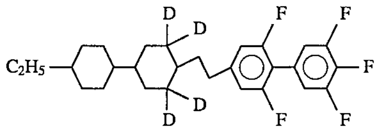
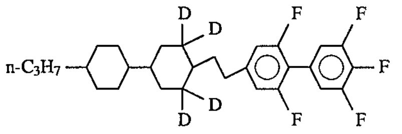
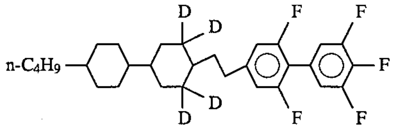

-continued
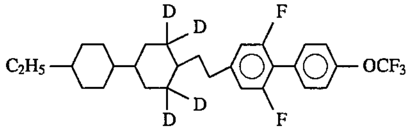
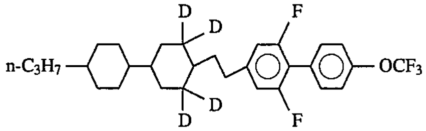
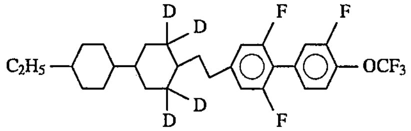
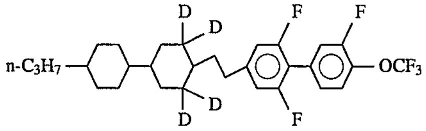
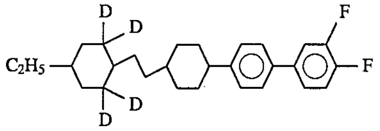
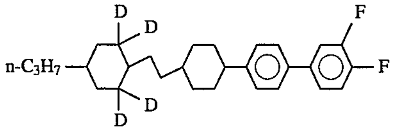
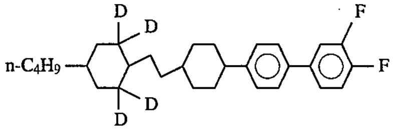
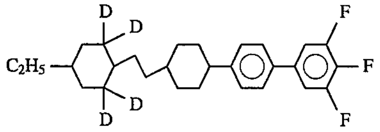
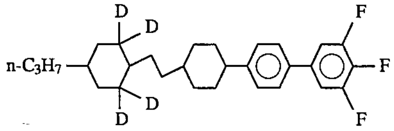
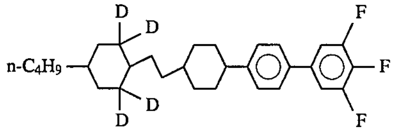
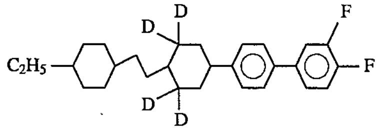
-continued
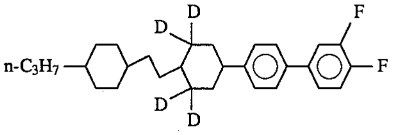
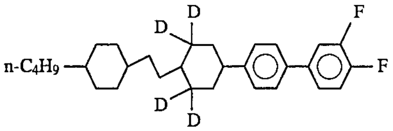
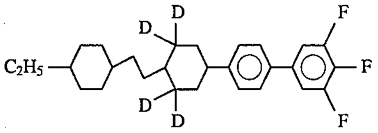
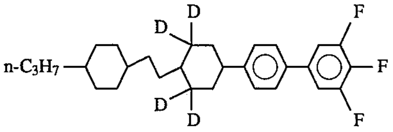
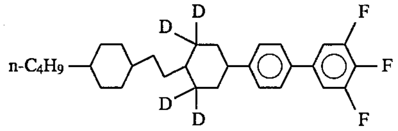
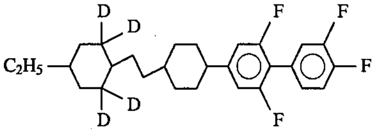
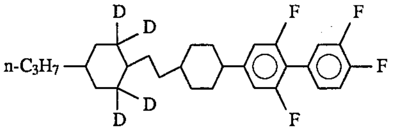
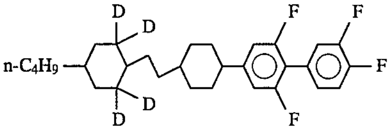
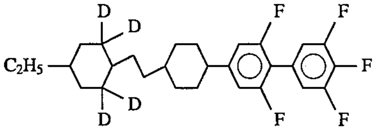
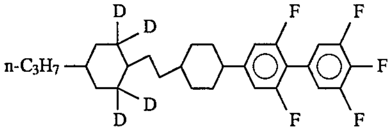
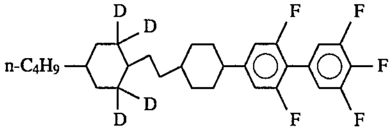
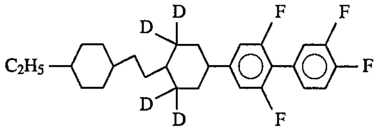

-continued
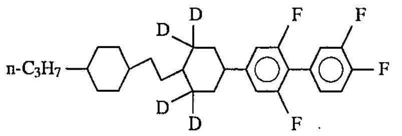
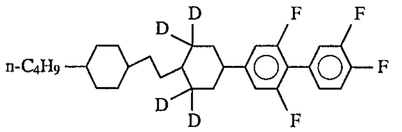
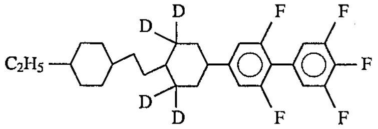
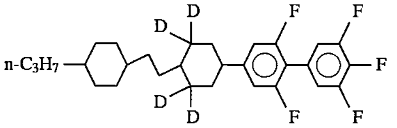
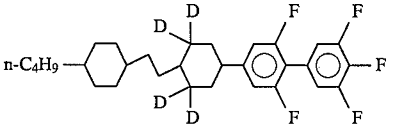
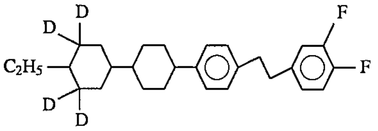
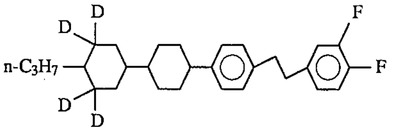
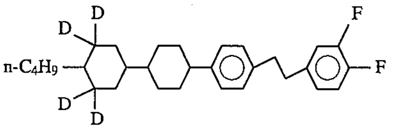
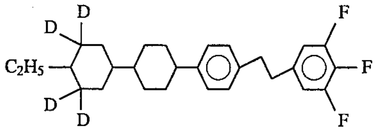
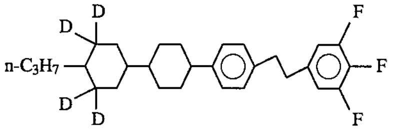
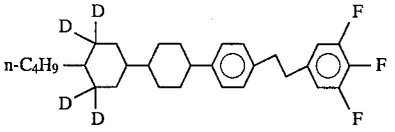
-continued
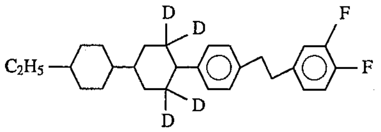
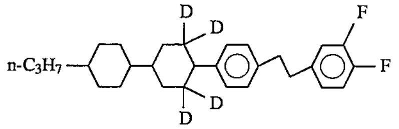
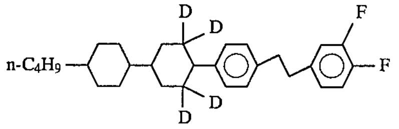
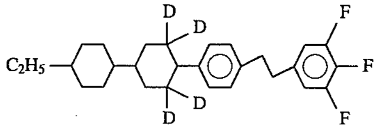
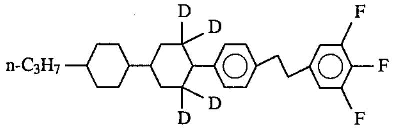
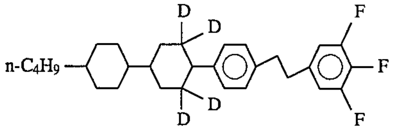
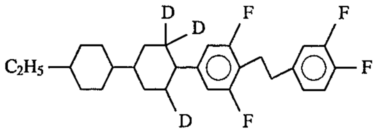
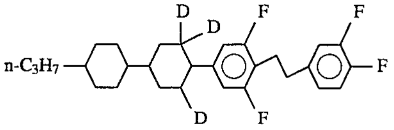
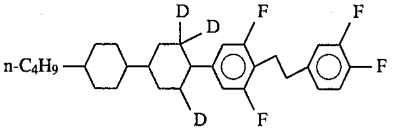
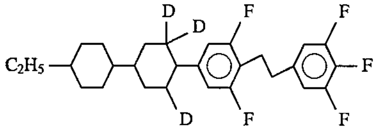
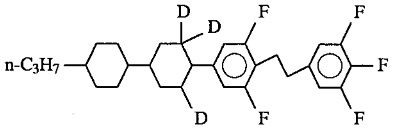
[C 114 N 170 I]

-continued
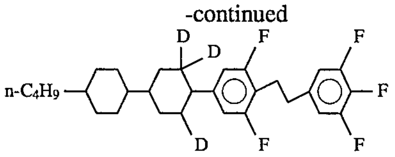
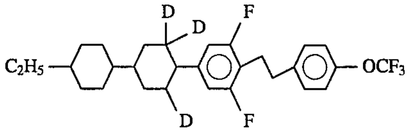
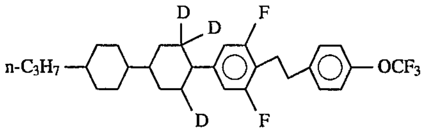
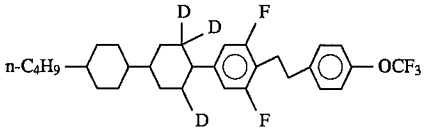
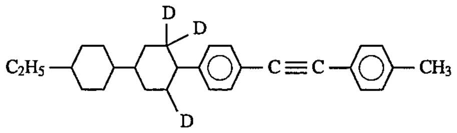
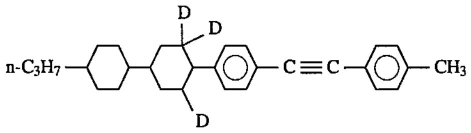
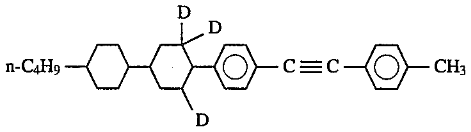
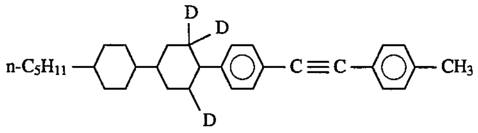
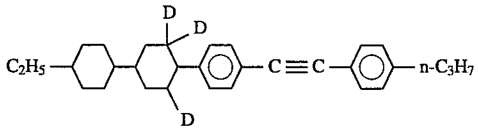
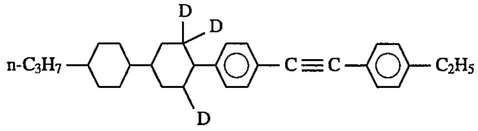
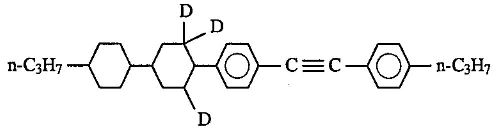
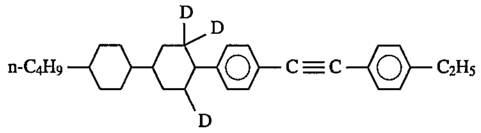
-continued
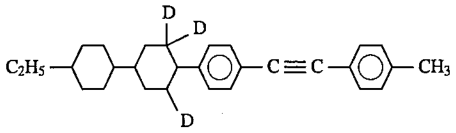
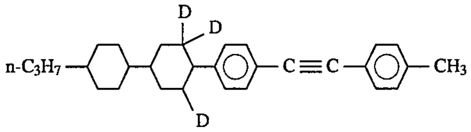
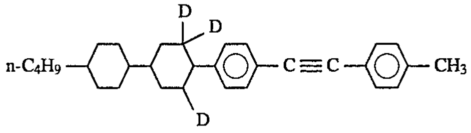
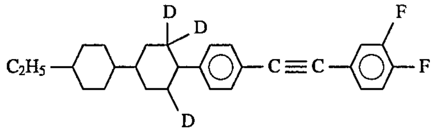
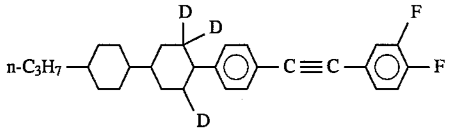
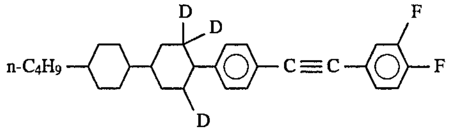
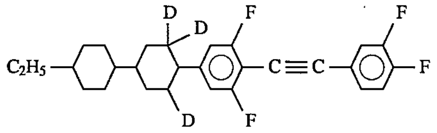
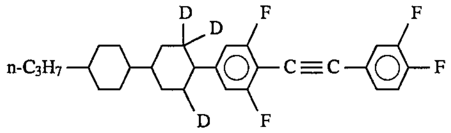
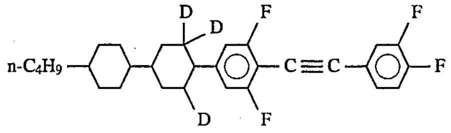
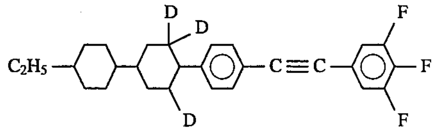
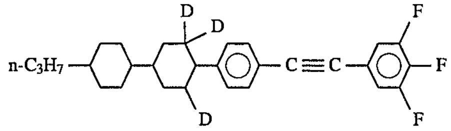

-continued

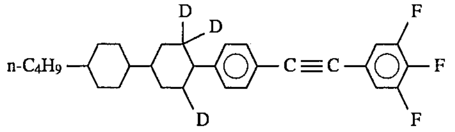

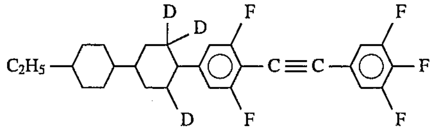

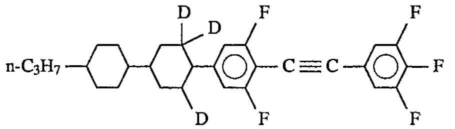

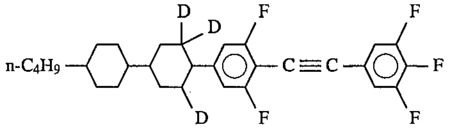

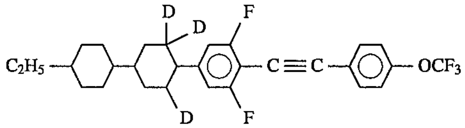

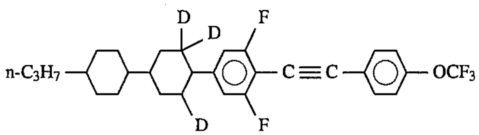

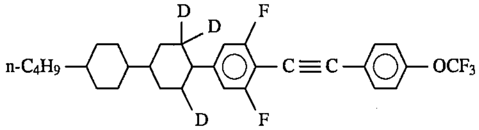

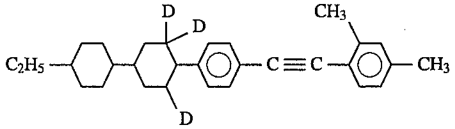

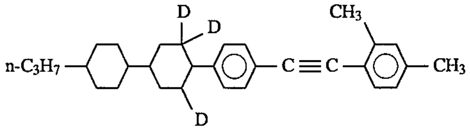

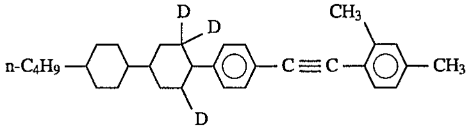

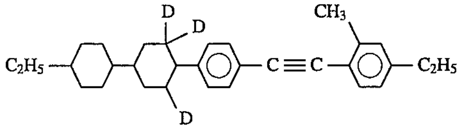

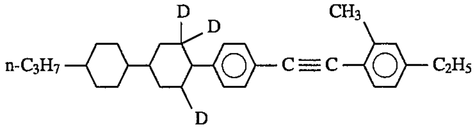

-continued

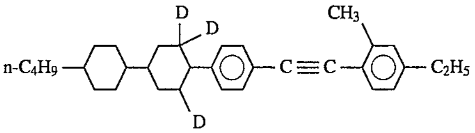

In the above-described compounds, it is preferable that ring A is represented by formula (II) wherein 1 to 8 of $X^2$, $X^3$, $X^4$, $X^5$, $X^6$, $X^7$, $X^8$, and $X^9$ are deuterium atoms (D).

Of these deuterated cyclohexane rings, preferred are those represented by formulae (II-a), (III-a), (II-b), (III-b), (II-c), and (III-c):

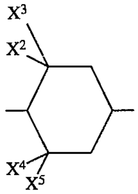

(II-a)

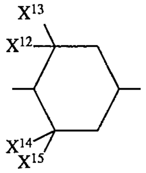

(III-a)

wherein at least one of $X^2$, $X^3$, $X^4$, and $X^5$ and at least one of $X^{12}$, $X^{13}$, $X^{14}$, and $X^{15}$ each represent a deuterium atom (D).

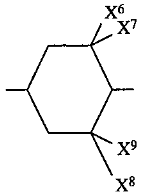

(II-b)

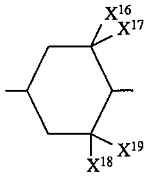

(III-b)

wherein at least one of $X^6$, $X^7$, $X^8$, and $X^9$ and at least one of $X^{16}$, $X^{17}$, $X^{18}$, and $X^{19}$ each represent a deuterium atom (D).

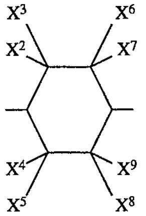

(II-c)

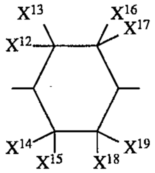

(III-c)

wherein at least one of $X^2$, $X^3$, $X^4$, and $X^5$, at least one of $X^6$, $X^7$, $X^8$, and $X^9$, at least three of $X^{12}$, $X^{13}$, $X^{14}$, and $X^{15}$, and at least one of $R^{16}$, $R^{17}$, $R^{18}$, and $R^{19}$ each represent a deuterium atom (D).

The compounds of formula (I) according to the present invention can be prepared in the same manner as for corresponding compounds of formula (I) wherein the group of formula (II) and the group of formula (III) are each a 1,4-cyclohexylene group having no deuterium, with the exception that deuterated cyclohexanone derivatives, etc. are used as starting materials or a deuteration step is introduced in the stage of intermediates, while depending on the central skeleton composed of rings and linking groups and the position and the number the deuterium atoms (D) bonded to the ring(s).

For example, a bicyclic liquid crystal compound represented by formula (R-1):

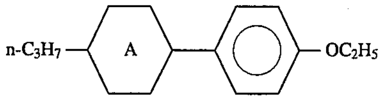

(R-1)

wherein ring A is a cyclohexane ring having one or more deuterium atoms (D), which is deuterated 1-(trans-4-propylcyclohexyl)-4-ethoxybenzene, can be prepared through processes A to J hereinafter illustrated. In what follows, "$d_n$-" attached to a chemical name or a structural formula indicates that the hydrogen atoms (H) bonded to the cyclohexane ring are substituted by n deuterium atom or atoms (D).

Process A:

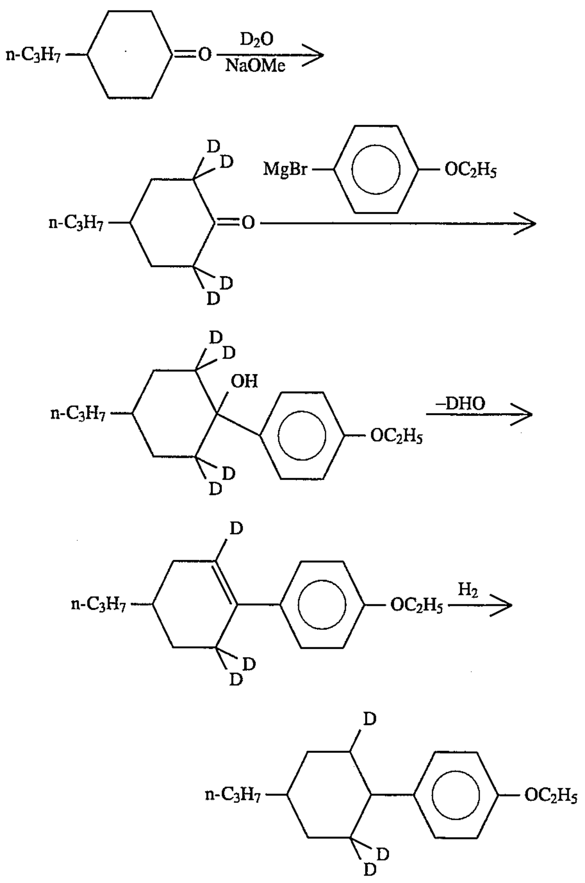

4-Propylcyclohexanone is dissolved in a solvent, e.g., dichloromethane, and heated with heavy water ($D_2O$) in the presence of a base to obtain 4-propylcyclohexanone-2,2,6,6-$d_4$, which is then reacted with a Grignard reagent prepared from 1-ethoxy-4-bromobenzene. The resulting $d_4$-phenylcyclohexanol derivative is dehydrated to obtain a $d_3$-phenylcyclohexene derivative. The $d_3$-phenylcyclohexene derivative is catalytically reduced, and the cis-compound is removed to obtain 1-(trans-4-propylcyclohexyl-2,2,6-$d_3$)-4-ethoxybenzene.

Process B:

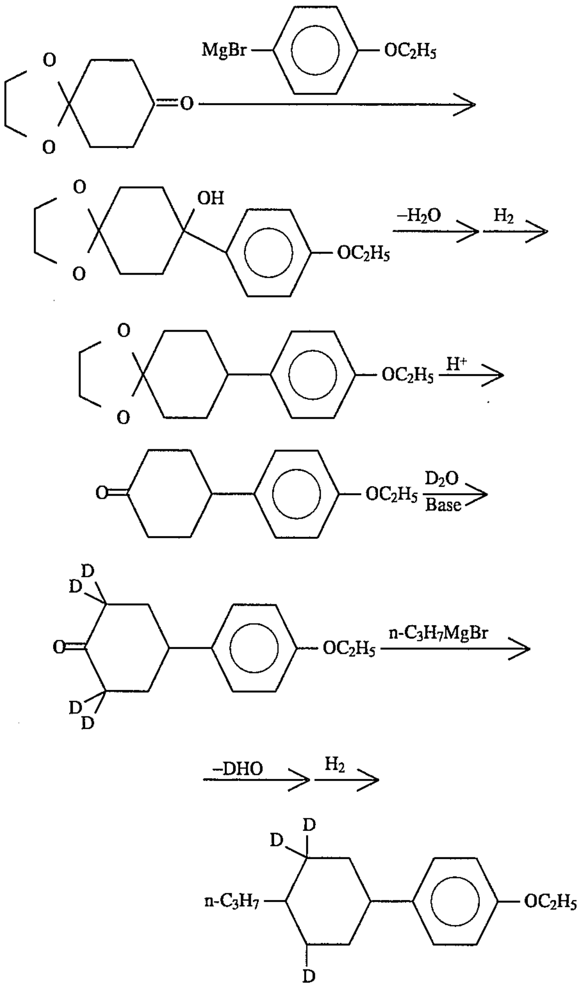

Cyclohexane-1,4-dione monoethyleneacetal is reacted with a Grignard reagent prepared from 1-ethoxy-4-bromobenzene, and the product is dehydrated and then hydrogenated in the same manner as in process A (if desired, ethyleneacetal is re-introduced). The acetal moiety is removed to obtain 4-(4-ethoxyphenyl)cyclohexanone, which is then deuterated in the same manner as in process A to obtain 4-(4-ethoxyphenyl)cyclohexanone-2,2,6,6-$d_4$. The deuterated compound is reacted with a Grignard reagent prepared from propyl bromide, and the product is dehydrated and hydrogenated. The cis-compound is separated to obtain 1-(trans-4-propylcyclohexyl-3,3,5-$d_3$)-4-ethoxybenzene.

Process C:

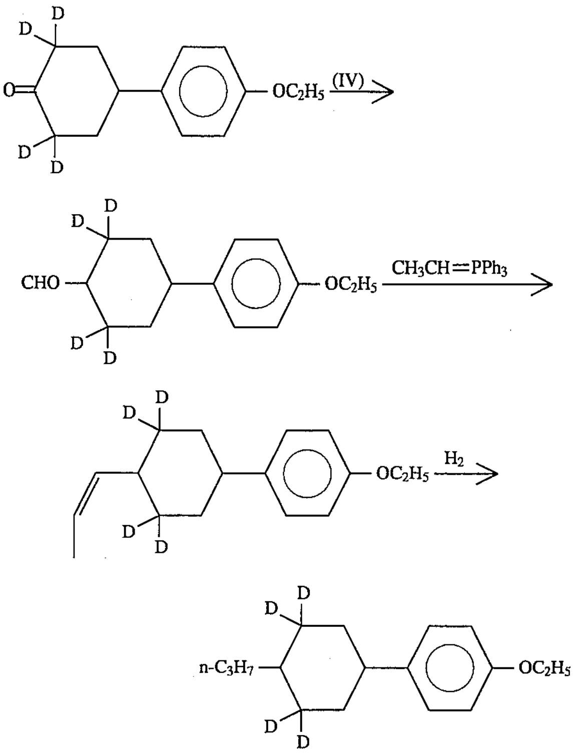

The 4-(4-ethoxyphenyl)cyclohexanone-2,2,6,6-$d_4$ obtained in process B as an intermediate is reacted with a Wittig reagent represented by formula (IV):

$CH_3OCH{=}PPh_3$ (IV)

wherein Ph represents a phenyl group, which is prepared with methoxymethyltriphenylphosphonium chloride. The product is then treated with an acid to obtain 4-(4-ethoxyphenyl)cyclohexane-2,2,6,6-$d_4$-carbaldehyde, which is isomerized to a trans-form and reacted with a Wittig reagent prepared from ethyltriphenylphosphonium salt, followed by hydrogenation to obtain 1-(trans-4-propylcyclohexyl-3,3,5,5,-$d_4$)-4-ethoxybenzene.

Process D:

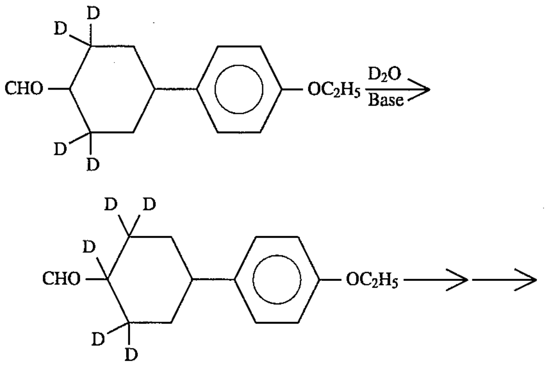

-continued

Process D:

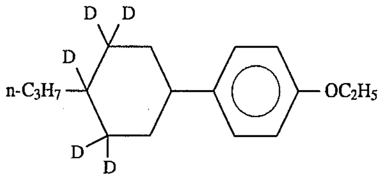

Isomerization of the carbaldehyde derivative described in process C is carried out in the presence of heavy water ($D_2O$) to obtain 4-(4-ethoxyphenyl)cyclohexane-1,2,2,6,6-$d_5$-carbaldehyde, which is then treated in the same manner as in process C to obtain 1-(trans-4-propylcyclohexyl-3,3,4,5,5-$d_5$)-4-ethoxybenzene.

Process E:

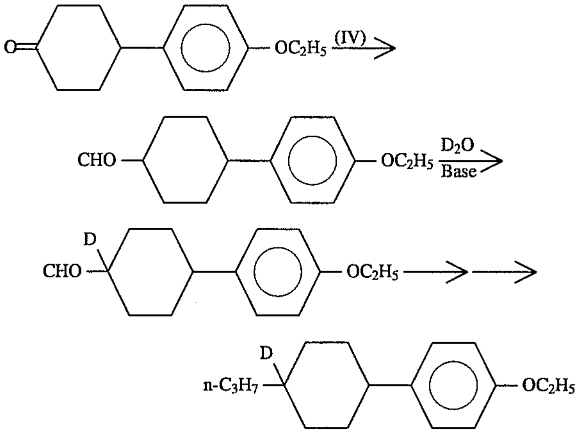

The 4-(4-ethoxyphenyl)cyclohexanone obtained in process B as an intermediate is reacted with a Wittig reagent of formula (IV) to obtain 4-(4-ethoxyphenyl)cyclohexanecarbaldehyde, which is led to 1-(trans-4-propylcyclohexyl-4-d)-4-ethoxybenzene via 4-(4-ethoxyphenyl)cyclohexane-1-d-carbaldehyde in the same manner as in process D.

Process F:

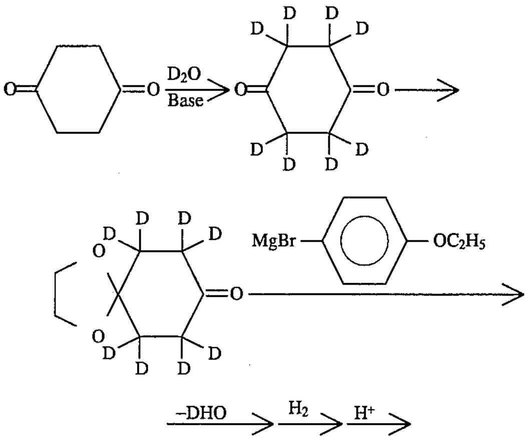

-continued

Process F:

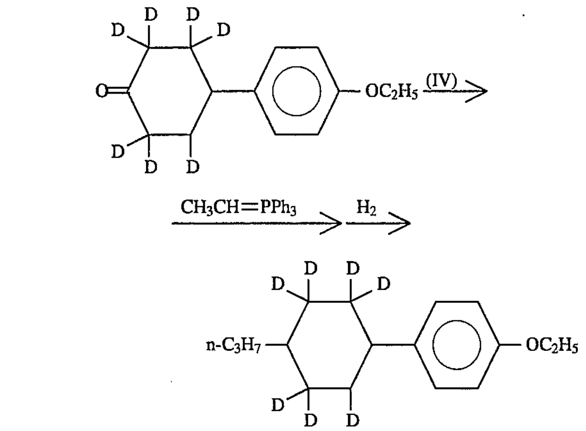

Cyclohexane-1,4-dione is deuterated in the same manner as in process A to obtain $d_8$-cyclohexane-1,4-dione. The product is converted to a monoethyleneacetal, which is then reacted in the same manner as in process C to obtain 1-(trans-4-propylcyclohexyl-2,2,3,3,5,5,6-$d_7$)-4 -ethoxybenzene.

Process G:

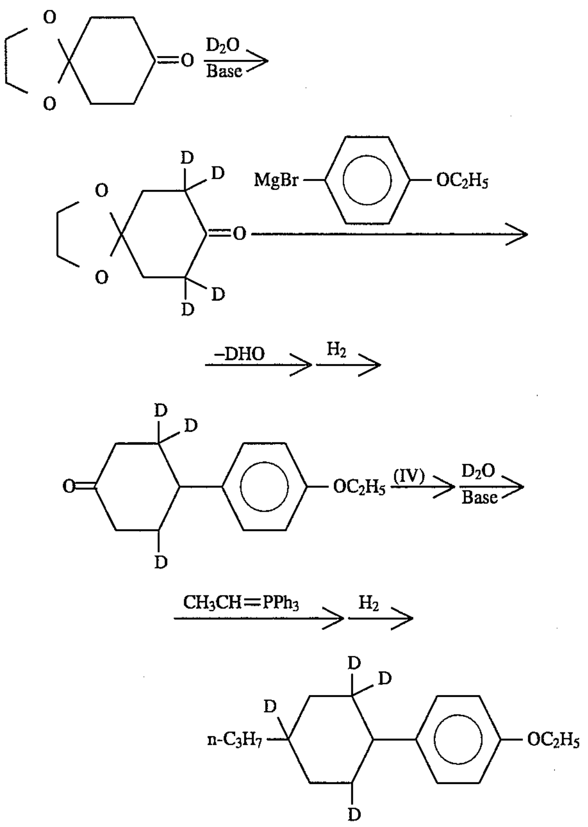

Cyclohexane-1,4-dione monoethyleneacetal is deuterated, and the product is treated in the same manner as in process B to obtain 4-(4-ethoxyphenyl)cyclohexanone-3,3,5-$d_3$. From the product is obtain 1-(trans-4-propylcyclohexyl-2,2,4,6-$d_4$)-4-ethoxybenzene in the same manner as in process E.

Process H:

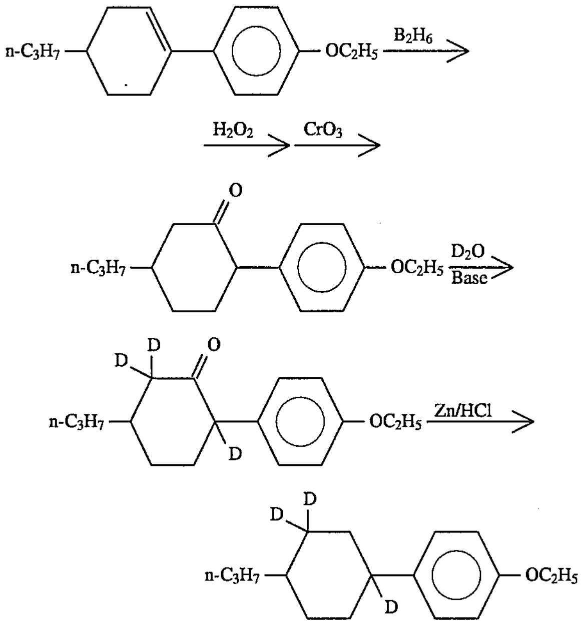

1-(4-Ethoxyphenyl)-4-propylcyclohexene which is used as an intermediate for a compound having a non-deuterated cyclohexane ring as ring A of formula (R-1), is subjected to hydroboration and then oxidized with chromic acid, etc. to obtain 2-(4-ethoxyphenyl)-5-propylcyclohexanone. This compound is then subjected to deuteration and isomerization to a trans-form in the same manner as in process D, and the carbonyl group is removed by reduction to obtain 1-(trans-4-propylcyclohexyl-1,3,3-$d_3$)-4-ethoxybenzene.

Process I:

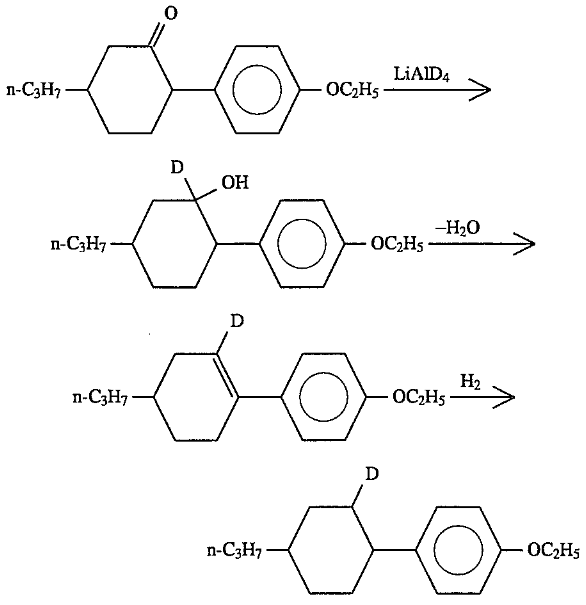

2-(4-Ethoxyphenyl)-5-propylcyclohexanone, which is the intermediate in process H, is reduced with lithium aluminum hydride-$d_4$, dehydrated, hydrogenated, and then isomerized to a trans-form to obtain 1-(trans-4-propylcyclohexyl-2-d)-4-ethoxybenzene.

Process J:

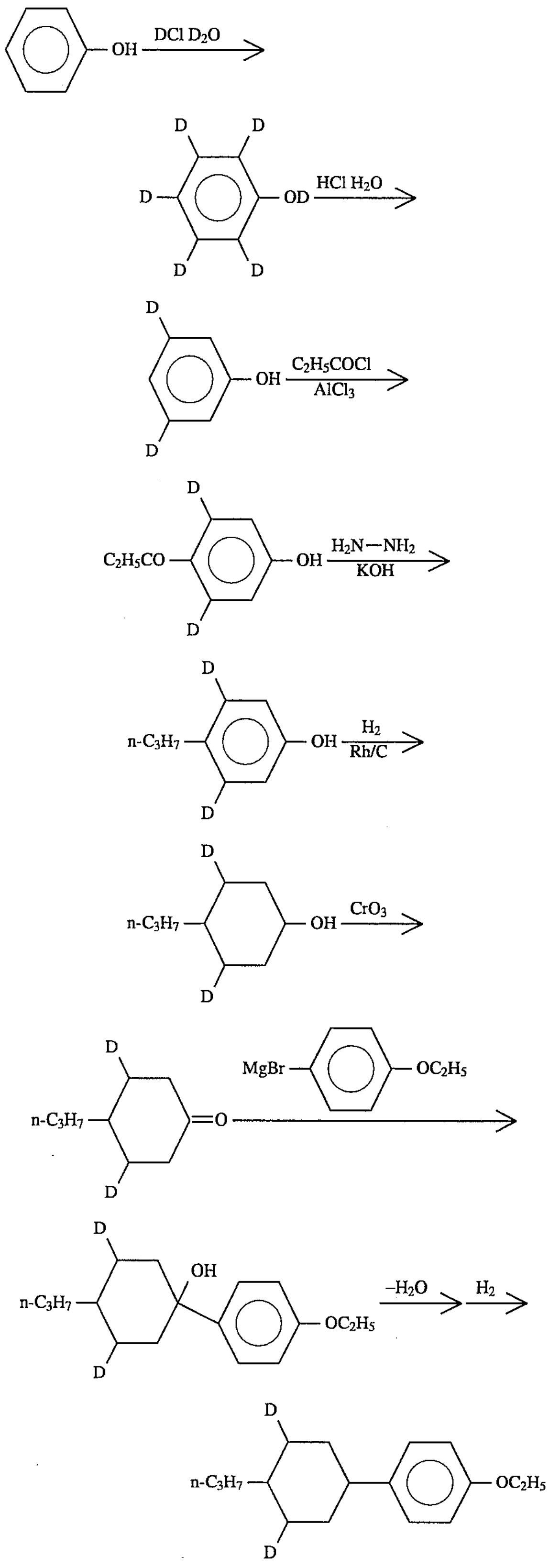

Phenol is reacted in heavy water and low-concentration deuterium chloride (DCl) at a high temperature (230° to 250° C.) under pressure to obtain $d_6$-phenol. $d_6$-Phenol is refluxed in hydrochloric acid to obtain 3,5-$d_2$-phenol. 3,5-$d_2$-Phenol is reacted with propionyl chloride in the presence of aluminum chloride, and the product is subjected to Wolff-Kishner reduction to obtain 4-propyl-(3,5-$d_2$)-phenol, which is then hydrogenated using rhodium-on-carbon as a catalyst. The resulting cyclohexanol derivative is oxidized with chromic anhydride, etc. to obtain 4-propyl-(3,5-$d_2$)-cyclohexanone, which is led to 1-(trans-4-propylcyclohexyl-3,5-$d_2$)-4-ethoxybenzene in the same manner as in process A.

Bicyclic deuterated liquid crystal compounds other than the compound of formula (R-1) can also be obtained with ease in accordance with processes A to J or an appropriate combination thereof.

A tricyclic deuterated liquid crystal compound represented by formula (R-2):

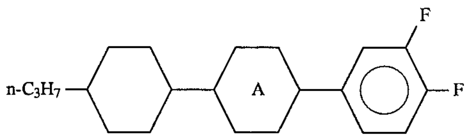

(R-2)

wherein ring A is a cyclohexane ring having one or more deuterium atoms (D), which is deuterated 1-[4-(trans-4-propylcyclohexyl)cyclohexyl]-3,4-difluorobenzene, can be prepared through any of the following processes K to O.

Process K:

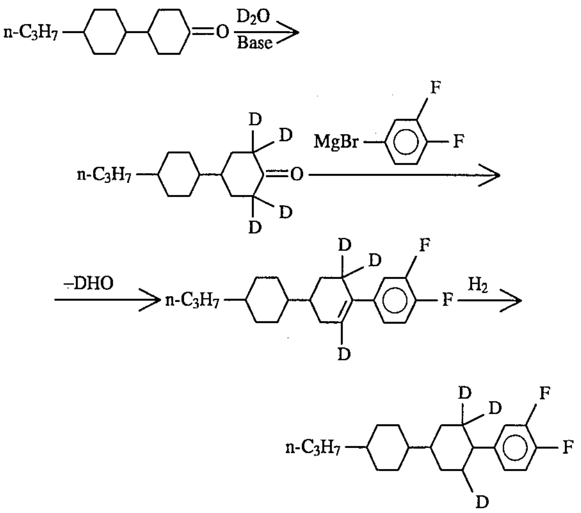

4-(Trans-4-propylcyclohexyl)cyclohexanone is deuterated in the same manner as in process A to obtain 4-(trans-propylcyclohexyl)cyclohexanone-2,2,6,6-$d_4$. This compound is reacted with a Grignard reagent prepared from 1-bromo-3,4-difluorobenzene, and the product is further treated in the same manner as in process A to obtain 1-[4-(trans-4-propylcyclohexyl)cyclohexyl-2,2,6-$d_3$]-3,4-difluorobenzene.

Process L:

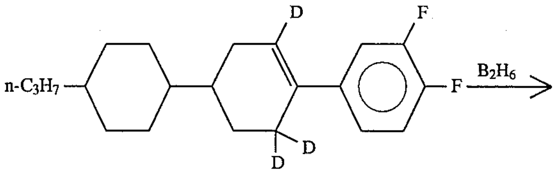

-continued

Process L:

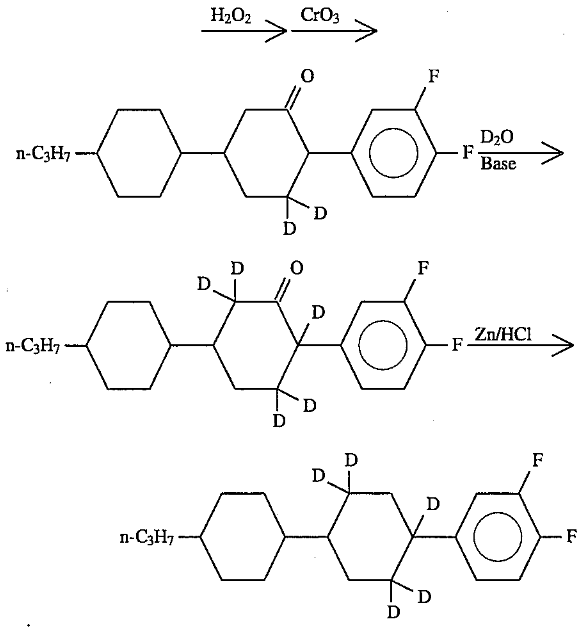

1-(3,4-Difluorophenyl)-4-(trans-4-propylcyclohexyl)cyclohexene-2,6,6-$d_3$, the intermediate of process K, is subjected to hydroboration and then oxidation in the same manner as in process H to obtain 2-(3,4-difluorophenyl)-5-(trans-4-propylcyclohexyl)cyclohexanone-3,3 -$d_2$. The product is subjected to deuteration and isomerization to a trans-form in the same manner as in process D, and the carbonyl group is removed by reduction to obtain 1-[4-(trans-4-propylcyclohexyl)cyclohexyl-1,2,2,5,5-$d_5$]-3,4-difluorobenzene.

Process M:

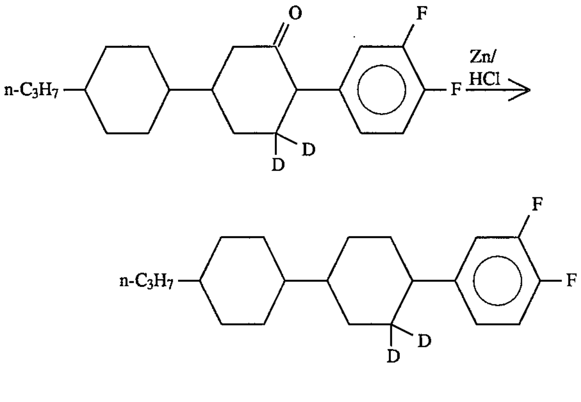

The same reactions as in process L are carried out, except that after the hydroboration deuteration was not conducted and only isomerization is conducted, to obtain 1-[4-(trans-4-propylcyclohexyl)cyclohexyl-2,2-$d_2$]-3,4-difluorobenzene.

Process N:

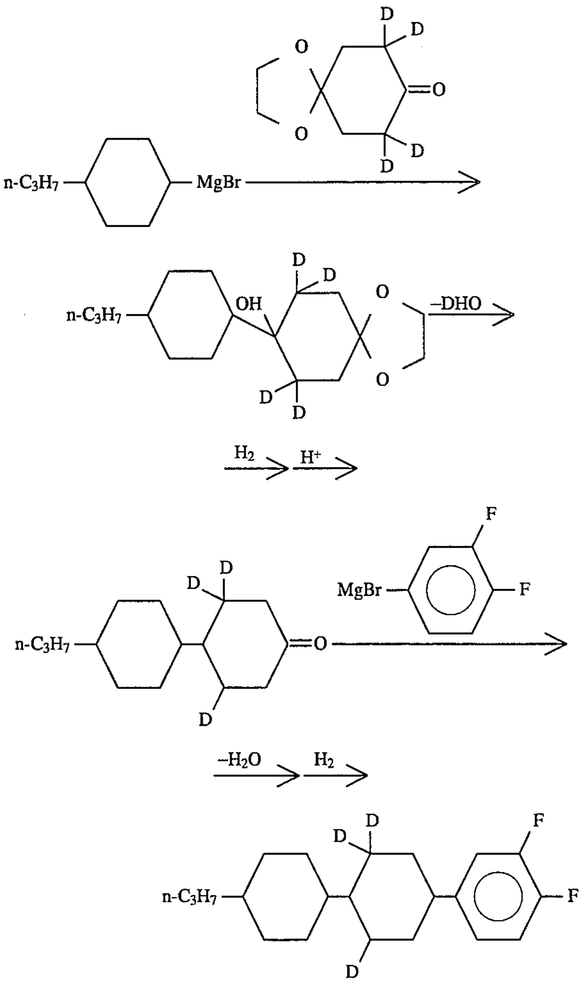

The deuterated cyclohexane-1,4-dione monoethyleneacetal obtained in process G is reacted with a Grignard reagent prepared from 4-propylcyclohexyl bromide, and the product is dehydrated and then hydrogenated in the same manner as in process G to obtain 4-(trans-4-propylcyclohexyl)cyclohexanone-3,3,5-$d_3$, from which is obtained 1-[4-(trans-4-propylcyclohexyl)cyclohexyl-3,3,5-$d_3$]-3,4-difluorobenzene in the same manner as in process K.

Process O:

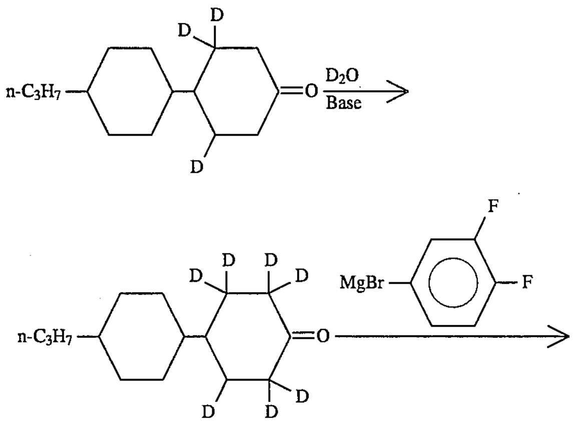

-continued

Process O:

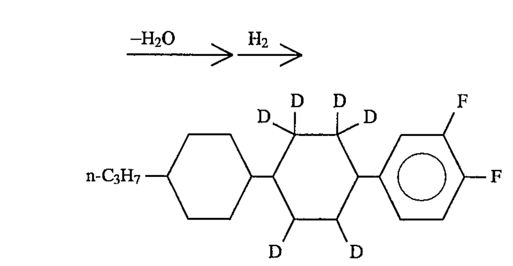

and

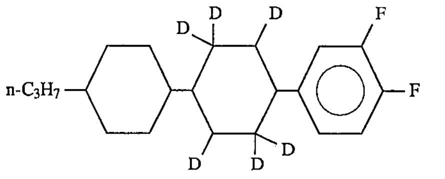

The 4-(trans-4-propylcyclohexyl)cyclohexanone-3,3,5-$d_3$ obtained in process N is further deuterated to obtain 4-(trans-4-propylcyclohexyl)cyclohexanone-2,2,3,3,5,6,6-$d_7$. From this compound are obtained 1-[4-(trans-4-propylcyclohexyl)cyclohexyl-2,2,3,3,5,6-$d_6$]-3,4 -difluorobenzene and 1-[4-(trans-4-propylcyclohexyl)cyclohexyl-2,2,3,5,5,6-$d_6$]-3,4-difluorobenzene in the same manner as in process K.

Tricyclic deuterated liquid crystal compounds other than the compound of formula (R-2) can also be obtained with ease in accordance with processes K to O or an appropriate combination thereof.

Further, tetracyclic deuterated liquid crystal compounds are also prepared easily in accordance with processes A to O or an appropriate combination thereof.

While the deuterated liquid crystal compounds hereinabove described are those in which the saturated hydrocarbon ring is a cyclohexane ring, compounds having a saturated hydrocarbon ring having 3 to 5 carbon atoms are also preferred.

The deuterated liquid crystal compounds which can be used in the present invention can be prepared by applying the syntheses described in the above-mentioned literature. Therefore, the positions of deuterium atoms (D) are not limited to those specifically described in processes A to O and may be at any of the positions on the saturated hydrocarbon ring. While it will suffice if at least one deuterium atom (D) should be bonded, all the hydrogen atoms (H) on the saturated hydrocarbon ring may be substituted with deuterium atoms (D).

In process J, for example, the intermediate of formula:

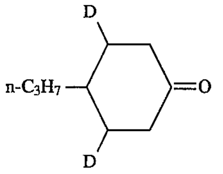

may be replaced with any of compounds of the following formulae to obtain a large variety of deuterated liquid crystal compounds.

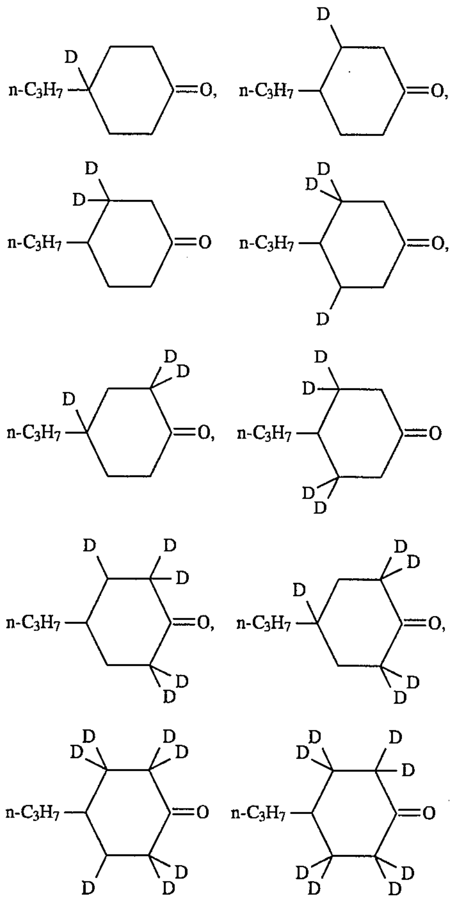

Typical examples of compounds which can be used for preference to obtain the liquid crystal composition of the present invention are shown below.

Unless otherwise indicated, in compounds (1) to (425) hereinafter given, $R^1$ represents an alkyl, alkoxylalkyl or alkenyl group having from 1 to 20 carbon atoms; $R^2$ represents an alkyl group or an alkoxyl group; $R^3$ and $R^4$ each represent an alkyl group having from 1 to 20 carbon atoms; and $R^5$ represents an alkyl or alkenyl group having from 1 to 20 carbon atoms. Rings A, A' and B in compounds (1), (2), (21) to (28), (41) to (43), (45) to (59), (90) to (104), (150) to (179), (210) to (303), and (335) to (349), and rings A and A' in compounds (75) to (89), (350) to (364), (265) to (378), (382) to (388), (403) to (409), (416), (417), (424), and (425) each represent a group selected from the groups:

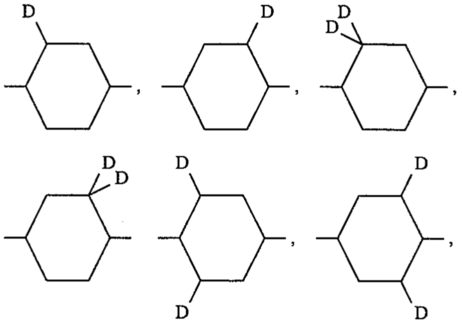

-continued
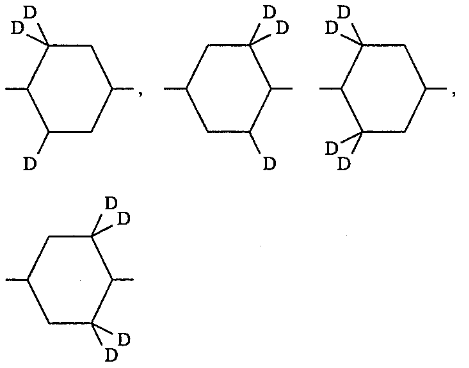
Rings A and A' in compounds (3) to (20), (39), (40), (44), (60) to (74), (105) to (149), (180) to (209), (304) to (334), (379) to (381), (389) to (402), (410) to (415), and (418) to (423), and rings B and B' in compounds (75) to (89) and (350) to (364) each represent a group selected from the groups:
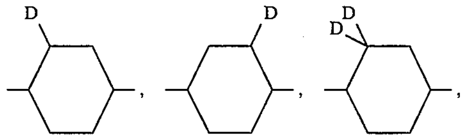
-continued
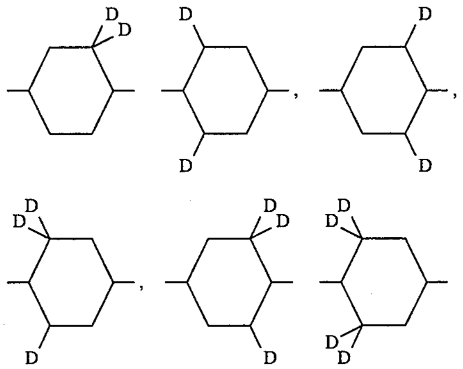
Rings A and B or rings A' and B' in compounds (75) to (89), (255) to (269), (301), (303), and (350) to (364) may be the same or different. The above illustrated groups are those merely showing the position of the substituent(s), deuterium atom(s).
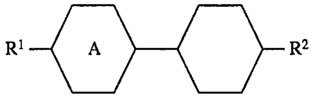
(1)
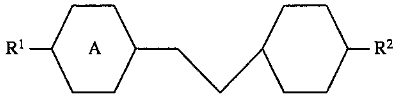
(2)
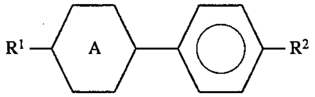
(3)
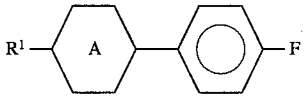
(4)
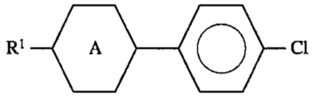
(5)
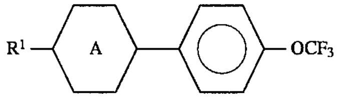
(6)
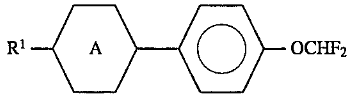
(7)
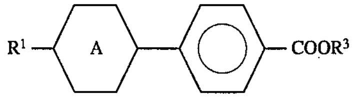
(8)

-continued
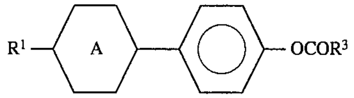
(9)
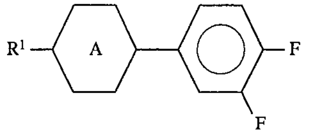
(10)
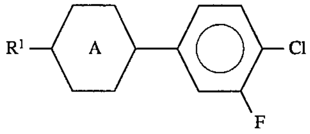
(11)
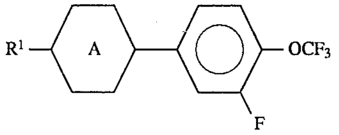
(12)
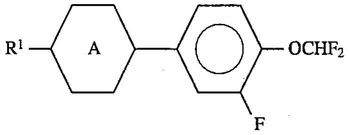
(13)
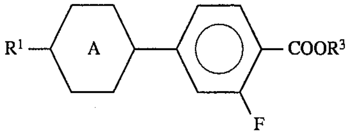
(14)
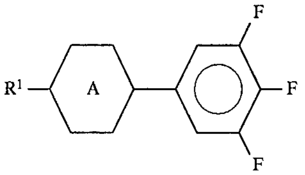
(15)
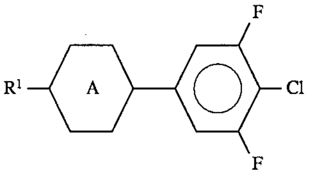
(16)
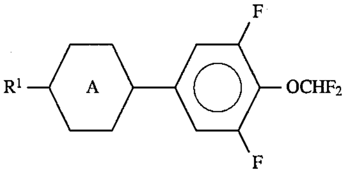
(17)
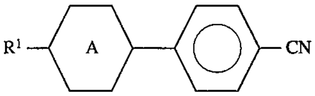
(18)
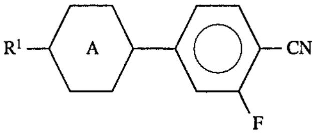
(19)

-continued
(20)
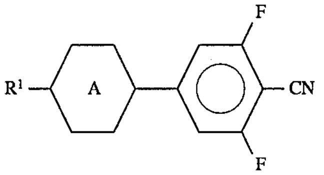
(21)
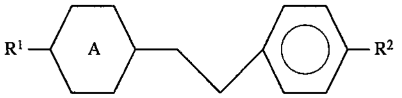
(22)
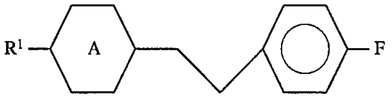
(23)
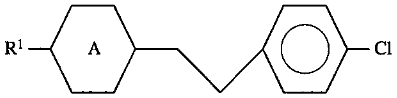
(24)
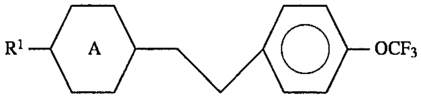
(25)
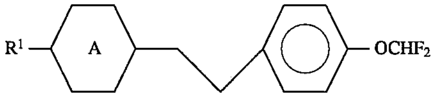
(26)
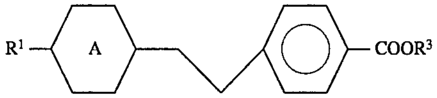
(27)
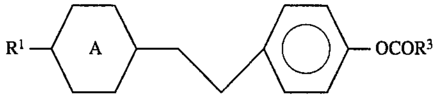
(28)
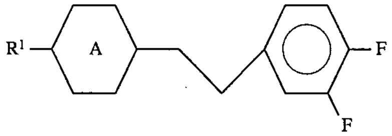
(29)
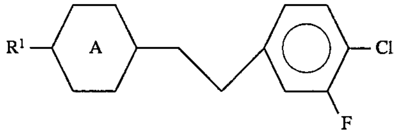
(30)
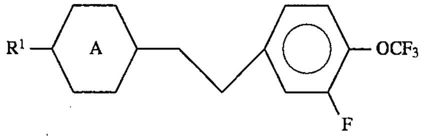
(31)
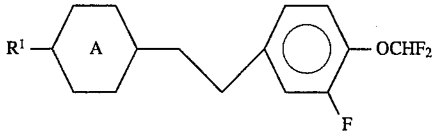
(32)
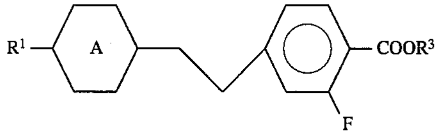

-continued
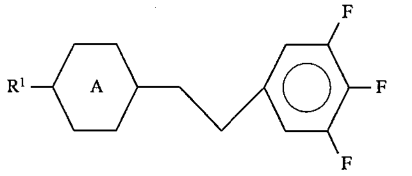
(33)
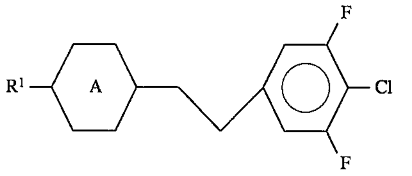
(34)
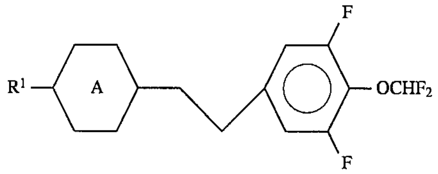
(35)
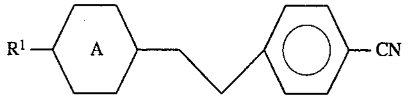
(36)
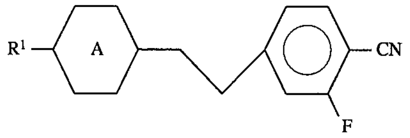
(37)
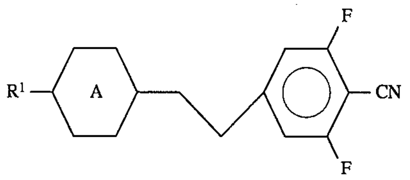
(38)
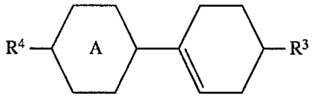
(39)
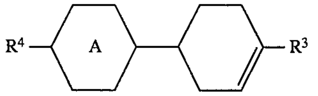
(40)
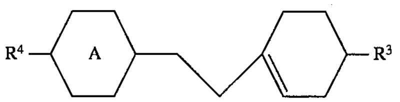
(41)
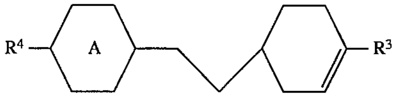
(42)
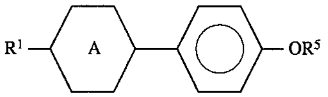
(43)
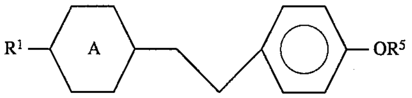
(44)

-continued
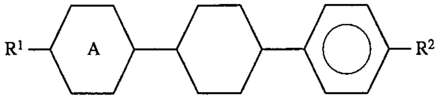
(45)
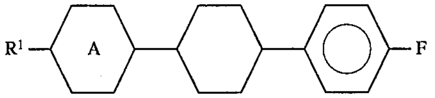
(46)
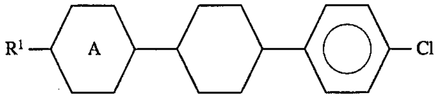
(47)
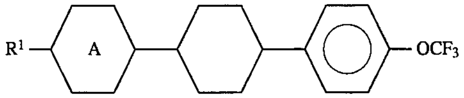
(48)
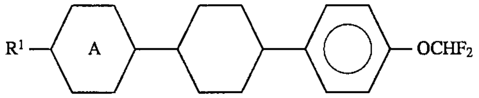
(49)
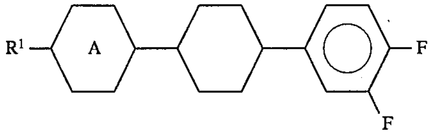
(50)
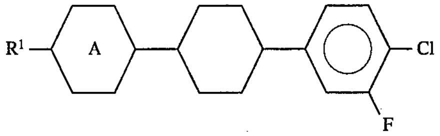
(51)
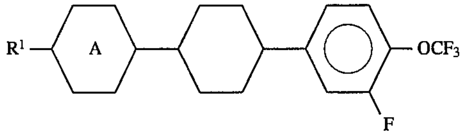
(52)
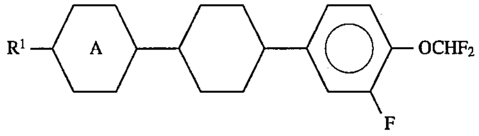
(53)
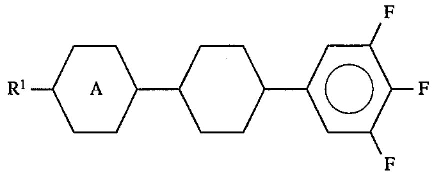
(54)
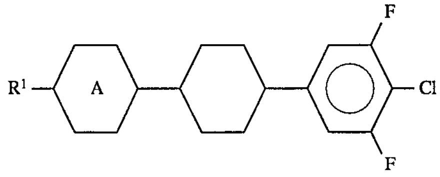
(55)
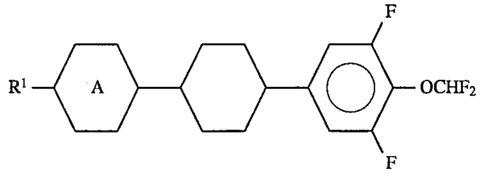
(56)

-continued
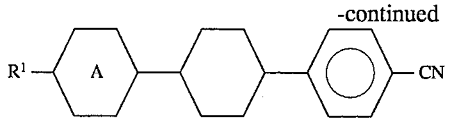
(57)
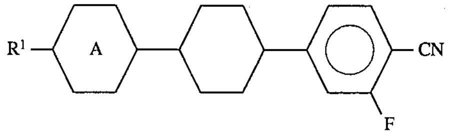
(58)
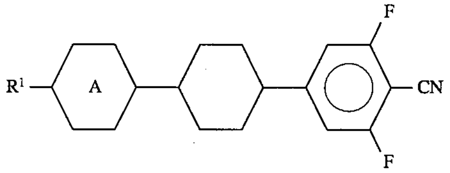
(59)
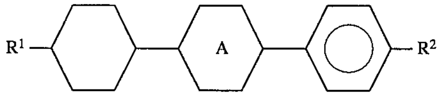
(60)
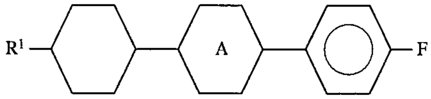
(61)
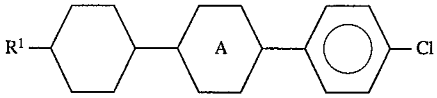
(62)
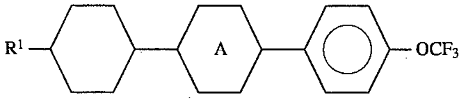
(63)
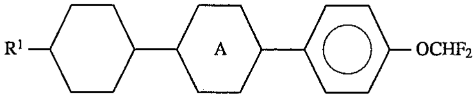
(64)
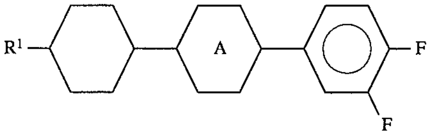
(65)
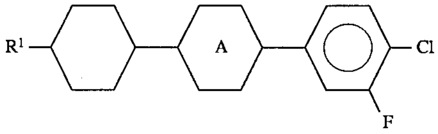
(66)
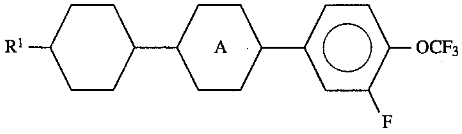
(67)
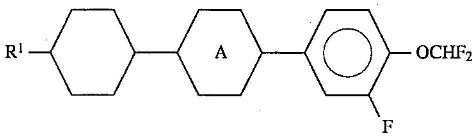
(68)

-continued
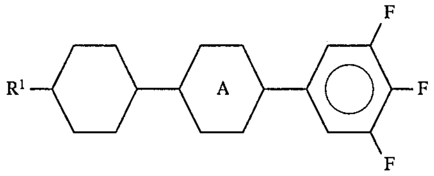
(69)
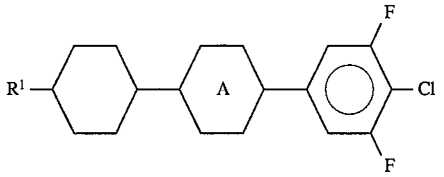
(70)
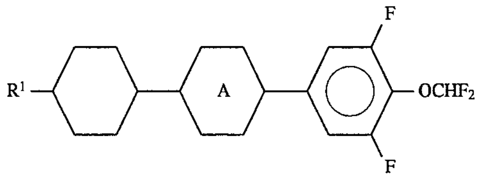
(71)
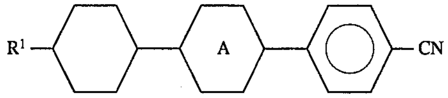
(72)
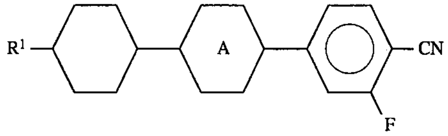
(73)
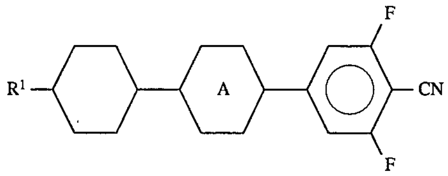
(74)
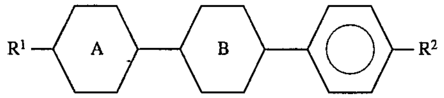
(75)
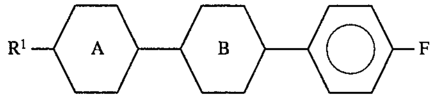
(76)
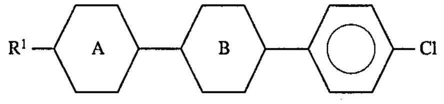
(77)
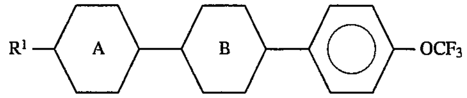
(78)
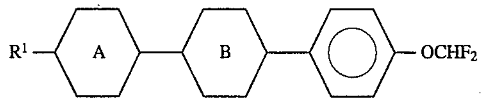
(79)
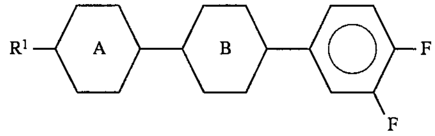
(80)

-continued
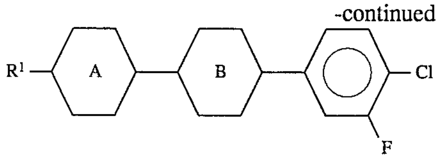
(81)
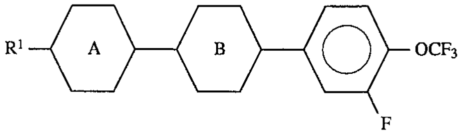
(82)
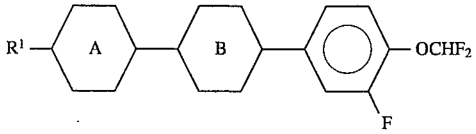
(83)
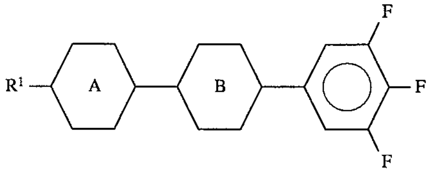
(84)
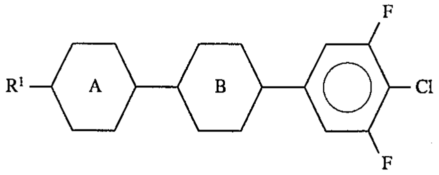
(85)
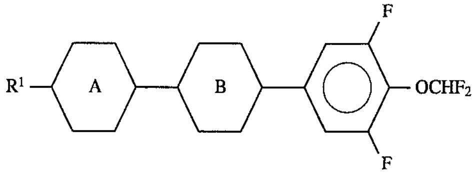
(86)
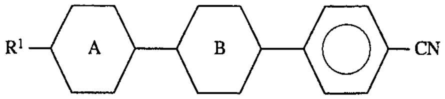
(87)
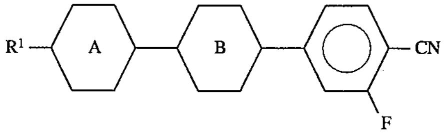
(88)
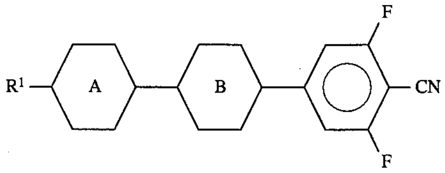
(89)
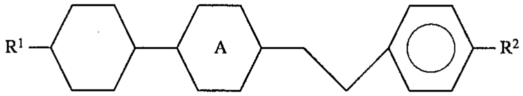
(90)
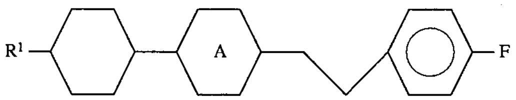
(91)

-continued
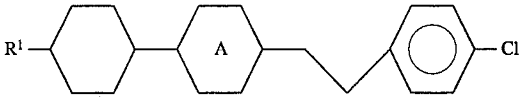
(92)
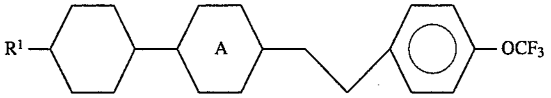
(93)
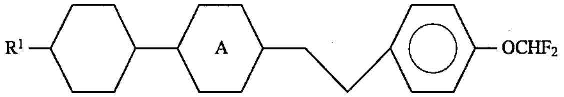
(94)
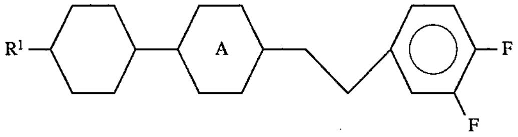
(95)
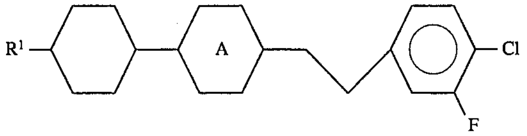
(96)
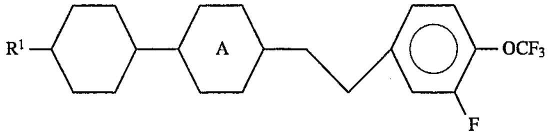
(97)
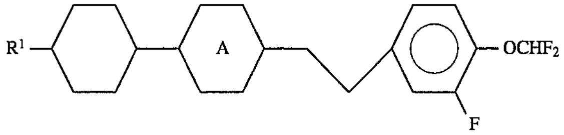
(98)
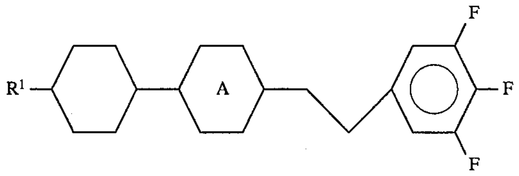
(99)
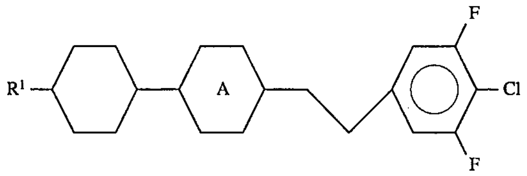
(100)
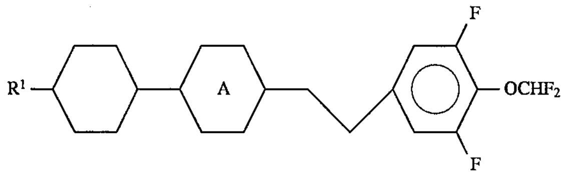
(101)
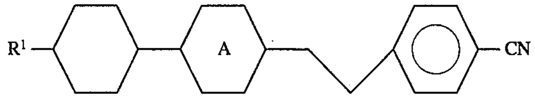
(102)
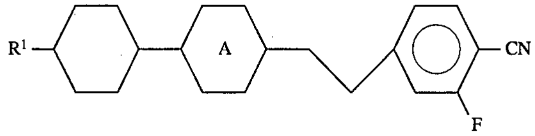
(103)

-continued
(104)
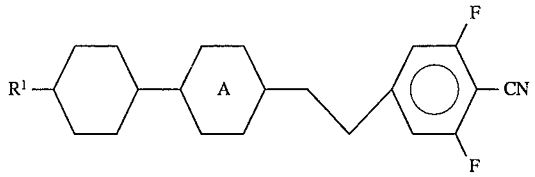
(105)
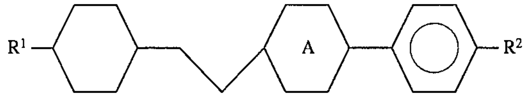
(106)
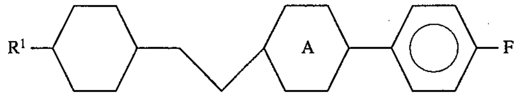
(107)
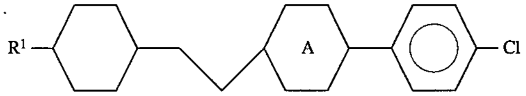
(108)
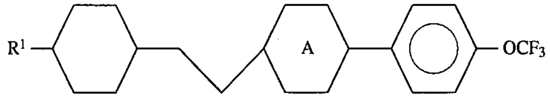
(109)
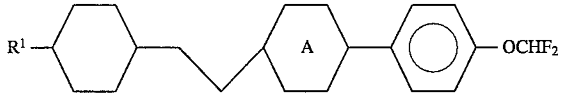
(110)
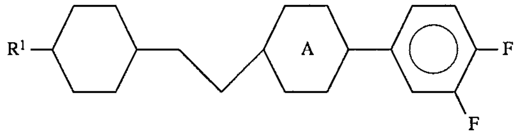
(111)
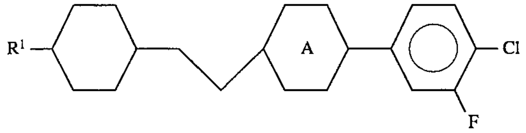
(112)
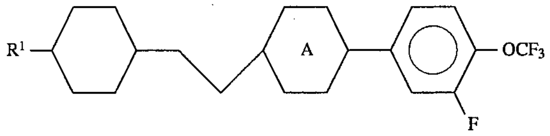
(113)
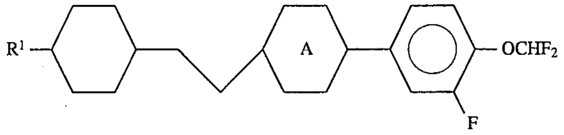
(114)
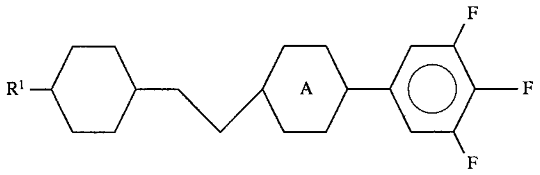
(115)
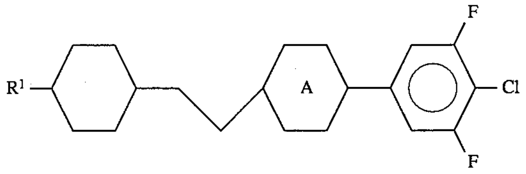

-continued
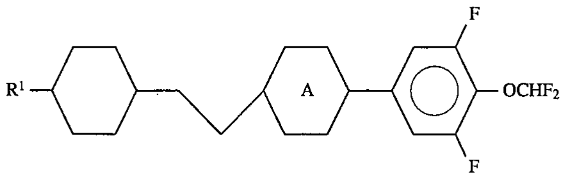
(116)
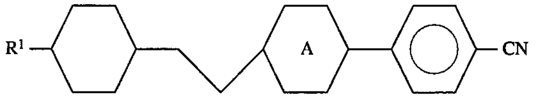
(117)
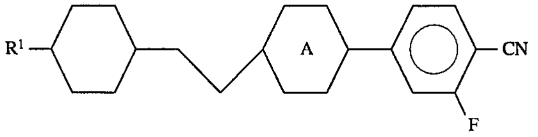
(118)
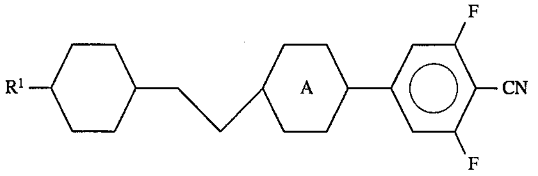
(119)
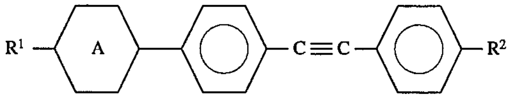
(120)
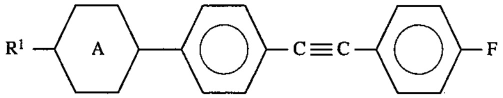
(121)
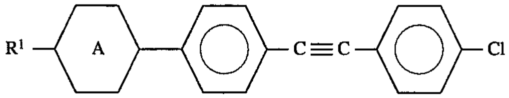
(122)
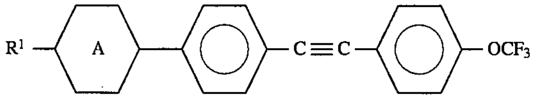
(123)
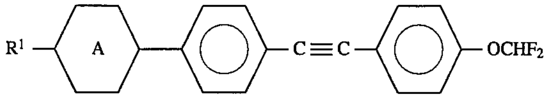
(124)
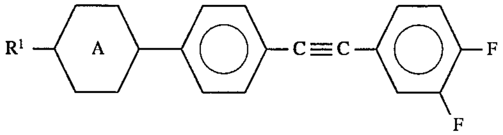
(125)
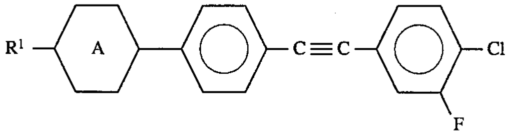
(126)
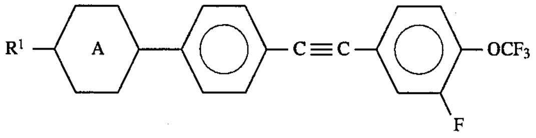
(127)

-continued
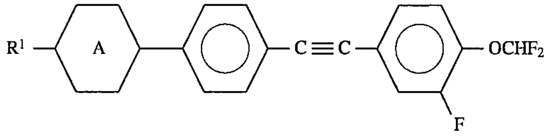
(128)
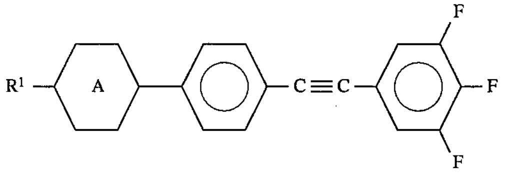
(129)
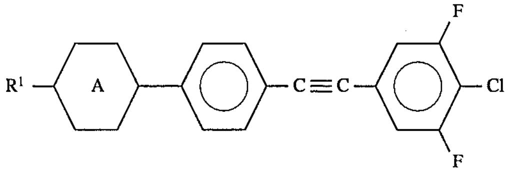
(130)
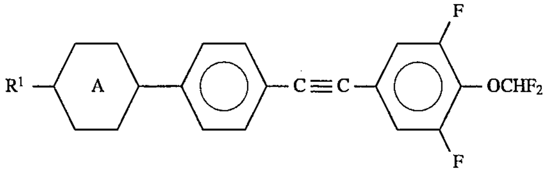
(131)
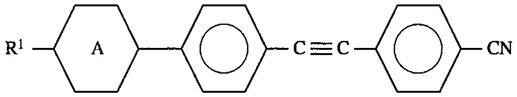
(132)
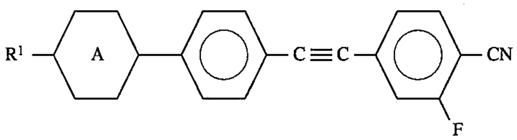
(133)
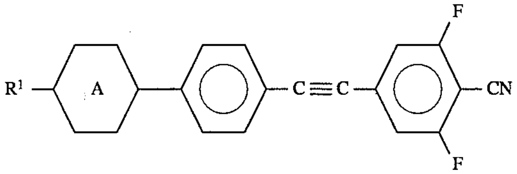
(134)
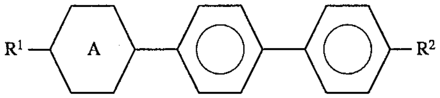
(135)
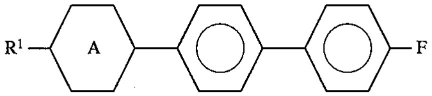
(136)
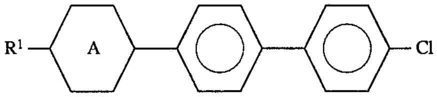
(137)
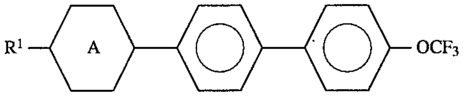
(138)
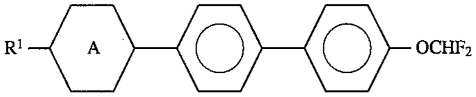
(139)

-continued
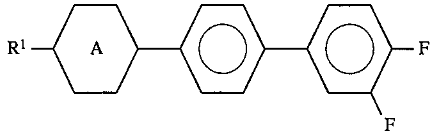
(140)
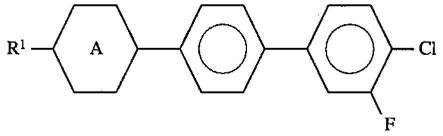
(141)
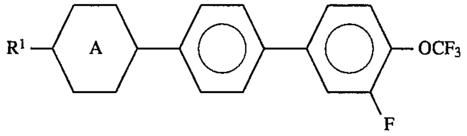
(142)
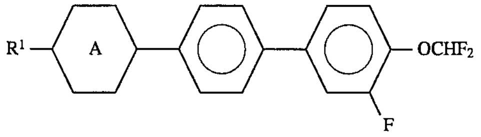
(143)
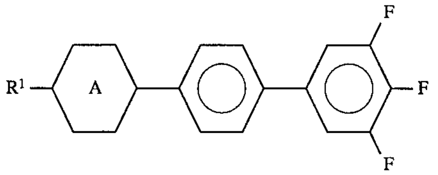
(144)
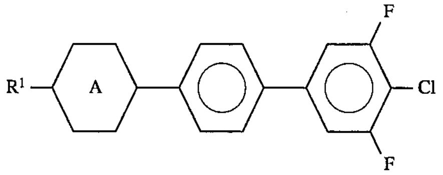
(145)
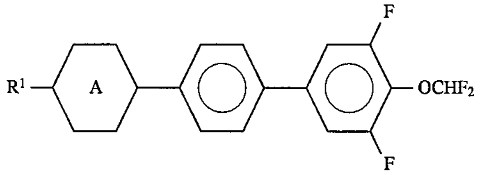
(146)
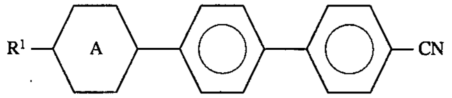
(147)
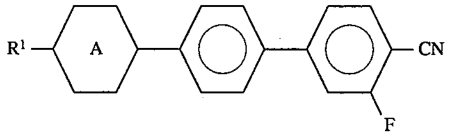
(148)
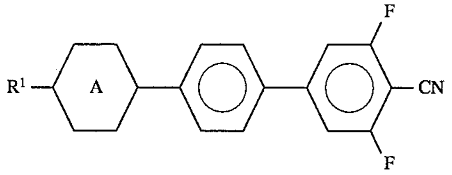
(149)
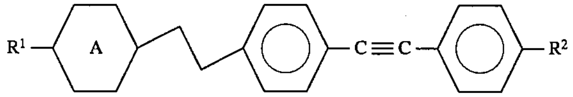
(150)

-continued
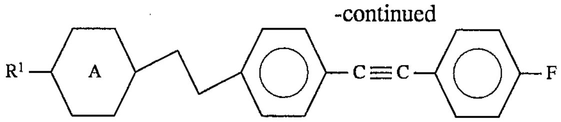
(151)
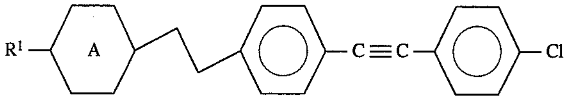
(152)
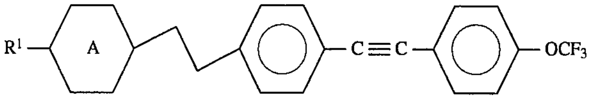
(153)
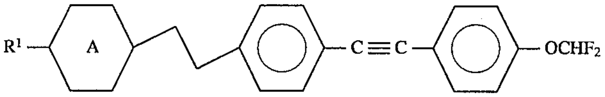
(154)
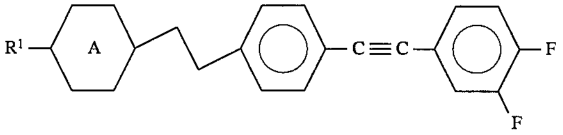
(155)
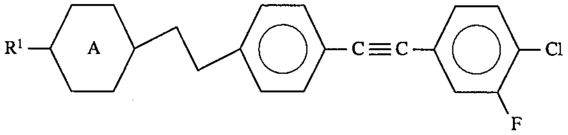
(156)
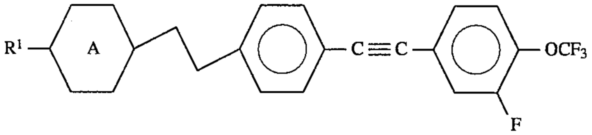
(157)
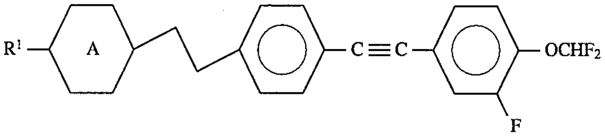
(158)
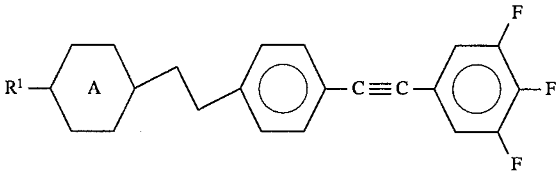
(159)
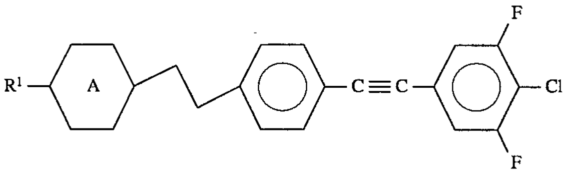
(160)
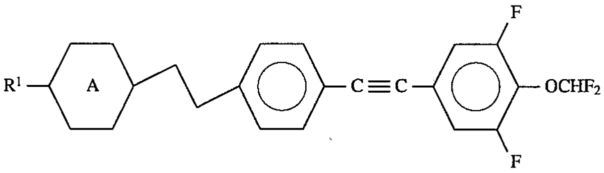
(161)
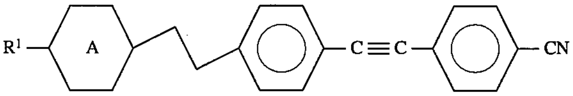
(162)

-continued
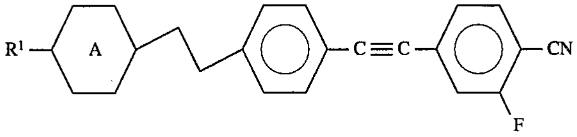
(163)
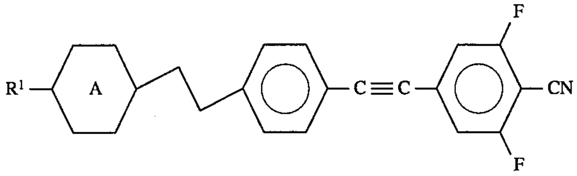
(164)
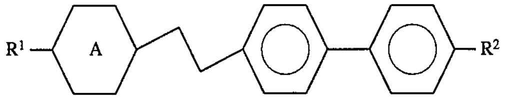
(165)
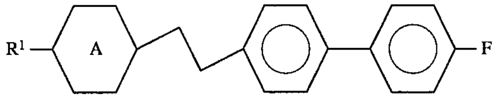
(166)
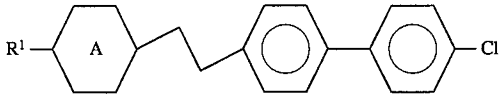
(167)
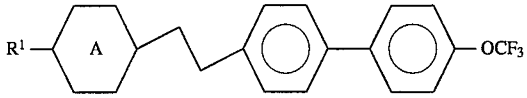
(168)
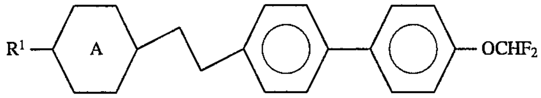
(169)
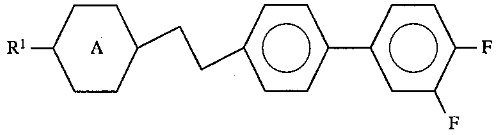
(170)
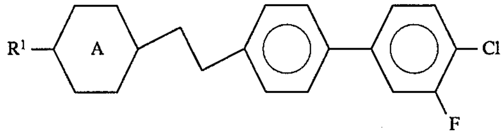
(171)
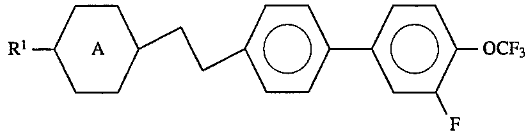
(172)
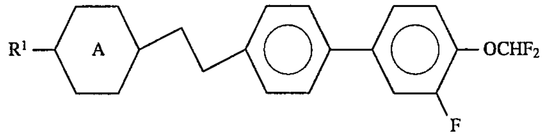
(173)
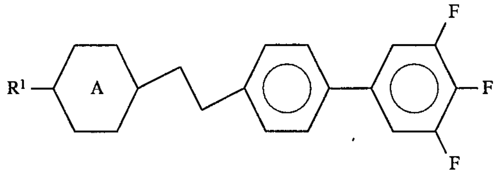
(174)

-continued
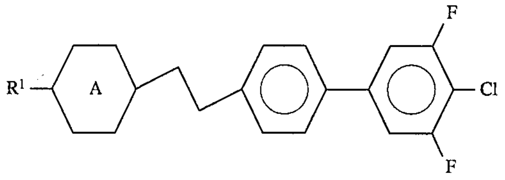
(175)
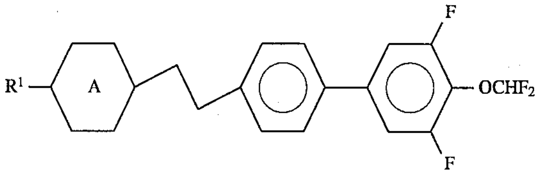
(176)
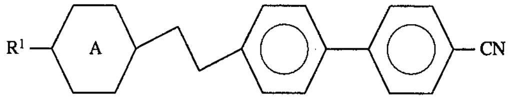
(177)
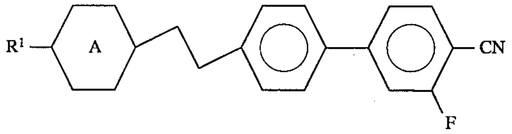
(178)
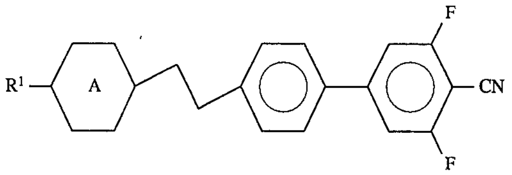
(179)
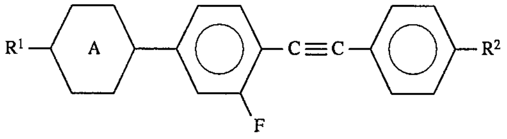
(180)
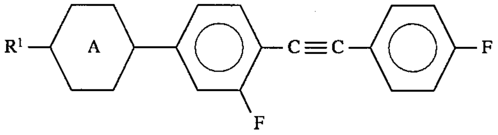
(181)
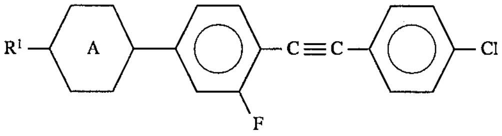
(182)
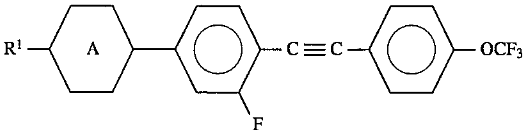
(183)
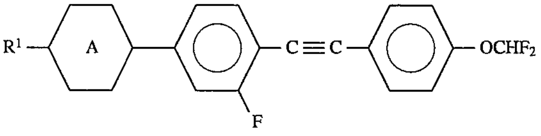
(184)
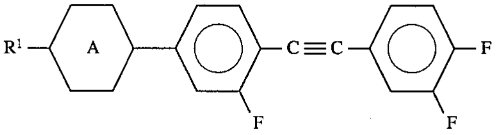
(185)

-continued
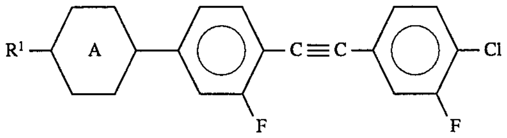
(186)
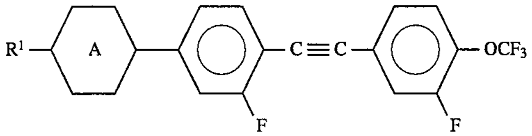
(187)
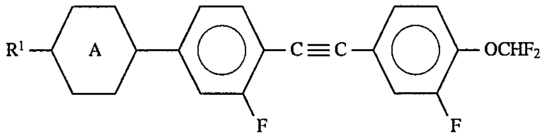
(188)
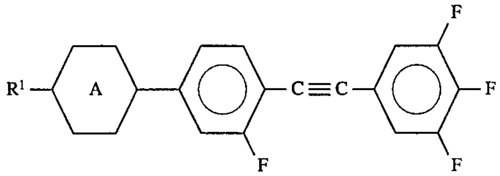
(189)
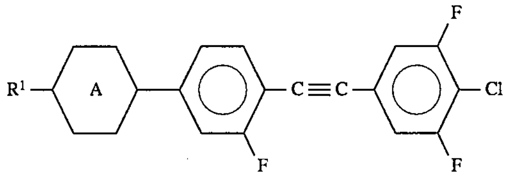
(190)
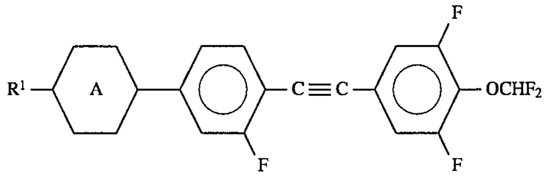
(191)
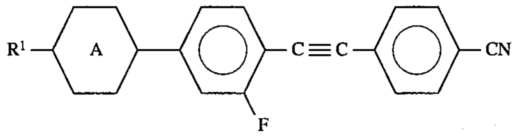
(192)
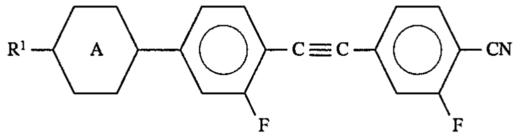
(193)
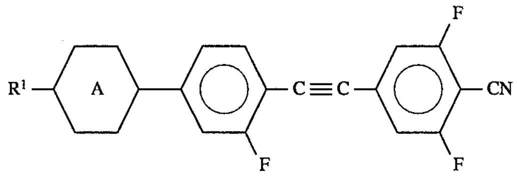
(194)
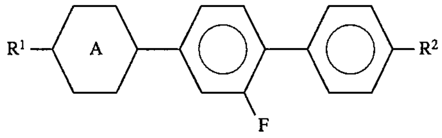
(195)

-continued
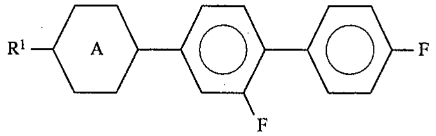
(196)
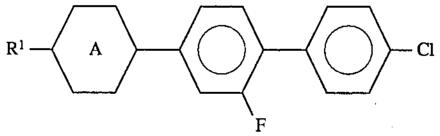
(197)
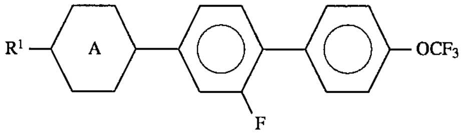
(198)
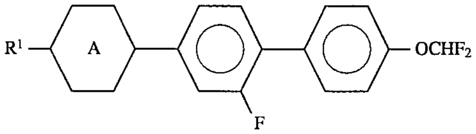
(199)
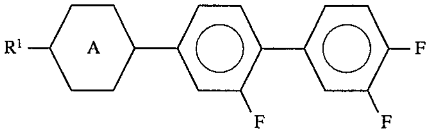
(200)
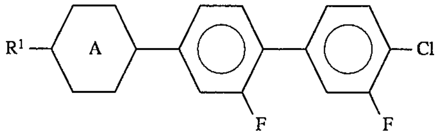
(201)
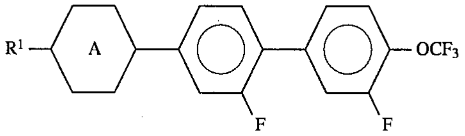
(202)
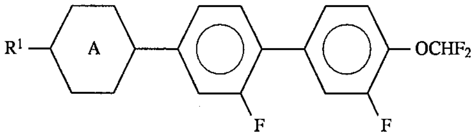
(203)
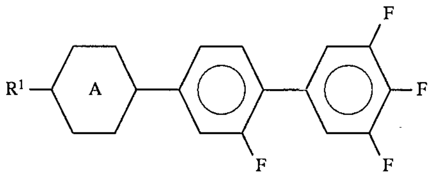
(204)
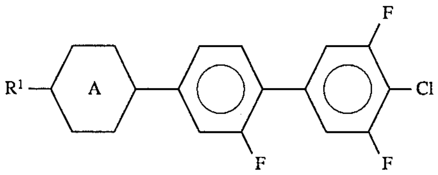
(205)
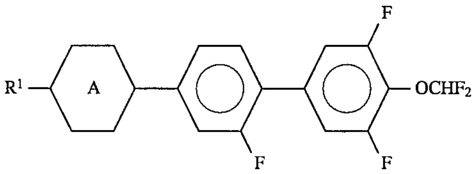
(206)

-continued
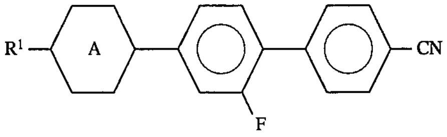
(207)
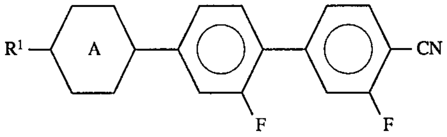
(208)
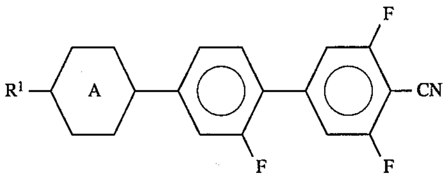
(209)
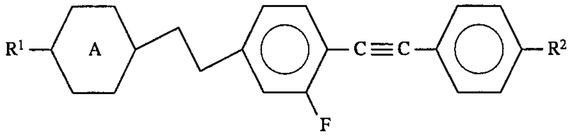
(210)
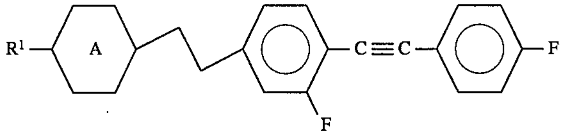
(211)
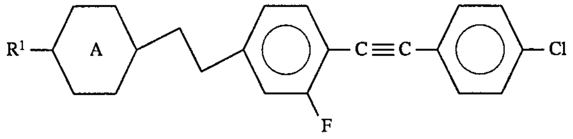
(212)
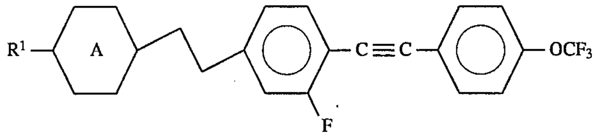
(213)
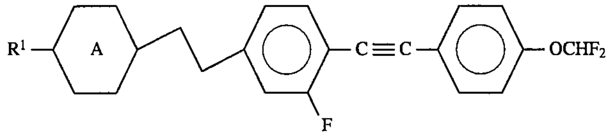
(214)
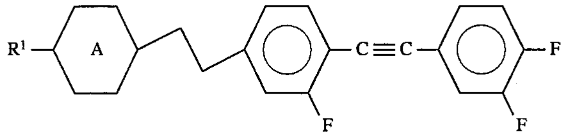
(215)
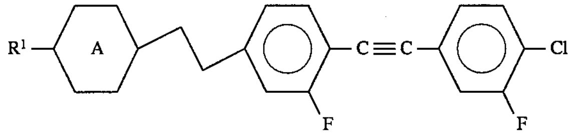
(216)
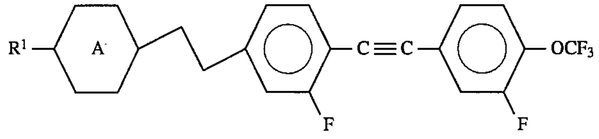
(217)

-continued
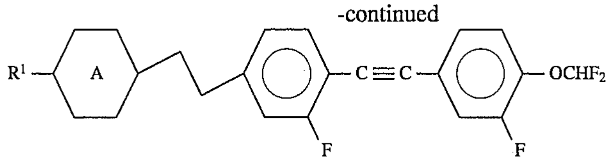
(218)
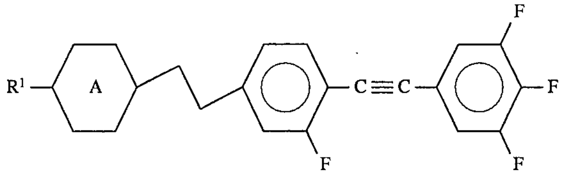
(219)
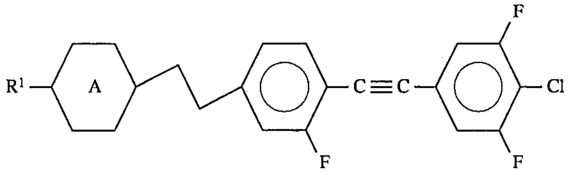
(220)
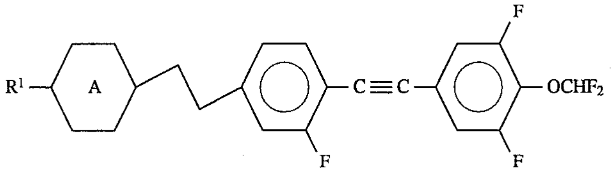
(221)
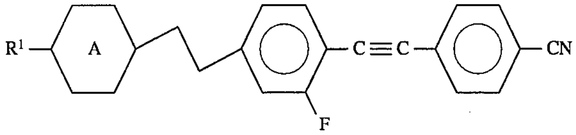
(222)
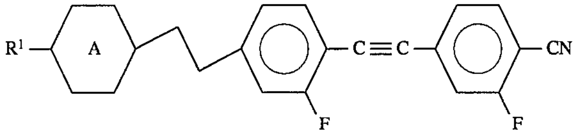
(223)
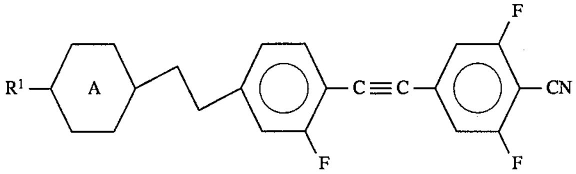
(224)
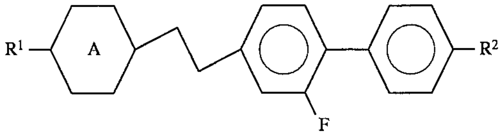
(225)
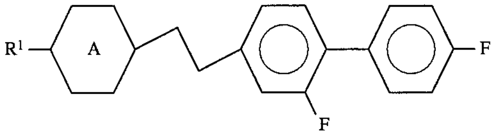
(226)
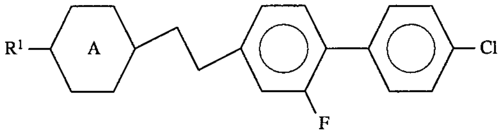
(227)

-continued
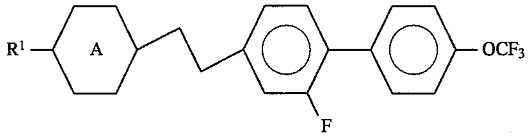
(228)
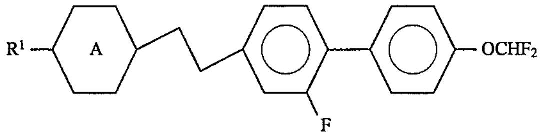
(229)
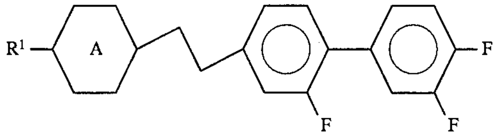
(230)
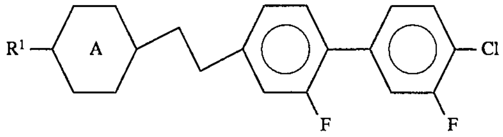
(231)
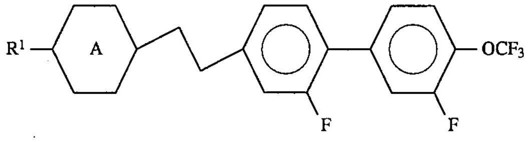
(232)
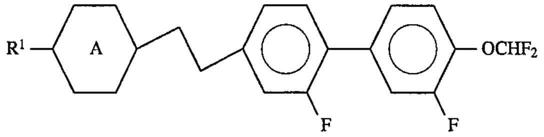
(233)
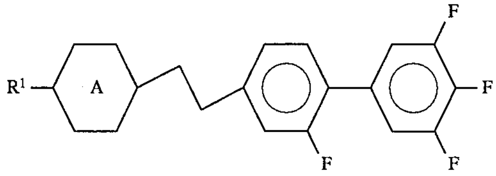
(234)
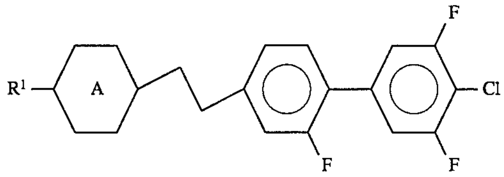
(235)
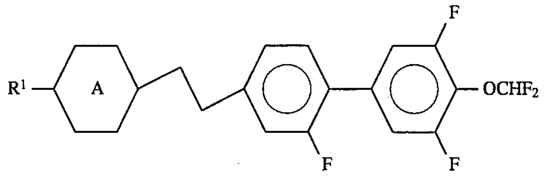
(236)
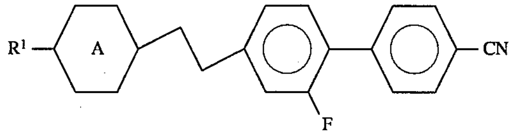
(237)
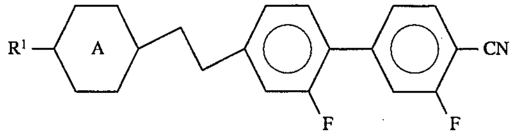
(238)

-continued
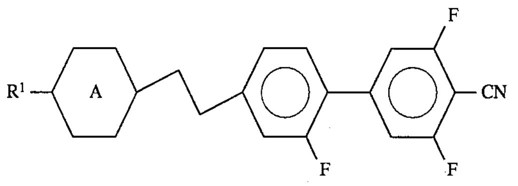
(239)
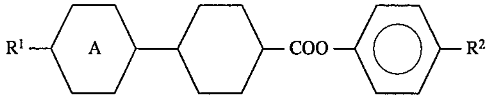
(240)
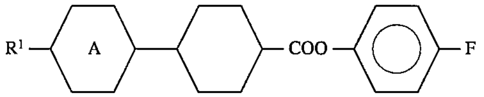
(241)
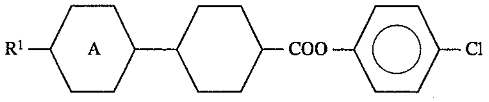
(242)
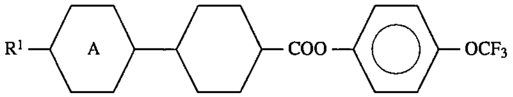
(243)
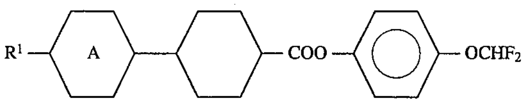
(244)
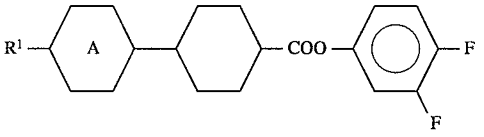
(245)
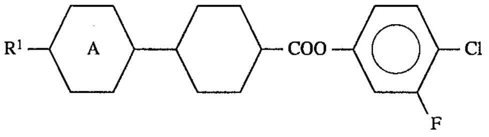
(246)
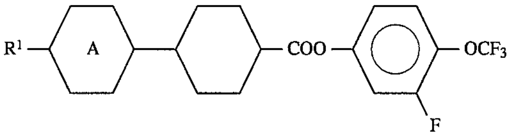
(247)
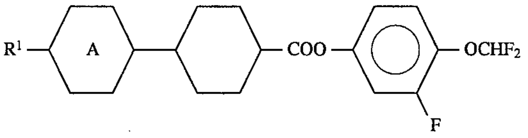
(248)
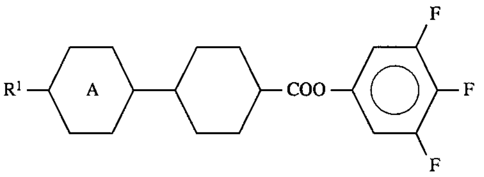
(249)
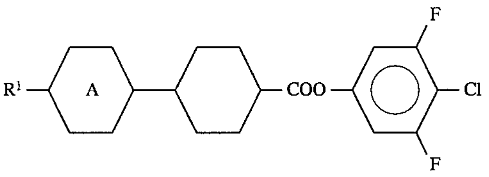
(250)

-continued
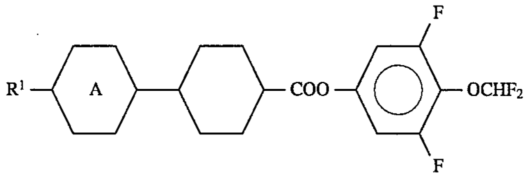
(251)
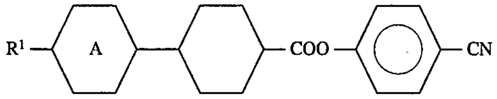
(252)
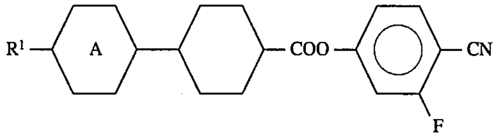
(253)
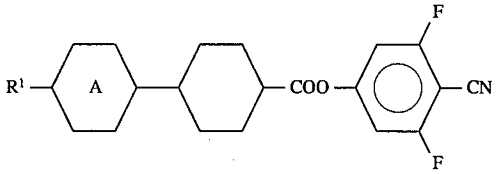
(254)
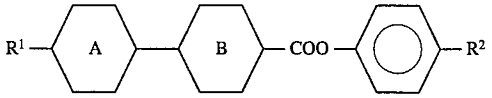
(255)
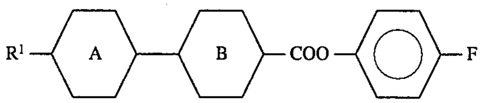
(256)
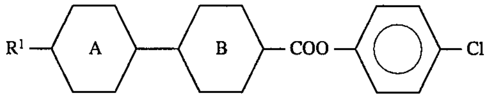
(257)
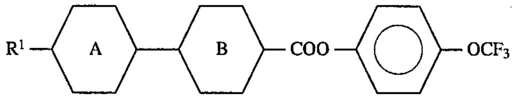
(258)
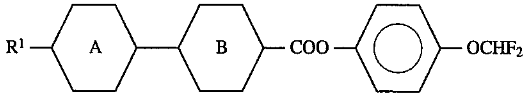
(259)
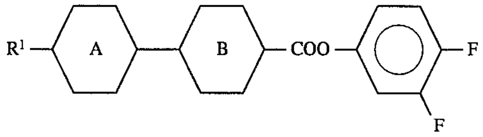
(260)
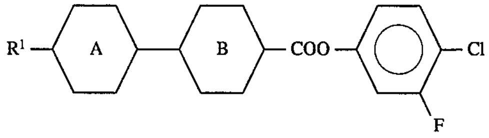
(261)
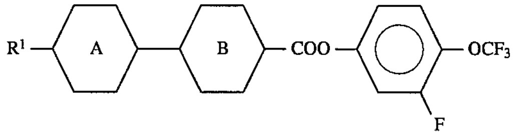
(262)

-continued
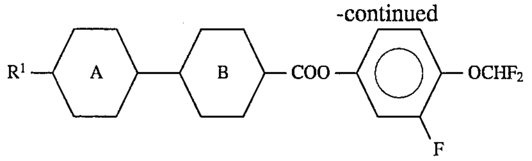
(263)
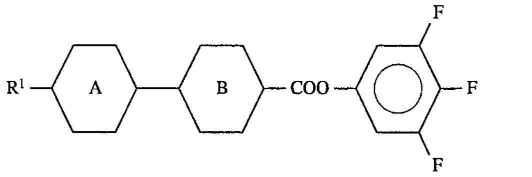
(264)
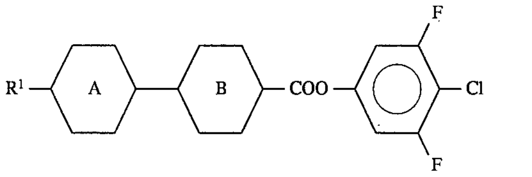
(265)
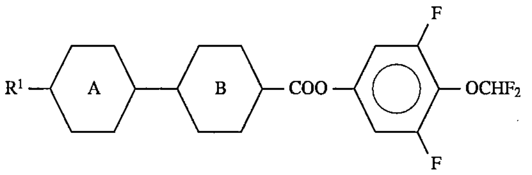
(266)
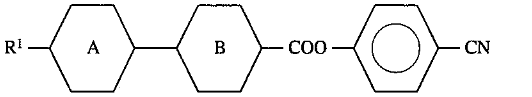
(267)
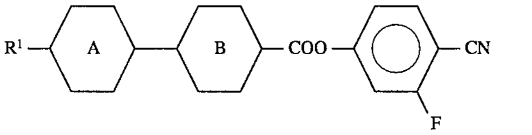
(268)
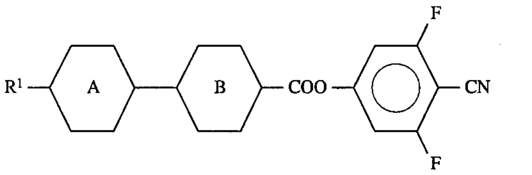
(269)
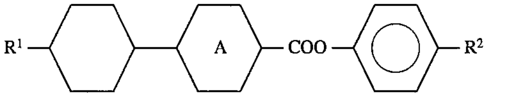
(270)
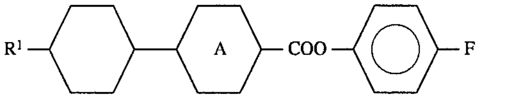
(271)
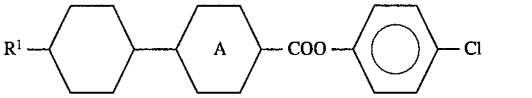
(272)
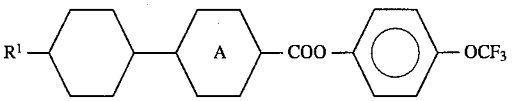
(273)
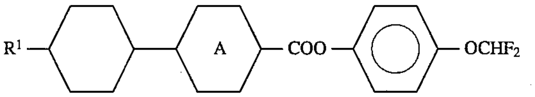
(274)

-continued
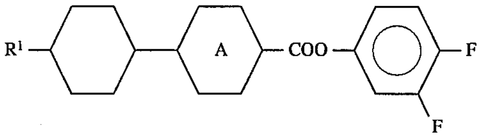
(275)
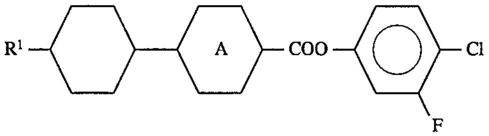
(276)
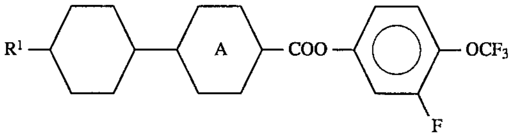
(277)
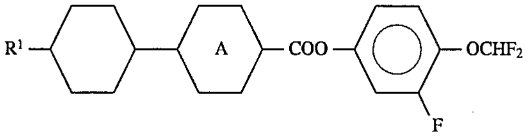
(278)
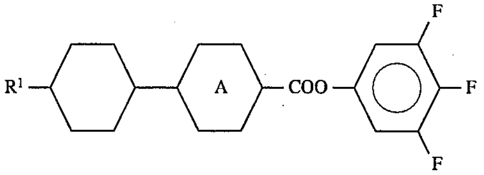
(279)
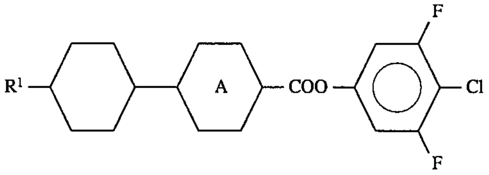
(280)
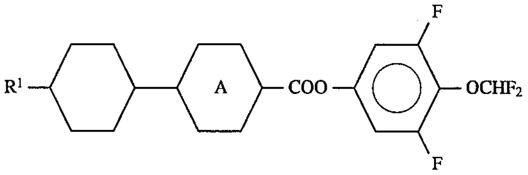
(281)
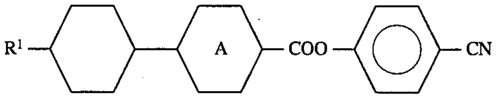
(282)
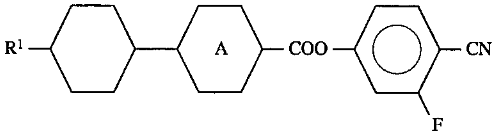
(283)
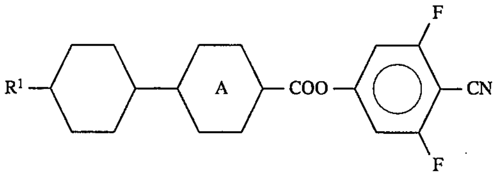
(284)
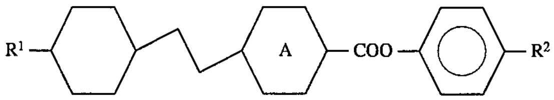
(285)

-continued
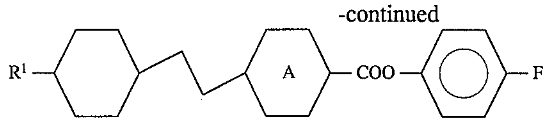
(286)
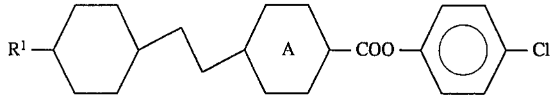
(287)
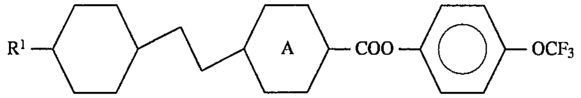
(288)
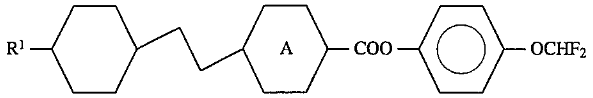
(289)
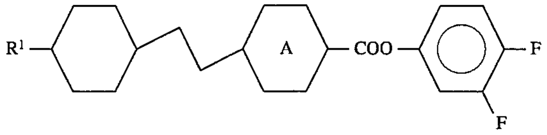
(290)
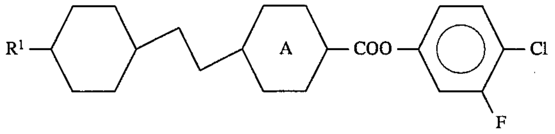
(291)
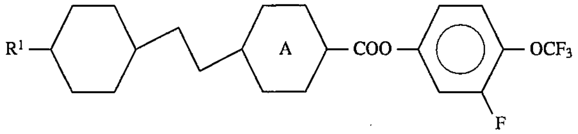
(292)
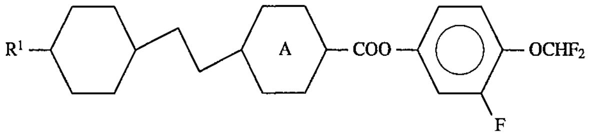
(293)
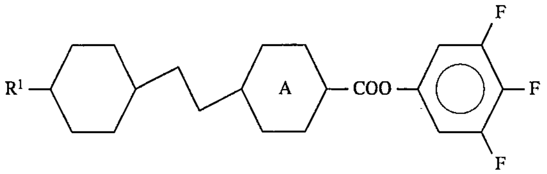
(294)
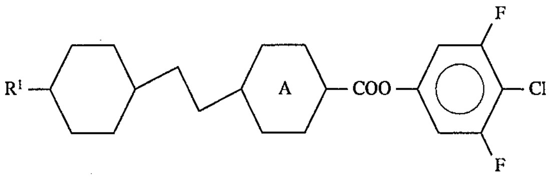
(295)
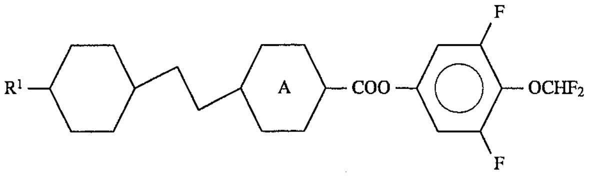
(296)
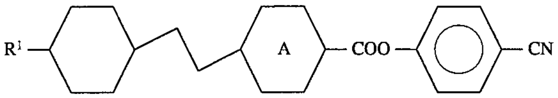
(297)

-continued
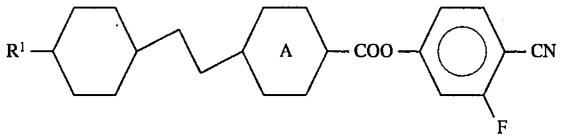
(298)
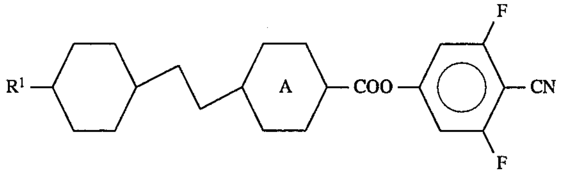
(299)
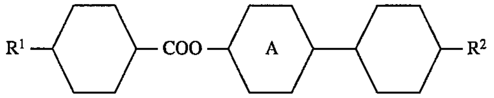
(300)
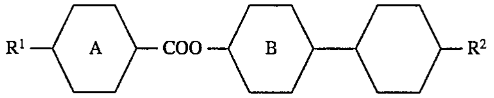
(301)
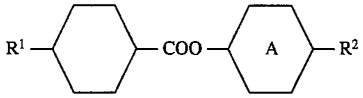
(302)
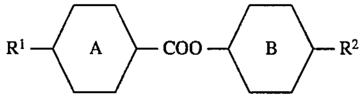
(303)
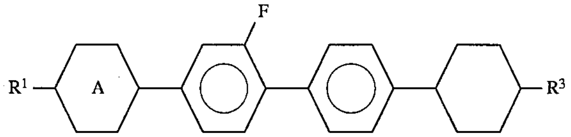
(304)
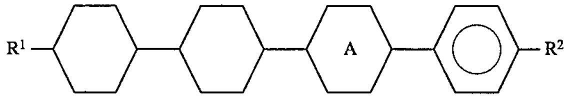
(305)
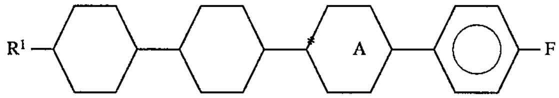
(306)
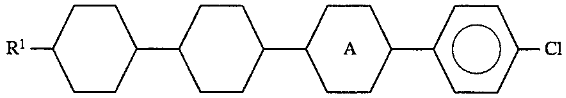
(307)
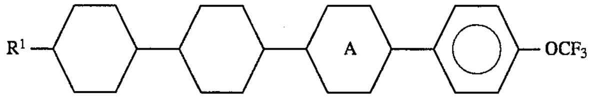
(308)
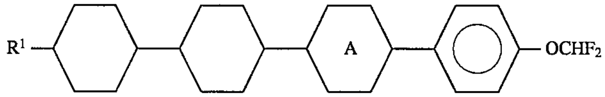
(309)
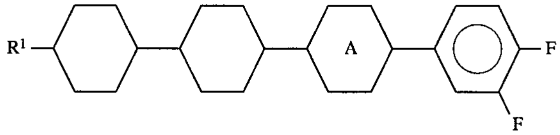
(310)

-continued
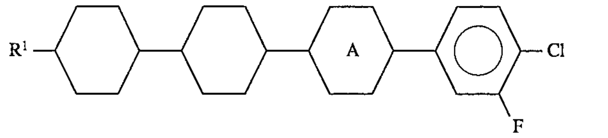
(311)
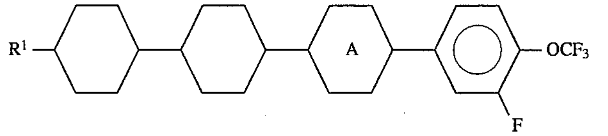
(312)
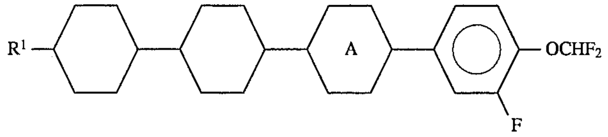
(313)
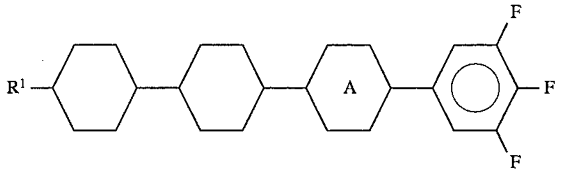
(314)
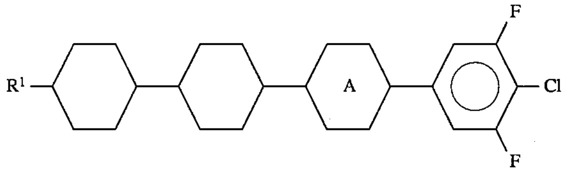
(315)
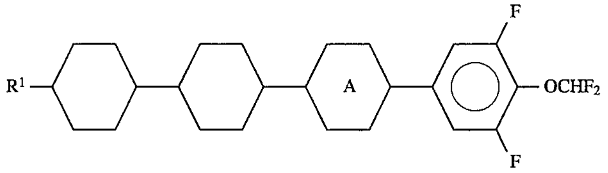
(316)
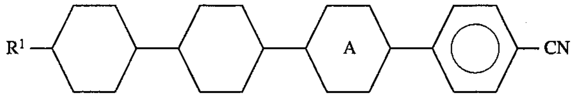
(317)
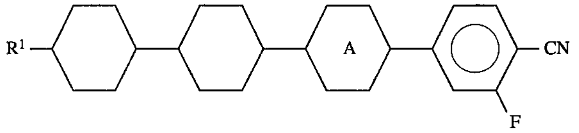
(318)
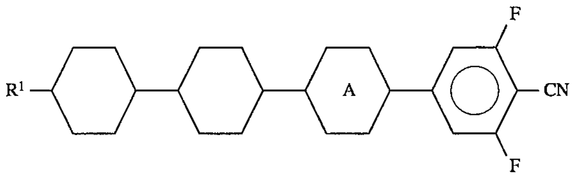
(319)
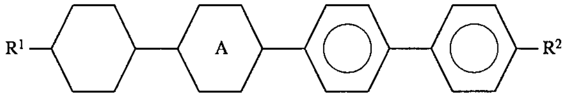
(320)
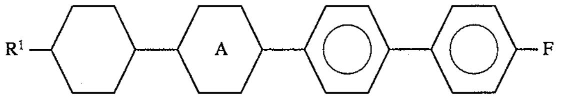
(321)

-continued
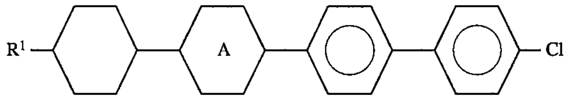
(322)
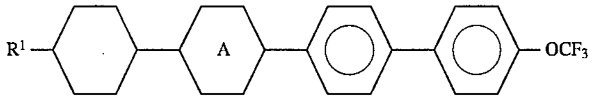
(323)
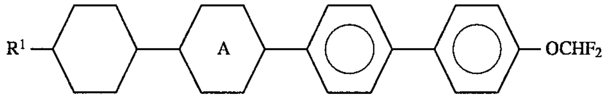
(324)
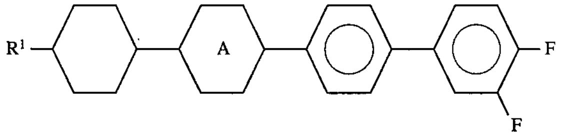
(325)
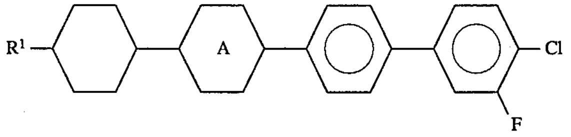
(326)
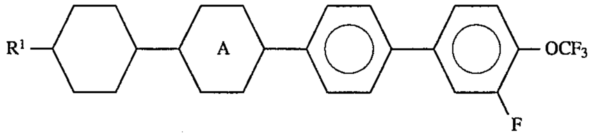
(327)
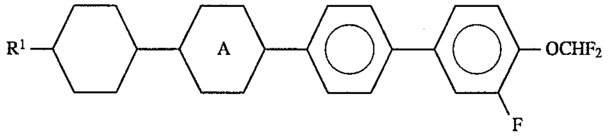
(328)
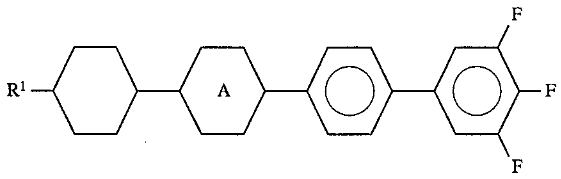
(329)
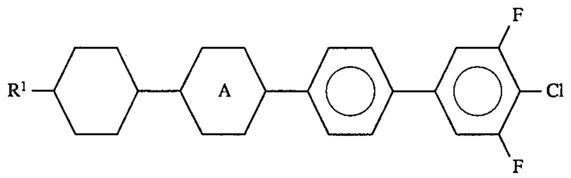
(330)
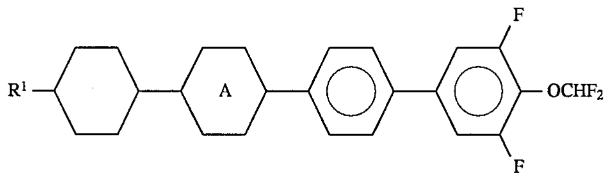
(331)
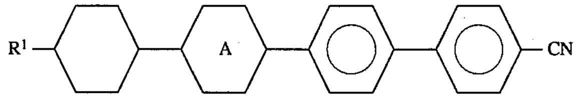
(332)
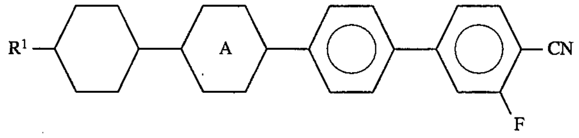
(333)

-continued
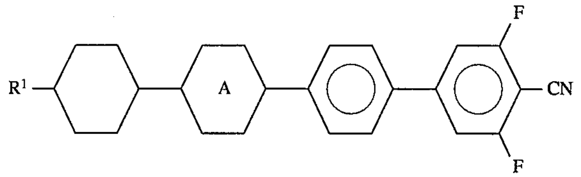
(334)
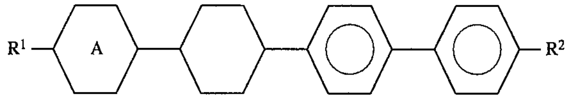
(335)
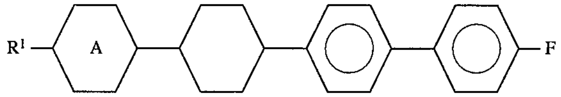
(336)
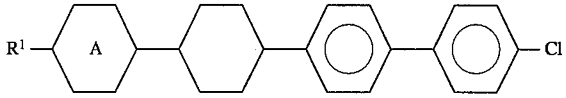
(337)
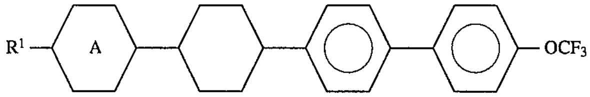
(338)
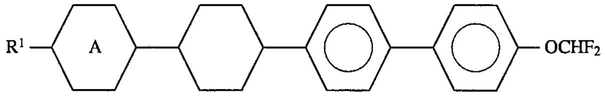
(339)
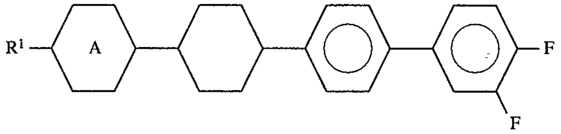
(340)
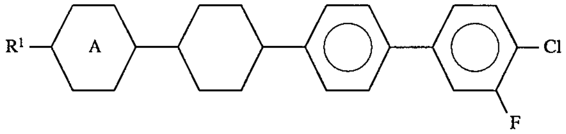
(341)
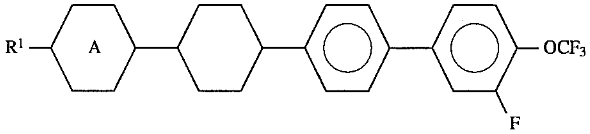
(342)
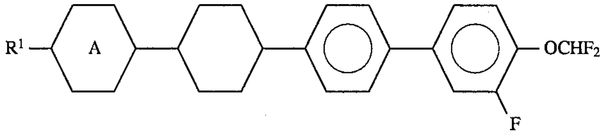
(343)
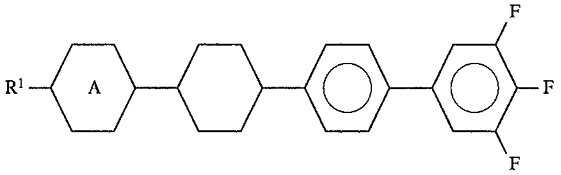
(344)
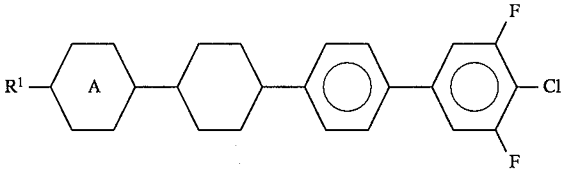
(345)

-continued
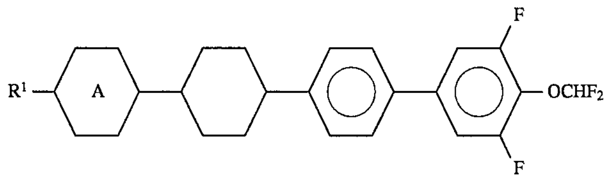
(346)
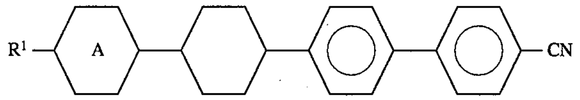
(347)
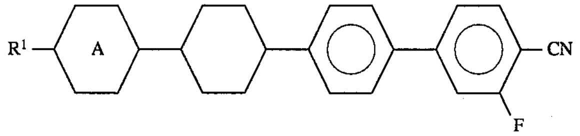
(348)
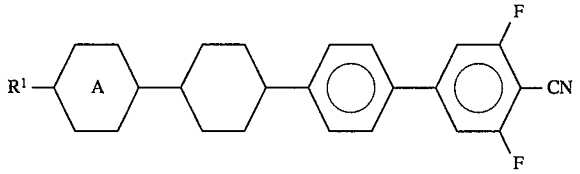
(349)
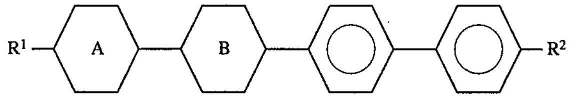
(350)
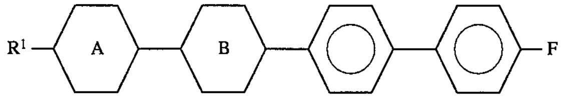
(351)
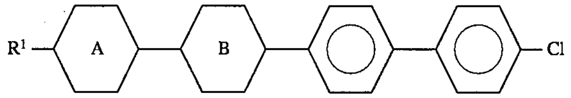
(352)
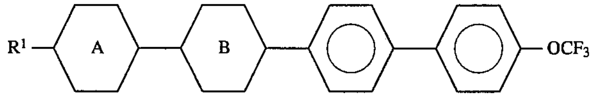
(353)
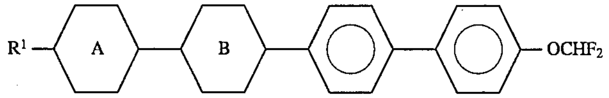
(354)
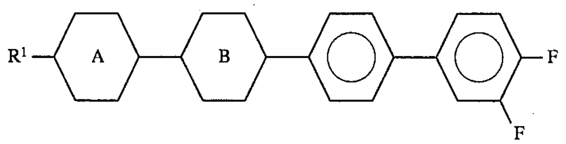
(355)
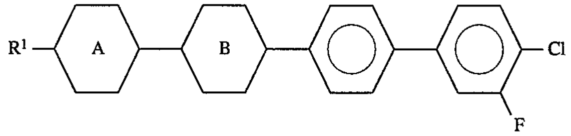
(356)
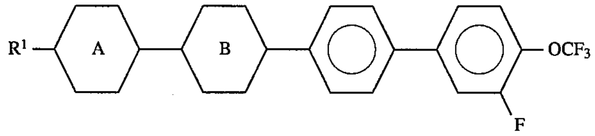
(357)

-continued
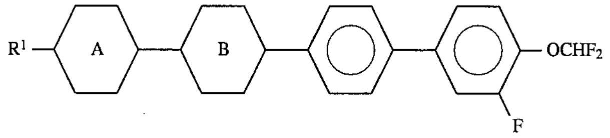
(358)
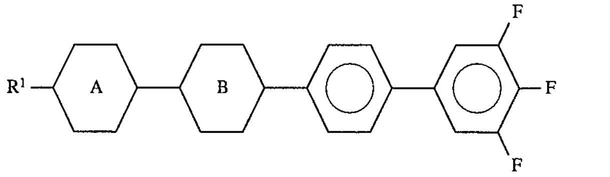
(359)
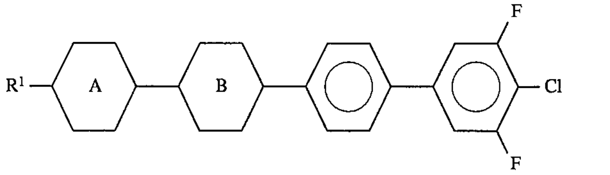
(360)
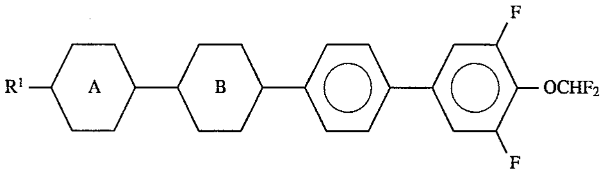
(361)
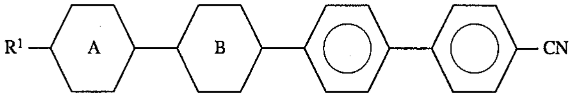
(362)
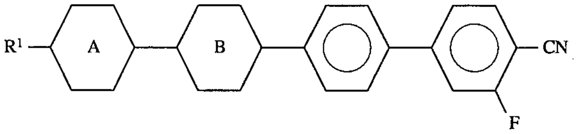
(363)
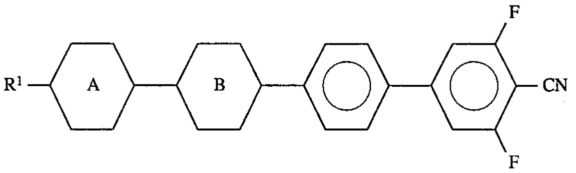
(364)
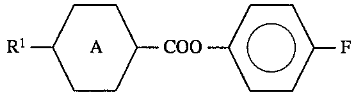
(365)
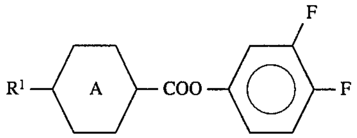
(366)
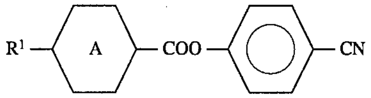
(367)
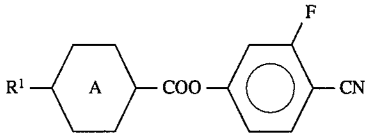
(368)

-continued
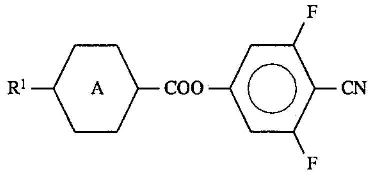
(369)
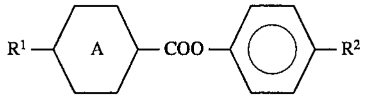
(370)
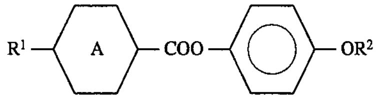
(371)
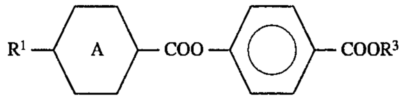
(372)
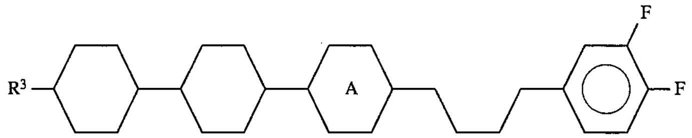
(373)
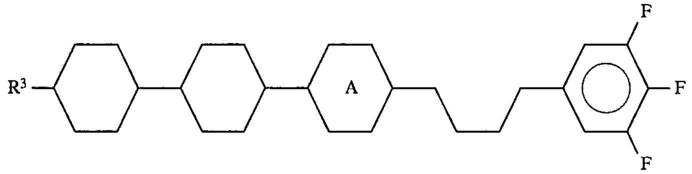
(374)
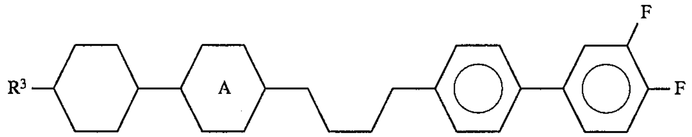
(375)
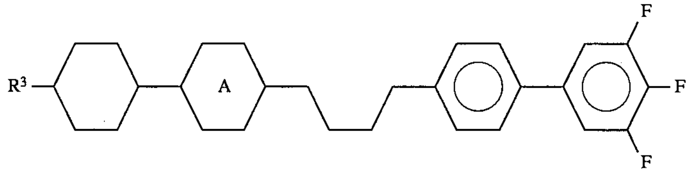
(376)
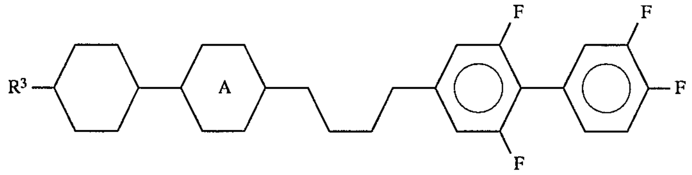
(377)
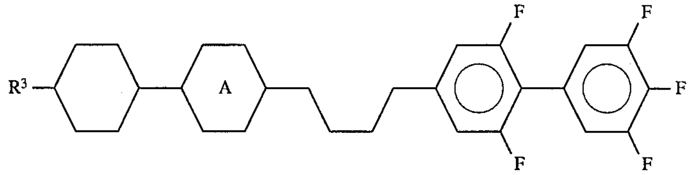
(378)
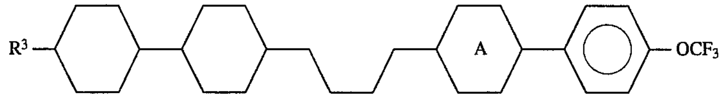
(379)

-continued
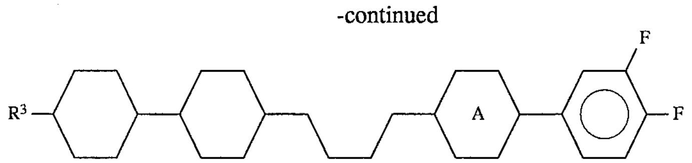
(380)
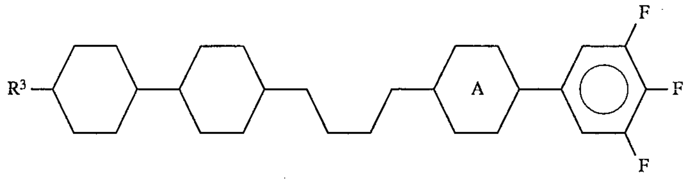
(381)
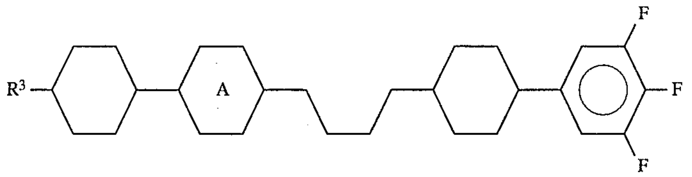
(382)
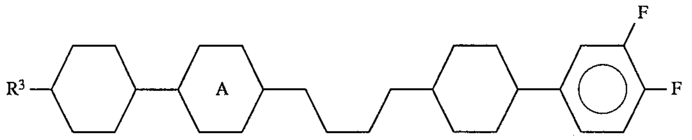
(383)
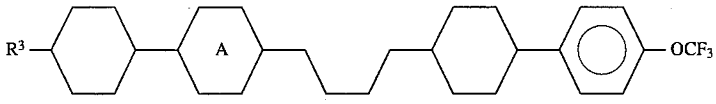
(384)
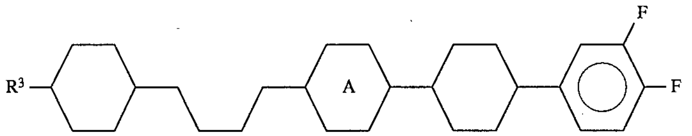
(385)
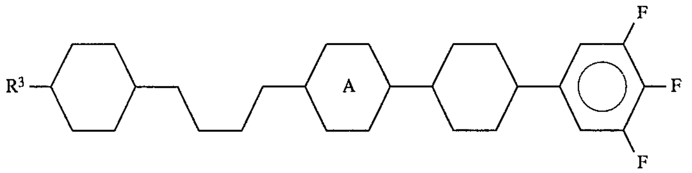
(386)
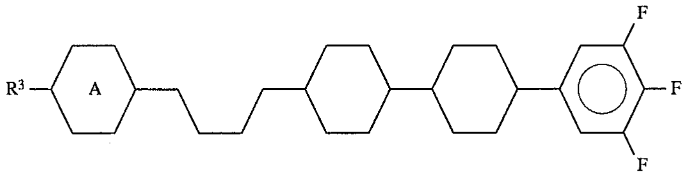
(387)
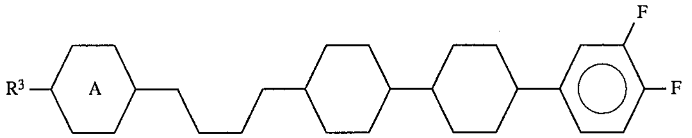
(388)
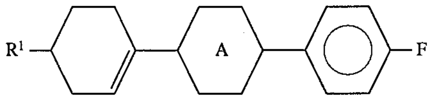
(389)
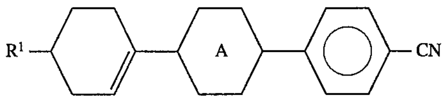
(390)

-continued
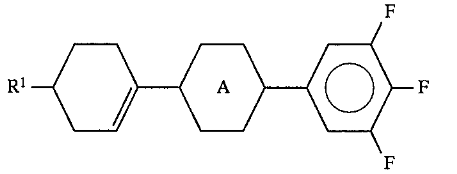
(391)
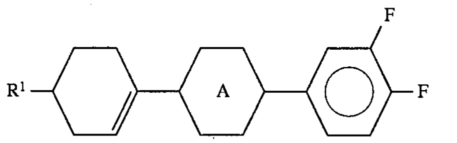
(392)
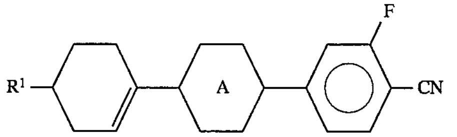
(393)
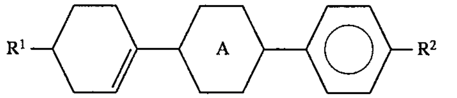
(394)
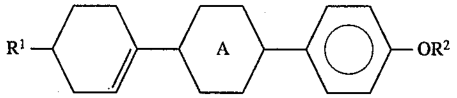
(395)
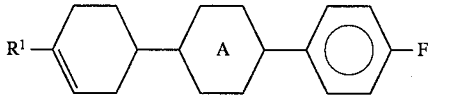
(396)
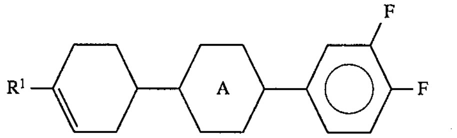
(397)
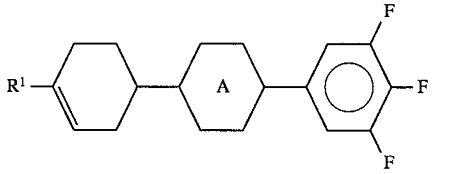
(398)
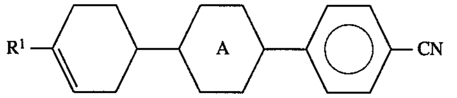
(399)
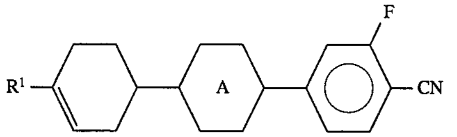
(400)
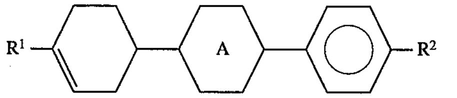
(401)
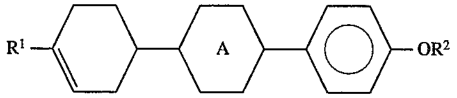
(402)

-continued
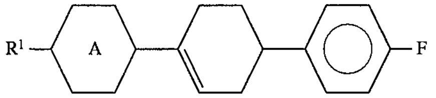
(403)
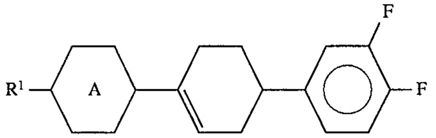
(404)
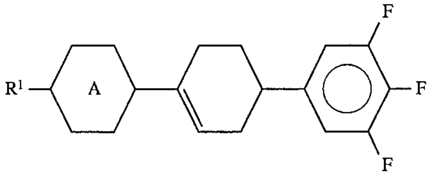
(405)
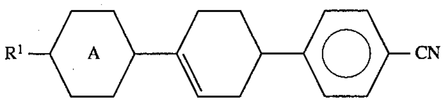
(406)
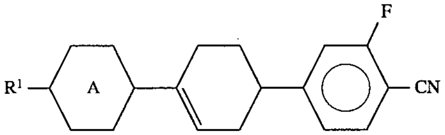
(407)
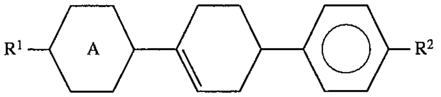
(408)
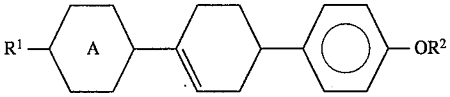
(409)
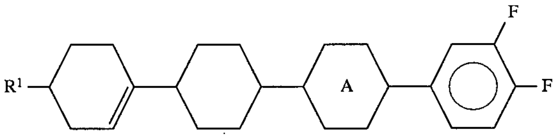
(410)
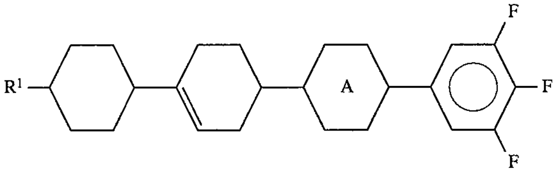
(411)
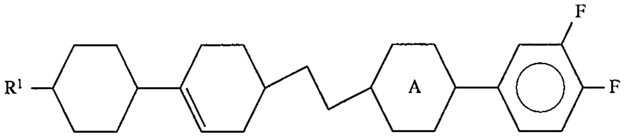
(412)
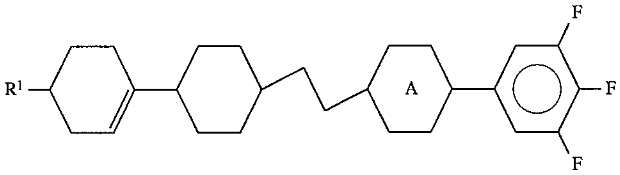
(413)

-continued
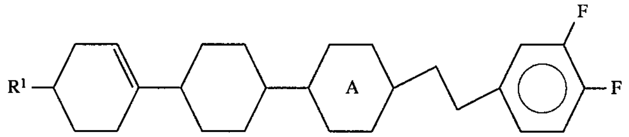
(414)
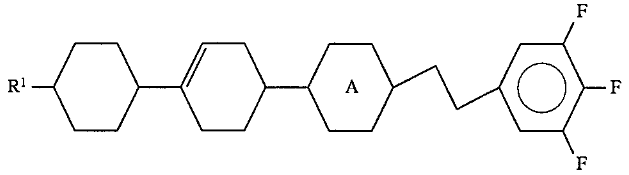
(415)
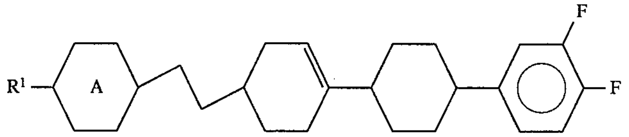
(416)
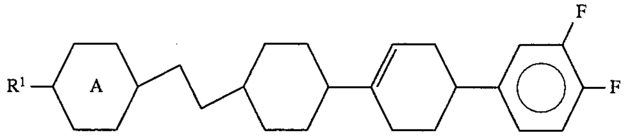
(417)
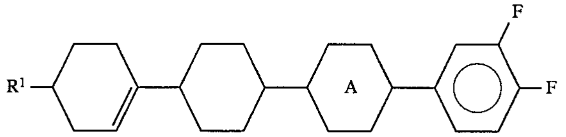
(418)
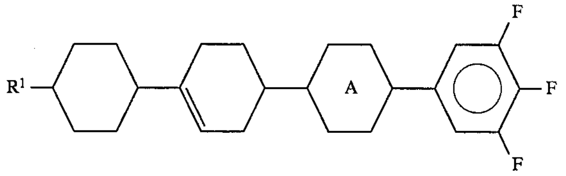
(419)
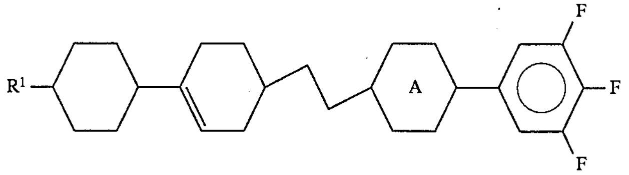
(420)
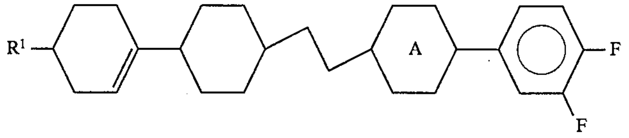
(421)
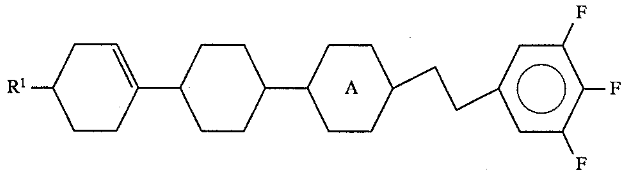
(422)
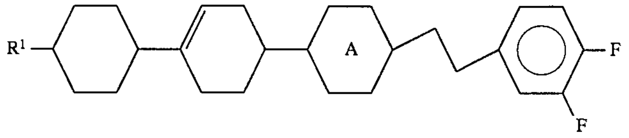
(423)

-continued

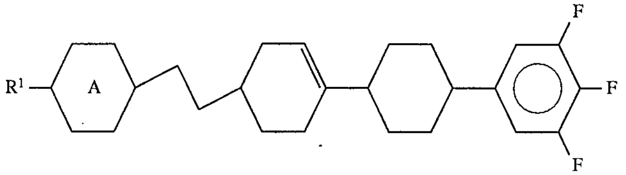

(424)

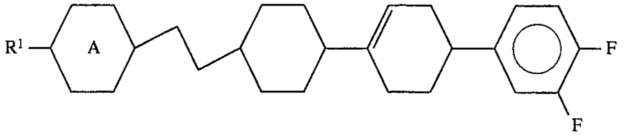

(425)

Preparation Examples of compounds (1) to (364) are shown below.

PREPARATION EXAMPLE 1

Preparation of Compound (1)

Compound (1) can be prepared by processes A, B or F, except for replacing 4-ethoxyphenylmagnesium bromide with a 4-alkyl(or alkoxyl)cyclohexylmagnesium bromide or by processes C, D, E or G, except for replacing 4-(4-ethoxyphenyl)cyclohexanone with a 4-(4-alkyl or alkoxylcyclohexyl)cyclohexanone.

PREPARATION EXAMPLE 2

Preparation of Compound (2)

Compound (2) can be prepared in the same manner as in Preparation Example 1, except for replacing the 4-alkyl(or alkoxyl)cyclohexylmagnesium bromide with a 2-[4-alkyl(or alkoxyl)cyclohexyl]ethylmagnesium bromide or replacing the 4-(4-alkyl or alkoxylcyclohexyl)cyclohexanone with a 4-[2-(4-alkyl or alkoxylcyclohexyl)ethyl]cyclohexanone.

PREPARATION EXAMPLE 3

Preparation of Compound (3)

Compound (3) can be prepared in accordance with processes A to J.

PREPARATION EXAMPLE 4

Preparation of Compound (4)

Compound (4) can be prepared in the same manner as in Preparation Example 3, except for replacing the 4-alkyl(or alkoxyl)phenylmagnesium bromide as a Grignard reagent with 4-fluorophenylmagnesium bromide.

PREPARATION EXAMPLE 5

Preparation of Compound (5)

A compound of formula (P1):

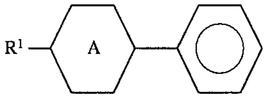

(P1)

is prepared in the same manner as in Preparation Example 3, except for replacing the 4-alkyl(or alkoxyl)phenylmagnesium bromide as a Grignard reagent with phenylmagnesium bromide. Compound (P1) is directly chlorinated with sulfuryl chloride, etc. in the presence of a catalyst to obtain compound (5). Alternatively, compound (P1) is once nitrated and then reduced to obtain an aniline derivative represented by formula (P2):

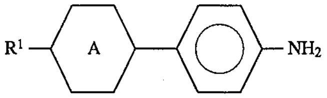

(P2)

which is then diazotized and decomposed to obtain compound (5).

PREPARATION EXAMPLE 6

Preparation of Compound (6)

Compound (6) is prepared in the same manner as in Preparation Example 3, except for using a Grignard reagent prepared from 4-bromo-1-trifluoromethoxybenzene.

PREPARATION EXAMPLE 7

Preparation of Compound (7)

Compound (3) wherein $R^2$ is $OCH_3$, which is prepared in Preparation Example 3, is demethylated using hydrobromic acid, trimethylsilyl iodide, aluminum chloride or boron tribromide, or aluminum chloride and dimethyl sulfide (or ethanethiol) to obtain a phenol derivative represented by formula (P3):

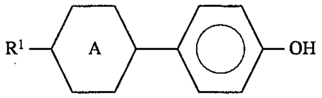

(P3)

The phenol derivative (P3) is reacted with chlorodifluoromethane in the presence of a base to obtain compound (7). Alternatively, the phenol derivative (P3) is converted to a formic ester and then reacted with dimethylaminosulfur trifluoride (hereinafter abbreviated as DAST), etc. to obtain compound (7).

PREPARATION EXAMPLE 8

Preparation of Compound (8)

The intermediate compound (P1) is reacted with oxalyl dichloride in the presence of a Lewis acid, e.g., aluminum chloride, to obtain a benzoyl chloride derivative represented by formula (P4):

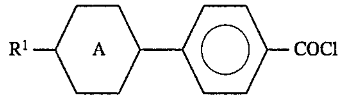
(P4)

Compound (P4) is esterified with an alcohol $R^3OH$ to obtain compound (8).

PREPARATION EXAMPLE 9

Preparation of Compound (9)

The intermediate compound (P3) is esterified with a carboxylic acid $R^3COOH$ or $R^3COCl$ in a usual manner to obtain compound (9).

PREPARATION EXAMPLE 10

Preparation of Compound (10)

Compound (10) can be prepared in the same manner as in Preparation Example 3, except for replacing the 4-alkyl(or alkoxyl)phenylmagnesium bromide with a Grignard reagent prepared from 1-bromo-3,4-difluorobenzene.

PREPARATION EXAMPLE 11

Preparation of Compound (11)

Compound (11) can be prepared in the same manner as in Preparation Example 10, except for using a Grignard reagent prepared from 1-bromo-4-chloro-3-fluorobenzene. Alternatively, an intermediate compound represented by formula (P5):

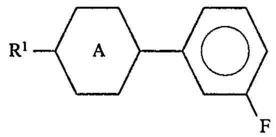
(P5)

is prepared b using 1-bromo-3-fluorobenzene, and compound (P5) is chlorinated in the same manner as in Preparation Example 5.

PREPARATION EXAMPLE 12

Preparation of Compound (12)

Compound (12) can be prepared in the same manner as in Preparation Example 3, except for replacing the 4-alkyl(or alkoxyl)phenylmagnesium bromide with a Grignard reagent prepared from 4-bromo-2-fluoro-1-trifluoromethoxybenzene.

PREPARATION EXAMPLE 13

Preparation of Compound (13)

A phenol derivative represented by formula (P6):

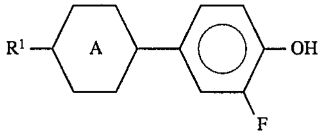
(P6)

in obtained in the same manner as in Preparation Example 7, except for replacing the 4-methoxyphenylmagnesium bromide with a Grignard reagent prepared from 4-bromo-2-fluoroanisole. Compound (P6) is then led to compound (13) in the same manner as in Preparation Example 7.

PREPARATION EXAMPLE 14

Preparation of Compound (14)

The intermediate compound (P5) is converted to an acid chloride of formula (P7):

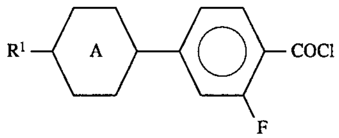
(P7)

which is then led to compound (14) in the same manner as in Preparation Example 8.

PREPARATION EXAMPLE 15

Preparation of Compound (15)

Compound (15) can be prepared in the same manner as in Preparation Example 3, except for replacing the 4-alkyl(or alkoxyl)phenylmagnesium bromide with a Grignard reagent prepared from 1-bromo-3,4,5-trifluorobenzene.

PREPARATION EXAMPLE 16

Preparation of Compound (16)

Compound (16) can be prepared in the same manner as in Preparation Example 3, except for replacing the 4-alkyl(or alkoxyl)phenylmagnesium bromide with a Grignard reagent prepared from 1-bromo-4-chloro-3,5-difluorobenzene. Alternatively, a compound represented by formula (P8):

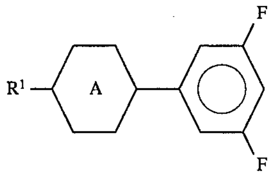
(P8)

is obtained by using a Grignard reagent prepared from 1-bromo-3,5-difluorobenzene, and compound (P8) is chlorinated in the same manner as in Preparation Example 5.

PREPARATION EXAMPLE 17

Preparation of Compound (17)

2,6-Difluorophenol is brominated and then reacted with methyl iodide, etc. to obtain 4-bromo-2,6-difluoroanisole, which is led to compound (17) in the same manner as in Preparation Example 13.

PREPARATION EXAMPLE 18

Preparation of Compound (18)

The intermediate compound (P4) is reacted with aqueous ammonia to obtain an amide derivative represented by formula (P9):

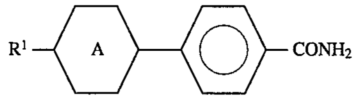
(P9)

The amide derivative (P9) is dehydrated with thionyl chloride, etc. for cyanogenation to obtain compound (18). Alternatively, the intermediate compound (P1) is iodinated with iodine-periodic acid to obtain a compound of formula (P10):

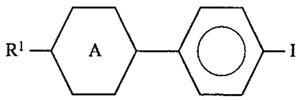

(P10)

which is then reacted with cuprous cyanide to obtain compound (18).

PREPARATION EXAMPLE 19

Preparation of Compound (19)

Compound (19) can be prepared from the intermediate compound (P7) or (P5) according to Preparation Example 18.

PREPARATION EXAMPLE 20

Preparation of Compound (20)

Compound (20) can be prepared in the same manner as in Preparation Example 18, except for replacing compound (P1) with compound (P8). Alternatively, compound (P8) is reacted with an alkyl lithium to obtain a phenyllithium derivative, which is then reacted with carbon dioxide to obtain a benzoic acid derivative of formula (P11):

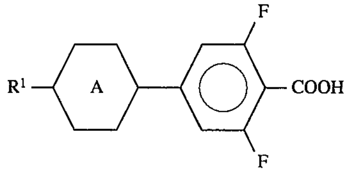

(P11)

Compound (P11) is converted to an acid chloride by using thionyl chloride, etc., which is further reacted in the same manner as in Preparation Example 18 to obtain compound (20).

PREPARATION EXAMPLE 21

Preparation of Compound (21)

A monoethyleneacetal of cyclohexane-1,4-dione is reacted with a Wittig reagent of formula (IV) to obtain a cyclohexanecarbaldehyde derivative represented by formula (P12):

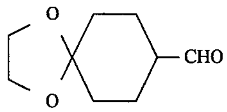

(P12)

which is again reacted with the compound of formula (IV) to obtain a cyclohexaneethanal derivative of formula (P13):

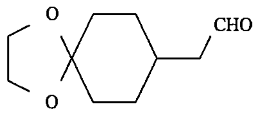

(P13)

Compound (P13) is reacted with a 4-alkyl(or alkoxyl)phenylmagnesium bromide, and the product is dehydrated with an acid. Where the acetal moiety has been removed, an acetal moiety is again introduced into the product. The acetal compound is hydrogenated, followed by decomposition of the acetal moiety to obtain a cyclohexanone derivative represented by formula (P15):

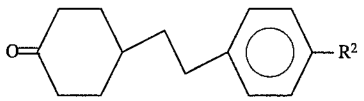

(P15)

From compound (P15) is obtained compound (21) in accordance with process B, C, D or E. The above-described process may be carried out by starting with a compound prepared by previously deuterating cyclohexane-1,4-dione monoethyleneacetal as in process G or a compound prepared by deuterating cyclohexane-1,4-dione and then introducing a monoacetal moiety thereinto as in process F. Further, compound (21) wherein $R^1$ is an alkyl group or an alkoxylalkyl group can also be prepared by deuterating a 4-substituted cyclohexanone according to process A, reacting the resulting deuterated cyclohexanone derivative with a Wittig reagent of formula (VI) twice to obtain a 4-substituted cyclohexaneethanal, and using this compound in place of compound (P13) in the above-described process.

PREPARATION EXAMPLE 22

Preparation of Compound (22)

Compound (22) can be prepared in the same manner as in Preparation Example 21, except for replacing the 4-alkyl(or alkoxyl)phenylmagnesium bromide with 4-fluorophenylmagnesium bromide.

PREPARATION EXAMPLE 23

Preparation of Compound (23)

Compound (23) can be prepared in the same manner as in Preparation Example 21,except for using a Grignard reagent prepared from 1-bromo-4-chlorobenzene. Alternatively, it is also prepared by once obtaining a compound of formula (P16):

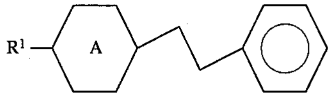

(P16)

by using phenylmagnesium bromide in Preparation Example 21, and then treating compound (P16) in the same manner as in Preparation Example 5.

PREPARATION EXAMPLE 24

Preparation of Compound (24)

Compound (24) can be prepared in the same manner as in Preparation Example 21, except for using a Grignard reagent prepared from 4-bromo-1-trifluoromethoxybenzene.

PREPARATION EXAMPLE 25

Preparation of Compound (25)

Compound (21) wherein $R^2$ is $OCH_3$, which is prepared in Preparation Example 21, is demethylated in the same manner as in Preparation Example 7 to obtain a phenol derivative represented by formula (P17):

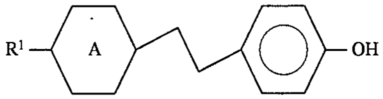

(P17)

Compound (25) can be prepared from this phenol derivative (P17) in the same manner as in Preparation Example 7.

PREPARATION EXAMPLE 26

Preparation of Compound (26)

Compound (26) can be prepared from compound (P16) in the same manner as in Preparation Example 8.

PREPARATION EXAMPLE 27

Preparation of Compound (27)

Compound (27) can be prepared form compound (P17) in the same manner as in Preparation Example 9.

PREPARATION EXAMPLE 28

Preparation of Compound (28)

Compound (28) can be prepared in the same manner as in Preparation Example 21, except for using a Grignard reagent prepared from 4-bromo-1,2-difluorobenzene.

PREPARATION EXAMPLE 29

Preparation of Compound (29)

Compound (29) can be prepared in the same manner as in Preparation Example 21, except for using a Grignard reagent prepared from 1-bromo-4-chloro-3-fluorobenzene. Alternatively, an intermediate compound of formula (P18):

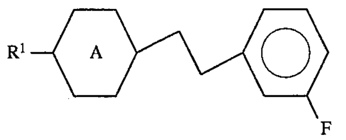

(P18)

which is obtained by using 1-bromo-3-fluorobenzene, is chlorinated in the same manner as in Preparation Example 5 to obtain compound (29).

PREPARATION EXAMPLE 30

Preparation of Compound (30)

Compound (30) can be prepared in the same manner as in Preparation Example 21, except for replacing the 4-alkyl(or alkoxyl)phenylmagnesium with a Grignard reagent prepared from 4-bromo-2-fluoro-1-trifluoromethoxybenzene.

PREPARATION EXAMPLE 31

Preparation of Compound (31)

A phenol derivative represented by formula (P19):

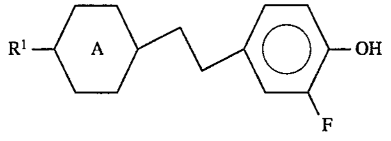

(P19)

is obtained in the same manner as in Preparation Example 25, except for replacing 4-methoxyphenylmagnesium bromide with a Grignard reagent prepared from 4-bromo-2-fluoroanisole. Compound (31) can be prepared from compound (P19) in the same manner as in Preparation Example 7.

PREPARATION EXAMPLE 32

Preparation of Compound (32)

An acid chloride represented by formula (P20):

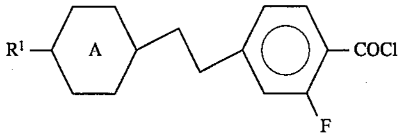

(P20)

is obtained from compound (P18), and compound (P20) is treated in the same manner as in Preparation Example 8 to obtain compound (32).

PREPARATION EXAMPLE 33

Preparation of Compound (33)

Compound (33) can be prepared in the same manner as in Preparation Example 21, except for using a Grignard reagent prepared from 1-bromo-3,4,5-trifluorobenzene.

PREPARATION EXAMPLE 34

Preparation of Compound (34)

Compound (34) can be prepared in the same manner as in Preparation Example 21, except for using a Grignard reagent prepared from 1-bromo-4-chloro-3,5-difluorobenzene. Alternatively, a compound of formula (P21):

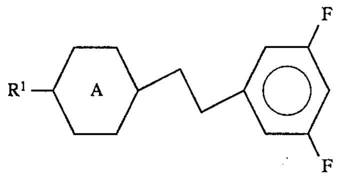

(P21)

is once prepared by using a Grignard reagent prepared from 1-bromo-3,5-difluorobenzene, which is then chlorinated in the same manner as in Preparation Example 5 to obtain compound (34).

PREPARATION EXAMPLE 35

Preparation of Compound (35)

2,6-Difluorophenol is brominated and then methylated with methyl iodide, etc. to obtain 4-bromo-2,6-difluoroanisole. A phenol derivative of formula (P22):

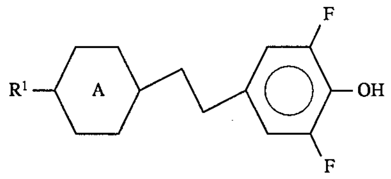

(P22)

is obtained using the resulting 4-bromo-2,6-difluoroanisole, which is then led to compound (35) in the same manner as in Preparation Example 31.

PREPARATION EXAMPLE 36

Preparation of Compound (36)

In the same manner as in Preparation Example 18, an amide derivative of formula (P23):

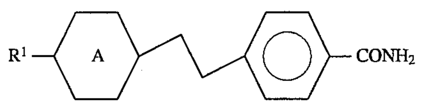

(P23)

is obtained. Compound (P23) is dehydrated with thionyl chloride, etc. for cyanogenation to obtain compound (36). Alternatively, the intermediate compound (P16) is iodinated with iodine-periodic acid to obtain an iodobenzene derivative of formula (P24):

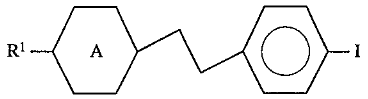

(P24)

which is then reacted with cuprous cyanide to obtain compound (36).

PREPARATION EXAMPLE 37

Preparation of Compound (37)

Compound (37) can be prepared from compound (P18) or compound (P20) in the same manner as in Preparation Example 36.

PREPARATION EXAMPLE 38

Preparation of Compound (38)

Compound (38) can be prepared in the same manner as in Preparation Example 36, except for replacing compound (P16) with compound (P21). Alternatively, compound (P21) is reacted with an alkyl lithium to obtain a phenyllithium derivative, which is then reacted with carbon dioxide to obtain a benzoic acid derivative of formula (P25):

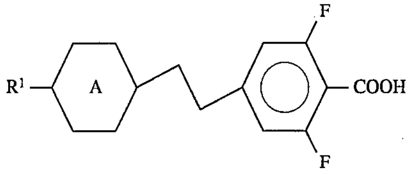

(P25)

Compound (P25) is converted to an acid chloride by using thionyl chloride, etc., which is further reacted in the same manner as in Preparation Example 36 to obtain compound (38).

PREPARATION EXAMPLES 39 AND 40

Preparation of Compounds (39) and (40)

A compound represented by formula (P26):

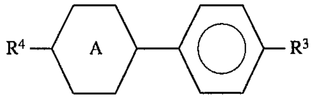

(P26)

which corresponds to compound (3) wherein $R^1$ is an alkyl group or an alkoxylalkyl group; and $R^2$ is an alkyl group, is reduced with metallic lithium or metallic sodium to obtain a mixture of compounds (39) and (40). The mixture as obtained is usually usable as such. If desired, the mixture can be separated into each compound.

Where only compound (39) is desired, it is prepared as follows. A compound of formula (P27):

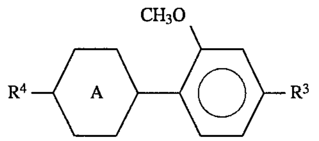

(P27)

is prepared by using a Grignard reagent prepared from a 2-bromo-5-alkylanisole. Compound (P27) is demethylated and then hydrogenated to obtain a cyanohexanone derivative of formula (P28):

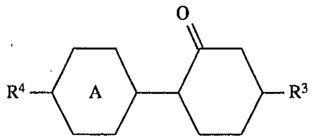

(P28)

Compound (P28) is reduced with lithium aluminum hydride or sodium borohydride and then dehydrated to obtain compound (39).

Where only compound (40) is desired, it can be prepared in the same manner as for compound (39), except for using a Grignard reagent prepared from a 5-bromo-2-alkylanisole.

PREPARATION EXAMPLES 41 AND 42

Preparation of Compounds (41) and (42)

A compound represented by formula (P29):

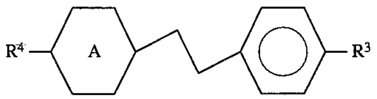

(P29)

which corresponds to compound (21) wherein $R^1$ is an alkyl group or an alkoxylalkyl group; and $R^2$ is an alkyl group, is reduced with metallic lithium or metallic sodium to obtain a mixture of compounds (41) and (42). The mixture as produced is usually usable as such. If desired, the mixture can be separated into each compound.

Where only compound (41) is desired, it is prepared as follows. A compound of formula (P30):

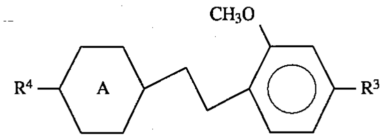

(P30)

is obtained by using a Grignard reagent prepared from a 2-bromo-5-alkylanisole. Compound (P30) is demethylated and then hydrogenated to obtain a cyanohexanone derivative of formula (P31):

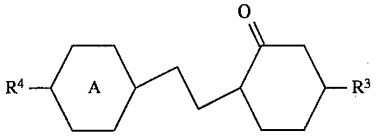

(P31)

Compound (P31) is reduced with lithium aluminum hydride or sodium borohydride and then dehydrated to obtain compound (41).

Where only compound (42) is desired, it can be prepared in the same manner as for compound (41), except for using a Grignard reagent prepared from a 5-bromo-2-alkylanisole.

PREPARATION EXAMPLE 43

Preparation of Compound (43)

Compound (43) can be prepared by reacting the compound of formula (P3) with a compound of formula X-$R^5$, wherein X represents a chlorine atom, a bromine atom, an iodine atom, or a leaving group, such as a p-toluenesulfonyl group; and $R^5$ represents an alkenyl group, in the presence of a base.

PREPARATION EXAMPLE 44

Preparation of Compound (44)

Compound (44) can be prepared in the same manner as in Preparation Example 43, except for using the intermediate compound of formula (P17).

PREPARATION EXAMPLE 45

Preparation of Compound (45)

Compound (45) can be prepared in accordance with process B, C, D or E, except for replacing the monoacetal of cyclohexane-1,4-dione with a monoacetal of bicyclohexane-4,4'-dione. Alternatively, compound (45) wherein $R^1$ is an alkyl or alkoxylalkyl group can be prepared by hydrogenating compound (P3) to obtain a cyclohexanone derivative of formula (P32):

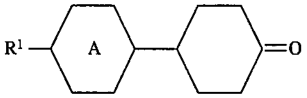
(P32)

reacting compound (P32) with a Grignard reagent, and subjecting the product to dehydration and hydrogenation in accordance with process A. If desired, the cis-cyclohexane ring is isomerized to a trans-form.

PREPARATION EXAMPLE 46

Preparation of Compound (46)

Compound (46) can be prepared in the same manner as in Preparation Example 45, except for using 4-fluorophenylmagnesium bromide as a Grignard reagent.

PREPARATION EXAMPLE 47

Preparation of Compound (47)

Compound (47) can be prepared in the same manner as in Preparation Example 45, except for using a Grignard reagent prepared from 1-bromo-4-chlorobenzene. Alternatively, a compound of formula (33):

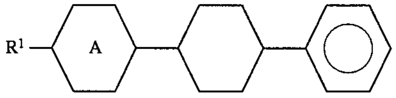
(P33)

is obtained in the same manner but using phenylmagnesium bromide as a Grignard reagent, and compound (P33) is led to compound (47) in the same manner as in Preparation Example 5.

PREPARATION EXAMPLE 48

Preparation of Compound (48)

Compound (48) can be prepared in the same manner as in Preparation Example 45, except for using a Grignard reagent prepared from 4-bromo-1-trifluoromethoxybenzene.

PREPARATION EXAMPLE 49

Preparation of Compound (49)

Compound (45) wherein $R^2$ is $OCH_3$ as prepared in Preparation Example 45 is demethylated in the same manner as in Preparation Example 3 to obtain a phenol derivative of formula (P34):

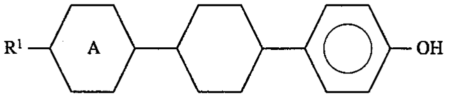
(P34)

from which Compound (49) can be prepared in the same manner as in Preparation Example 3.

PREPARATION EXAMPLE 50

Preparation of Compound (50)

Compound (50) can be prepared in the same manner as in Preparation Example 45, except for replacing the 4-alkyl(or alkoxyl)phenylmagnesium bromide with a Grignard reagent prepared from 1-bromo-3,4-difluorobenzene.

PREPARATION EXAMPLE 51

Preparation of Compound (51)

Compound (51) is prepared in the same manner as in Preparation Example 45, except for using a Grignard reagent prepared from 1-bromo-4-chloro-3-fluorobenzene. Alternatively, an intermediate compound of formula (P35):

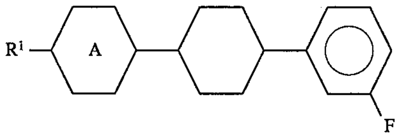
(P35)

is once prepared in the same manner but using a Grignard reagent prepared from 1-bromo-3-fluorobenzene, and compound (P35) is chlorinated in the same manner as in Preparation Example 5 to obtain compound (51).

PREPARATION EXAMPLE 52

Preparation of Compound (52)

Compound (52) can be obtained in the same manner as in Preparation Example 45, except for replacing the 4-alkyl(or alkoxyl)phenylmagnesium bromide with a Grignard reagent prepared from 4-bromo-2-fluoro-1-trifluoromethoxybenzene.

PREPARATION EXAMPLE 53

Preparation of Compound (53)

A phenol derivative represented by formula (P36):

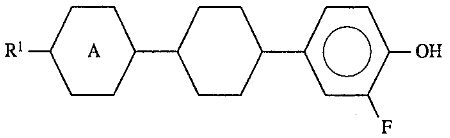
(P36)

is prepared in the same manner as in Preparation Example 49, except for replacing 4-methoxyphenylmagnesium bromide with a Grignard reagent prepared from 4-bromo-3-fluoroanisole. Compound (53) can be prepared from compound (P36) in the same manner as in Preparation Example 7.

PREPARATION EXAMPLE 54

Preparation of Compound (54)

Compound (54) can be prepared in the same manner as in Preparation Example 45, except for replacing the 4-alkyl(or alkoxyl)phenylmagnesium bromide with a Grignard reagent prepared from 1-bromo-3,4,5-trifluorobenzene.

PREPARATION EXAMPLE 55

Preparation of Compound (55)

Compound (55) can be prepared in the same manner as in Preparation Example 45, except for using a Grignard reagent prepared from 1-bromo-4-chloro-3,5-difluorobenzene. Alternatively, compound (55) can also be obtained by chlorinating a compound of formula (P37):

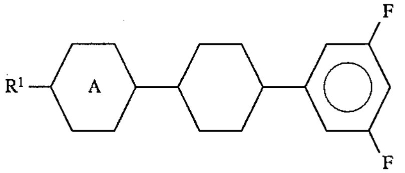
(P37)

which is similarly obtained by using a Grignard reagent prepared from 1-bromo-3,5-difluorobenzene, in the same manner as in Preparation Example 5.

PREPARATION EXAMPLE 56

Preparation of Compound (56)

Compound (56) can be obtained in the same manner as in Preparation Example 53, except for using a Grignard reagent prepared from 4-bromo-2,6-difluoroanisole, the intermediate prepared in Preparation Example 17.

PREPARATION EXAMPLE 57

Preparation of Compound (57)

An acid chloride of formula (P38):

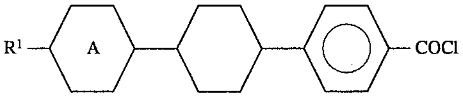
(P38)

is obtained from compound (P33) in the same manner as in Preparation Example 8. The acid chloride (P38) is reacted with aqueous ammonia to obtain an amide derivative of formula (P39):

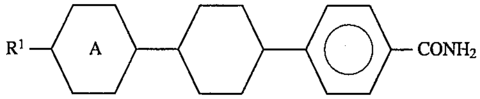
(P39)

The amide derivative (P39) is dehydrated with thionyl chloride, etc. for cyanogenation to obtain compound (57). Alternatively, the intermediate of formula (P33) is iodinated with iodine-periodic acid to obtain a compound of formula (P40):

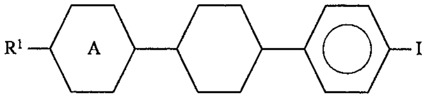
(P40)

which is then reacted with cuprous cyanide to obtain compound (57).

PREPARATION EXAMPLE 58

Preparation of Compound (58)

Compound (58) can be obtained from the intermediate compound (P35) in the same manner as in Preparation Example 57.

PREPARATION EXAMPLE 59

Preparation of Compound (59)

Compound (59) can be prepared in the same manner as in Preparation Example 57, except for replacing compound (P33) with compound (P37). Alternatively, compound (37) is reacted with an alkyl lithium to obtain a phenyllithium derivative, which is then reacted with carbon dioxide to obtain a benzoic acid derivative of formula (P41):

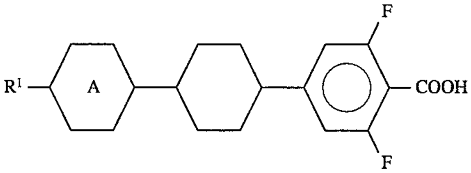
(P41)

Compound (P41) is converted to an acid chloride by using thionyl chloride, etc., which is further reacted in the same manner as in Preparation Example 57 to obtain compound (59).

PREPARATION EXAMPLE 60

Preparation of Compound (60)

Compound (60) can be prepared in accordance with process K, L, M, N or O, except for replacing 3,4-difluorophenylmagnesium bromide as a Grignard reagent with a 4-alkyl(or alkoxyl)magnesium bromide.

PREPARATION EXAMPLE 61

Preparation of Compound (61)

Compound (61) can be prepared in the same manner as in Preparation Example 60, except for using 4-fluorophenylmagnesium bromide as a Grignard reagent.

PREPARATION EXAMPLE 62

Preparation of Compound (62)

Compound (62) can be prepared in the same manner as in Preparation Example 60, except for using a Grignard reagent prepared from 1-bromo-4-chlorobenzene. Alternatively, a compound of formula (P42):

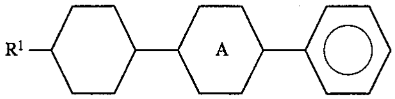

(P42)

is obtained in the same manner but using phenylmagnesium bromide as a Grignard reagent, and compound (62) is prepared therefrom in the same manner as in Preparation Example 5.

PREPARATION EXAMPLE 63

Preparation of Compound (63)

Compound (63) can be prepared in the same manner as in Preparation Example 60, except for using a Grignard reagent prepared from 4-bromo-1-trifluoromethoxybenzene.

PREPARATION EXAMPLE 64

Preparation of Compound (64)

Compound (60) prepared in Preparation Example 60 wherein $R^2$ is $OCH_3$ is demethylated to obtain a phenol derivative of formula (P43):

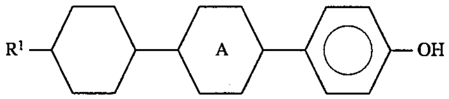

(P43)

which is then led to compound (64) in the same manner as in Preparation Example 3.

PREPARATION EXAMPLE 65

Preparation of Compound (65)

Compound (65) is obtained in accordance with process K, L, M, N or O.

PREPARATION EXAMPLE 66

Preparation of Compound (66)

Compound (66) can be prepared in the same manner as in Preparation Example 60, except for using a Grignard reagent prepared from 1-bromo-4-chloro-3-fluorobenzene. Alternatively, compound (66) can be obtained by once preparing a compound of formula (P44):

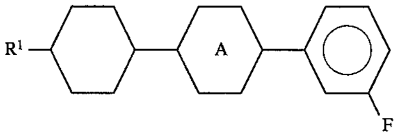

(P44)

in the same manner but using 1-bromo-3-fluorobenzene and chlorinating compound (P44) in the same manner as in Preparation Example 5.

PREPARATION EXAMPLE 67

Preparation of Compound (67)

Compound (67) can be prepared in the same manner as in Preparation Example 60, except for replacing the 4-alkyl(or alkoxyl)phenylmagnesium bromide with a Grignard reagent prepared from 4-bromo-2-fluoro-1-trifluoromethoxybenzene.

PREPARATION EXAMPLE 68

Preparation of Compound (68)

A phenol derivative represented by formula (P45):

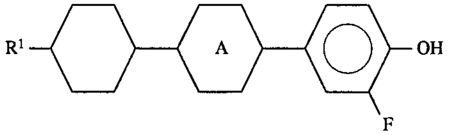

(P45)

is prepared in the same manner as in Preparation Example 64, except for replacing 4-methoxyphenylmagnesium bromide with a Grignard reagent prepared from 4-bromo-2-fluoroanisole. Compound (64) can be obtained from compound (P45) in the same manner as in Preparation Example 7.

PREPARATION EXAMPLE 69

Preparation of Compound (69)

Compound (69) can be obtained in the same manner as in Preparation Example 60, except for replacing the 4-alkyl(or alkoxyl)phenylmagnesium with a Grignard reagent prepared from 1-bromo-3,4,5-trifluorobenzene.

PREPARATION EXAMPLE 70

Preparation of Compound (70)

Compound (70) can be prepared in the same manner as in Preparation Example 60, except for using a Grignard reagent prepared from 1-bromo-4-chloro-3,5-difluorobenzene. Alternatively, a compound of the formula (P46):

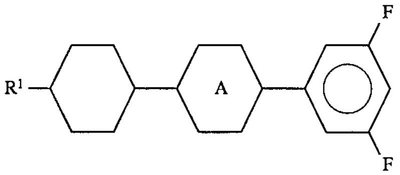

(P46)

which is obtained in the same manner but using a Grignard reagent prepared from 1-bromo-3,5-difluorobenzene, is chlorinated in the same manner as in Preparation Example 5 to obtain compound (70).

PREPARATION EXAMPLE 71

Preparation of Compound (71)

Compound (71) can be prepared in the same manner as in Preparation Example 68, except for using 4-bromo-2,6-difluoroanisole, the intermediate compound obtained in Preparation Example 17.

PREPARATION EXAMPLE 72

Preparation of Compound (72)

An acid chloride of formula (P47):

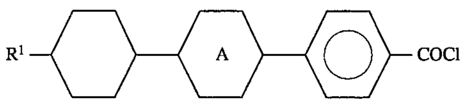
(P47)

is obtained from the intermediate compound of formula (P42) in the same manner as in Preparation Example 8, and the acid chloride (P47) is reacted with aqueous ammonia to obtain an amide derivative of formula (P48):

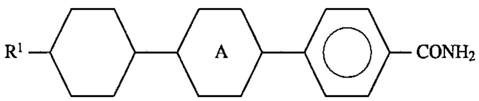
(P48)

The amide derivative (P48) is dehydrated with thionyl chloride, etc. for cyanogenation to obtain compound (72). Alternatively, the intermediate of formula (P42) is iodinated with iodine-periodic acid to obtain a compound of formula (P49):

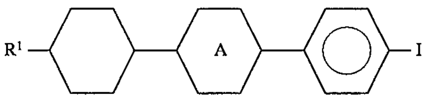
(P49)

which is then reacted with cuprous cyanide to obtain compound (72).

PREPARATION EXAMPLE 73

Preparation of Compound (73)

Compound (73) can be prepared from the compound of formula (P44) in the same manner as in Preparation Example 72.

PREPARATION EXAMPLE 74

Preparation of Compound (74)

Compound (74) can be prepared in the same manner as in Preparation Example 72, except for replacing compound (P42) with compound (P44). Alternatively, it can be prepared from compound (P46) via a benzoic acid derivative of formula (P50):

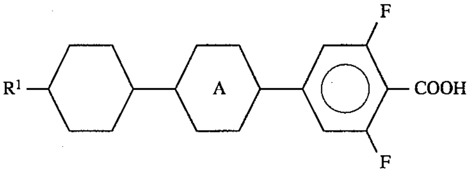
(P50)

in the same manner as in Preparation Example 59.

PREPARATION EXAMPLE 75

Preparation of Compound (75)

Compound (75) can be prepared in accordance with process K to O, except for using a deuterated compound of formula (P51):

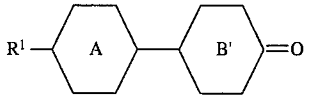
(P51)

in place of the 4-(4-substituted cyclohexyl)cyclohexanone and replacing 3,4-difluorophenylmagnesium bromide as a Grignard reagent with a 4-alkyl(or alkoxyl)phenylmagnesium bromide. It can also be prepared by using compound (P32) in place of compound (P51) in accordance with processes H to L. Further, it may be prepared in the same manner as in Preparation Example 45, except for starting with a monoethyleneacetal of deuterated bicyclohexane-4,4'-dione represented by formula (P52):

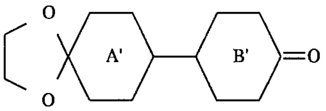
(P52)

Alternatively, a compound of formula (P53):

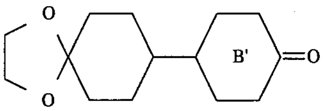
(P53)

is reacted in the same manner in place of compound (P52) to obtain a cyclohexanone derivative of formula (P54):

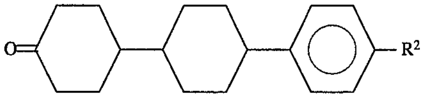
(P54)

from which compound 75) can be prepared in accordance with processes B to G.

Compound (P51) can be obtained by deuteration of compound (P32). Compound (P52) can be obtained by deuteration of bicyclohexane-4,4'-dione followed by introduction of a monoacetal moiety. Compound (P53) can be obtained by deuteration of bicyclohexane-4,4-dione monoethyleneacetal.

PREPARATION EXAMPLE 76

Preparation of Compound (76)

Compound (76) can be prepared in the same manner as in Preparation Example 75, except for using 4-fluorophenylmagnesium bromide as a Grignard reagent.

PREPARATION EXAMPLE 77

Preparation of Compound (77)

Compound (77) can be prepared in the same manner as in Preparation Example 75, except for using a Grignard reagent prepared from 1-bromo-4-chlorobenzene. Alternatively, a compound of formula (P55):

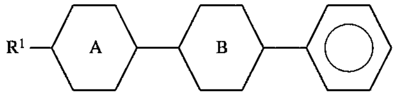
(P55)

is once obtained in the same manner but using phenylmagnesium bromide as a Grignard reagent, from which compound (77) can be prepared in the same manner as in Preparation Example 5.

PREPARATION EXAMPLE 78

Preparation of Compound (78)

Compound (78) can be obtained in the same manner as in Preparation Example 75, except for using a Grignard reagent prepared from 4-bromo-1-trifluoromethoxybenzene.

PREPARATION EXAMPLE 79

Preparation of Compound (79)

Compound (75) prepared in Preparation Example 75 wherein $R^2$ is $OCH_3$ is demethylated according to process A to J to obtain a phenol derivative of formula (P56):

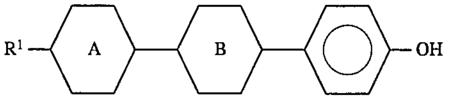

(P56)

which is then led to compound (79) in the same manner as in Preparation Example 3.

PREPARATION EXAMPLE 80

Preparation of Compound (80)

Compound (80) can be prepared in the same manner as in Preparation Example 75, except for replacing the 4-alkyl(or alkoxyl)phenylmagnesium bromide with a Grignard reagent prepared from 1-bromo-3,4-difluorobenzene.

PREPARATION EXAMPLE 81

Preparation of Compound (81)

Compound (81) can be prepared in the same manner as in Preparation Example 75, except for replacing the 4-alkyl(or alkoxyl)phenylmagnesium bromide with a Grignard reagent prepared from 1-bromo-4-chloro-3-fluorobenzene. Alternatively, a Grignard reagent prepared from 1-bromo-3-fluorobenzene may be used to obtain an intermediate compound of formula (P57):

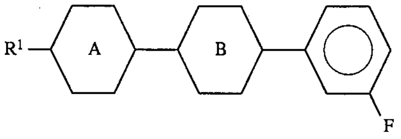

(P57)

which is then chlorinated in the same manner as in Preparation Example 5 to obtain compound (81).

PREPARATION EXAMPLE 82

Preparation of Compound (82)

Compound (82) can be prepared in the same manner as in Preparation Example 75, except for replacing the 4-alkyl(or alkoxyl)phenylmagnesium bromide with a Grignard reagent prepared from 4-bromo-2-fluoro-1-trifluoromethoxybenzene.

PREPARATION EXAMPLE 83

Preparation of Compound (83)

A phenol derivative of formula (P58):

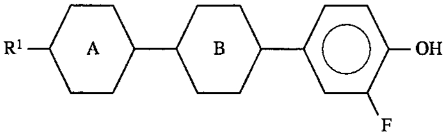

(P58)

is prepared in the same manner as in Preparation Example 79, except for replacing 4-methoxyphenylmagnesium bromide with a Grignard reagent prepared from 4-bromo-2-fluoroanisole. Compound (P58) can be led to compound (83) in the same manner as in Preparation Example 7.

PREPARATION EXAMPLE 84

Preparation of Compound (84)

Compound (84) can be prepared in the same manner as in Preparation Example 75, except for replacing the 4-alkyl(or alkoxyl)phenylmagnesium bromide with a Grignard reagent prepared from 1-bromo-3,4,5-trifluorobenzene.

PREPARATION EXAMPLE 85

Preparation of Compound (85)

Compound (85) can be prepared in the same manner as in Preparation Example 75, except for replacing the 4-alkyl(or alkoxyl)phenylmagnesium bromide with a Grignard reagent prepared from 1-bromo-4-chloro-3,5-difluorobenzene. Alternatively, a Grignard reagent prepared from 1-bromo-3,5-difluorobenzene may be used to obtain an intermediate compound of formula (P59):

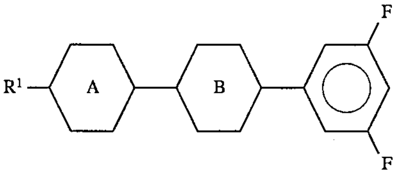

(P59)

which is then chlorinated in the same manner as in Preparation Example 5 to obtain compound (85).

PREPARATION EXAMPLE 86

Preparation of Compound (86)

Compound (86) can be prepared in the same manner as in Preparation Example 83, except for using 4-bromo-2,6-difluoroanisole, which is an intermediate product of Preparation Example 17.

PREPARATION EXAMPLE 87

Preparation of Compound (87)

Compound (P55) is treated in the same manner as in Preparation Example 8 to obtain an acid chloride of formula (P60):

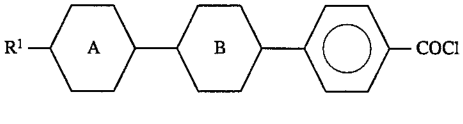

(P60)

The acid chloride (P60) is reacted with aqueous ammonia to obtain an amide derivative of formula (P61):

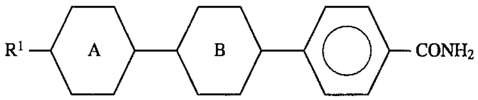

(P61)

which is then dehydrated with thionyl chloride, etc. for cyanogenation to obtain compound (87). Alternatively, compound (P55) is iodinated with iodine-periodic acid to obtain a compound of formula (P62):

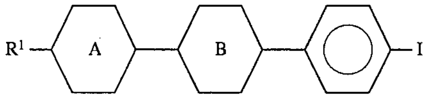

(P62)

which is then reacted with cuprous cyanide to obtain compound (87).

PREPARATION EXAMPLE 88

Preparation of Compound (88)

Compound (88) can be prepared from compound (P57) in the same manner as in Preparation Example 87.

PREPARATION EXAMPLE 89

Preparation of Compound (89)

Compound (89) can be prepared in the same manner as in Preparation Example 87, except for replacing compound (P55) with compound (P59). Alternatively, compound (59) is reacted with an alkyl lithium to obtain a phenyllithium derivative, which is then reacted with carbon dioxide to obtain a benzoic acid derivative of formula (P64):

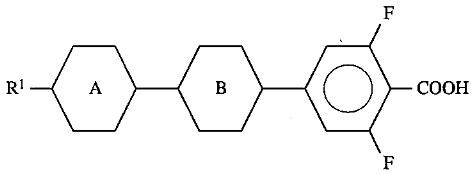

(P46)

Compound (P64) is converted to an acid chloride by using thionyl chloride, etc., which is further reacted in the same manner as in Preparation Example 87 to obtain compound (89).

PREPARATION EXAMPLE 90

Preparation of Compound (90)

Compound (90) can be prepared by reacting a deuterated bicyclohexaneethanal derivative of formula (P65):

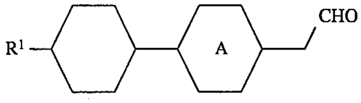

(P65)

with a 4-alkyl(or alkoxyl)phenylmagnesium bromide, and subjecting the product to dehydration and then hydrogenation. Compound (P65) can be obtained by deuterating a 4-(4-substituted cyclohexyl)cyclohexanone, reacting the deuterated compound with a Wittig reagent of formula (IV), if desired again deuterating the product, and again reacting the product with the Wittig reagent of formula (IV).

PREPARATION EXAMPLE 91

Preparation of Compound (91)

Compound (91) can be prepared in the same manner as in Preparation Example 90, except for using 4-fluorophenylmagnesium bromide as a Grignard reagent.

PREPARATION EXAMPLE 92

Preparation of Compound (92)

Compound (92) can be prepared in the same manner as in Preparation Example 90, except for using a Grignard reagent prepared from 1-bromo-4-chlorobenzene. Alternatively, phenylmagnesium bromide may be used as a Grignard reagent to obtain a compound of formula (P66):

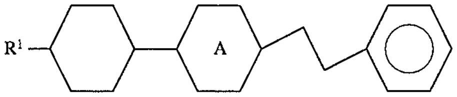

(P66)

which can then be led to compound (92) in the same manner as in Preparation Example 5.

PREPARATION EXAMPLE 93

Preparation of Compound (93)

Compound (93) can be prepared in the same manner as in Preparation Example 90, except for using a Grignard reagent prepared from 4-bromo-1-trifluoromethoxybenzene.

PREPARATION EXAMPLE 94

Preparation of Compound (94)

Compound (90) prepared in Preparation Example 90 wherein $R^2$ is $OCH_3$ is demethylated in the same manner as in Preparation Example 3 to obtain a phenol derivative of formula (P67):

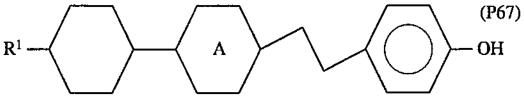

(P67)

which is then led to compound (94) in the same manner as in Preparation Example 3.

PREPARATION EXAMPLE 95

Preparation of Compound (95)

Compound (95) can be prepared in the same manner as in Preparation Example 90, except for using a Grignard reagent prepared from 1-bromo-3,4-difluorobenzene.

PREPARATION EXAMPLE 96

Preparation of Compound (96)

Compound (96) can be prepared in the same manner as in Preparation Example 90, except for using a Grignard reagent prepared from 1-bromo-4-chloro-3-fluorobenzene. Alternatively, a Grignard reagent prepared from 1-bromo-3-fluorobenzene may be used to obtain a compound of formula (P68):

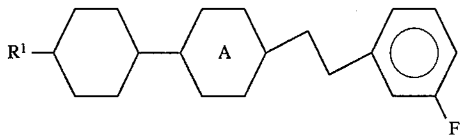

(P68)

which can then be led to compound (96) in the same manner as in Preparation Example 5.

PREPARATION EXAMPLE 97

Preparation of Compound (97)

Compound (97) can be prepared in the same manner as in Preparation Example 90, except for replacing the 4-alkyl(or alkoxyl)phenylmagnesium bromide with a Grignard reagent prepared from 4-bromo-3-fluoro-1-trifluoromethoxybenzene.

PREPARATION EXAMPLE 98

Preparation of Compound (98)

A phenol derivative of formula (P69):

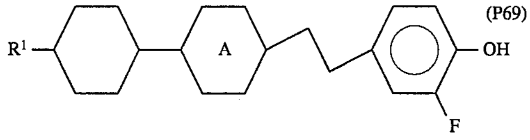

(P69)

is prepared in the same manner as in Preparation Example 94, except for replacing 4-methoxyphenylmagnesium bromide with a Grignard reagent prepared from 4-bromo-2-fluoroanisole. Compound (P69) is led to compound (98) in the same manner as in Preparation Example 7.

PREPARATION EXAMPLE 99

Preparation of Compound (99)

Compound (99) can be prepared in the same manner as in Preparation Example 90, except for replacing the 4-alkyl(or alkoxyl)phenylmagnesium bromide with a Grignard reagent prepared from 1-bromo-3,4,5-trifluorobenzene.

PREPARATION EXAMPLE 100

Preparation of Compound (100)

Compound (100) can be prepared in the same manner as in Preparation Example 90, except for using a Grignard reagent prepared from 1-bromo-4-chloro-3,5-difluorobenzene. Alternatively, a Grignard reagent prepared from 1-bromo-3,5-difluorobenzene may be used to obtain a compound of formula (P70):

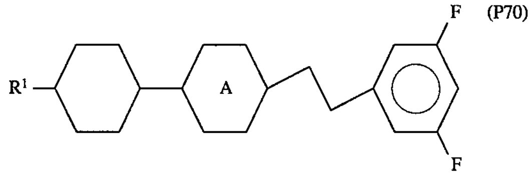

(P70)

which is then chlorinated in the same manner as in Preparation Example 5 to obtain compound (100).

PREPARATION EXAMPLE 101

Preparation of Compound (101)

Compound (101) can be prepared in the same manner as in Preparation Example 98, except for using 4-bromo-2,6-difluoroanisole, which is an intermediate product of Preparation Example 17.

PREPARATION EXAMPLE 102

Preparation of Compound (102)

Compound (P66) is treated in the same manner as in Preparation Example 8 to obtain an acid chloride of formula (P71):

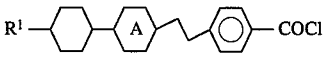

(P71)

The acid chloride (P71) is reacted with aqueous ammonia to obtain an amide derivative of formula (P72):

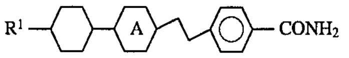

(P72)

which is then dehydrated with thionyl chloride, etc. for cyanogenation to obtain compound (102). Alternatively, the intermediate of formula (P66) is iodinated with iodine-periodic acid to obtain a compound of formula (P73):

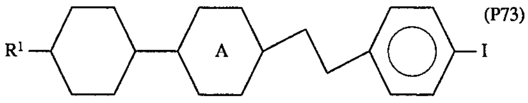

(P73)

which is then reacted with cuprous cyanide to obtain compound (102).

PREPARATION EXAMPLE 103

Preparation of Compound (103)

Compound (103) can be prepared from compound (P68) in the same manner as in Preparation Example 102.

PREPARATION EXAMPLE 104

Preparation of Compound (104)

Compound (104) can be prepared in the same manner as in Preparation Example 102, except for replacing compound (P66) with compound (P70). Alternatively, compound (P70) is treated in the same manner as in Preparation Example 56 to obtain a benzoic acid derivative of formula (P74):

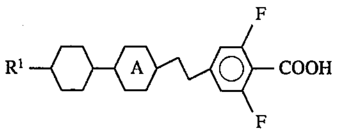

(P74)

which is then converted to an acid chloride with thionyl chloride, etc., and the acid chloride is treated in the same manner as in Preparation Example 102 to obtain compound (104).

PREPARATION EXAMPLES 105 TO 119

Preparation of Compounds (105) to (119)

Compounds (105) to (119) can be prepared in the same manner as in Preparation Examples 60 to 74, respectively, except for replacing the intermediate 4-(4-substituted cyclohexyl)cyclohexanone with a corresponding 4-[2-(4-substituted cyclohexyl)ethyl]cyclohexanone of formula (P75):

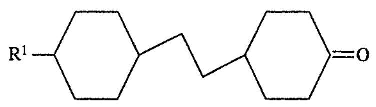

(P75)

PREPARATION EXAMPLE 120

Preparation of Compound (120)

Compound (P10) and 2-methyl-3-butyn-2-ol are reacted in the presence of a catalyst, e.g., palladium chloride, and the reaction product is treated with a base while heating to obtain a phenylacetylene derivative of formula (P76):

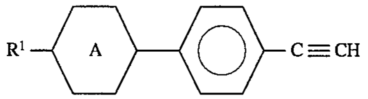

(P76)

This compound (P76) is then reacted with a 4-alkyl(or alkoxyl)phenylmagnesium bromide in the presence of a catalyst to obtain compound (120).

PREPARATION EXAMPLE 121

Preparation of Compound (121)

Compound (121) can be prepared in the same manner as in Preparation Example 120, except for using 4-fluorophenylmagnesium bromide as a Grignard reagent.

PREPARATION EXAMPLE 122

Preparation of Compound (122)

Compound (122) can be prepared in the same manner as in Preparation Example 120, except for using a Grignard reagent prepared from 1-bromo-4-chlorobenzene. Alternatively, phenylmagnesium bromide may be used as a Grignard reagent to obtain a compound of formula (P77):

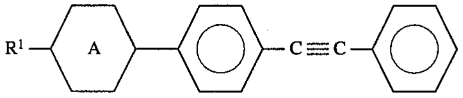

(P77)

Compound (P77) is nitrated and reduced to obtain an aniline derivative, which is then diazotized and decomposed in the same manner as in Preparation Example 5 to obtain compound (122).

PREPARATION EXAMPLE 123

Preparation of Compound (123)

Compound (123) can be prepared in the same manner as in Preparation Example 120, except for using a Grignard reagent prepared from 4- bromo-1-trifluoromethoxybenzene.

PREPARATION EXAMPLE 124

Preparation of Compound (124)

Compound (120) prepared in Preparation Example 120 wherein $R^2$ is $OCH_3$ is demethylated in the same manner as in Preparation Example 3 to obtain a phenol derivative of formula (P78):

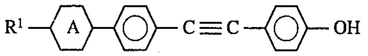

(P78)

which is then led to compound (124) in the same manner as in Preparation Example 3.

PREPARATION EXAMPLE 125

Preparation of Compound (125)

Compound (125) can be prepared in the same manner as in Preparation Example 120, except for using a Grignard reagent prepared from 1-bromo-3,4-difluorobenzene.

PREPARATION EXAMPLE 126

Preparation of Compound (126)

Compound (126) can be prepared in the same manner as in Preparation Example 120, except for using a Grignard reagent prepared from 1-bromo-4-chloro-3-fluorobenzene. Alternatively, a Grignard reagent prepared from 1-bromo-3-fluorobenzene may be used to obtain a compound of formula (P79):

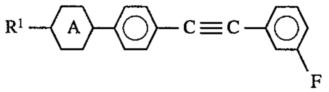

(P79)

which is then chlorinated in the same manner as in Preparation Example 5 to obtain compound (126).

PREPARATION EXAMPLE 127

Preparation of Compound (127)

Compound (127) can be prepared in the same manner as in Preparation Example 120, except for replacing the 4-alkyl(or alkoxyl)phenylmagnesium bromide with a Grignard reagent prepared from 4-bromo-2-fluoro-1-trifluoromethoxybenzene.

PREPARATION EXAMPLE 128

Preparation of Compound (128)

A phenol derivative of formula (P80):

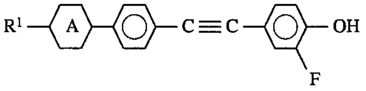

(P80)

is prepared in the same manner as in Preparation Example 124, except for replacing 4-methoxyphenylmagnesium bromide with a Grignard reagent prepared from 4-bromo-2-fluoroanisole. Compound (P80) can be led to compound (128) in the same manner as in Preparation Example 7.

PREPARATION EXAMPLE 129

Preparation of Compound (129)

Compound (129) can be prepared in the same manner as in Preparation Example 120, except for replacing the 4-alkyl(or alkoxyl)phenylmagnesium bromide with a Grignard reagent prepared from 1-bromo-3,4,5-trifluorobenzene.

PREPARATION EXAMPLE 130

Preparation of Compound (130)

Compound (130) can be prepared in the same manner as in Preparation Example 120, except for using a Grignard reagent prepared from 1-bromo-4-chloro-3,5-difluorobenzene. Alternatively, a Grignard reagent prepared from 1-bromo-3,5-difluorobenzene may be used to obtain a compound of formula (P81):

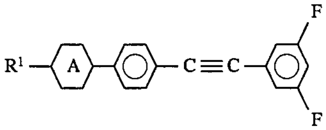

(P81)

which is then chlorinated in the same manner as in Preparation Example 5 to obtain compound (130).

PREPARATION EXAMPLE 131

Preparation of Compound (131)

Compound (131) can be prepared in the same manner as in Preparation Example 128, except for using a Grignard reagent prepared from 4-bromo-2,6-difluoroanisole.

PREPARATION EXAMPLE 132

Preparation of Compound (132)

Compound (P77) is treated in the same manner as in Preparation Example 8 to obtain an acid chloride of formula (P82):

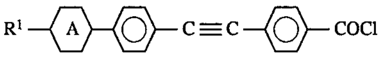

(P82)

The acid chloride (P82) is reacted with aqueous ammonia to obtain an amide derivative of formula (P83):

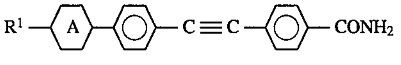

(P83)

which is then dehydrated with thionyl chloride, etc. for cyanogenation to obtain compound (132).

PREPARATION EXAMPLE 133

Preparation of Compound (133)

Compound (133) can be prepared from compound (P79) in the same manner as in Preparation Example 132.

PREPARATION EXAMPLE 134

Preparation of Compound (134)

Compound (134) can be prepared in the same manner as in Preparation Example 132, except for replacing compound (P77) with compound (P81). Alternatively, compound (P81) is treated in the same manner as in Preparation Example 57 to obtain a benzoic acid derivative of formula (P84):

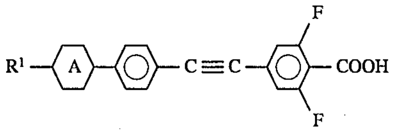

(P84)

which is then led to compound (134) in the same manner as in Preparation Example 57.

PREPARATION EXAMPLE 135

Preparation of Compound (135)

(a) Compound (P10) and a 4-alkyl(or alkoxyl)phenylmagnesium bromide are reacted in the presence of a palladium or nickel catalyst to obtain compound (135).

(b) Compound (P32) and a 4-alkyl(or alkoxyl)phenylmagnesium bromide are reacted, followed by dehydration to obtain a cyclohexene derivative of formula (P85):

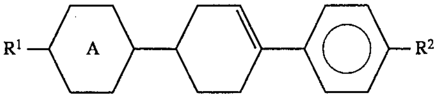

(P85)

Compound (P85) is oxidatively dehydrogenated using chloranil, dichlorodicyanobenzoquinone (hereinafter abbreviated as DDQ), etc. to obtain compound (135).

(c) Compound (135) can also be prepared in accordance with process A to J, except for using a Grignard reagent prepared from a 4'-bromo-4-alkyl(or alkoxyl)biphenyl of formula (P86):

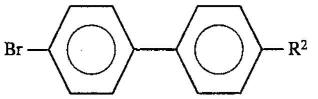

(P86)

Compound (P86) used here can be obtained by direct bromination of a 4-alkyl(or alkoxyl)biphenyl or by reacting a 4-alkyl(or alkoxyl)phenylmagnesium bromide with 4-bromo-1-iodobenzene in the presence of a palladium or nickel catalyst.

PREPARATION EXAMPLE 136

Preparation of Compound (136)

Compound (136) can be prepared in the same manner as in Preparation Example 135-(a) or (b), except for using 4-fluorophenylmagnesium bromide as a Grignard reagent. It can also be prepared in the same manner as in Preparation Example 135-(c), except for using the above Grignard reagent and 4-bromo-4'-fluorobiphenyl prepared from 4-bromo-1-iodobenzene.

PREPARATION EXAMPLE 137

Preparation of Compound (137)

Compound (137) can be prepared in the same manner as in Preparation Example 135-(a) or (b), except for using a Grignard reagent prepared from 1-bromo-4-chlorobenzene. Alternatively, a compound of formula (P87):

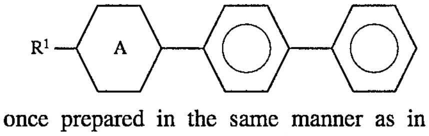

(P87)

is once prepared in the same manner as in Preparation Example 135-(a) or (b) except for using phenylmagnesium bromide, or in the same manner as in Preparation Example 135(c) except for starting with 4-bromobiphenyl. Compound (P87) is nitrated and reduced to obtain an aniline derivative, which is then diazotized and decomposed to obtain compound (137) in the same manner as in Preparation Example 5.

PREPARATION EXAMPLE 138

Preparation of Compound (138)

Compound (138) can be prepared in the same manner as in Preparation Example 135-(a) or (b), except for using a Grignard reagent prepared from 4-bromo-1-trifluoromethoxybenzene. It can also be prepared in the same manner as in Preparation Example 135-(c), except for using the above Grignard reagent and 4'-bromo-4-trifluoromethoxybiphenyl prepared from 4-bromo-1-iodobenzene.

PREPARATION EXAMPLE 139

Preparation of Compound (139)

Compound (135) prepared in Preparation Example 135 wherein $R^2$ is $OCH_3$ is demethylated in the same manner as in Preparation Example 3 to obtain a bisphenol derivative of formula (P88):

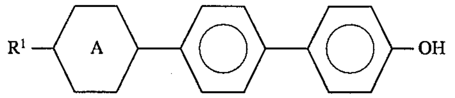

(P88)

which is then led to compound (139) in the same manner as in Preparation Example 3.

PREPARATION EXAMPLE 140

Preparation of Compound (140)

Compound (140) can be prepared in the same manner as in Preparation Example 135-(a) or (b), except for using a Grignard reagent prepared from 1-bromo-3,4-difluorobenzene. It can also be prepared in the same manner as in Preparation Example 135-(c), except for using the above Grignard reagent and 4-bromo-3',4'-difluorobiphenyl prepared from 4-bromo-1-iodobenzene.

PREPARATION EXAMPLE 141

Preparation of Compound (141)

Compound (141) can be prepared in the same manner as in Preparation Example 135-(a) or (b), except for using a Grignard reagent prepared from 1-bromo-4-chloro-3-fluorobenzene. Alternatively, a compound of formula (P89):

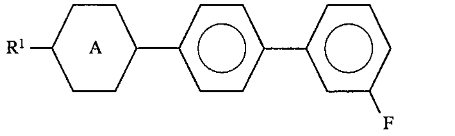

(P89)

is once prepared in the same manner as in Preparation Example 135-(a) or (b) except for using 1-bromo-3-fluorobenzene, and compound (P89) is then chlorinated in the same manner as in Preparation Example 5 to obtain compound (141).

Compound (P89) can also be obtained from 4-bromo-3'-fluorobiphenyl according to Preparation Example 135-(c).

PREPARATION EXAMPLE 142

Preparation of Compound (142)

Compound (142) can be prepared in the same manner as in Preparation Example 135-(a) or (b), except for replacing the 4-alkyl(or alkoxyl)phenylmagnesium bromide with a Grignard reagent prepared from 4-bromo-2-fluoro-1-trifluoromethoxybenzene. It can also be prepared in the same manner as in Preparation Example 135-(c), except for using the above Grignard reagent and 4'-bromo-3-fluoro-4-trifluoromethoxybiphenyl prepared from 4-bromo-1-iodobenzene.

PREPARATION EXAMPLE 143

Preparation of Compound (143)

An intermediate compound of formula (P90):

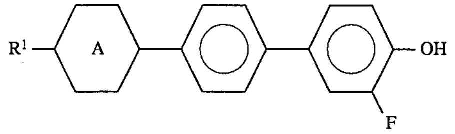

(P90)

is prepared in the same manner as in Preparation Example 139-(a) or (b), except for replacing 4-methoxyphenylmagnesium bromide with a Grignard reagent prepared from 4-bromo-2-fluoroanisole, and compound (P90) is then led to compound (143) in the same manner as in Preparation Example 7.

Compound (90) may also be obtained by reacting the above Grignard reagent with 4'-bromo-3-fluoro-4-methoxybiphenyl prepared from 4-bromo-1-iodobenzene, followed by demethylation in accordance with Preparation Example 135-(c).

PREPARATION EXAMPLE 144

Preparation of Compound (144)

Compound (144) can be prepared in the same manner as in Preparation Example 135-(a) or (b), except for replacing the 4-alkyl(or alkoxyl)phenylmagnesium with a Grignard reagent prepared from 1-bromo-3,4,5-trifluorobenzene. It can also be prepared in the same manner as in Preparation Example 135-(c), except for using the above Grignard reagent and 4'-bromo-3,4,5-trifluorobiphenyl prepared from 4-bromo-1-iodobenzene.

PREPARATION EXAMPLE 145

Preparation of Compound (145)

Compound (145) can be prepared in the same manner as in Preparation Example 135-(a) or (b), except for using a Grignard reagent prepared from 1-bromo-4-chloro-3,5-difluorobenzene. It can also be prepared in the same manner as in Preparation Example 135-(c), except for using the above Grignard reagent and 4'-bromo-4-chloro-3,5-difluorobiphenyl prepared from 4-bromo-1-iodobenzene. Alternatively, compound (145) can be prepared by obtaining a compound of formula (P91):

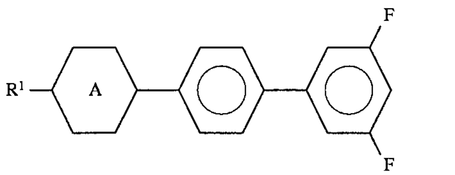

(P91)

in the same manner as in (a) or (b) except for using a Grignard reagent prepared from 1-bromo-3,5-difluorobenzene, and then chlorinating compound (P91) in the same manner as in Preparation Example 5. Compound (P91) may be prepared by using the above Grignard reagent and 4-bromo-3',5'-difluorobiphenyl prepared from 4-bromo-1-iodobenzene in accordance with (c).

PREPARATION EXAMPLE 146

Preparation of Compound (146)

Compound (146) can be prepared in the same manner as in Preparation Example 143-(a) or (b), except for using a Grignard reagent prepared from 4-bromo-2,6-difluoroanisole, the intermediate compound of Preparation Example 17.

PREPARATION EXAMPLE 147

Preparation of Compound (147)

Compound (P87) is treated in the same manner as in Preparation Example 8 to obtain an acid chloride of formula (P92):

(P92)

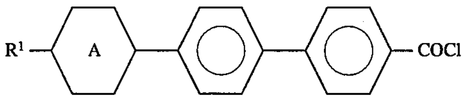

The acid chloride (P92) is reacted with aqueous ammonia to obtain an amido derivative of formula (P93):

(P93)

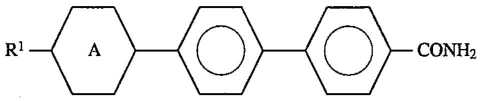

which is then dehydrated with thionyl chloride, etc. for cyanogenation to obtain compound (147).

PREPARATION EXAMPLE 148

Preparation of Compound (148)

Compound (148) can be prepared in the same manner as in Preparation Example 147, except for starting with compound (P89).

PREPARATION EXAMPLE 149

Preparation of Compound (149)

Compound (149) can be prepared in the same manner as in Preparation Example 147, except for replacing compound (P87) with compound (P91). Alternatively, compound (P91) is treated in the same manner as in Preparation Example 57 to obtain a benzoic acid derivative of formula (P94):

(P94)

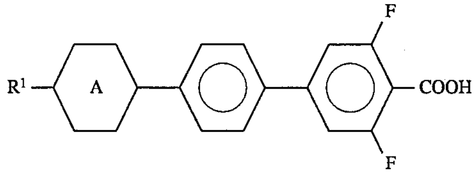

which is then led to compound (149) in the same manner as in Preparation Example 57.

PREPARATION EXAMPLE 150

Preparation of Compound (150)

Compound (150) can be prepared in the same manner as in Preparation Example 120, except for replacing compound (P10) with compound (P24).

PREPARATION EXAMPLES 151 TO 164

Preparation of Compounds (151) to (164)

Compounds (151) to (164) can be prepared in the same manner as in Preparation Examples 121 to 134, respectively, except for replacing compound (P10) with corresponding compound (P24).

PREPARATION EXAMPLE 165

Preparation of Compound (165)

Compound (165) can be prepared in the same manner as in Preparation Example 135-(a), except for replacing compound (P10) with compound (P24). It can also be prepared in the same manner as in Preparation Example 135-(b), except for replacing compound (P32) with a compound of formula (P95):

(P95)

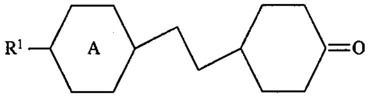

which is obtained by hydrogenation of compound (P17).

PREPARATION EXAMPLES 166 TO 179

Preparation of Compounds (166) to (179)

Compounds (166) to (179) can be prepared in the same manner as in Preparation Examples 136 to 149, respectively, except for replacing compound (P10) with corresponding compound (P24) or replacing compound (P32) with corresponding compound (P95).

PREPARATION EXAMPLE 180

Preparation of Compound (180)

Compound (180) can be prepared in the same manner as in Preparation Example 120, except for replacing compound (P10) with a compound of formula (P96):

(P96)

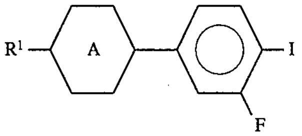

Compound (P96) is obtained either by direct iodination of compound (P5) with iodine-periodic acid or by nitrating compound (P5) followed by reduction to prepare an aniline derivative of formula (P97):

(P97)

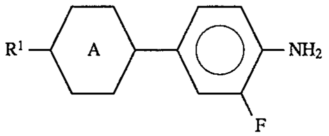

and decomposing its diazonium salt with potassium iodide, etc.

PREPARATION EXAMPLES 181 TO 194

Preparation of Compounds (181) to (194)

Compounds (181) to (194) can be prepared in the same manner as in Preparation Examples 121 to 134, respectively, except for replacing compound (P10) with corresponding compound (P96).

PREPARATION EXAMPLE 195

Preparation of Compound (195)

Compound (195) can be prepared in the same manner as in Preparation Example 135, except for replacing compound (P10) with compound (P96).

PREPARATION EXAMPLES 196 TO 209

Preparation of Compounds (196) to (209)

Compounds (196) to (209) can be prepared in the same manner as in Preparation Examples 136 to 149, respectively, except for replacing compound (P10) with compound (P96).

PREPARATION EXAMPLE 210

Preparation of Compound (210)

Compound (210) can be prepared in the same manner as in Preparation Example 120, except for replacing compound (P10) with a compound of formula (P98):

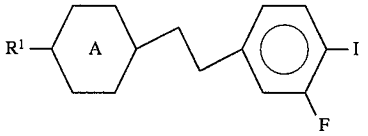

(P98)

Compound (P98) is obtained either by direct iodination of compound (P18) with iodine-periodic acid or by nitrating compound (P18) followed by reduction to prepare an aniline derivative of formula (P99):

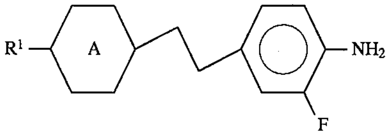

(P99)

and decomposing its diazonium salt with copper iodide, etc.

PREPARATION EXAMPLES 211 TO 224

Preparation of Compounds (211) to (224)

Compounds (211) to (224) can be prepared in the same manner as in Preparation Examples 121 to 134, respectively, except for replacing compound (P10) with corresponding compound (P98)

PREPARATION EXAMPLE 225

Preparation of Compound (225)

Compound (225) can be prepared in the same manner as in Example 135-(a), except for replacing compound (P10) with compound (P98).

PREPARATION EXAMPLES 226 TO 239

Preparation of Compounds (226) to (239)

Compounds (226) to (239) can be prepared in the same manner as in Preparation Examples 136 to 149, respectively, except for replacing compound (P10) with corresponding compound (P98).

PREPARATION EXAMPLE 240

Preparation of Compound (240)

Compound (P32) is reacted with a Wittig reagent of formula (IV), and the product is isomerized to a trans-form in the presence of a base to obtain a bicyclohexanecarbaldehyde derivative of formula (P100):

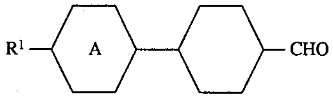

(P100)

Compound (P100) is oxidized and then reacted thionyl chloride to obtain an acid chloride of formula (P101):

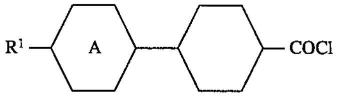

(P101)

Compound (P101) is then reacted with a 4-alkyl(or alkoxyl)phenol of formula (P102):

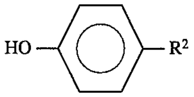

(P102)

in the presence of a base to obtain compound (240.

PREPARATION EXAMPLE 241

Preparation of Compound (241)

Compound (241) can be prepared in the same manner as in Preparation Example 240, except for replacing compound (P102) with 4-fluorophenol.

PREPARATION EXAMPLE 242

Preparation of Compound (242)

Compound (242) can be prepared in the same manner as in Preparation Example 240, except for replacing compound (P102) with 4-chlorophenol.

PREPARATION EXAMPLE 243

Preparation of Compound (243)

Compound (243) can be prepared in the same manner as in Preparation Example 240, except for replacing compound (P102) with 4-trifluoromethoxyphenol. The 4-trifluoromethoxyphenol can be obtained by acetylating 4-trifluoromethoxybenzene with acetyl chloride in the presence of a Lewis acid, e.g., aluminum chloride, oxidizing the acetylated compound with hydrogen peroxide in formic acid, followed by hydrolysis. 4-Trifluoromethoxyphenol may be prepared by reacting a Grignard reagent prepared from 4-bromo-1-trifluoromethoxybenzene with t-butyl hydroperoxide or reacting the Grignard reagent with boric acid and oxidizing the ester with hydrogen peroxide in a basic condition. It is also obtainable by nitrating (trifluoromethoxy)benzene, reducing the product to 4-trifluoromethoxyaniline, converting it to a diazonium salt, and decomposing the diazonium salt in sulfuric acid.

PREPARATION EXAMPLE 244

Preparation of Compound (244)

Compound (244) can be prepared in the same manner as in Preparation Example 240, except for replacing compound (P102) with 4-difluoromethoxyphenol. The 4-difluoromethoxyphenol can be obtained by converting hydroquinone monobenzyl ether to a formic ester, fluorinating the ester with DAST, and reductively debenzylating the product. It may also be obtained by nitrating(difluoromethoxy)benzene, reducing the nitro-compound to 4-difluoromethoxyaniline, converting it to a diazonium salt, and decomposing the diazonium salt in sulfuric acid. It is also obtainable by converting 4-bromophenol to a formic ester, fluorinating the ester with DAST to obtain 4-bromo-1-difluoromethoxybenzene, preparing a Grignard reagent therefrom, and reacting the Grignard reagent with t-butyl hydroperoxide, or reacting the Grignard reagent with boric acid and oxidizing the boric ester with hydrogen peroxide in a basic condition.

PREPARATION EXAMPLE 245

Preparation of Compound (245)

Compound (245) can be prepared in the same manner as in Preparation Example 240, except for replacing compound (P102) with 3,4-difluorophenol.

PREPARATION EXAMPLE 246

Preparation of Compound (246)

Compound (246) can be prepared in the same manner as in Preparation Example 240, except for replacing compound (P102) with 3-fluoro-4-chlorophenol.

PREPARATION EXAMPLE 247

Preparation of Compound (247)

Compound (247) can be prepared in the same manner as in Preparation Example 243, except for replacing 4-trifluoromethoxyphenol with 3-fluoro-4-trifluoromethoxyphenol. The 3-fluoro-4-trifluoromethoxyphenol can be obtained by acetylating 3-fluoro-4-trifluoromethoxybenzene with acetyl chloride in the presence of a Lewis acid, e.g., aluminum chloride, oxidizing the acetylated compound with hydrogen peroxide in formic acid, followed by hydrolysis. It can also be obtained by reacting a Grignard reagent prepared from 4-bromo-1-trifluoromethoxybenzene with t-butyl hydroperoxide or reacting the Grignard reagent with boric acid, and oxidizing the boric ester with hydrogen peroxide in a basic condition. It is also obtainable by nitrating 3-fluoro-4-trifluoromethoxyphenol or 3-fluoro-4-trifluoromethoxybenzene, reducing the nitro-compound to 4-trifluoromethoxybenzene, reducing the nitro-compound to 4-trifluoromethoxyaniline, converting it to a diazonium salt, and decomposing the diazonium salt in sulfuric acid.

PREPARATION EXAMPLE 248

Preparation of Compound (248)

Compound (248) can be prepared in the same manner as in Preparation Example 244, except for replacing 4-difluoromethoxyphenol with 3-fluoro-4-difluoromethoxyphenol. The 3-fluoro-4-difluoromethoxyphenol can be prepared by converting 2-fluoro-4-benzyloxyphenol to a formic ester, fluorinating the ester with DAST, and reductively debenzylating the product. It may also be obtained by nitrating 3-fluoro-4-difluoromethoxybenzene, reducing the product to 3-fluoro-4-trifluoromethoxyaniline, converting it to a diazonium salt, and decomposing the diazonium salt in sulfuric acid. It is also obtainable by brominating 3-fluoro-4-difluoromethoxybenzene, preparing a Grignard reagent from the resulting 4-bromo-2-fluoro-1-difluoromethoxybenzene, reacting the Grignard reagent with t-butyl hydroperoxide or reacting the Grignard reagent with boric acid, and oxidizing the boric ester with hydrogen peroxide under a basic condition.

PREPARATION EXAMPLE 249

Preparation of Compound (249)

Compound (249) can be prepared in the same manner as in Preparation Example 240, except for replacing compound (P102) with 2,4,5-trifluorophenol. The 3,4,5-trifluorophenol can be prepared by decomposition of a diazonium salt of 3,4,5-trifluoroaniline in sulfuric acid. It is also obtained by reacting a Grignard reagent prepared from 1-bromo-3,4,5-trifluorobenzene with t-butyl peroxide or converting the same Grignard reagent to a boric ester, and oxidizing the ester with hydrogen peroxide under a basic condition.

PREPARATION EXAMPLE 250

Preparation of Compound (250)

Compound (250) can be prepared in the same manner as in Preparation Example 240, except for replacing compound (P102) with 4-chloro-3,5-difluorophenol. The 4-chloro-3,5-difluorophenol can be prepared by reacting a Grignard reagent prepared from 1-bromo-4-chloro-3,5-difluorobenzene with t-butyl hydroperoxide or converting the same Grignard reagent to a boric ester, and oxidizing the product with hydrogen peroxide under a basic condition. It is also prepared by nitrating 2-chloro-1,3-difluorobenzene (obtainable by decomposing a diazonium salt of 2,6-difluoroaniline in the presence of cuprous chloride or in hydrochloric acid), reducing the nitro-compound to obtain 4-chloro-3,5-difluoroaniline, and decomposing its diazonium salt in sulfuric acid.

PREPARATION EXAMPLE 251

Preparation of Compound (251)

Compound (251) can be prepared in the same manner as in Preparation Example 248, except for replacing 3-fluoro-4-difluoromethoxyphenol with 3,5-difluoro-4-difluoromethoxyphenol. The 3,5-difluoro-4-difluoromethoxyphenol can be obtained by converting 2,6-difluorophenol to a formic ester, fluorinating the ester with DAST, brominating the resulting 2,6-difluoro-1-difluoromethoxybenzene, preparing a Grignard reagent from the resulting 4-bromo-2,6-difluoro-1-difluoromethoxybenzene, and reacting the Grignard reagent with t-butyl hydroperoxide or converting the Grignard reagent to a boric ester, and oxidizing the ester with hydrogen peroxide under a basic condition. Alternatively, 3,5-difluoro-4-difluoromethoxyphenol can also be obtained by nitrating 3,5-difluoro-4-difluoromethoxybenzene, reducing the product to 3-fluoro-4-trifluoromethoxyaniline, and decomposing a diazonium salt of the 3-fluoro-4-trifluoromethoxyaniline in sulfuric acid.

PREPARATION EXAMPLE 252

Preparation of Compound (252)

Compound (252) can be prepared in the same manner as in Preparation Example 240, except for replacing compound (P102) with 4-cyanophenol.

PREPARATION EXAMPLE 253

Preparation of Compound (253)

Compound (253) can be prepared in the same manner as in Preparation Example 240, except for replacing compound (P102) with 3-fluoro-4-cyanophenol.

PREPARATION EXAMPLE 254

Preparation of Compound (254)

Compound (254) can be prepared in the same manner as in Preparation Example 240, except for replacing compound (P102) with 3,5-difluoro-4-cyanophenol. The 3,5-difluoro-4-cyanophenol can be obtained by nitrating 2,6-difluoroaniline, diazotizing the resulting 4-nitro-2,6-difluoroaniline, decomposing the diazonium salt in the presence of a cuprous cyanide to obtain 4-nitro-2,6-difluoro-1-cyanobenzene, reducing the product to obtain 4-cyano-3,5-difluoroaniline, and decomposing its diazonium salt in sulfuric acid.

PREPARATION EXAMPLE 255

Preparation of Compound (255)

Compound (255) can be prepared in the same manner as in Preparation Example 240, except by using an acid chloride of formula (P103):

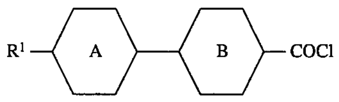

(P103)

Compound (P103) can be obtained by reacting compound (P51) with a Wittig reagent of formula (IV), isomerizing the product to a trans-form, and, if desired, further deuterating the product.

PREPARATION EXAMPLES 256 TO 269

Preparation of Compounds (256) to (269)

Compounds (256) to (269) can be prepared in the same manner as in Preparation Examples 241 to 254, respectively, except for using a corresponding compound (P103) as an acid chloride.

PREPARATION EXAMPLE 270

Preparation of Compound (270)

Compound (270) can be prepared in the same manner as in Preparation Example 240, except for using an acid chloride of formula (P104):

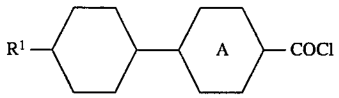

(P104)

Compound (P104) is obtained from a deuterated 4-(4-substituted cyclohexyl)cyclohexanone (obtainable by processes K, N or O) in the same manner as in Preparation Example 255.

PREPARATION EXAMPLES 271 TO 284

Preparation of Compounds (271) to (284)

Compounds (271) to (284) can be prepared in the same manner as in Preparation Examples 241 to 254, respectively, except for using a corresponding compound (P104) as an acid chloride.

PREPARATION EXAMPLE 285

Preparation of Compound (285)

Compound (285) can be prepared in the same manner as in Preparation Example 240, except for using an acid chloride of formula (P105):

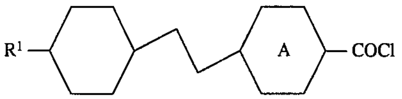

(P105)

Compound (P105) is obtained from a deuterated cyclohexanone derivative of formula (P106):

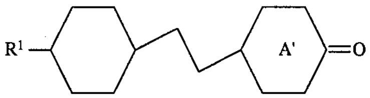

(P106)

in accordance with Preparation Example 255. Compound (P106) is obtained by deuterating compound (P75). Compound (P106) is also obtainable by reacting a Grignard reagent of formula (P107):

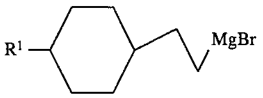

(P107)

which is prepared from a 4-substituted cyclohexaneethanal by reduction and bromination, with a monoethyleneacetal of deuterated cyclohexane-1,4-dione, followed by dehydration and hydrogenation

PREPARATION EXAMPLES 286 TO 299

Preparation of Compounds (286) to (299)

Compounds (286) to (299) can be prepared in the same manner as in Preparation Example 241 to 254, respectively, except for using a corresponding acid chloride of formula (P105).

PREPARATION EXAMPLE 300

Preparation of Compound (300)

Compound (300) can be prepared by reacting a 4-substituted cyclohexanecarboxylic acid chloride of formula (P108):

(P108)

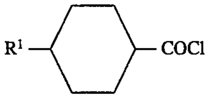

with a 4'-substituted-bicyclohexan-4-ol of formula (P109):

(P109)

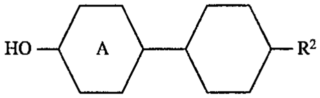

in the presence of a basic catalyst. Compound (P109) is obtainable by reducing a deuterated 4-(4-substituted cyclohexyl)cyclohexanone (obtainable by process K, N or O) using lithium aluminum hydride (or a deuterated compound thereof), sodium borohydride, etc.

PREPARATION EXAMPLE 301

Preparation of Compound (301)

Compound (301) can be prepared in the same manner as in Preparation Example 300, except for replacing compound (P108) with a deuterated 4-substituted-cyclohexanecarboxylic acid chloride of formula (P110):

(P110)

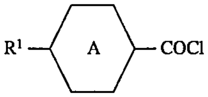

Compound (P110) can be prepared by deuteration of compound (P108). It can also be prepared from a compound of formula (P111):

(P111)

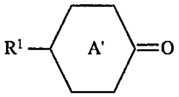

which is obtained by deuteration of a 4-substituted cyclohexanone, in the same manner as in Preparation Example 255. Compound (P111) can be obtained by deuterating cyclohexane-1,4-dione monoethyleneacetal and reacting the deuterated product with a Wittig reagent, followed by hydrogenation and decomposition of the acetal moiety. Alternatively, the deuterated product may be reacted with a Grignard reagent, followed by dehydration, hydrogenation, and decomposition of the acetal moiety. Compound (P111) can also be obtained by deuterating cyclohexane-1,4-dione and then introducing a monoethyleneacetal moiety, which is then treated in the same manner as described above.

PREPARATION EXAMPLE 302—PREPARATION OF COMPOUND (302)

Compound (302) can be prepared in the same manner as in Preparation Example 300, except for replacing compound (P109) with a compound of formula (P112):

(P112)

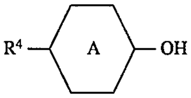

Compound (P112) can be obtained by reducing compound (P111) wherein $R^1$ is an alkyl or alkoxyl group with lithium aluminum hydride (or a deuterated compound thereof), sodium borohydride, etc.

PREPARATION EXAMPLE 303—PREPARATION OF COMPOUND (303)

Compound (303) can be prepared in the same manner as in Preparation Example 300, except for using compound (P110) and compound (P112).

PREPARATION EXAMPLE 304—PREPARATION OF COMPOUND (304)

A Grignard reagent prepared from a bromobenzene derivative of formula (P113):

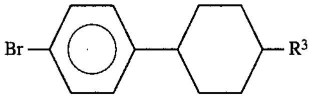

(P113)

is reacted with a fluoroiodobenzene derivative of formula (P96) in the presence of a palladium or nickel catalyst to obtain compound (304). Compound (304) can also be prepared by reacting a Grignard reagent prepared from a compound of formula (P114):

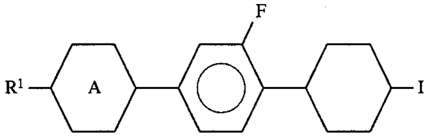

(P114)

with a 4-substituted cyclohexanone, followed by dehydration and hydrogenation.

PREPARATION EXAMPLE 305—PREPARATION OF COMPOUND (305)

Compound (305) can be prepared in the same manner as in Preparation Example 60, except for replacing the deuterated 4-(4-substituted cyclohexyl)cyclohexanone with a deuterated 4"-substituted-tercyclohexan-4-one of formula (P115):

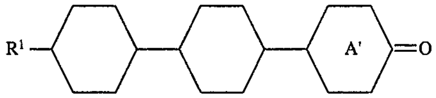

(P115)

Compound (P115) is obtained by hydrogenating a phenol derivative of formula (P116):

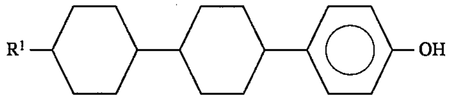

(P116)

and deuterating the resulting 4"-substituted tercyclohexan-4-one. It is also obtained by reacting a Grignard reagent prepared from a brominated bicyclohexane derivative of formula (P117):

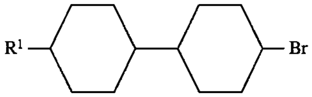

(P117)

with deuterated cyclohexane-1,4-dione monoethyleneacetal, followed by dehydration, hydrogenation, and removal of the acetal moiety.

PREPARATION EXAMPLES 306 TO 319—PREPARATION OF COMPOUNDS (306) TO (319)

Compounds (306) to (319) can be prepared in the same manner as in Preparation Examples 61 to 74, respectively, except for using a corresponding compound (P115).

PREPARATION EXAMPLE 320—PREPARATION OF COMPOUND (320)

Compound (320) can be prepared in the same manner as in Preparation Example 135, except for replacing compound (P10) with compound (P49).

PREPARATION EXAMPLES 321 TO 334—PREPARATION OF COMPOUNDS (321) TO (334)

Compounds (321) to (334) can be prepared in the same manner as in Preparation Examples 136 to 149, respectively, except for using a corresponding compound (P49).

PREPARATION EXAMPLE 335—PREPARATION OF COMPOUND (335)

Compound (335) can be prepared in the same manner as in Preparation Example 135, except for replacing compound (P10) with compound (P40).

PREPARATION EXAMPLES 336 TO 349—PREPARATION OF COMPOUNDS (336) TO (349)

Compounds (336) to (349) can be prepared in the same manner as in Preparation Examples 136 to 149, respectively, except for using a corresponding compound (P40).

PREPARATION EXAMPLE 350—Preparation of Compound (350)

Compound (350) can be prepared in the same manner as in Preparation Example 135, except for replacing compound (P10) with compound (P62).

PREPARATION EXAMPLES 351 TO 364—

Preparation of Compounds (351) to (364)

Compounds (351) to (364) can be prepared in the same manner as in Preparation Examples 136 to 149, respectively, except for using a corresponding compound (P62).

As hereinabove illustrated, while the deuterated liquid crystal compounds which can be used in the present invention take on an infinite variety of skeleton structure and substituents, those having one or two saturated hydrocarbon groups substituted with deuterium atom (D) and, as a whole, having 2 to 4 cyclic structures, inclusive of the deuterated saturated hydrocarbon rings, are preferred. Inter alia, compounds represented by formulae (I-A) to (I-L) shown below are preferred.

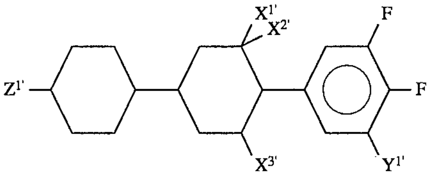
(I-A)

wherein $Z^1$ represents a straight-chain alkyl group having from 1 to 20 carbon atoms; $X^{1'}$, $X^{2'}$, and $X^{3'}$ each represent a hydrogen atom (H) or a deuterium atom (D), provided that at least one of them is a deuterium atom (D); and $Y_1$ represents a hydrogen atom or a fluorine atom.

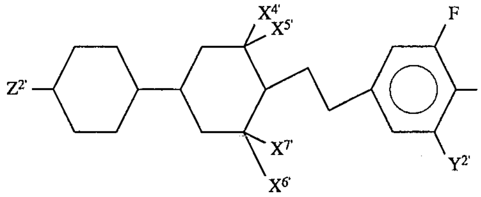
(I-B)

wherein $Z^{2'}$ represents a straight-chain alkyl group having from 1 to 20 carbon atoms; $X^{4'}$, $X^{5'}$, $X^{6'}$, and $X^{7'}$ each represent a hydrogen atom (H) or a deuterium atom (D), provided that at least one of them is a deuterium atom (D); and $Y^{2'}$ represents a hydrogen atom or a fluorine atom.

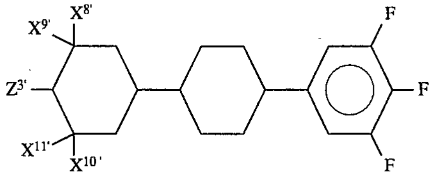
(I-C)

wherein $Z^{3'}$ represents an alkyl or alkenyl group having from 1 to 20 carbon atoms; and $X^{8'}$, $X^{9'}$, $X^{10'}$, and $X^{11'}$ each represent a hydrogen atom (H) or a deuterium atom (D), provided that at least one of them is a deuterium atom (D).

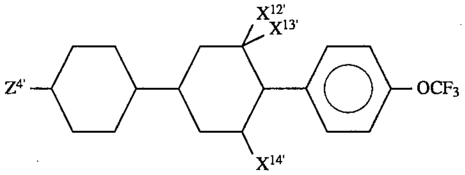
(I-D)

wherein $Z^{4'}$ represents a straight-chain alkyl group having from 1 to 20 carbon atoms; and $X^{12'}$, $X^{13'}$, and $X^{14'}$ each represent a hydrogen atom (H) or a deuterium atom (D), provided that at least one of them is a deuterium atom (D).

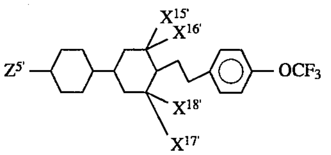
(I-E)

wherein $Z^{5'}$ represents an alkyl group having from 1 to 20 carbon atoms; and $X^{15'}$, $X^{16'}$, $X^{17'}$, and $X^{18'}$ each represent a hydrogen atom (H) or a deuterium atom (D), provided that at least one of them is a deuterium atom (D).

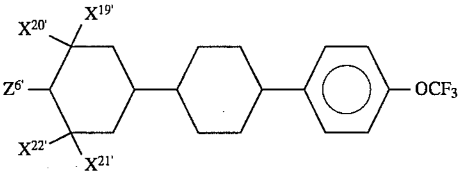
(I-F)

wherein $Z^{6'}$ represents a straight-chain alkyl or alkenyl group having from 1 to 20 carbon atoms; and $X^{19'}$, $X^{20'}$, $X^{21'}$, and $X^{22'}$ each represent a hydrogen atom (H) or a deuterium atom (D), provided that at least one of them is a deuterium atom (D).

(I-G)

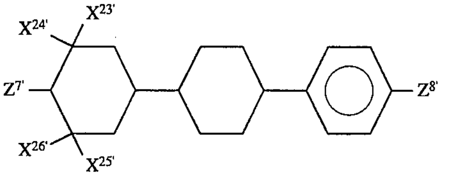

wherein $Z^{7'}$ represents an alkyl or alkenyl group having from 1 to 20 carbon atoms; $Z^{8'}$ represents an alkyl group having from 1 to 20 carbon atoms; and $X^{23'}$, $X^{24'}$, $X^{25'}$, and $X^{26'}$ each represent a hydrogen atom (H) or a deuterium atom (D), provided that at least one of them is a deuterium atom (D).

(I-H)

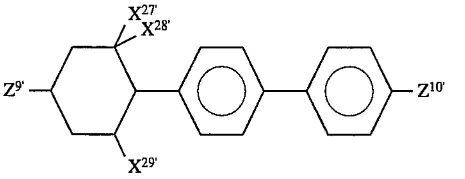

wherein $Z^{9'}$ represents an alkyl group having from 1 to 20 carbon atoms; $Z^{10'}$ represents an alkyl group having from 1 to 20 carbon atoms; and $X^{27'}$, $X^{28'}$, and $X^{29'}$ each represent a hydrogen atom (H) or a deuterium atom (D), provided that at least one of them is a deuterium atom (D).

(I-I)

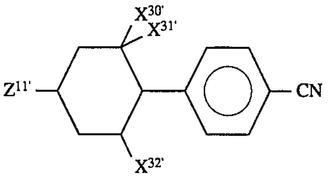

wherein $Z^{11'}$ represents an alkyl group having from 1 to 20 carbon atoms or $Z^{12'}$—O—$(CH_2)_m$—, wherein $Z^{12'}$ represents an alkyl group having from 1 to 10 carbon atoms, and n represents an integer of from 2 to 7; and $X^{30'}$, $X^{31'}$, and $X^{32'}$ each represent a hydrogen atom (H) or a deuterium atom (D), provided that at least one of them is a deuterium atom (D).

(I-J)

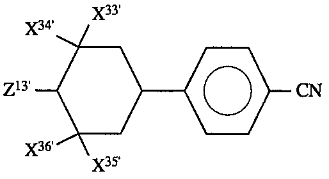

wherein $Z^{13'}$ represents an alkyl group having from 1 to 20 carbon atoms; and $X^{33'}$, $X^{34'}$, $X^{35'}$, and $X^{36'}$ each represent a hydrogen atom (H) or a deuterium atom (D), provided that at least one of them is a deuterium atom (D).

(I-K)

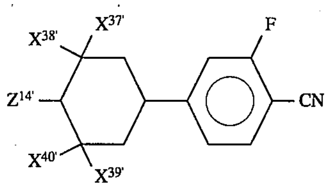

wherein $Z^{14'}$ represents an alkenyl group having from 2 to 18 carbon atoms; and $X^{37'}$, $X^{38'}$, $X^{39'}$, and $X^{40'}$ each represent a hydrogen atom (H) or a deuterium atom (D), provided that at least one of them is a deuterium atom (D).

(I-L)

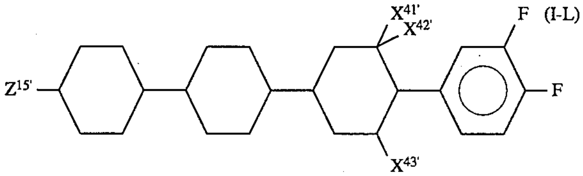

wherein $Z^{15'}$ represents an alkyl group having from 1 to 15 carbon atoms; and $X^{41'}$, $X^{42'}$, and $X^{43'}$ each represent a hydrogen atom (H) or a deuterium atom (D), provided that at least one of them is a deuterium atom (D).

Specific examples of the above-described deuterated liquid crystal compounds of formula (I) are shown in Tables 1 to 3 together with their phase transition temperatures. In the Tables, Cr, Sm, N, and I represent a crystal phase, a smectic phase, a nematic phase, and an isotropic liquid phase, respectively. In the column "Phase Transition Temperature", the parentheses indicate that the phase is monotropic, and the numeral between two phases is the transition temperature from the left phase to the right one. For example, "C 42 N 46 I" means that the transition temperature from a crystal phase to a nematic phase is 42° C. and that from a nematic phase to an isotropic liquid phase is 46° C.

TABLE 1

| Compound No. | Structural Formula | Phase Transition Temperature (°C.) |
|---|---|---|
| 1 | 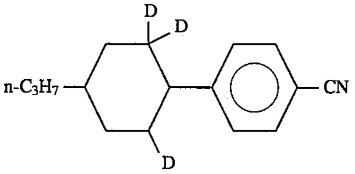 | C42 N46 I |

TABLE 1-continued
| Compound No. | Structural Formula | Phase Transition Temperature (°C.) |
|---|---|---|
| 2 | 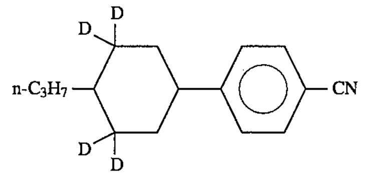 | C40 N45 I |
| 3 | 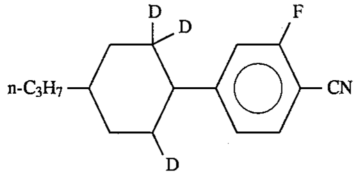 | C9 (N5) I |
| 4 | 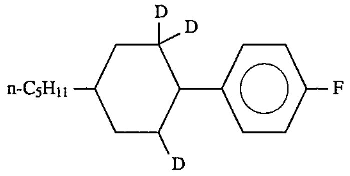 | C29 (N-24) I |
| 5 | 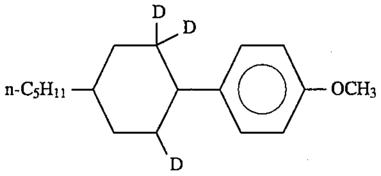 | C37 N30 I |
| 6 | 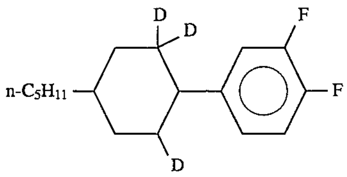 | C-2 (N-30) I |
| 7 | 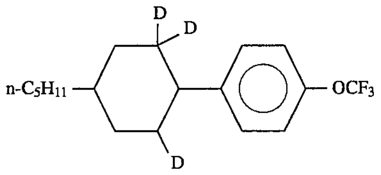 | C10 I |
| 8 | 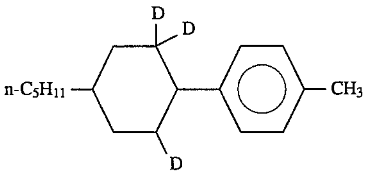 | C19 (N-3) I |
| 9 | 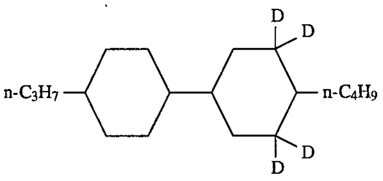 | C-11 Sm92 I |

TABLE 1-continued
| Compound No. | Structural Formula | Phase Transition Temperature (°C.) |
|---|---|---|
| 10 | 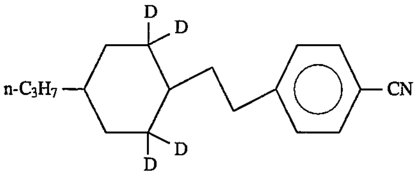 | C32 N44 I |
TABLE 2
| Compound No. | Structural Formula | Phase Transition Temperature (°C.) |
|---|---|---|
| 11 | 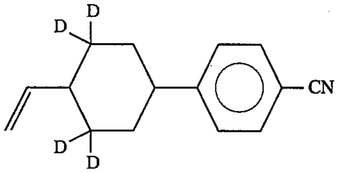 | C52 (N29) I |
| 12 | 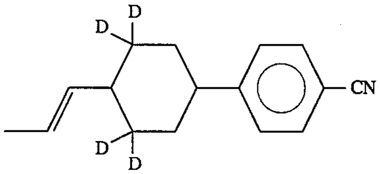 | C62 N73 I |
| 13 | 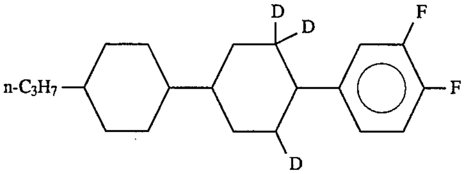 | C42 N119 I |
| 14 | 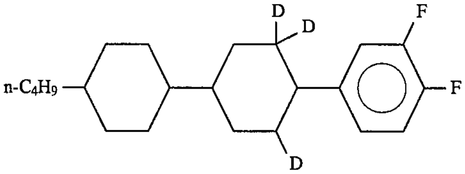 | C44 N120 I |
| 15 | 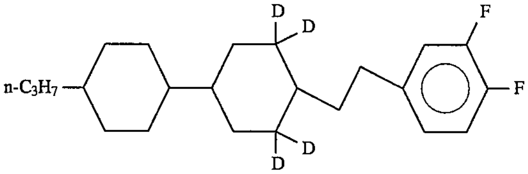 | C12 Sm49 N118 I |
| 16 | 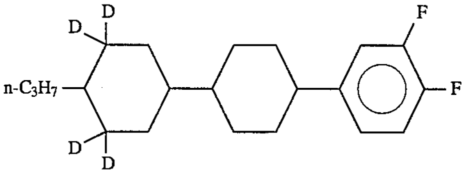 | C41 N122 I |

TABLE 2-continued
| Compound No. | Structural Formula | Phase Transition Temperature (°C.) |
|---|---|---|
| 17 | 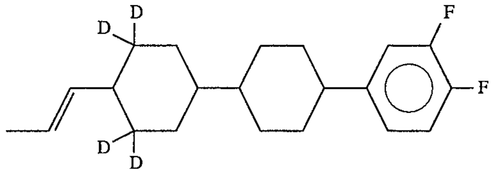 | C99 N193 I |
| 18 | 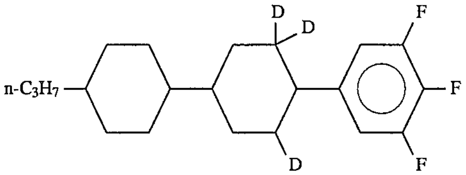 | C64 N94 I |
| 19 | 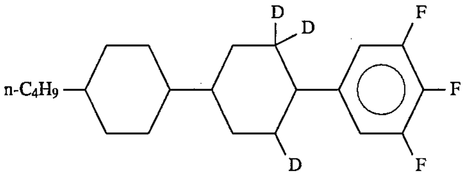 | C67 N91 I |
| 20 | 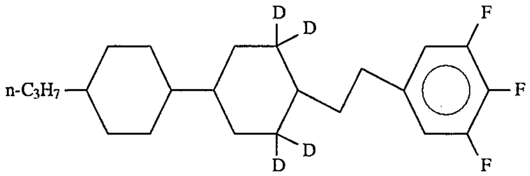 | C41 N98 I |
TABLE 3
| Compound No. | Structural Formula | Phase Transition Temperature (°C.) |
|---|---|---|
| 21 | 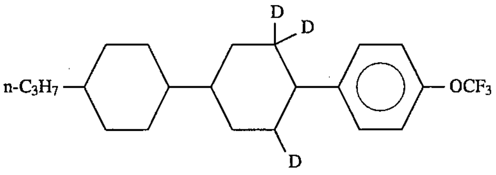 | C45 Sm71 N153 I |
| 22 | 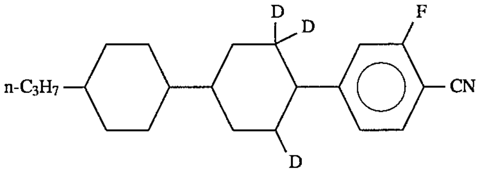 | C49 Sm87 N206 I |
| 23 | 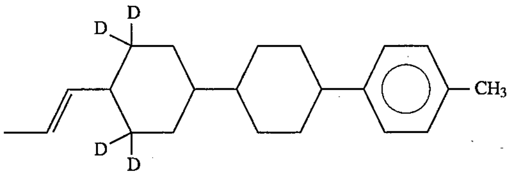 | C69 N214 I |

TABLE 3-continued

| Compound No. | Structural Formula | Phase Transition Temperature (°C.) |
| --- | --- | --- |
| 24 | 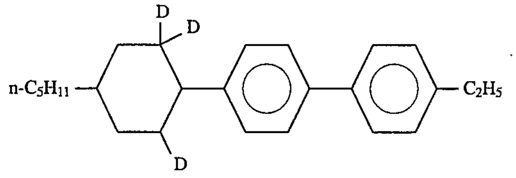 | C29 Sm142 N162 I |
| 25 | 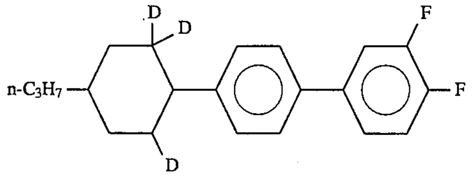 | C63 N97 I |
| 26 | 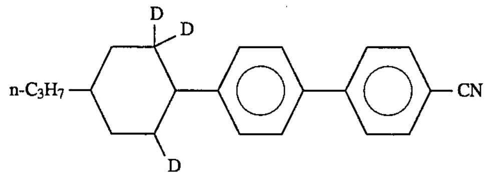 | C88 N218 I |
| 27 | 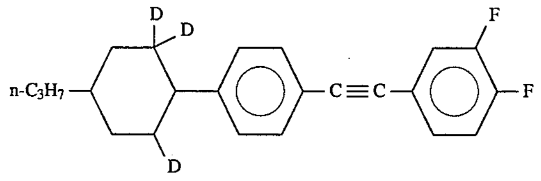 | C83 N148 I |
| 28 | 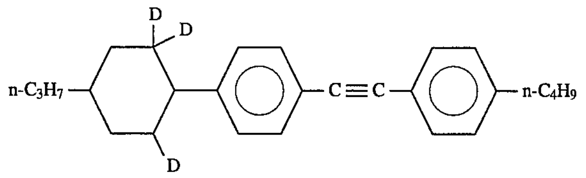 | C82 N200 I |
| 29 | 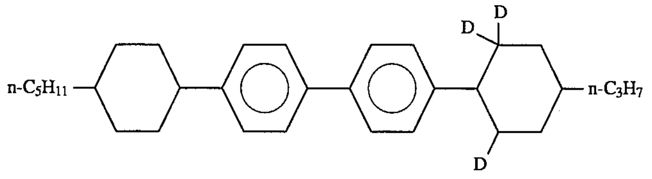 | C-13 Sm249 N310 I |
| 30 | 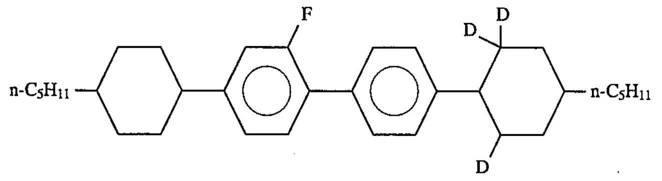 | C74 N276 I |

Compound with corresponding non-deuterated compounds, the deuterated liquid crystal compounds of formula (I) according to the present invention have approximately equal or slightly lower phase transition temperatures, and they appear to produce no considerable difference. However, because the compounds of formula (I) are extremely superior to the corresponding non-deuterated compounds in compatibility with general-purpose liquid crystal materials, particularly in a low temperature range, they produce such an excellent effect that crystals are hardly crystallized in liquid crystal materials. The following typical example of liquid crystal compositions is to demonstrate the above-described effect.

A liquid crystal composition was prepared from 85% by weight of a currently employed, general-purpose mother liquid crystal material having the following composition and 15% by weight of Compound No. 13 in Table 2.

Composition of General-Purpose Liquid Crystal Material:

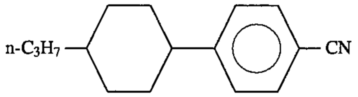

20%

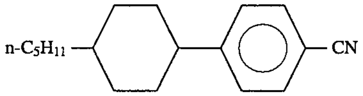

16%

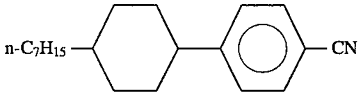

16%

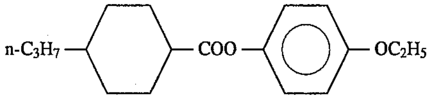

8%

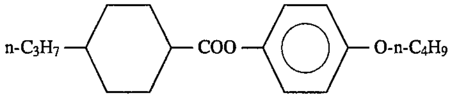

8%

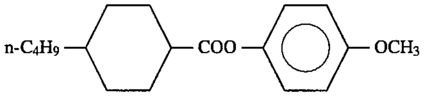

8%

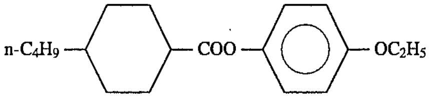

8%

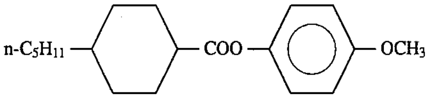

8%

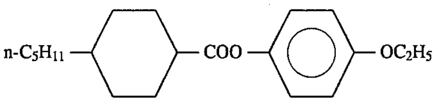

8%

This liquid crystal composition was not crystallized even after storage at −20° C. for 1 month.

For comparison, a liquid crystal composition was prepared from 85% by weight of the same general-purpose liquid crystal material as used above and 15% by weight of a compound represented by formula:

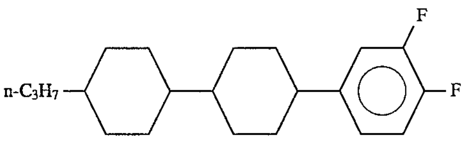

which has the same skeleton as Compound No. 13 but is not deuterated. When this comparative liquid crystal composition was similarly preserved at −20° C., crystallization was observed after 5 days.

It is thus understood that the compounds of formula (1) having a deuterated cyclohexane ring exhibit excellent compatibility with a general-purpose liquid crystal material to provide a practically useful liquid crystal material which is hardly crystallized even at a low temperature.

Further, addition of the deuterated liquid crystal compound of the present invention to a liquid crystal composition provides a liquid crystal composition which is not crystallized in a low temperature region and also exhibits improved electro-optical characteristics. These effects will be apparent from the following examples.

The electro-optical characteristics of liquid crystal compositions were measured as follows unless otherwise specified.

A liquid crystal display composed of a pair of electrode-backed substrates, at least one of the substrates being transparent, at a cell gap of 6 μm, and a liquid crystal composition sealed therebetween is prepared for characteristic measurement. A threshold voltage and a response time are measured at 25° C. A response time is the time where the rise time and the decay time become equal, the rise time being the time required from voltage application to occurrence of a change in light transmittance, and the decay time being the time required from power cut-off to restoration of the initial state. $\Delta n$ is a refractive index anisotropy. All the percents of the compositions are by weight.

A liquid crystal mixture (a-1) comprising 50% by weight of a compound of formula:

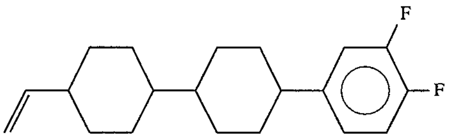

50% and 50% by weight of a compound of formula:

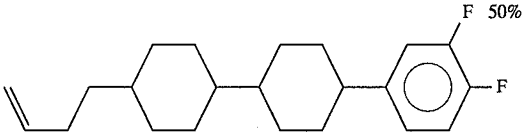

50% has the following characteristics:

$T_{N-I}$ Point: 117° C.

$T_{C-N}$ Point: 11° C.

Threshold Voltage: 2.14 V $\Delta\epsilon$: 4.8

$\Delta n$: 0.090

Response Time: 25 msec

Since the above compounds constituting liquid crystal mixture (a-1) have a relatively high voltage holding ratio, they are widely used as liquid crystal material particularly for active matrix driving.

A liquid crystal composition (b) for active matrix driving having the following composition was prepared from 70% of liquid crystal mixture (a-1) and 30% of a non-deuterated liquid crystal compound for active matrix driving.

Composition of Liquid Crystal Composition (b):

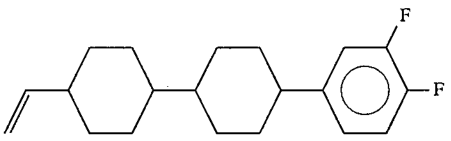

35%

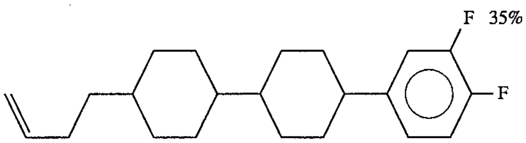

35%

-continued

30%

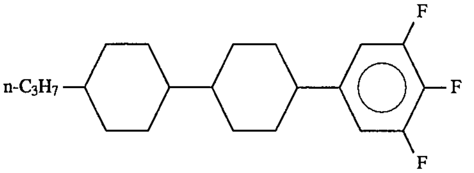

Liquid crystal composition (b) had the following characteristics.

$T_{N-I}$ Point: 111° C.

Threshold Voltage: 1.83 V $\Delta\epsilon$: 7.0

$\Delta n$: 0.087

Response Time: 30 msec

A liquid crystal composition (B) was also prepared from 70% of liquid crystal mixture (a-1) and 30% of Compound No. 18 in Table 2.

Composition of Liquid Crystal Composition (B):

35%

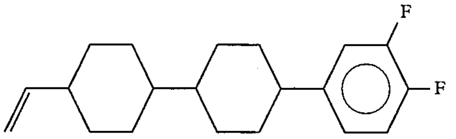

35%

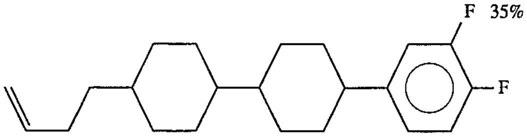

30%

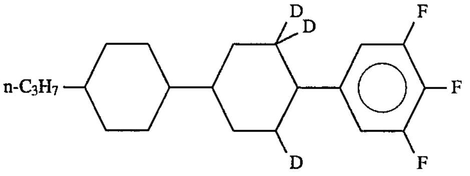

Liquid crystal composition (B) had the following characteristics.

$T_{N-I}$ Point: 110° C.

Threshold Voltage: 1.81 V $\Delta\epsilon$: 7.0

$\Delta n$: 0.087

Response Time: 28 msec

It is obvious from these results that liquid crystal composition (B) has a lower threshold voltage and a shorter response time. Further, when each of liquid crystal mixture (a-1), liquid crystal composition (b), and liquid crystal composition (B) was preserved at +10° C., the former two compositions are crystallized after 3 days, while composition (B) showed no crystallization even after 1 month's storage. It is now understood that the liquid crystal composition according to the present invention has improved electro-optical characteristics and is not crystallized even in a low temperature region.

Further, a liquid crystal composition (p) having the following composition was prepared using compounds generally used for an STN mode.

Composition of Liquid Crystal Composition (p):

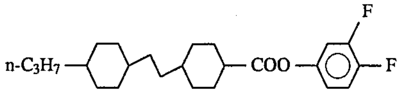

17%

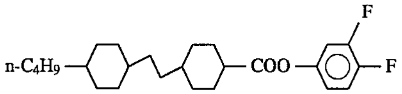

16.5%

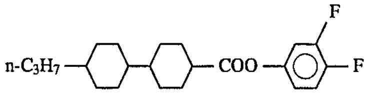

16.5%

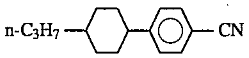

20%

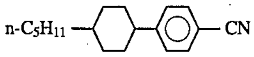

15%

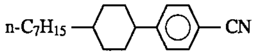

15%

Liquid crystal composition (p) had the following characteristics.

$T_{N-I}$ Point: 84° C.

Threshold Voltage: 1.60 V $\Delta\epsilon$: 9.9

$\Delta n$: 0.099

$K_{33}/K_{11}$: 2.3

A liquid crystal composition (P) was also prepared in the same manner, except for replacing the three bicyclic compounds having a cyano group with those which have the same structure but have their cyclohexane ring deuterated.

Composition of Liquid Crystal Composition (P):

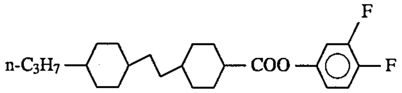

17%

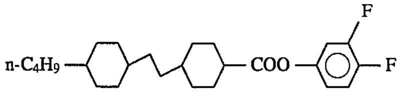

16.5%

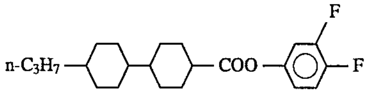

16.5%

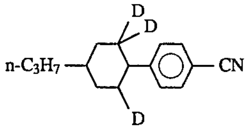

20%

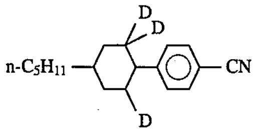

15%

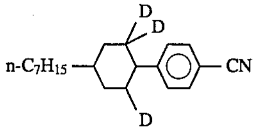

15%

-continued

Liquid crystal composition (P) had the following characteristics.

$T_{N-I}$ Point: 84° C.

Threshold Voltage: 1.59 V $\Delta\epsilon$: 9.9

$\Delta n$: 0.099

$K_{33}/K_{11}$: 2.4

It is obvious that liquid crystal composition (P) has a lower threshold voltage and a higher $K_{33}/K_{11}$ value. When each of liquid crystal compositions (p) and (P) was preserved at 0° C., composition (p) was crystallized after 1 day's storage, while it was after 14 days' storage that composition (P) showed crystallization. It is now understood that the liquid crystal composition according to the present invention has improved electro-optical characteristics and is hardly crystallized even in a low temperature region.

As can be seen from the above-described processes for preparing the compounds (I) and Tables 1 to 3, the compounds of the present invention take on an infinite variety in the number or position of deuterium atoms (D) or steric configuration, while the skeleton being equal.

For example, where Compound No. 18, which is useful for active matrix driving, is prepared in accordance with process J, there are obtained 8 analogues different in degree of deuteration as shown below.

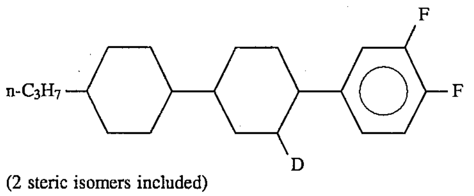

(2 steric isomers included)

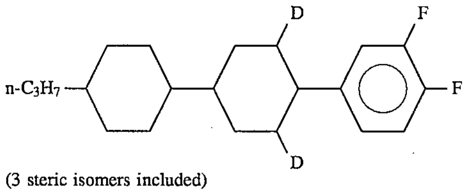

(3 steric isomers included)

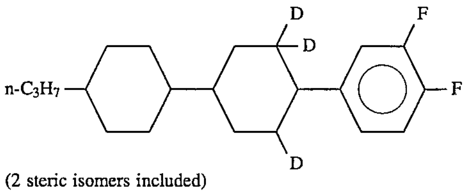

(2 steric isomers included)

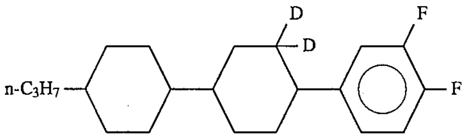

Where process C is followed, there would be obtained 9 analogues shown below.

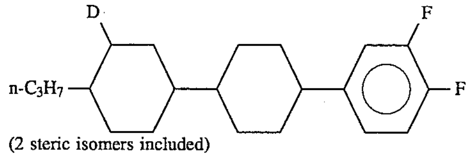

(2 steric isomers included)

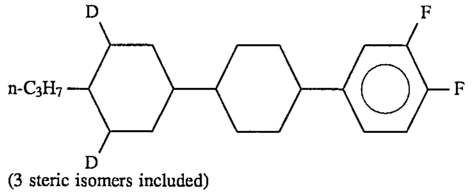

(3 steric isomers included)

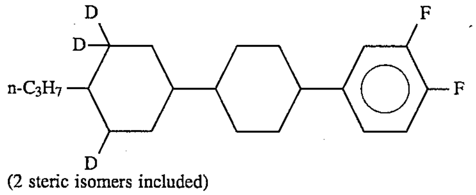

(2 steric isomers included)

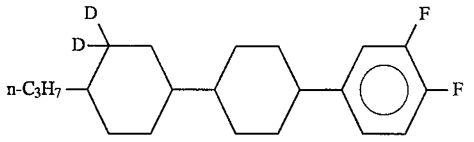

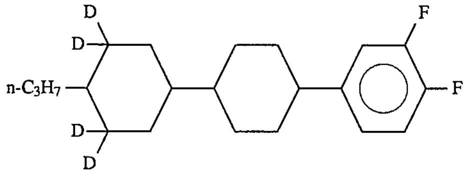

Thus, only two processes provide as many analogues as 17. Application of other processes will further increase the number of analogues obtained.

While incorporation of only one of the deuterated liquid crystal compounds of the present invention into a liquid crystal composition suffices to produce the above-mentioned effects, a liquid crystal composition containing two or more analogues prepared through the above-described various processes is particularly preferred because the effect of preventing crystallization in a low temperature region is pronouncedly manifested. An increase in number of analogues combined shows no tendency to deterioration of electro-optical characteristic. Therefore, liquid crystal displays using the liquid crystal composition of the present invention exhibit satisfactory driving characteristics even at an extremely low temperature at which conventional displays could not serve.

The effects of the composition containing two or more analogues of the deuterated liquid crystal compounds will be demonstrated below.

A comparative liquid crystal composition (a-2) containing conventional compounds for active matrix driving and a liquid crystal composition (A) containing several analogues of the deuterated compounds having the similar structures to the conventional compounds were prepared.

Composition of Liquid Crystal Composition (a-2):

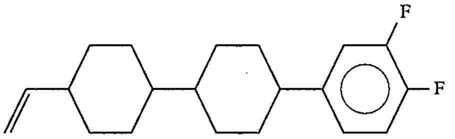
30%

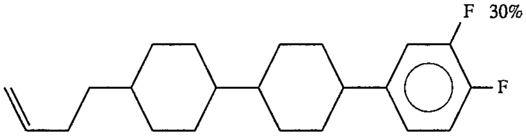
30%

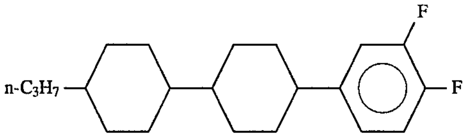
40%

Composition of Liquid Crystal Composition (A):

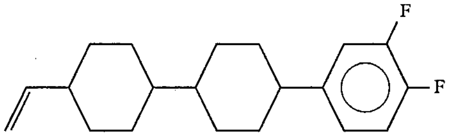
30%

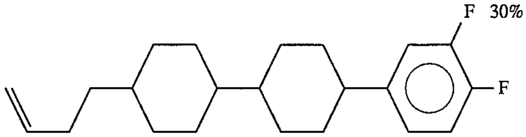
30%

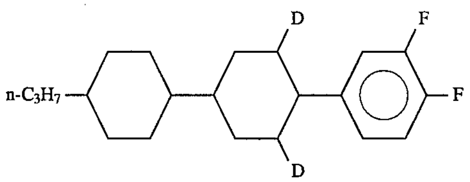
8%

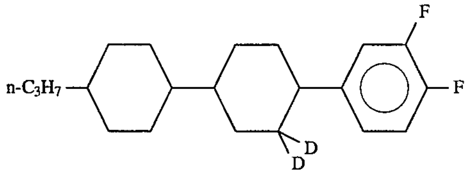
8%

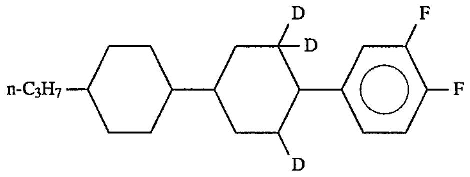
20%

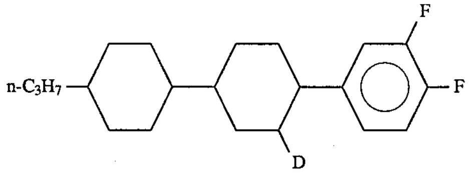
4%

The electro-optical characteristics of liquid crystal compositions (A) and (a-2) were as follows.

| | (A) | (a-2) |
|---|---|---|
| $T_{N-I}$ Point | 117° C. | 119° C. |
| Threshold Voltage | 1.91 V | 1.96 V |
| Δg | 5.5 | 5.5 |
| Δn | 0.086 | 0.086 |
| Response Time | 28 msec | 33 msec |

It is apparent that composition (A) according to the present invention has a lower threshold voltage and a shorter response time. In storage at +10° C., composition (A) of the present invention was not crystallized even after 1 month's storage, whereas composition (a-2) did after only 1 day.

Other various liquid crystal compositions of the present invention containing the deuterated liquid crystal compounds similarly exhibit improved electro-optical characteristics and the effect of preventing crystallization in low temperatures, as will be demonstrated in Examples hereinafter given.

Further, the present invention provides such a liquid crystal composition that is not crystallized even in storage for 3 months or longer at −55° C., at which it has been said any known liquid crystal composition for active matrix driving necessarily is crystallized. A liquid crystal composition (M) having the following composition and characteristics affords a typical example.

Composition of Liquid Crystal Composition (M):

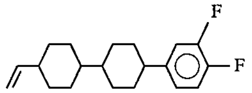
12.5%

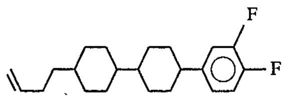
12.5%

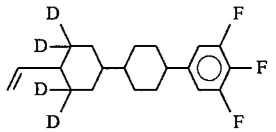
3%

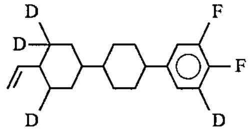
4%

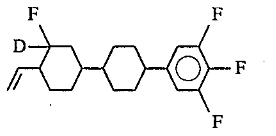
1%

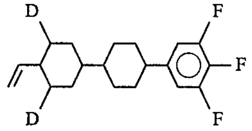
1%

-continued

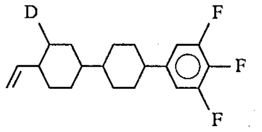
1%

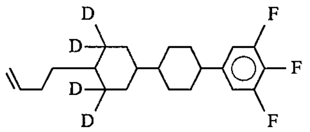
3%

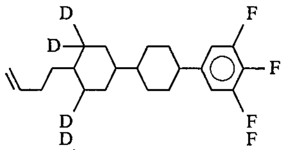
4%

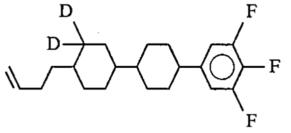
1%

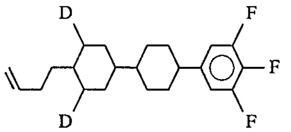
1%

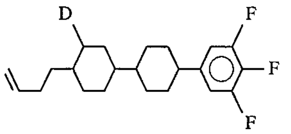
1%

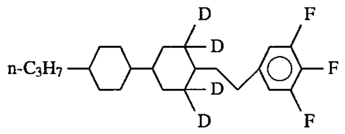
3%

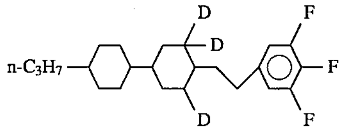
4%

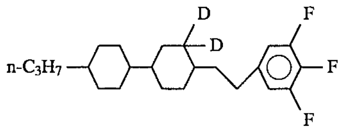
1%

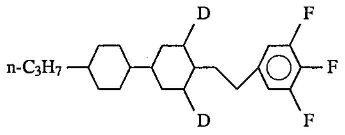
1%

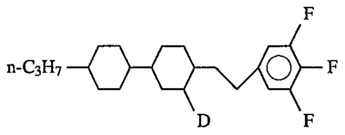
1%

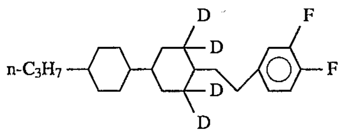
3%

-continued

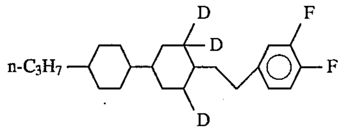
4%

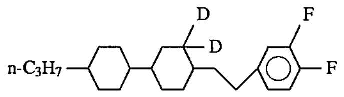
1%

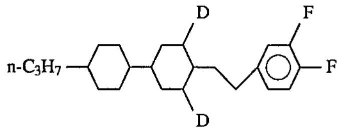
1%

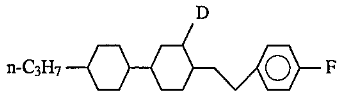
1%

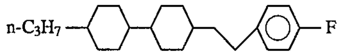
10%

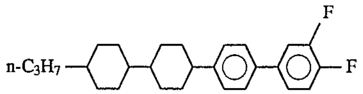
5%

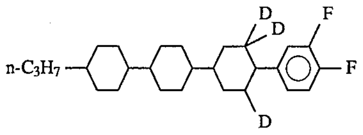
5%

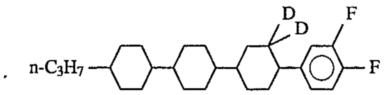
2%

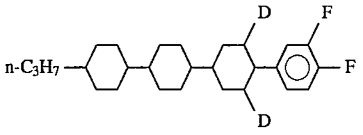
2%

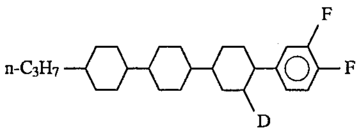
1%

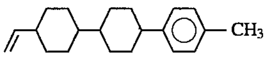
10%

$T_{N-I}$ Point: 112° C.
$T_{C-N}$ Point: −70° C.
Threshold Voltage: 1.9 V
$\Delta\epsilon$: 5.5
$\Delta n$: 0.086
Response Time: 24 msec
Voltage Holding Ratio: 99% (/100° C.)

A liquid crystal display prepared by using liquid crystal composition (M) exhibits satisfactory driving characteristics even in a low temperature region. Therefore, the liquid crystal composition of the present invention provides an epoch-making liquid crystal display that serves in a low temperature region in which conventional liquid crystal displays for active matrix driving could never be used. Such a liquid crystal display is extremely useful as a component of equipment which is demanded to be stably operated even in low temperatures, such as equipment installed in the automobile console box or the cockpit of aircraft.

In order for a liquid crystal display for active matrix driving to be general-purpose for office automation (OA) equipment, it is keenly demanded that the liquid crystal composition to be used should have a threshold voltage of not more than 1.2 V. However, as previously stated, a liquid crystal composition designed to meet this demand involves a tendency toward crystallization. In application to OA equipment, a liquid crystal composition which is not crystallized at −25° C. for at least 1 month is generally regarded to be practical, but such a composition that has a threshold voltage of not more than 1.2 V and a $T_{N-I}$ point of not lower than 85° C. and yet is not crystallized at −25° C. for 1 month or longer has not yet been developed.

For example, a liquid crystal composition (n) having the following composition affords an example of a conventional composition having a low threshold voltage.

Composition of Liquid Crystal Composition (n):

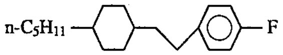
5%

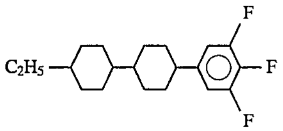
20%

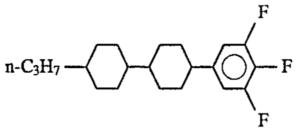
16%

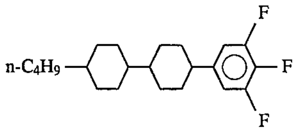
15%

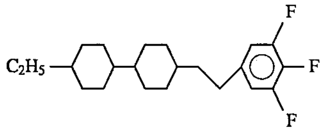
8.5%

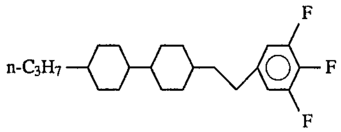
8.5%

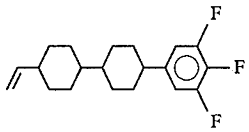
8.5%

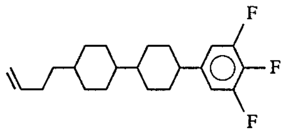
8.5%

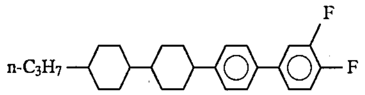
10%

The characteristics of liquid crystal composition (n) were as follows. The measurement was made using a liquid crystal cell with a cell gap of 4.5 μm.

$T_{N-I}$ Point: 87° C.

Threshold Voltage: 1.15 V $\Delta\epsilon$: 9.1

$\Delta n$: 0.080

Response Time: 38 msec

Composition (n), while having a low threshold voltage and a high $T_{N-I}$ point, was crystallized in storage at 0° C. for 1 day or longer and therefore proved impractical.

To the contrary, a liquid crystal composition (N) containing the deuterated liquid crystal compounds was prepared.

Composition of Liquid Crystal Composition (N):

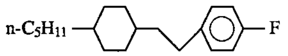
5%

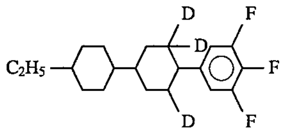
5%

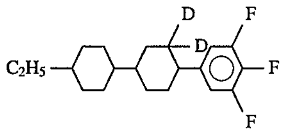
2%

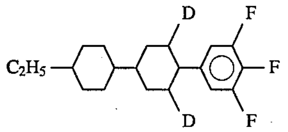
2%

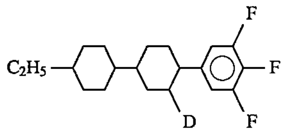
1%

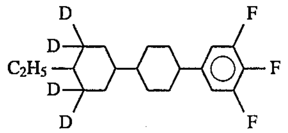
3%

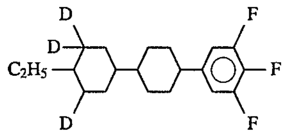
4%

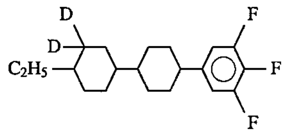
1%

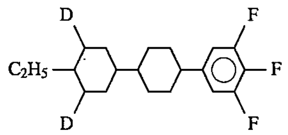
1%

-continued
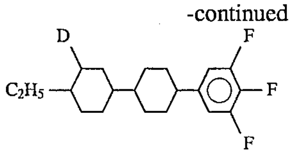
1%
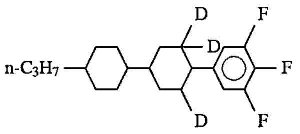
4%
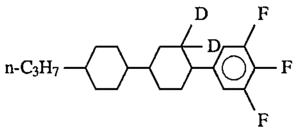
1.6%
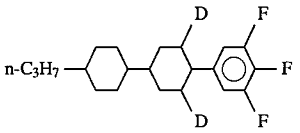
1.6%
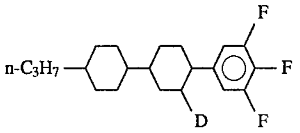
0.8%
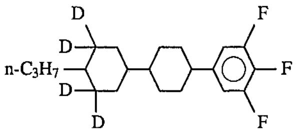
2.4%
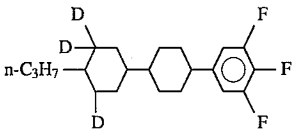
3.2%
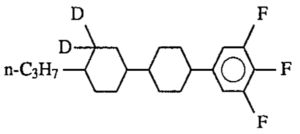
0.8%
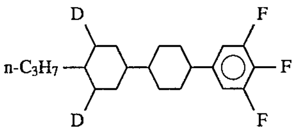
0.8%
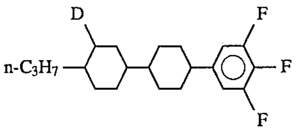
0.8%
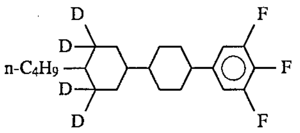
4.5%
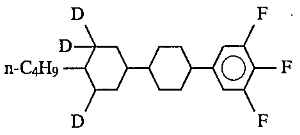
6%
-continued
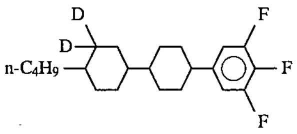
1.5%
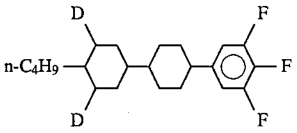
1.5%
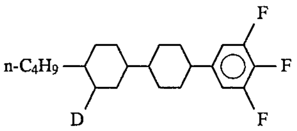
1.5%
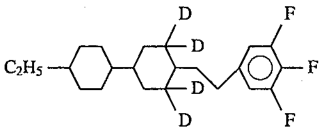
2.55%
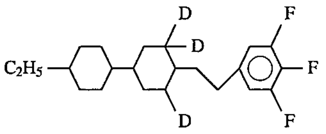
3.4%
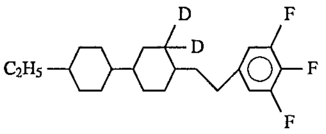
0.85%
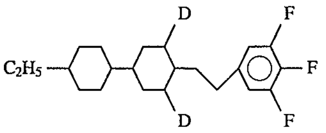
0.85%
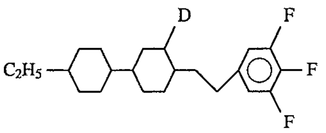
0.85%
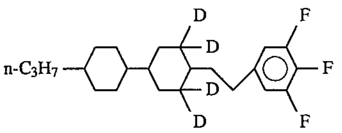
2.55%
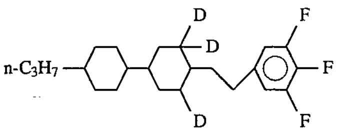
3.4%
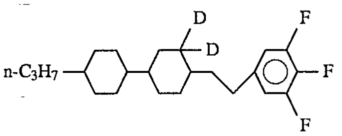
0.85%

-continued

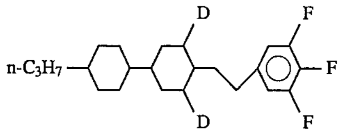

0.85%

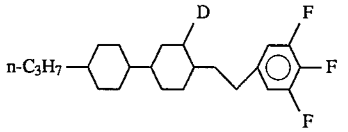

0.85%

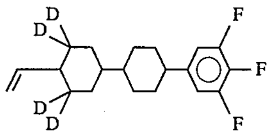

2.55%

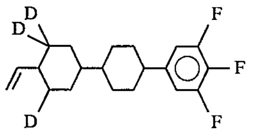

3.4%

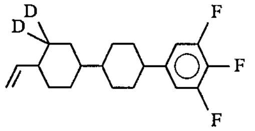

0.85%

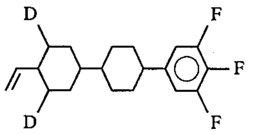

0.85%

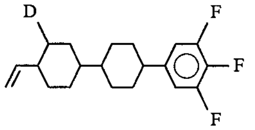

0.85%

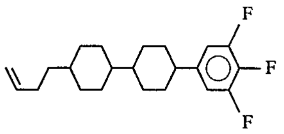

8.5%

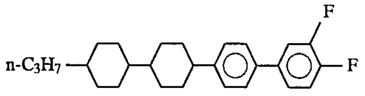

10%

The electro-optical characteristics of composition (N) as measured in the same manner as for composition (n) were as follows.

$T_{N-I}$ Point: 86° C.

$T_{C-N}$ Point: −30° C.

Threshold Voltage: 1.10 V $^{\Delta}\epsilon$: 9.2

$^{\Delta}n$: 0.080

Response Time; 33 msec

Voltage Holding Ratio: 98.5% (/100° C.)

It is seen that composition (N) has a high $T_{N-I}$ point and a threshold voltage of 1.2 V or lower, and a short response time. When composition (N) was preserved at −25° C. for 1 months or longer, it was not crystallized. A liquid crystal display for TFT driving prepared by using composition (N) shows satisfactory driving characteristics even in a low temperature region.

It has thus been proved that the liquid crystal compositions of the present invention exhibit improved electro-optical characteristics and also are not crystallized in a low temperature region.

A liquid crystal composition (t) having the following composition is offered as an example of a liquid crystal composition containing the above-mentioned bicyclic compounds having a cyano group which are useful in STN liquid crystal displays.

Composition of Liquid Crystal Composition (t):

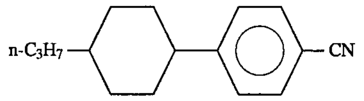

20%

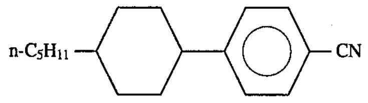

10%

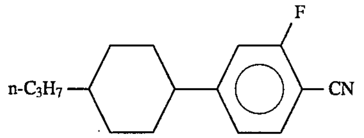

10%

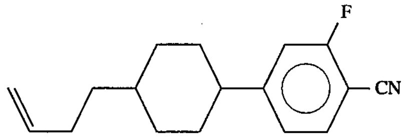

10%

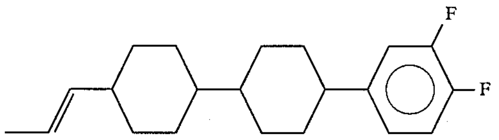

10%

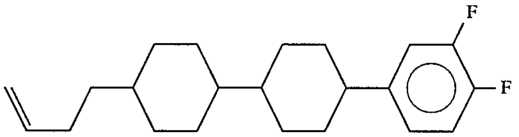

10%

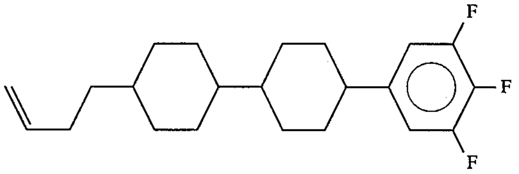

10%

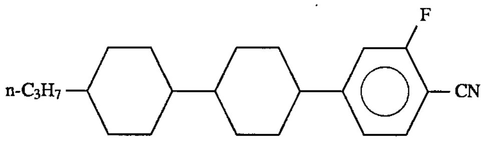

10%

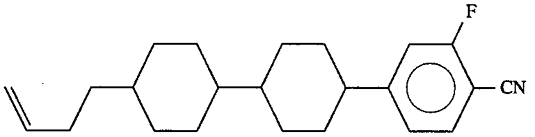

10%

The characteristics of liquid crystal composition (t) are shown below.

$T_{N-I}$ Point: 83° C.

Threshold Voltage: 1.12 V $^{\Delta}\epsilon$: 17

$^{\Delta}n$: 0.116

$K_{33}/K_{11}$: 2.5

Composition (t) is an excellent liquid crystal composition for STN mode with which low power driving and high contrast display can be achieved as seen from its low threshold voltage and large $K_{33}/K_{11}$ value. Composition (t) is also excellent in scarcely involving such problems as an increase of electric current value. Nevertheless, this composition is crystallized in storage at −25° C. for 5 days.

The problem of crystallization can be solved by a liquid crystal composition (T) having the following composition and characteristics.

Composition of Liquid Crystal Composition (T):

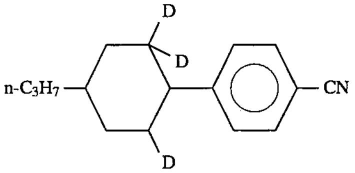
5%

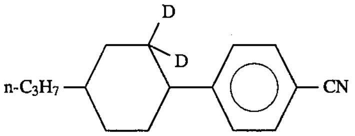
2%

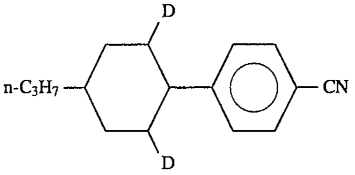
2%

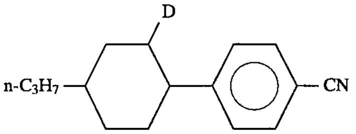
1%

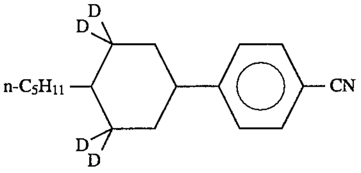
3%

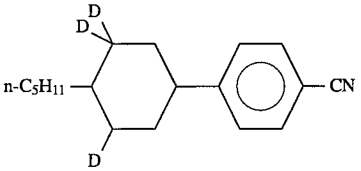
4%

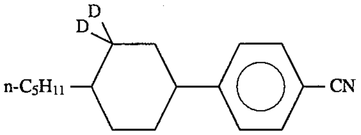
1%

-continued

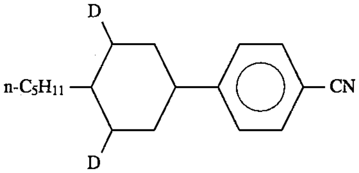
1%

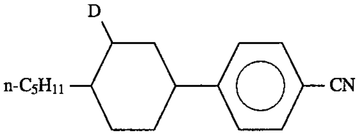
1%

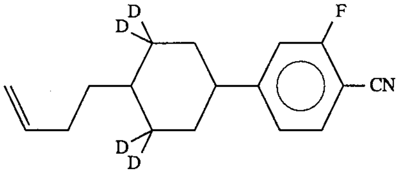
3%

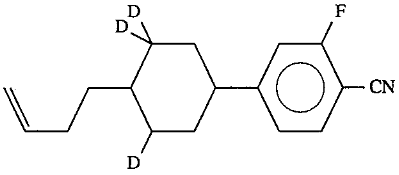
4%

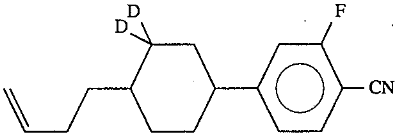
1%

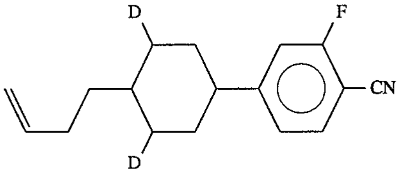
1%

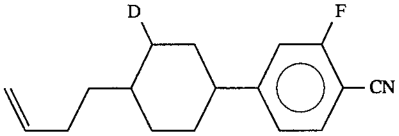
1%

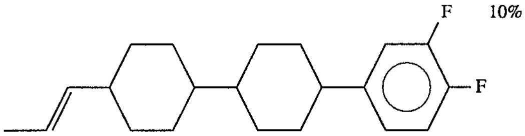
10%

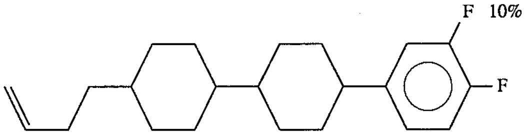
10%

-continued

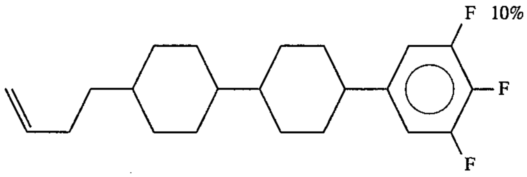
10%

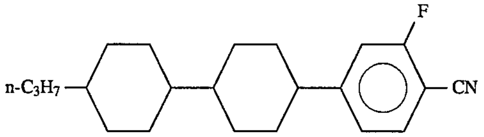
10%

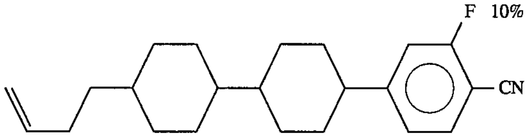
10%

$T_{N-I}$ Point: 82° C.
Threshold Voltage: 1.10 V
$^{\Delta}\epsilon$: 17
$^{\Delta}n$: 0.116
$K_{33}/K_{11}$: 2.5
Contrast: Satisfactory It is seen that composition (T) has a lower threshold voltage than composition (t). An STN display having a twisted angle of 260° which is prepared by using composition (T) exhibits satisfactory driving characteristics even in a low temperature region. Further, composition (T) is not crystallized even in storage at −40° C. for 3 months or longer, which is a great advantage for practical use.

Thus, the liquid crystal compositions according to the present invention bring about the happiest solution to the problem of crystallization in low temperatures and are expected to be useful in a low-temperature environment where a conventional display has been of no practical use. As a matter of course, the liquid crystal display of the present invention is useful for an ordinary TN mode as well as for an active matrix driving system and an STN mode.

The liquid crystal compositions according to the present invention comprises at least one deuterated liquid crystal compound having, as a partial structure, a saturated hydrocarbon ring with its one or more hydrogen atoms (H) substituted with deuterium atoms (D). The liquid crystal compositions of the present invention preferably contains a liquid crystal compound having one or more deuterated cyclohexane rings. More preferred are those containing a deuterated liquid crystal compound having 2 to 4 cyclic structures per molecule, one or two of which are deuterated cyclohexane rings.

A total content of the deuterated liquid crystal compounds in the liquid crystal composition of the present invention is preferably from 5 to 100% by weight, still preferably from 30 to 90% by weight.

As will be demonstrated in Examples hereinafter described, the liquid crystal composition for active matrix driving preferably has a dielectric anisotropy ($^{\Delta}\epsilon$) of from +3 to +12 as a whole, and that for TN and STN modes preferably comprises the deuterated liquid crystal compound having a $^{\Delta}\epsilon$ of not less than +8.

The present invention will now be illustrated in greater detail with reference to Examples, but it should be understood that the present invention is not construed as being limited thereto.

In Examples, the structure of deuterated compounds were confirmed by comparing with known non-deuterated compounds having the same retention time or the same Rf value in capillary gas chromatography and thin layer chromatography, taking the nuclear magnetic resonance spectrum (NMR), mass spectrum (MS), and infrared absorption spectrum (IR) as factors for comparison. The degree of deuteration was determined with JNM-GSX400 (400 MHz; $^{1}H$), manufactured by JEOL Ltd.

All the percents and ratios are given by weight unless otherwise indicated.

EXAMPLE 1

Synthesis of 1-Cyano-4-(trans-4-propylcyclohexyl-2, 2,6-$d_3$)benzene

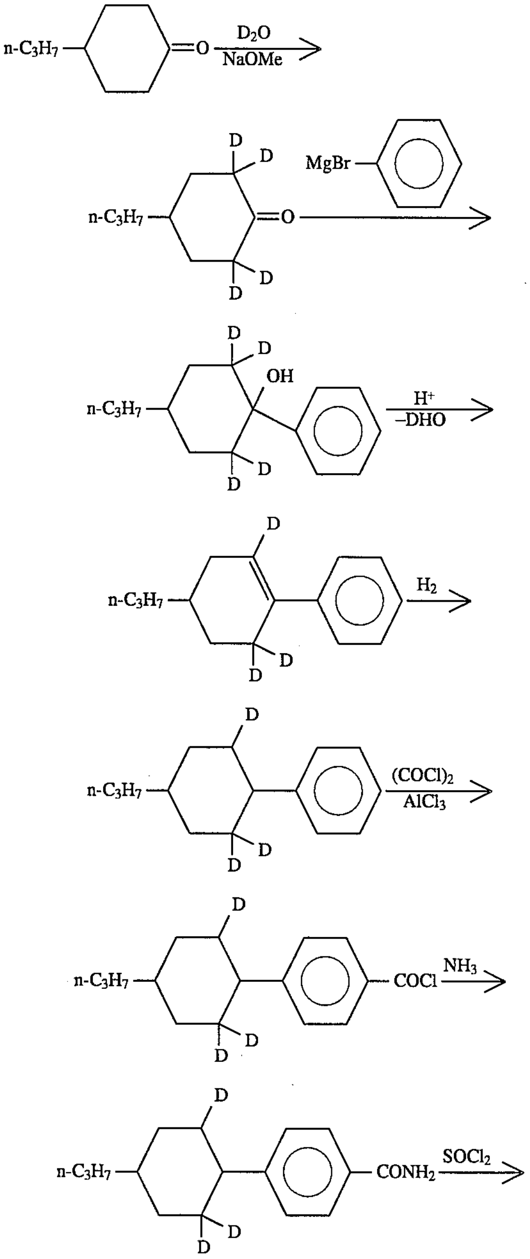

-continued

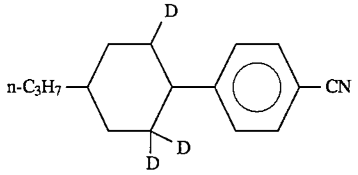

(1-a) Deuteration of 4-propylcyclohexane:

In 100 ml of heavy water (degree of deuteration: 99.8%) was dissolved 11.5 g of sodium methoxide. To the solution was added a solution of 88.9 g of 4-propylcyclohexanone and 1.0 g of tetrabutylammonium bromide in 100 ml of dichloromethane, and the mixture was stirred at the refluxing temperature of the solvent for 6 hours. After completion of the reaction, the reaction mixture was allowed to cool to room temperature, and the aqueous layer was separated and extracted with 50 ml of dichloromethane. The extract and the above separated organic layer were combined and added to 50 ml of heavy water (degree of deuteration: 99.96%) having dissolved therein 4.0 g of sodium methoxide. The mixture was stirred at the refluxing temperature of the solvent for 10 hours. The organic layer was separated, and the aqueous layer was extracted with dichloromethane. The extract and the organic layer were combined, washed with water, and dried over anhydrous sodium sulfate. The solvent was removed by distillation to obtain 88.6 g of 4-propylcyclohexanone-2,2,6,6-$d_4$.

(1-b) Synthesis of 1-phenyl-4-propyl-1-cyclohexene-2,6,6-$d_3$:

In 20 ml of dried tetrahydrofuran (THF) was added 10.2 g of magnesium shavings, and a solution of 56.0 g of bromobenzene in 240 ml of THF was added thereto dropwise at such a rate that mild refluxing might continue. After the addition, the mixture was stirred for 1 hour. To the mixture was added dropwise a solution of 33.0 g of 4-propylcyclohexanone-2, 2,6,6-$d_4$ prepared in (1-a) in 100 ml of THF over a period of 1 hour while cooling with ice with care so that the inner temperature might not exceed 40° C. After stirring at room temperature for 1 hour, dilute hydrochloric acid was added thereto until the aqueous layer became weakly acidic. The reaction product was extracted with two 300 ml portions of ethyl acetate, and the organic layer was washed with a saturated sodium chloride aqueous solution, and dried over anhydrous sodium sulfate. The solvent was removed by distillation under reduced pressure to obtain crude 1-phenyl-4-propyl-1-cyclohexanol-2, 2,6,6-$d_4$ as an oily substance.

The whole portion of the crude product was dissolved in 200 ml of toluene, and 2.5 g of potassium bisulfate was added thereto. The mixture was heated under reflux with stirring for 1 hour while removing water as a distillate. After allowing to cool to room temperature, the reaction mixture was washed successively with water, saturated aqueous solution of sodium bicarbonate, water, and saturated aqueous solution of sodium chloride, and dried over anhydrous sodium sulfate. Removal of the solvent by distillation under reduced pressure gave 47.5 g of 1-phenyl-4-propyl-1-cyclohexene-2,6,6-$d_3$.

(1-c) Synthesis of (trans-4-propylcyclohexyl-2,2,6-$d_4$)benzene:

In an autoclave was put 40.0 g of the 1-phenyl-4-propyl-1-cyclohexene-2, 6,6-$d_3$ obtained in (1-b), and 340 ml of ethyl acetate was added thereto to dissolve. To the solution was added 4.0 g of palladium-on-carbon, and the mixture was stirred at room temperature under a hydrogen pressure of 4 kg/$cm^2$ for 3 hours. The reaction mixture was filtered using Celite to remove the catalyst, and the solvent was removed by distillation under reduced pressure to obtain a cis/trans mixture of (4-propylcyclohexyl-2,2,6-$d_3$)benzene. The isomeric mixture was dissolved in 200 ml of N,N-dimethylformamide (DMF), and 17.0 g of potassium t-butoxide was added thereto, followed by stirring at 110° C. for 3 hours. After completion of the reaction, 100 ml of water was added thereto, the mixture was neutralized with dilute hydrochloric acid and the product was extracted twice with hexane. The hexane layer was washed with water and dried over anhydrous sodium sulfate. The solvent was removed by distillation under reduced pressure, and the resulting crude product was purified by silica gel column chromatography using hexane as an eluent to obtain 34.2 g of a 86/14 isomeric mixture of (trans-4-propylcyclohexyl-2,2,6-$d_3$)benzene and (cis-4-propylcyclohexyl-2,2,6-$d_3$) benzene.

(1-d) Synthesis of 4-(trans-4-propylcyclohexyl-2,2,6-$d_3$) benzamide:

In 100 ml of dichloromethane was dissolved 20.0 g of the 86/14 isomeric mixture prepared in (1-c), and 17 g of anhydrous aluminum chloride was added thereto, followed by cooling with ice. A solution of 14 g of oxalyl dichloride in 70 ml of dichloromethane was added thereto dropwise with care so that the inner temperature might not exceed 10° C. After stirring for 1 hour with ice-cooling, the reaction mixture was poured into ice-dilute hydrochloric acid, and the product was extracted with dichloromethane. The dichloromethane layer was added dropwise to 250 ml of 29% aqueous ammonia at 10° C. or lower. After stirring at 5° to 10° C. for 1 hour, the precipitated crystals were collected by filtration and dried under reduced pressure to obtain 20.0 g crude crystals of 4-(trans-4-propylcyclohexyl-2, 2,6-$d_3$)benzamide (containing a small amount of the cis-form).

(1-e) Synthesis of 1-cyano-4-(trans-4-propylcyclohexyl-2,2,6-$d_3$)benzene:

The whole portion of the 4-(trans-4-propylcyclohexyl-2,2,6-$d_3$)benzamide prepared in (1-d) was added to 100 ml of thionyl chloride, followed by refluxing for 1 hour with stirring. The excess thionyl chloride was removed by distillation under reduced pressure, the residue was allowed to cool, water and toluene were added thereto, followed by stirring, and the organic layer was separated. The aqueous layer was extracted with toluene. The organic layer and the extract were combined, washed with water, and dried over anhydrous sodium sulfate. The solvent was removed by distillation, and the resulting crude product was purified by silica gel column chromatography using toluene as an eluent. Recrystallization from methanol afforded 9.4 g of 1-cyano-4-(trans-4-propylcyclohexyl-2, 2,6-$d_3$)benzene. The phase transition temperatures of this compound were as follows.

42° C. (m.p.) (Cr→N), 46° C. (N-I)

For reference, non-deuterated 1-cyano-4-(trans-4-propylcyclohexyl) benzene has the following phase transition temperatures according to literature (Koji Okano Shunsuke Kobayashi (ed.), *EKISHO KISOHEN*, Baihukan (1985)).

42° C. (m.p.) (Cr→N), 45° C. (N-I)

EXAMPLE 2

Synthesis of 1-Cyano-4-(trans-4-propylcyclohexyl-3, 3,5,5-$d_4$)benzene

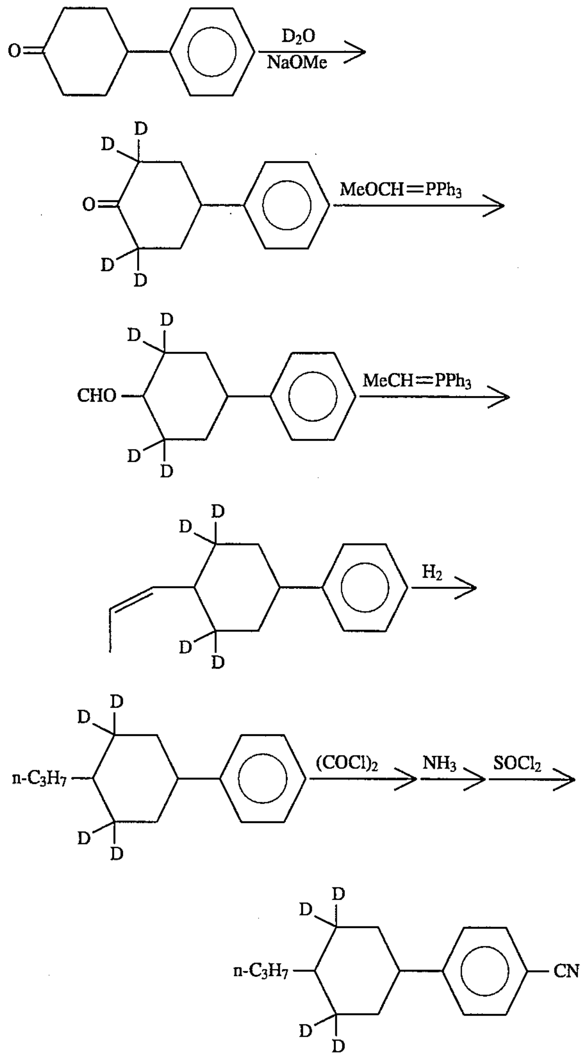

(2-a) Deuteration of 4-phenylcyclohexanone;

Commercially available 4-phenylcyclohexanone was deuterated in the same manner as in Example 1-(1-a) to obtain 4-phenylcyclohexanone-2,2,6,6-$d_4$.

(2-b) Synthesis of trans-4-phenylcyclohexane-2,2,6,6-$d_4$ carbaldehyde:

In 35 ml of THF was suspended 14.2 g of methoxymethyltriphenylphosphonium chloride, and the solution was cooled to −5° C. To the solution was added 4.6 g of potassium t-butoxide, followed by stirring at room temperature for 1 hour to prepare a Wittig reagent. To the Wittig reagent was added dropwise a solution of 5.7 g of 4-phenylcyclohexanone-2, 2,6,6-$d_4$ prepared in (2-a) in 10 ml of THF at −5° C. over 5 minutes. After stirring at room temperature for 5 hours, the reaction mixture was poured into water, and hexane was added thereto. The organic layer was separated, and the triphenylphosphine oxide precipitate was removed by filtration. The filtrate was washed with water and dried over anhydrous sodium sulfate. The solvent was removed by distillation, and the resulting crude product was purified by silica gel column chromatography using a 5:1 mixed solvent of hexane and ethyl acetate as an eluent to recover 5.2 g of 4-phenylcyclohexane-2,2,6,6-$d_4$ carbaldehyde as an oily substance, which was a mixture of diastereomers assigned to the cis and trans configurations of the cyclohexane ring. The product was dissolved in 50 ml of ethanol, and 1 ml of a 20% sodium hydroxide aqueous solution was added thereto, followed by stirring at room temperature for 3 hours. Water was added thereto, the mixture neutralized with 1N hydrochloric acid, the reaction product extracted with ethyl acetate, and the extract washed with water and dried over anhydrous sodium sulfate. The solvent was distilled off, and the resulting crude product was purified by silica gel column chromatography using a 5:1 mixed solvent of hexane and ethyl acetate. Recrystallization from hexane yielded 3.1 g of trans-4-phenylcyclohexane-2, 2,6,6-$d_4$ carbaldehyde as white crystals.

(2-c) Synthesis of trans-1-phenyl-4-(1-propenyl)cyclohexane-3, 3,5,5-$d_4$:

In a mixture of 3 ml of THF and 10 ml of toluene was suspended 1.8 g of ethyltriphenylphosphonium iodide, and the suspension was cooled to 15° C. To the suspension was added 0.52 g of potassium t-butoxide, followed by stirring at room temperature for 1 hour to prepare a Wittig reagent. To the thus prepared Wittig reagent was added dropwise a solution of 0.60 of the trans-4-phenylcyclohexane-2,2,6,6-$d_4$ carbaldehyde prepared in (2-b) in 2 ml of toluene at 15° C. over 5 minutes. After stirring at room temperature for 2 hours, the reaction mixture was poured into water, toluene added thereto, and the organic layer separated and concentrated. Hexane was added to the organic layer, and the triphenylphosphine oxide precipitate was removed by filtration. The filtrate was washed with a 1:1 mixed solvent of water and methanol and dried over anhydrous sodium sulfate. The solvent was removed by distillation, and the resulting crude product was purified by silica gel column chromatography using hexane as an eluent to obtain 0.56 g of trans-1-phenyl-4-(1-propenyl)cyclohexane-3,3,5,5-$d_4$.

(2-d) Synthesis of trans-1-phenyl-4-propylcyclohexane-3, 3,5,5-$d_4$:

The whole portion of the trans-1-phenyl-4-(1-propenyl) cyclohexane-3,3,5,5-$d_4$ obtained in (2-c) was hydrogenated in the same manner as in Example 1-(1-c), except for replacing the palladium-on-carbon with Raney nickel, to obtain 0.55 g of trans-1-phenyl-4-propylcyclohexane-3,3,5, 5-$d_4$.

(2-e) Synthesis of 1-cyano-4-(trans-4-propylcyclohexyl-3,3, 5,5-$d_4$)benzene:

The whole portion of the trans-1-phenyl-4-propylcyclohexane-3, 3,5,5-$d_4$ obtained in (2-d) was treated in the same manner as in (1-d) and (1-e) to obtain 0.28 g of 1-cyano-(trans-4-propylcyclohexyl-3, 3,5,5-$d_4$)benzene. The phase transition temperatures of this compound are shown in Table 1 above.

EXAMPLE 3

Synthesis of 1-Cyano-2-fluoro-4-(trans-4-propylcyclohexyl-2, 2,6-$d_3$)benzene The title compound was prepared in the same manner as in Example 1, except for replacing bromobenzene with 3-fluoro-1-bromobenzene. The phase transition temperatures of this compound are shown in Table 1.

EXAMPLE 4

Synthesis of 1-Fluoro-4-(trans-4-pentylcyclohexyl-2, 2,6-$d_3$)benzene

The title compound was prepared in the same manner as in Example 1, except for replacing bromobenzene with 4-fluoro-1-bromobenzene and replacing 4-propylcyclohexanone with 4-pentylcyclohexanone. The phase transition temperatures of this compound are shown in Table 1.

EXAMPLE 5

Synthesis of 1-Methoxy-4-(trans-4-pentylcyclohexyl-2, 2,6-$d_3$)benzene

The title compound was prepared in the same manner as in Example 1, except for replacing bromobenzene with 4-bromoanisole and replacing 4-propylcyclohexanone with 4-pentylcyclohexanone. The phase transition temperatures of this compound are shown in Table 1.

EXAMPLE 6

Synthesis of 1,2-Difluoro-4-(trans-4-pentylcyclohexyl-2, 2,6-$d_3$)benzene

The title compound was prepared in the same manner as in Example 1, except for replacing bromobenzene with 1-bromo-3, 4-difluorobenzene and replacing 4-propylcyclohexanone with 4-pentylcyclohexanone. The phase transition temperatures of this compound are shown in Table 1.

EXAMPLE 7

Synthesis of 1-Trifluoromethoxy-4-(trans-4-pentylcyclohexyl-2, 2,6-$d_3$)benzene The title compound was prepared in the same manner as in Example 1, except for replacing bromobenzene with 4-bromo-1-trifluoromethoxybenzene and replacing 4-propylcyclohexanone with 4-pentylcyclohexanone. The phase transition temperatures of this compound are shown in Table 1.

EXAMPLE 8

Synthesis of 1-Methyl-4-(trans-4-pentylcyclohexyl-2, 2,6-$d_3$)benzene

The title compound was prepared in the same manner as in Example 1, except for replacing bromobenzene with 4-bromotoluene and replacing 4-propylcyclohexanone with 4-pentylcyclohexanone. The phase transition temperatures of this compound are shown in Table 1.

EXAMPLE 9

Synthesis of Trans-4-(trans-4-propyl-cyclohexyl)-1-butylcyclohexane-2, 2,6,6-$d_4$

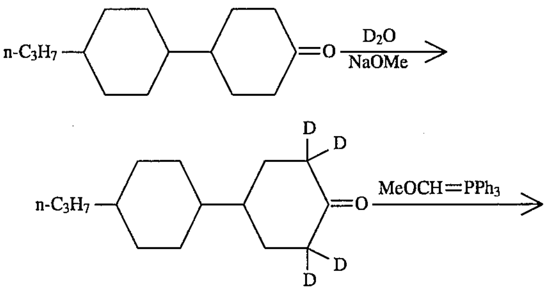

-continued

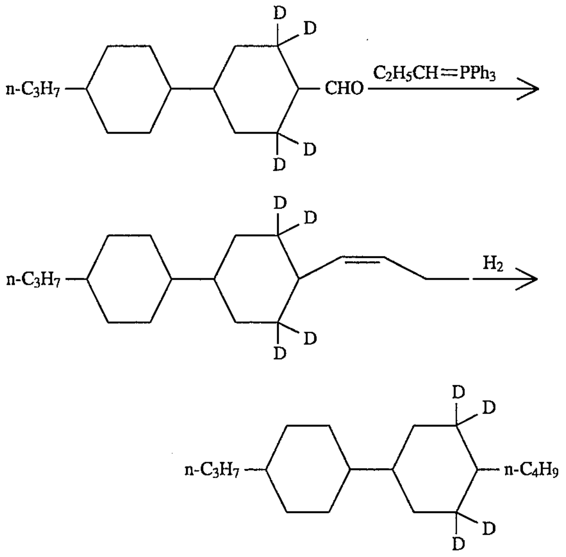

4-(Trans-4-propylcyclohexyl)cyclohexanone was deuterated in the same manner as in (1-a) to obtain 4-(trans-4-propylcyclohexyl) cyclohexanone-2,2,6,6-$d_4$, which was then reacted with a Wittig reagent in the same manner as in (2-b) to obtain 4-(trans-4-propylcyclohexyl)cyclohexane-2, 2,6,6-$d_4$ carbaldehyde. The carbaldehyde was reacted with a Wittig reagent prepared from propyltriphenylphosphonium bromide in the same manner as in (2-c), and the product was hydrogenated in the same manner as in (2-d) to obtain trans-4-(trans-4-propylcyclohexyl)-1-butylcyclohexane-2, 2,6,6-$d_4$. The phase transition temperatures of this compound are shown in Table 1.

EXAMPLE 10

Synthesis of 1-Cyano-4-[2-(trans-4-propylcyclohexyl-2, 2,6,6-$d_4$)ethyl]benzene

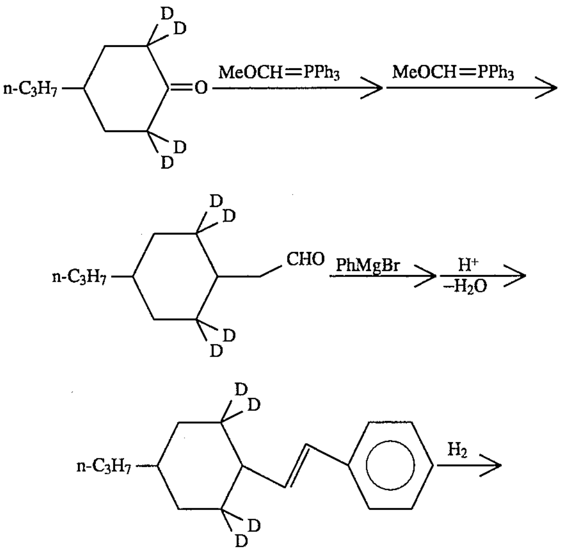

-continued

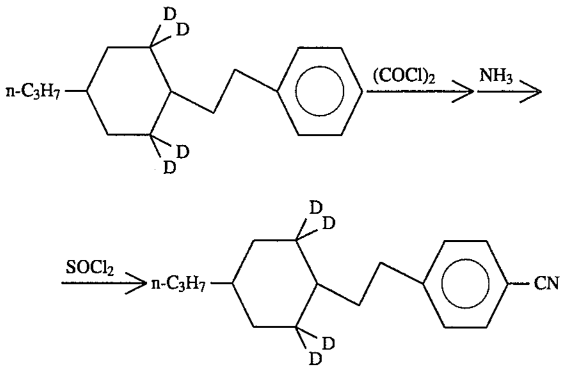

4-Propylcyclohexanone-2,2,6,6-$d_4$ obtained in (1-a) was reacted with a Wittig reagent prepared from methoxymethyltriphenylphosphonium chloride in the same manner as in (2-b) to obtain trans-4-propylcyclohexane-2,2,6,6-$d_4$ carbaldehyde. The reaction with the Wittig reagent was repeated once again to obtain trans-4-propylcyclohexane-2, 2,6,6-$d_4$ ethanal. The ethanal was reacted in the same manner as in (1-b) through (1-e) in place of trans-4-propylcyclohexanone-2, 2,6,6-$d_4$ to obtain the title compound. The phase transition temperatures of this compound are shown in Table 1.

EXAMPLE 11

Synthesis of 1-Cyano-4-(trans-4-ethenylcyclohexyl-3, 3,5,5-$d_4$)benzene

Trans-4-phenylcyclohexane-2,2,6,6-$d_4$ carbaldehyde prepared in (2-b) was reacted with a Wittig reagent prepared from methyltriphenylphosphonium iodide in the same manner as in (2-c) to obtain trans-1-ethenyl-4-phenylcyclohexane-2, 2,6,6-$d_4$. This compound was further reacted in the same manner as in (1-d) and (1-e) to obtain the title compound. The phase transition temperatures of this compound are shown in Table 2.

EXAMPLE 12

Synthesis of 1-Cyano-4-[trans-4-(trans-1-propenyl) cyclohexyl-3,3,5,5-$d_4$]benzene The same procedure as in Example 11 was repeated, except for replacing the Wittig reagent prepared from methyltriphenylphosphonium iodide with that prepared from ethyltriphenylphosphonium bromide, to obtain trans-1-(cis-1-propenyl)-4-phenylcyclohexane-2, 2,6,6-$d_4$. This compound (1.0 g) was dissolved in 5 ml of toluene, and 10 ml of 10% hydrochloric acid was added to the solution. To the mixture was further added 0.25 g of sodium benzenesulfinate, followed by heating under reflux for 10 hours. After allowing to cool, 50 ml of toluene was added to the reaction mixture, and the aqueous layer was separated. Any insoluble matter was removed, and the mother liquor was washed successively with 2% hydrochloric acid, saturated aqueous solution of sodium bicarbonate, and water. The solvent was removed by distillation under reduced pressure to obtain an about 3/1 isomeric mixture of trans-1-(trans-1-propenyl)-4-phenylcyclohexane-2, 2,6,6-$d_4$ and trans-1-(cis-1-propenyl)-4-phenylcyclohexane-2, 2,6,6-$d_4$. The resulting product was purified by silica gel column chromatography using a hexane-ethyl acetate mixed solvent as an eluent. Recrystallization from ethanol gave 0.62 g of trans-1-(trans-1-propenyl)-4-phenylcyclohexane-2, 2,6,6-$d_4$. This compound was further reacted in the same manner as in (1-d) and (1-e) to obtain the title compound. The phase transition temperatures of this compound are shown in Table 2.

EXAMPLE 13

Synthesis of 3,4-Difluoro-1-[trans-4-(trans-4-propylcyclohexyl) cyclohexyl-2,2,6-$d_3$]benzene

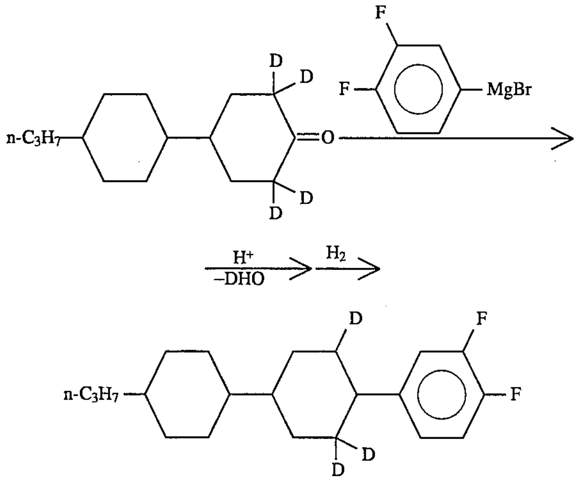

(13-a) Deuteration of 4-(trans-4-propylcyclohexyl) cyclohexanone:

4-(Trans-4-propylcyclohexyl)cyclohexanone-2,2,6,6-$d_4$ was obtained in the same manner as in (1-a), except for replacing trans-4-propylcyclohexanone with 4-(trans-4-propylcyclohexyl cyclohexanone.

(13-b) Synthesis of 3,4-difluoro-1-[trans-4-(trans-4-propylcyclohexyl) cyclohexyl-2,2,6-$d_3$]benzene:

3,4-Difluoro-1-[trans-4-(trans-4-propylcyclohexyl) cyclohexyl-2,2,6-$d_3$]benzene was obtained in the same manner as in Example 6, except for replacing 4-pentyloxycyclohexanone-2, 2,6,6-$d_4$ with 4-(trans-4-propylcyclohexyl) cyclohexanone-2,2,6,6-$d_4$ prepared in (13-a). The phase transition temperatures of this compound are shown in Table 2.

EXAMPLE 14

Synthesis of 3,4-Difluoro-1-[trans-4-(trans-4-butylcyclohexyl) cyclohexyl-2,2,6-$d_3$]benzene The title compound was prepared in the same manner as in Example 13, except for replacing 4-(trans-4-propylcyclohexyl) cyclohexanone with 4-(trans-4-butylcyclohexyl) cyclohexanone. The phase transition temperatures of this compound are shown in Table 2.

EXAMPLE 15

Synthesis of 3,4-Difluoro-1-[2-[trans-4-(trans-4-propylcyclohexyl) cyclohexyl-2,2,6,6-$d_4$]ethyl]benzene (15-a) Synthesis of 4-(trans-4-propylcyclohexyl)cyclohexane-2, 2,6,6-$d_4$ ethanal:

4-(Trans-4-propylcyclohexyl)cyclohexanone-2,2,6,6-$d_4$ obtained in (13-a) was treated in the same manner as in the first half of Example 10 to obtain 4-(trans-4-propylcyclohexyl) cyclohexane-2,2,6,6-$d_4$ ethanal.

(15-b) Synthesis of 3,4-difluoro-1-[2-[trans-4-(trans-4-propylcyclohexyl) cyclohexyl-2,2,6,6-$d_4$]ethyl]benzene:

A Grignard request was prepared from 1-bromo-3,4-difluorobenzene. 4-(Trans-4-propylcyclohexyl)cyclohexane-2, 2,6,6-$d_4$ ethanal prepared in (15-a) and the resulting Grignard reagent were reacted in the same manner as in Example 6 to obtain the title compound. The phase transition temperatures of this compound are shown in Table 2.

EXAMPLE 16

Synthesis of 3,4-Difluoro-1-[trans-4-(trans-4-propylcyclohexyl-3, 3,5,5-$d_4$)cyclohexyl]benzene

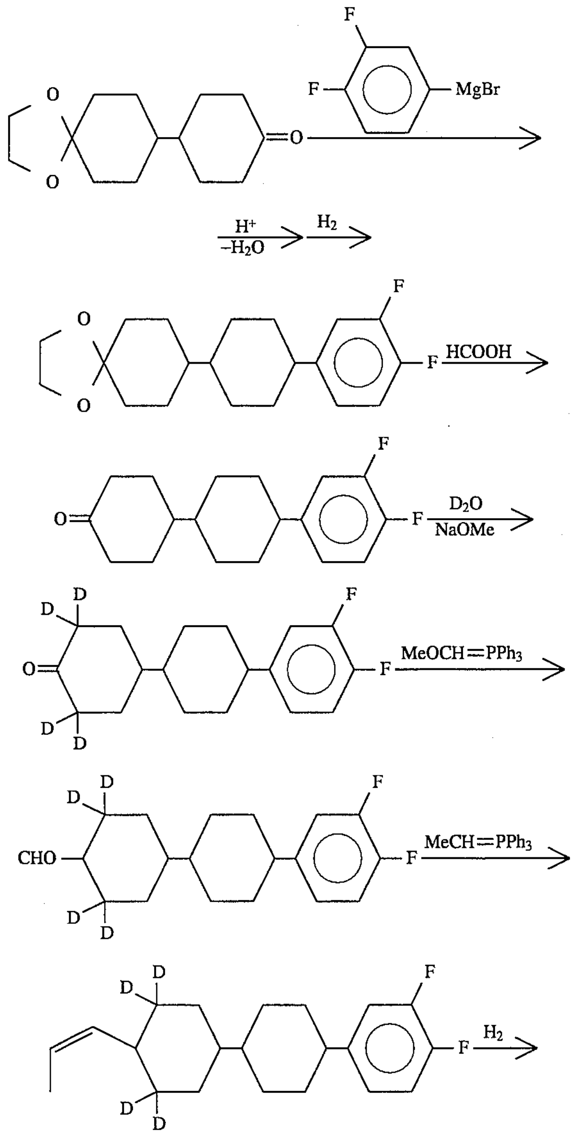

-continued

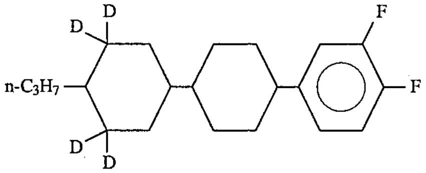

(16-a) Synthesis of 4-[trans-4-(3,4-difluorophenyl) cyclohexyl]cyclohexanone-2,2,6,6-$d_4$:

A Grignard reagent was prepared from 1-bromo-3,4-difluorobenzene and magnesium in THF, and a THF solution of bicyclohexane-4,4'-dione monoethyleneacetal was added thereto dropwise while cooling with ice. After allowing the mixture to react at room temperature for 1 hour, the reaction mixture was worked-up in a conventional manner to obtain crude crystals of 4-[4-hydroxy-4-(3,4-difluorophenyl) cyclohexyl]cyclohexanone ethyleneacetal. The crude crystals were dissolved in toluene, and a small amount of potassium bisulfate was added thereto, followed by refluxing for 10 hours while removing water. After cooling to room temperature, water was added to the reaction mixture, and the product was extracted with toluene. The solvent was removed by distillation to obtain white crystals of 4-[4-(3, 4-difluorophenyl)-3-cyclohexyl]cyclohexanone ethyleneacetal. Triethylamine and a catalytic amount of palladium-on-carbon were added to a toluene solution of the product, and the mixture was allowed to react in an autoclave at a hydrogen pressure of 5 kg/$cm^2$ for 3 hours. The catalyst was removed by filtration, and the filtrate was concentrated. The resulting crude product were recrystallized from ethanol to obtain white crystals of 4-[trans-4-(3,4-difluorophenyl) cyclohexyl]cyclohexanone ethyleneacetal. Formic acid was added to a toluene solution of the product, followed by stirring at room temperature for 4 hours. Water was added thereto, and the organic layer was separated, washed with a sodium bicarbonate aqueous solution, and dried. The solvent was removed by distillation, and the residue was recrystallized from ethanol to obtain white crystals of 4-[trans-4-(3, 4-difluorophenyl)cyclohexyl]cyclohexanone. The resulting product was deuterated in the same manner as in (1-a) to obtain 4-[trans-4-(3,4-difluorophenyl)cyclohexyl]cyclohexanone-2,2,6,6-$d_4$. (16-b) Synthesis of 4-[trans-4-(3,4-difluorophenyl) cyclohexyl]cyclohexane-2,2,6,6-$d_4$ carbaldehyde:

4-[Trans-4-(3,4-difluorophenyl)cyclohexyl]cyclohexane-2,2,6,6-$d_4$ carbaldehyde was obtained from 4 -[trans-4-(3, 4-difluorophenyl) cyclohexyl]cyclohexanone-2,2,6,6-$d_4$ obtained in (16-a) in the same manner as in (2-b). (16-c) Synthesis of 3,4-Difluoro-1-[trans-4-[trans-4-(cis-1-propenyl) cyclohexyl-3,3,5,5-$d_4$]cyclohexyl]benzene:

3,4-Difluoro-1-[trans-4-[trans-4-(cis-1-propenyl) cyclohexyl-3,3,5,5-$d_4$]cyclohexyl]benzene was obtained from 4-[trans-4-(3,4-difluorophenyl) cyclohexyl]cyclohexane-2, 2,6,6-$d_4$ carbaldehyde obtained in (16-b) in the same manner as in (2-c). (16-d) Synthesis of 3,4-difluoro-1-[trans-4-(trans-4-propylcyclohexyl-3, 3,5,5-$d_4$)cyclohexyl]benzene:

3,4-Difluoro-1-[trans-4-[trans-4-(cis-1-propenyl)cyclohexyl-3, 3,5,5-$d_4$]cyclohexyl]benzene obtained in (16-c) was hydrogenated in the same manner as in (2-d) to obtain 3,4-difluoro-1-[trans-4-(trans-4-propylcyclohexyl-3, 3,5,5-$d_4$)cyclohexyl]benzene. The phase transition temperatures of this compound are shown in Table 2.

EXAMPLE 17

Synthesis of 3,4-Difluoro-1-[trans-4-[trans-4-(trans-1-propenyl) cyclohexyl-3,3,5,5-$d_4$]cyclohexyl]benzene The title compound was obtained by isomerizing the side chain of 3,4-difluoro-1-[trans-4-[trans-4-(cis-1-propenyl- )cyclohexyl-3, 3,5,5-$d_4$]cyclohexyl]benzene obtained in (16-c) to a trans-form in the same manner as in Example 12. The phase transition temperatures of this compound are shown in Table 2.

EXAMPLE 18

Synthesis of 3,4,5-Trifluoro-1-[trans-4-(trans-4-propylcyclohexyl) cyclohexyl-2,2,6-$d_3$]benzene The title compound was obtained in the same manner as in Example 13, except for replacing 1-bromo-3,4-difluorobenzene with 1-bromo-3,4,5-trifluorobenzene. The phase transition temperatures of this compound are shown in Table 2.

EXAMPLE 19

Synthesis of 3,4,5-Trifluoro-1-[trans-4-(trans-4-butylcyclohexyl) cyclohexyl-2,2,6-$d_3$]benzene The title compound was obtained in the same manner as in Example 14, except for replacing 1-bromo-3,4-difluorobenzene with 1-bromo-3,4,5-trifluorobenzene. The phase transition temperatures of this compound are shown in Table 2.

EXAMPLE 20

Synthesis of 3,4,5-Trifluoro-1-[2-[trans-4-(trans-4-propylcyclohexyl) cyclohexyl-2,2,6,6-$d_4$]ethyl]benzene The title compound was obtained in the same manner as in Example 15, except for replacing 1-bromo-3,4-difluorobenzene with 1-bromo-3,4,5-trifluorobenzene. The phase transition temperatures of this compound are shown in Table 2.

EXAMPLE 21

Synthesis of 4-Trifluoromethoxy-1-[trans-4-trans-4-propylcyclohexyl) cyclohexyl-2,2,6-$d_3$]benzene The title compound was obtained in the same manner as in Example 13, except for replacing 1-bromo-3,4-difluorobenzene with 4-bromo-1-trifluoromethoxybenzene. The phase transition temperatures of this compound are shown in Table 2.

EXAMPLE 22

Synthesis of 3-Fluoro-4-cyano-1-[trans-4-(trans-4-propylcyclohexyl) cyclohexyl-2,2,6-$d_3$]benzene The title compound was obtained in the same manner as in Example 3, except for replacing 4-propylcyclohexanone-2, 2,6,6-$d_4$ with 4-(trans-4-propylcyclohexyl)cyclohexanone-2, 2,6,6-$d_4$. The phase transition temperatures of this compound are shown in Table 2.

EXAMPLE 23

Synthesis of 4-Methyl-1-[trans-4-[trans-4-(trans-1-propenyl) cyclohexyl-3,3,5,5-$d_4$]cyclohexyl]benzene 4-[Trans-4-(4-methylphenyl)cyclohexyl]cyclohexanone-2, 2,6,6-$d_4$ was obtained from bicyclohexane-4,4'-dione monoethyleneacetal and 4-bromoanisole in the same manner as in Example 16. The product was then led to the title compound as white crystals in the same manner as in Example 17. The phase transition temperatures of this compound are shown in Table 3.

EXAMPLE 24

Synthesis of 4-(Trans-4-pentyl-cyclohexyl-2, 2,6-$d_3$)-4'-ethylbiphenyl

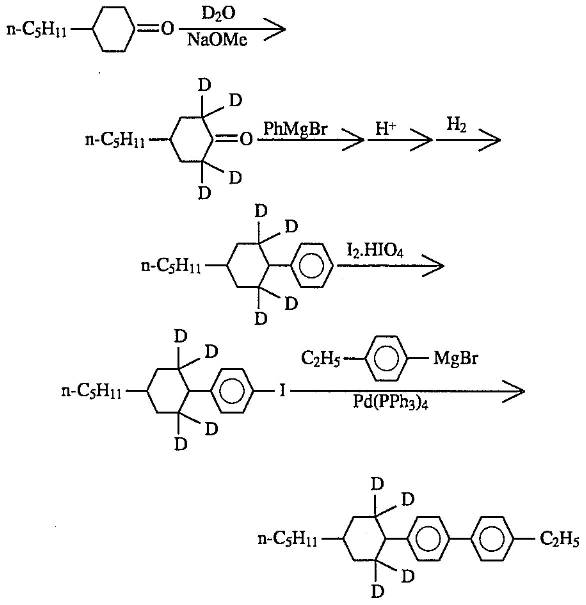

(24-a) Synthesis of (trans-4-pentylcyclohexyl-2,2,6-$d_3$) benzene:

(Trans-4-pentylcyclohexyl-2,2,6-$d_3$)benzene was obtained in the same manner as in (1-a) through (1-c), except for replacing 4-propylcyclohexanone with 4-pentylcyclohexanone.

(24-b) Synthesis of 1-(trans-4-pentylcyclohexyl-2,2,6-$d_3$)-4-iodobenzene:

In a mixed solvent of 200 ml of acetic acid, 7 ml of sulfuric acid, 40 ml of water, and 25 ml of 1,2-dichloroethane were dissolved in 57 g of (trans-4-pentylcyclohexyl-2, 2,6-$d_3$)benzene prepared in (24-a), 37.5 g of iodine, and 28.2 g of periodic acid dihydrate, and the mixture was heated for 1 hour with stirring. After allowing to cool, 200 ml of a 20% aqueous solution of sodium hydrogensulfite was added to the reaction mixture, followed by stirring for a while. The reaction product was extracted with 500 ml of hexane. The organic layer was washed with water and dried, and the solvent was distilled off. The residue was recrystallized from ethanol to obtain 58 g of 1-(trans-4-pentylcyclohexyl-2, 2,6-$d_3$)-4-iodobenzene.

(24-c) Synthesis of 4-(trans-4-pentylcyclohexyl-2,2,6-$d_3$)-4'-ethylbiphenyl:

A Grignard reagent was prepared from 15 g of 4-bromoethylbenzene and 2.4 g of magnesium in 100 ml of THF, and to the reaction system was added dropwise a solution of 19.5 g of 1-(trans-4-pentylcyclohexyl-2,2,6-$d_3$)-4-iodobenzene and 1.25 g of tetrakis (triphenylphosphine)palladium (0 ) in 100 ml of THF at 30° C. After stirring for 1 hour, 1% hydrochloric acid was added thereto, and the product was extracted with ethyl acetate. The extract was washed with water and dried. The solvent was distilled off, and the thus obtained oily crude product was purified by silica gel column chromatography using hexane as an eluent to obtain 19.0 g of 4-(trans-4-pentylcyclohexyl-2,2,6-$d_3$)-4'-ethylbiphenyl. The phase transition temperatures of this compound are shown in Table 3.

EXAMPLE 25

Synthesis of 4-(Trans-4-propylcyclohexyl-2, 2,6-$d_3$)-3',4'-difluorobiphenyl The title compound was obtained in the same manner as in Example 24, except for replacing (trans-4-pentylcyclohexyl-2, 2,6-$d_3$)benzene with (trans-4-propylcyclohexyl-2, 2,6-$d_3$)benzene in (24-b) and replacing 4-bromoethylbenzene with 1-bromo-3,4-difluorobenzene in (24-c). The phase transition temperatures of this compound are shown in Table 3.

EXAMPLE 26

Synthesis of 4-(Trans-4-propylcyclohexyl-2, 2,6-$d_3$)-4'-cyanobiphenyl 4-(Trans-4-propylcyclohexyl-2,2,6-$d_3$)biphenyl was obtained in the same manner as in Example 25, except for replacing 1-bromo-3,4-difluorobenzene with bromobenzene. The product was cyanogenated in the same manner as in (1-d) and (1-e) to obtain the title compound. The phase transition temperatures of this compound are shown in Table 3.

EXAMPLE 27

Synthesis of 3,4-Difluoro-1-[4-(trans-4 -propylcyclohexyl-2,2,6,6-$d_3$)phenyl]ethynylbenzene

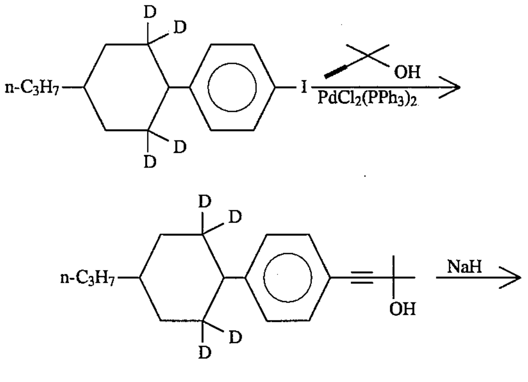

-continued

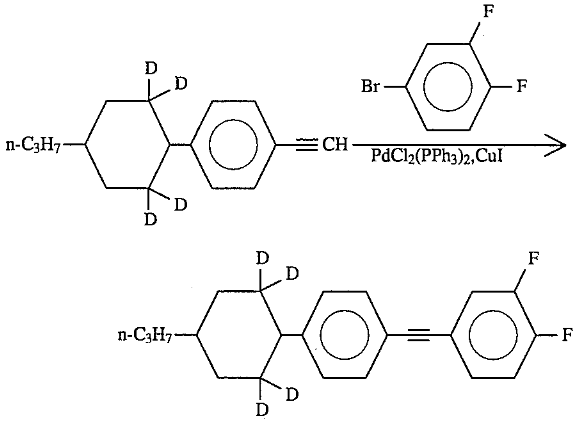

(27-a) Synthesis of 4-[4-(trans-4-propylcyclohexyl-2,2,6-$d_3$)phenyl]-2-methyl-3-butyn-2-ol:

In 40 ml of triethylamine were dissolved 14.4 g of 1 (trans-4-pentylcyclohexyl-2,2,6-$d_3$)-4-iodobenzene prepared in Example 25 and 5.1 g of 2-methyl-3-butyn-2-ol. To the solution were added 0.15 g of cuprous iodide and 0.2 g of dichlorobis(triphenylphosphine)palladium (II), followed by stirring at room temperature for 1 hour. To the reaction mixture was added 100 ml of water, and the product was extracted with 100 ml of ethyl acetate. The organic layer was washed with water and then with a saturated sodium chloride aqueous solution, and dried over anhydrous sodium sulfate. The solvent was distilled off, and the residue was purified by silica gel column chromatography using a 4:1 mixture of toluene and ethyl acetate as an eluent to obtain 12.2 g of 4-[4-(trans-4-propylcyclohexyl-2,2,6-$d_3$)phenyl]-2 -methyl-3-butyn-2-ol.

(27-b) Synthesis of 1-ethynyl-4-(trans-4-propylcyclox-hexyl-2,2,6-$d_3$)benzene:

In 30 ml of toluene was suspended 2.0 g of sodium hydride, and a solution of the whole portion of the 4-[4-(trans-4 -propylcyclohexyl-2,2,6-$d_3$)phenyl]-2-methyl-3-butyn-2-ol obtained in (27-a) in 70 ml of toluene was added dropwise to the suspension at room temperature over 30 minutes. The mixture was heated under reflux for 1 hour with stirring, followed by allowing the cool to room temperature. The reaction mixture was poured into 100 ml of water, and the organic layer was separated, washed successively with water and a saturated sodium chloride aqueous solution, and dried over anhydrous sodium sulfate. The solvent was removed by distillation, and the residue was purified by silica gel column chromatography using hexane as an eluent to obtain 8.8 g of 1-ethynyl-4-(trans-4-propylcyclohexyl-2,2,6-$d_3$)benzene.

(27-c) Synthesis of 3,4-difluoro-1-[4-(trans-4-propylcyclohexyl-2,2,6 -$d_3$)phenyl]ethynylbenzene:

In a mixture of 12 ml of triethylamine and 30 ml of DMF were dissolved 3.5 g of 1-ethynyl-4-trans-4 -propylcyclohexyl-2,2,6-$d_3$)benzene and 3.0 g of 1-bromo-3,4 -difluorobenzene. To the solution were added 0.06 g of cuprous idodide and 0.06 g of dichlorobis(triphenylphosphine)palladium (II), and the mixture was stirred at room temperature for 30 minutes and then heated under reflux for 3 hours. After cooling to room temperature, 100 ml of water was added thereto, and the reaction product was extracted with 100 ml of toluene. The organic layer was washed with water and then with a saturated sodium chloride aqueous solution, and dried over anhydrous sodium sulfate. The solvent was removed by distillation, and the residue was purified by silica gel column chromatography using hexane as an eluent and recrystallized from ethanol to obtain 3.8 g of 3,4-difluoro-1-[4-(trans-4-propylcyclohexyl-2,2,6-$d_3$)phenyl]ethynylbenzene. The phase transition temperatures of this compound are shown in Table 3.

EXAMPLE 28

Synthesis of 4-Butyl-1-[4-(trans-4-propyl-cyclohexyl-2,2,6-$d_3$)phenyl]ethynylbenzene The title compound was obtained in the same manner as in Example 27, except for replacing 1-bromo-3,4-difluorobenzene with 4-bromo-1-ethylbenzene. The phase transition temperatures of this compound are shown in Table 3.

EXAMPLE 29

Synthesis of 4-(Trans-4-pentylcyclohexyl)-4'-(trans-4-propylcyclohexyl-2,2,6-$d_3$)biphenyl (29-a) Synthesis of 1-bromo-4-(trans-4-pentylcyclohexyl)benzene:

In 30 ml of dichloromethane was dissolved 11.1. g of trans-4-pentylcyclohexylbenzene, and 0.1 g of iron powder and 0.05 g of iodine were added thereto. To the mixture was added dropwise 7.7 g of bromine dissolved in 20 ml of dichloromethane at 0° C. or lower. The mixture was stirred at −10° C. for 6 hours and then allowed to warm to room temperature. Water and then an aqueous solution of sodium hydrogensulfite were added to the reaction mixture, and the product was extracted with hexane. The extract was washed successively with a sodium bicarbonate aqueous solution, water and a saturated sodium chloride aqueous solution, and dried. The solvent was removed by distillation, and the resulting crude crystals were recrystallized from ethanol to give 4.8 g of 1-bromo-4-(trans-4-pentylcyclohexyl)benzene.

(29-b) Synthesis of 4-(trans-4-pentylcyclohexyl)-4'-(trans-4-propylcyclohexyl-2,2,6-$d_3$)biphenyl:

A Grignard reagent was prepared from 2.4 g of 1-bromo-4-(trans-4-pentylcyclohexyl)benzene prepared in (29-a) in the same manner as in (24-c). The resulting Grignard reagent was reacted with 2.2 g of 1-(trans-4-pentylcyclohexyl-2,2,6-$d_3$-4-iodobenzene prepared in Example 25 in the same manner as in (24-c) to obtain 2.6 g of 4-(trans-4-pentylcyclohexyl)-4'-(trans-4-propylcyclohexyl-2,2,6-$d_3$)biphenyl. The phase transition temperatures of this compound are shown in Table 3.

EXAMPLE 30

Synthesis of 2-Fluoro-4-(trans-4-pentylcyclo-hexyl)-4'-(trans-4-pentylcyclohexyl-2,2,6-$d_3$)biphenyl A Grignard reagent was prepared from commercially available 2-fluoro-4-bromobiphenyl, and the resulting Grignard reagent was reacted with 4-pentylcyclohexanone in the same manner as in (1-b) and (1-c) to obtain 2-fluoro-4-(trans-4-pentylcyclohexyl)biphenyl. The product was brominated in the same manner as in (29-a) to obtain 2-fluoro-4-(trans-4-pentylcyclohexyl)-4'-bromobiphenyl. A Grignard reagent was prepared therefrom and reacted with 4-pentylcyclohexanone-2,2,6,6-$d_4$ in the same manner as in Example 4 to obtain 2-fluoro-4-(trans-4-pentylcyclohexyl)-4'-(trans-4-pentylcyclohexyl-2,2,6-$d_3$)biphenyl. The phase transition temperatures of this compound are shown in Table 3.

EXAMPLE 31

Preparation of Liquid Crystal Composition

A mother liquid crystal composition (A) having the following composition was prepared.

Composition of Mother Liquid Crystal composition (A):

20%

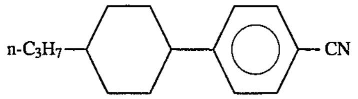

16%

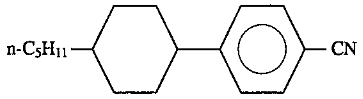

16%

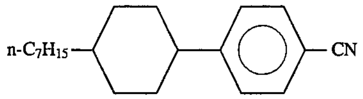

8%

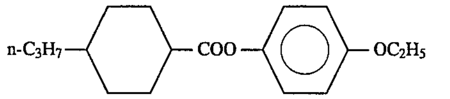

8%

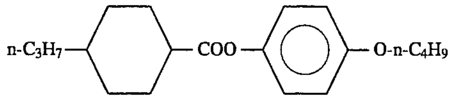

8%

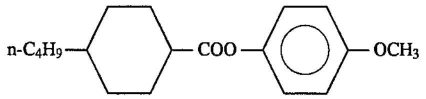

8%

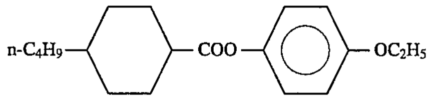

8%

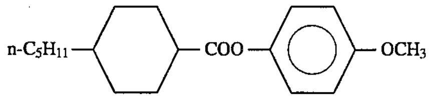

8%

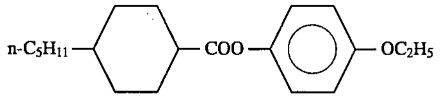

wherein the cyclohexane rings are in a trans-configuration.

Composition (A) showed a nematic (N) phase at 54.5° C. or lower.

A liquid crystal composition (B) was prepared from 85% of liquid crystal composition (A) and 15% of 3,4-difluoro-1-[trans-4-(trans-4-propylcyclohexyl)cyclohexyl-2,2,6-$d_3$] benzene obtained in Example 13 shown in Table 2 (Compound No. 13). The upper temperature limit for the N phase of composition (B) was 62.2° C. When composition (B) was preserved at −20° C., no crystallization was observed even after 1 month.

COMPARATIVE EXAMPLE 1

A liquid crystal composition (C) was prepared from 85% of composition (A) and 15% of non-deuterated 3,4-difluoro-1-[trans-4-(trans-4-propylcyclohexyl)cyclohexyl] benzene of formula:

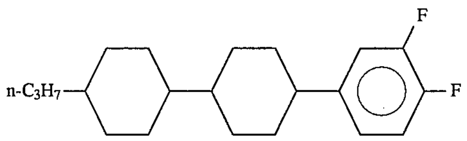

The upper temperature limit for the N phase of composition (C) was 62.3° C. When composition (C) was preserved at −20° C., crystallization was observed after 5 days.

From the results of Example 31 compared with Comparative Example 1, it is seen that the deuterated compound of formula (I) has excellent compatibility with a general-purpose liquid crystal material to provide a practical liquid crystal composition which is hardly crystallized even in a low temperature region.

EXAMPLE 32

Liquid crystal composition (B) having the following composition and characteristics was prepared.

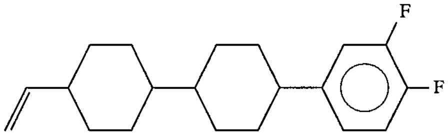

35%

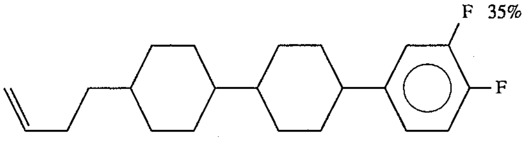

35%

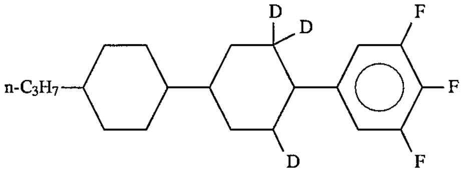

30%

$T_{N\text{-}I}$ Point: 110° C.

Threshold Voltage: 1.81 V $\Delta_\epsilon$: 7.0

$\Delta_n$: 0.087

Response Time: 28 msec

When composition (B) was preserved at 10° C., no crystallization was observed after 1 month.

EXAMPLE 33

Liquid crystal composition (B') having the following composition and characteristics was prepared.

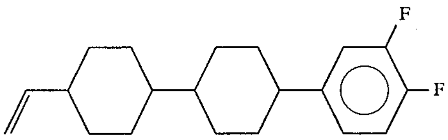

35%

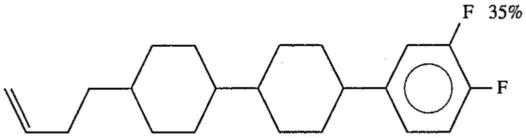

35%

-continued

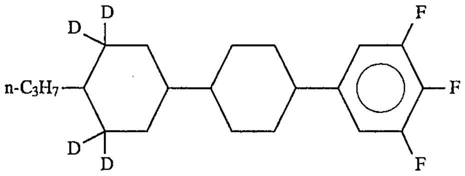

20%

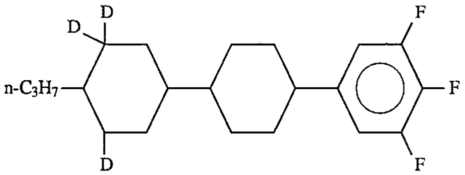

10%

$T_{N\text{-}I}$ Point: 108° C.

Threshold Voltage: 1.74 V $\Delta_\epsilon$: 7.2

$\Delta_n$: 0.086

Response Time: 24 msec

When composition (B') was preserved at 10° C., no crystallization was observed after 1 month.

COMPARATIVE EXAMPLE 2

Liquid crystal composition (a–1) having the following composition and characteristics was prepared.

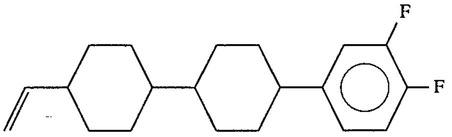

50%

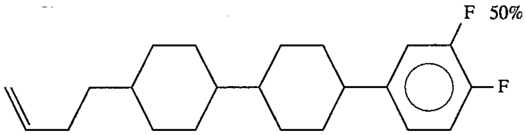

50%

$T_{N\text{-}I}$ Point: 117° C.

$T_{C\text{-}N}$ Point: 11° C.

Threshold Voltage: 2.14 V $\Delta_\epsilon$: 4.8

$\Delta_n$: 0.090

Response Time: 25 msec

When composition (a–1) was preserved at 10° C., crystallization was observed after 3 days.

COMPARATIVE EXAMPLE 3

Liquid crystal composition (b) having the following composition and characteristics was prepared.

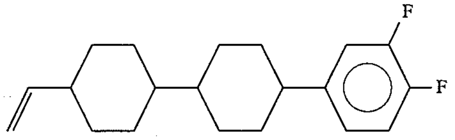

35%

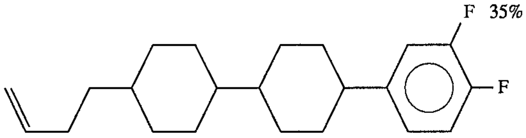

35%

-continued

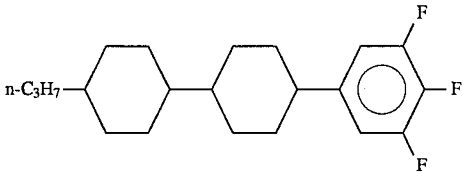

30%

$T_{N-I}$ Point: 111° C.

Threshold Voltage: 1.83 V $\Delta_\epsilon$: 7.0

$\Delta_n$: 0.087

Response Time: 30 msec

When composition (b) was preserved at 10° C., crystallization was observed after 3 days.

EXAMPLE 34

Liquid crystal composition (C) having the following composition and characteristics was prepared.

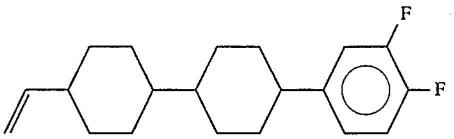

35%

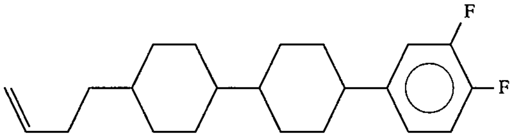

35%

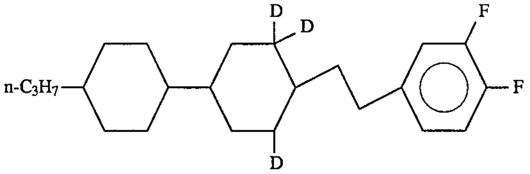

8%

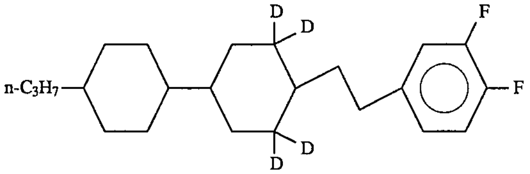

22%

$T_{N-I}$ Point: 116° C.

Threshold Voltage: 2.10 V $\Delta_\epsilon$: 5.2

$\Delta_n$: 0.086

Response Time: 25 msec

When composition (C) was preserved at 0° C., no crystallization was observed after 1 month.

COMPARATIVE EXAMPLE 4

Liquid crystal composition (c) having the following composition and characteristics was prepared.

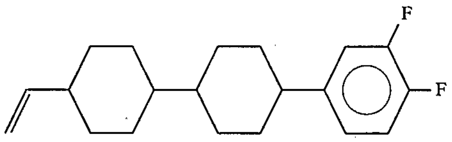

35%

-continued

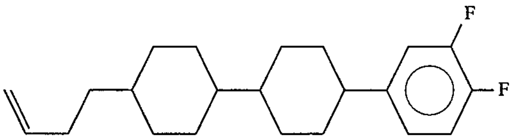

35%

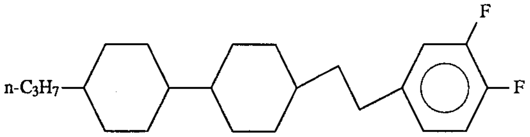

30%

$T_{N-I}$ Point: 116° C.

Threshold Voltage: 2.15 V $\Delta_\epsilon$: 5.1

$\Delta_n$: 0.086

Response Time: 28 msec

When composition (c) was preserved at 0° C., crystallization was observed after 4 days.

EXAMPLE 35

Liquid crystal composition (D) having the following composition was prepared.

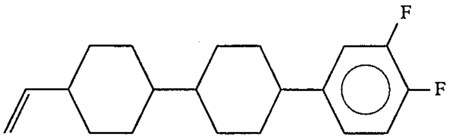

35%

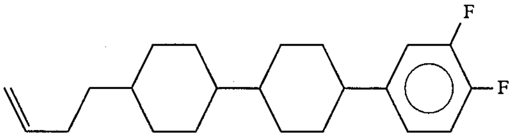

35%

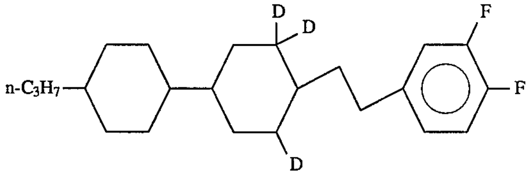

8%

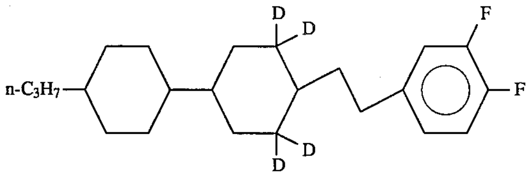

22%

$T_{N-I}$ Point: 109° C.

Threshold Voltage: 1.83 V $\Delta_\epsilon$: 6.2

$\Delta_n$: 0.085

Response Time: 29 msec

When composition (D) was preserved at 0° C., no crystallization was observed after 1 month.

COMPARATIVE EXAMPLE 5

Liquid crystal composition (d) having the following composition and characteristics was prepared.

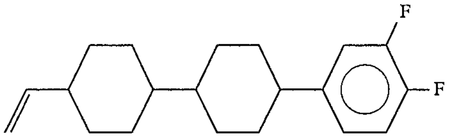
35%

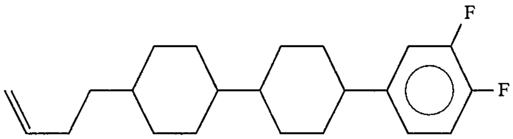
35%

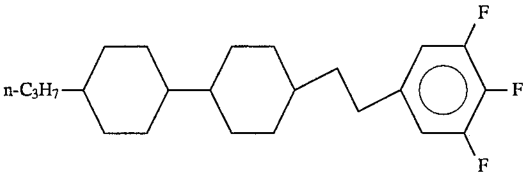
30%

$T_{N-I}$ Point: 110° C.
Threshold Voltage: 1.86 V
$\Delta_\epsilon$: 6.2
$\Delta_n$: 0.085
Response Time: 32 msec When composition (d) was preserved at 0° C., crystallization was observed after 3 days.

EXAMPLE 36

Liquid crystal composition (E) having the following composition and characteristics was prepared.

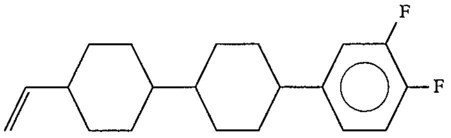
35%

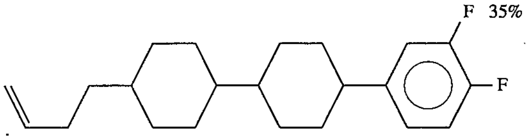
35%

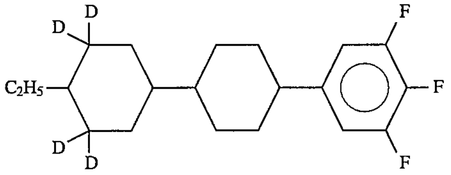
20%

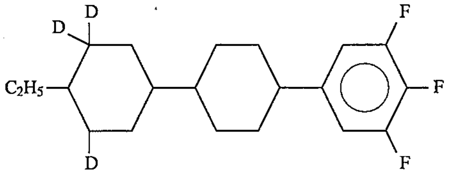
10%

$T_{N-I}$ Point: 94° C.
Threshold Voltage: 1.66 V
$\Delta_\epsilon$: 6.2
$\Delta_n$: 0.082
Response Time: 31 msec When composition (E) was preserved at 10° C., no crystallization was observed even after 1 month.

EXAMPLE 37

Liquid crystal composition (E') having the following composition and characteristics was prepared.

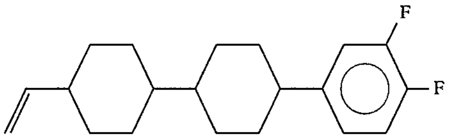
35%

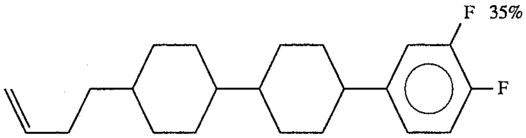
35%

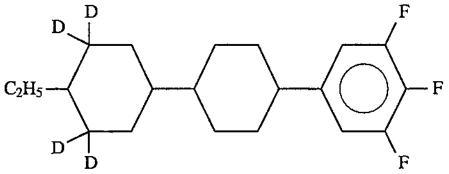
10%

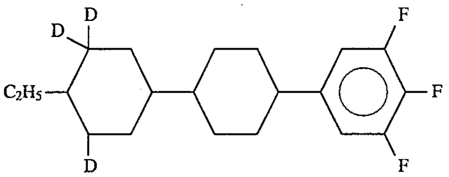
5%

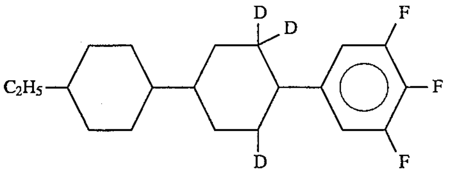
15%

$T_{N-I}$ Point: 95° C.
Threshold Voltage: 1.69 V
$\Delta_\epsilon$: 6.1
$\Delta_n$: 0.082
Response Time: 33 msec When composition (E') was preserved at 5° C., crystallization was observed after 1 month.

COMPARATIVE EXAMPLE 6

Liquid crystal composition (e) having the following composition and characteristics was prepared.

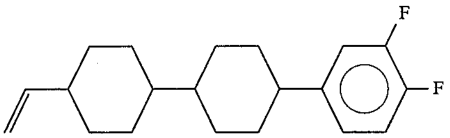
35%

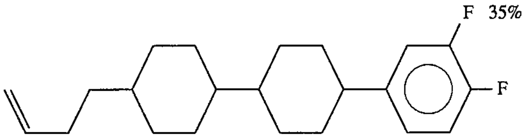
35%

-continued

30%

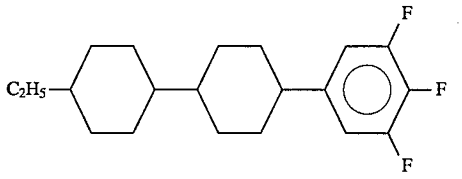

$T_{N-I}$ Point: 95° C.
Threshold Voltage: 1.74 V
$\Delta_\epsilon$: 6.1
$\Delta_n$: 0.082
Response Time: 35 msec When composition (e) was preserved at 10° C., crystallization was observed after 3 days.

EXAMPLE 38

Liquid crystal composition (F) having the following composition and characteristics was prepared.

35%

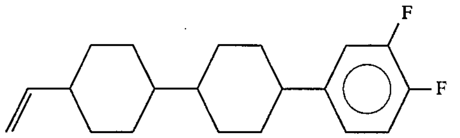

35%

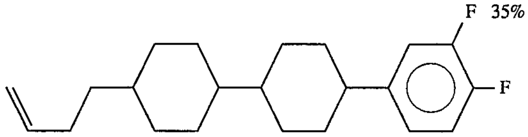

20%

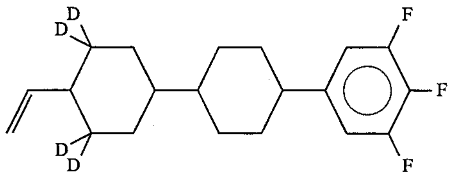

10%

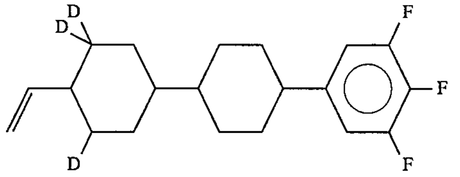

$T_{N-I}$ Point: 103° C.
Threshold Voltage: 1.70 V
$\Delta_\epsilon$: 6.1
$\Delta_n$: 0.087
Response Time: 23 msec When composition (F) was preserved at 10° C., no crystallization was observed after 1 month.

COMPARATIVE EXAMPLE 7

Liquid crystal composition (f) having the following composition and characteristics was prepared.

35%

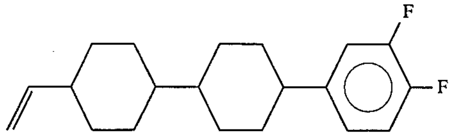

-continued

35%

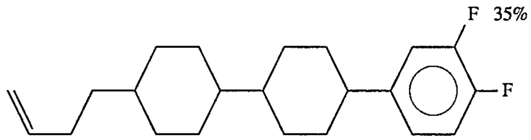

30%

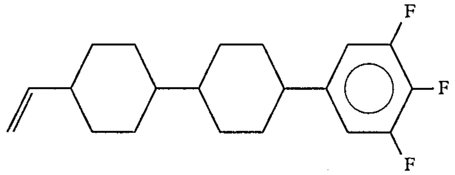

$T_{N-I}$ Point: 104° C.
Threshold Voltage: 1.79 V
$\Delta_\epsilon$: 6.0
$\Delta_n$: 0.087
Response Time: 27 msec When composition (f) was preserved at 10° C., crystallization was observed after 10 days.

EXAMPLE 39

Liquid crystal composition (G) having the following composition and characteristics was prepared.

35%

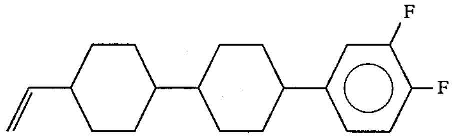

35%

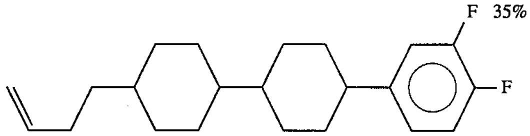

9%

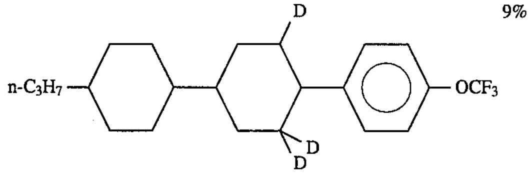

9%

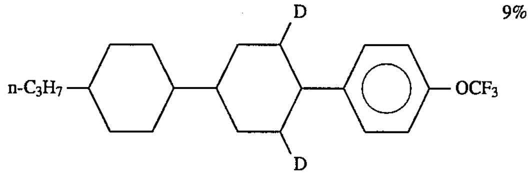

9%

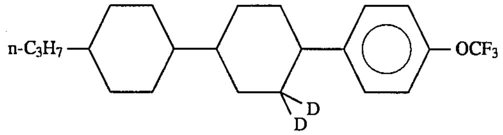

3%

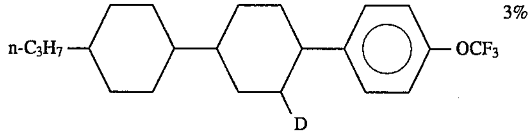

$T_{N-I}$ Point: 125° C.
Threshold Voltage: 2.18 V
$\Delta_\epsilon$: 5.4

$\Delta_n$: 0.089

Response Time: 21 msec

When composition (G) was preserved at 0° C., no crystallization was observed after 1 month.

COMPARATIVE EXAMPLE 8

Liquid crystal composition (g) having the following composition and characteristics was prepared.

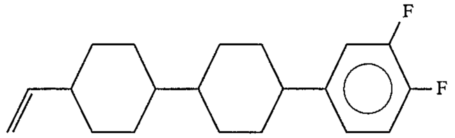

35%

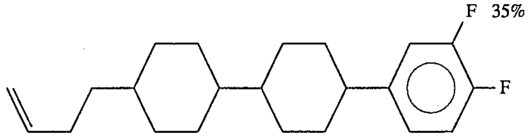

35%

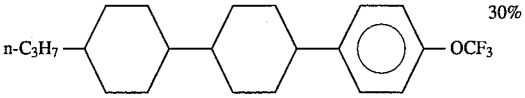

30%

$T_{N-I}$ Point: 125° C.

Threshold Voltage: 2.20 V $\Delta_\epsilon$: 5.3

$\Delta_n$: 0.089

Response Time: 24 msec

When composition (g) was preserved at 0° C., crystallization was observed after 3 days.

EXAMPLE 40

Liquid crystal composition (H) having the following composition and characteristics was prepared.

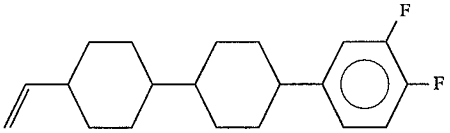

35%

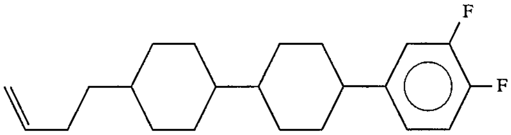

35%

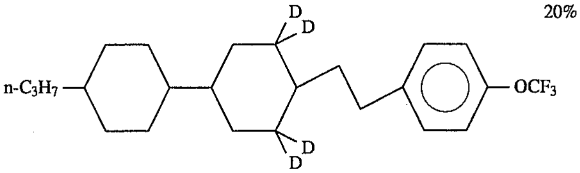

20%

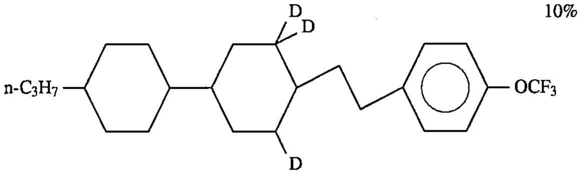

10%

$T_{N-I}$ Point: 121° C.

Threshold Voltage: 2.23 V $\Delta_\epsilon$: 5.1

$\Delta_n$: 0.088

Response Time: 25 msec

When composition (H) was preserved at −10° C., no crystallization was observed after 1 month.

COMPARATIVE EXAMPLE 9

Liquid crystal composition (h) having the following composition and characteristics was prepared.

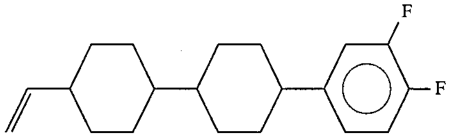

35%

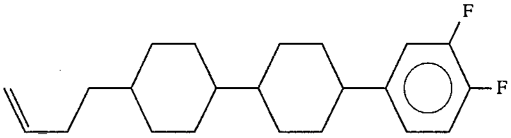

35%

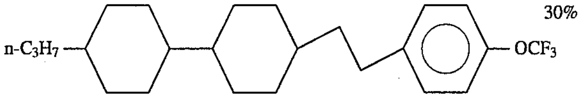

30%

$T_{N-I}$ Point: 121° C.

Threshold Voltage: 2.29 V $\Delta_\epsilon$: 5.0

$\Delta_n$: 0.089

Response Time: 27 msec

When composition (h) was preserved at −10° C., crystallization was observed after 4 days.

EXAMPLE 41

Liquid crystal composition (I) having the following composition and characteristics was prepared.

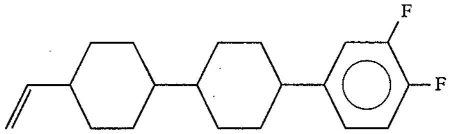

35%

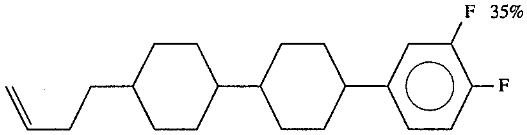

35%

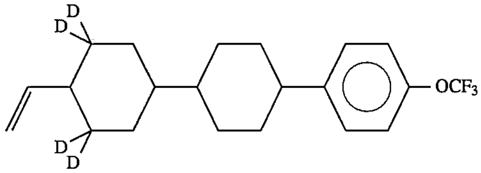

20%

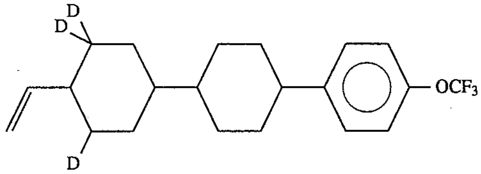

10%

$T_{N-I}$ Point: 120° C.

Threshold Voltage: 2.10 V $\Delta_\epsilon$: 4.8

$\Delta_n$: 0.090

Response Time: 17 msec

When composition (I) was preserved at 0° C., no crystallization was observed even after 1 month.

COMPARATIVE EXAMPLE 10

Liquid crystal composition (i) having the following composition and characteristics was prepared.

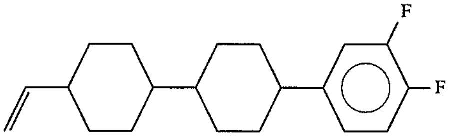

35%

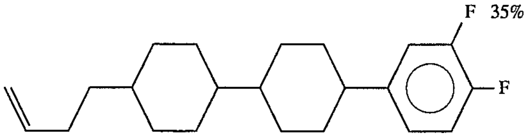

35%

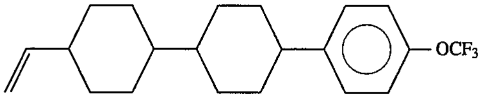

30%

$T_{N-I}$ Point: 121° C.

Threshold Voltage: 2.21 V $\Delta_\epsilon$: 4.7

$\Delta_n$: 0.091

Response Time: 20 msec

When composition (i) was preserved at 0° C., crystallization was observed after 3 days.

EXAMPLE 42

Liquid crystal composition (J) having the following composition and characteristics was prepared.

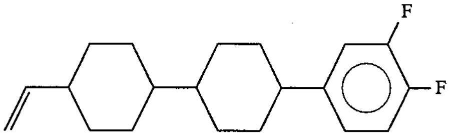

35%

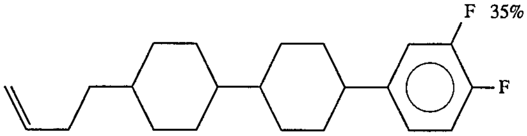

35%

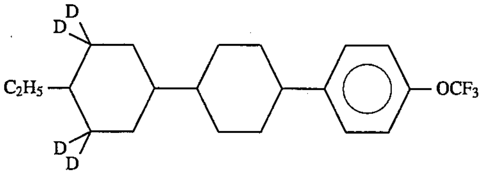

20%

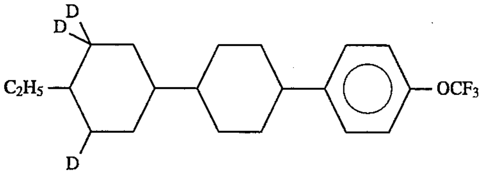

10%

$T_{N-I}$ Point: 115° C.

Threshold Voltage: 1.98 V $\Delta_\epsilon$: 5.2

$\Delta_n$: 0.088

Response Time: 19 msec

When composition (J) was preserved at 0° C., no crystallization was observed after 1 month.

COMPARATIVE EXAMPLE 11

Liquid crystal composition (j) having the following composition and characteristics was prepared.

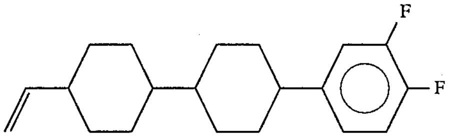

35%

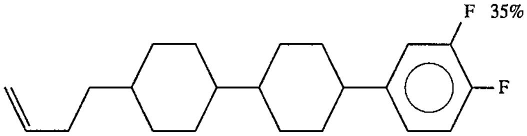

35%

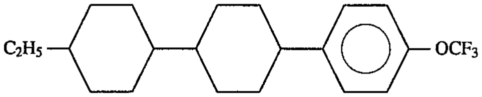

30%

$T_{N-I}$ Point: 115° C.

Threshold Voltage: 2.07 V $\Delta_\epsilon$: 5.0

$\Delta_n$: 0.088

Response Time: 23 msec

When composition (j) was preserved at 0° C., crystallization was observed after 2 days.

EXAMPLE 43

Liquid crystal composition (K) having the following composition and characteristics was prepared.

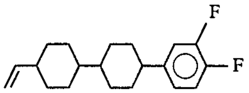

21.4%

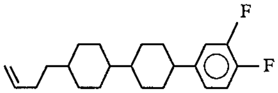

21.4%

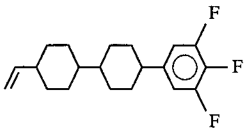

14.3%

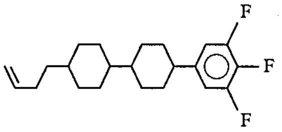

14.3%

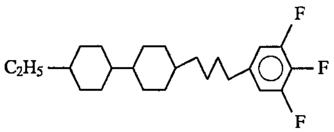

14.3%

-continued

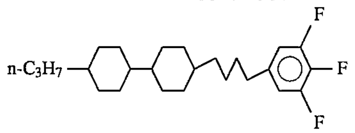

14.3%

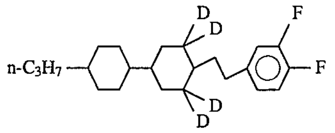

13%

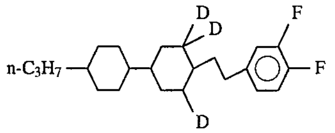

7%

$T_{N-I}$ Point: 98° C.

Threshold Voltage: 1.65 V $\Delta_\epsilon$: 6.6

$\Delta_n$: 0.080

Response Time: 33 msec

When composition (K) was preserved at −10° C., no crystallization was observed after 1 month.

COMPARATIVE EXAMPLE 12

Liquid crystal composition (k–1) having the following composition and characteristics was prepared.

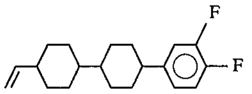

21.4%

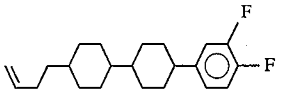

21.4%

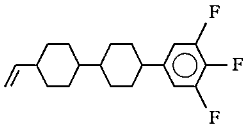

14.3%

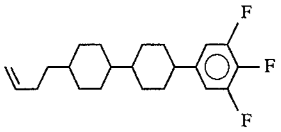

14.3%

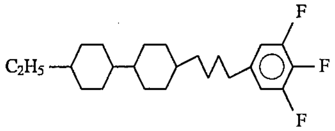

14.3%

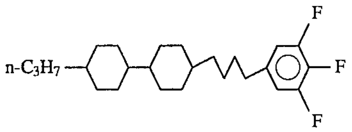

14.3%

$T_{N-I}$ Point: 92° C.

Threshold Voltage: 1.60 V $\Delta_\epsilon$: 6.8

$\Delta_n$: 0.080

Response Time: 38 msec

When composition (k–1) was preserved at −10° C., crystallization was observed after 5 days.

COMPARATIVE EXAMPLE 13

Liquid crystal composition (k–2) having the following composition and characteristics was prepared.

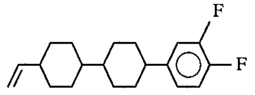

21.4%

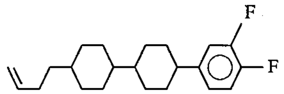

21.4

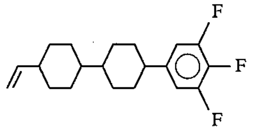

14.3%

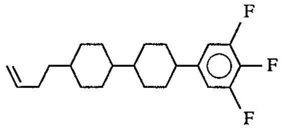

14.3%

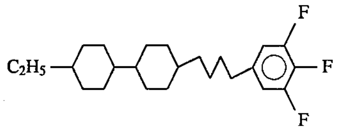

14.3%

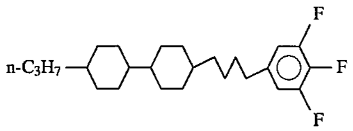

14.3%

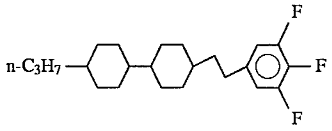

20%

$T_{N-I}$ Point: 98° C.

Threshold Voltage: 1.68 V $\Delta_\epsilon$: 6.5

$\Delta_n$: 0.080

Response Time: 35 msec

When composition (k–2) was preserved at −10° C., crystallization was observed after 9 days.

EXAMPLE 44

Liquid crystal composition (L) having the following composition and characteristics was prepared.

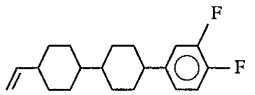

21.4%

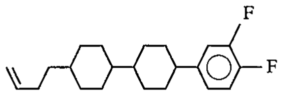

21.4%

-continued

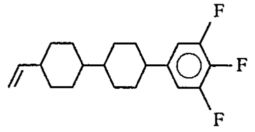

14.3%

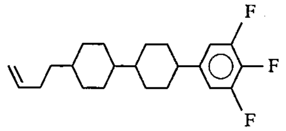

14.3%

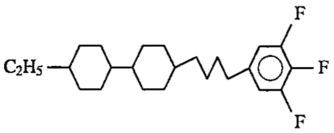

14.3%

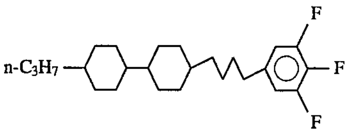

14.3%

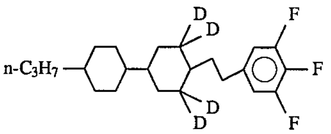

13%

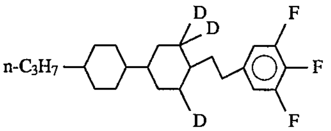

7%

$T_{N-I}$ Point: 93° C.

Threshold Voltage: 1.50 V $\Delta_\epsilon$: 7.3

$\Delta_n$: 0.079

Response Time: 35 msec

When composition (L) was preserved at −10° C., no crystallization was observed after 1 month.

COMPARATIVE EXAMPLE 14

Liquid crystal composition (l) having the following composition and characteristics was prepared.

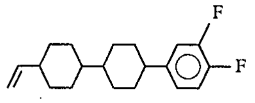

21.4%

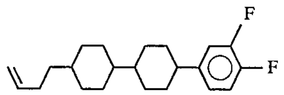

21.4%

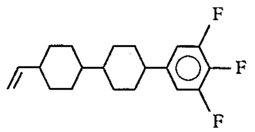

14.3%

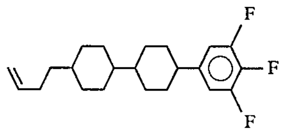

14.3%

-continued

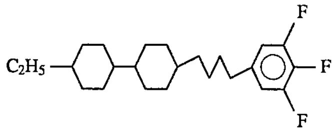

14.3%

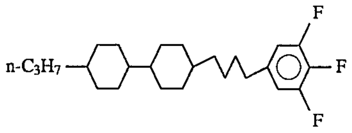

14.3%

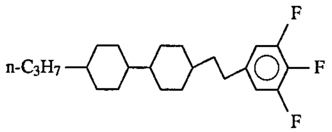

20%

$T_{N-I}$ Point: 94° C.

Threshold Voltage: 1.54 V $\Delta_\epsilon$: 7.2

$\Delta_n$: 0.080

Response Time: 38 msec

When composition (l) was preserved at −10° C., crystallization was observed after 7 days.

EXAMPLE 45

Liquid crystal composition (M) having the following composition and characteristics was prepared.

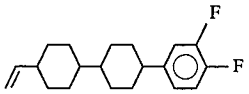

12.5%

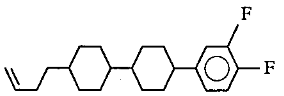

12.5%

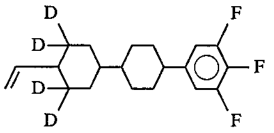

3%

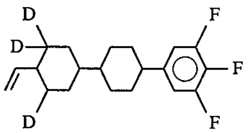

4%

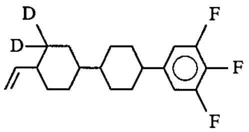

1%

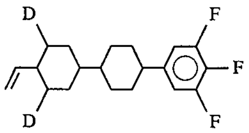

1%

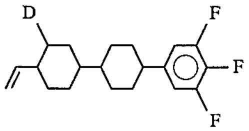

1%

-continued

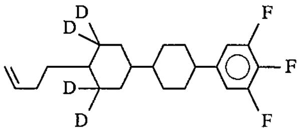
3%

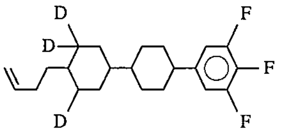
4%

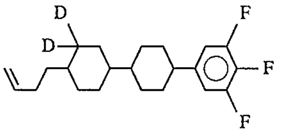
1%

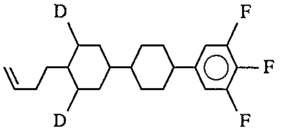
1%

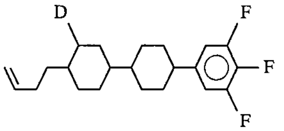
1%

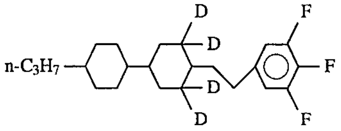
3%

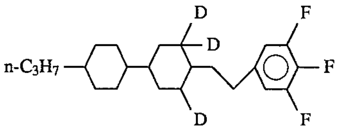
4%

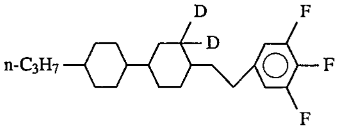
1%

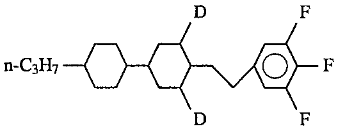
1%

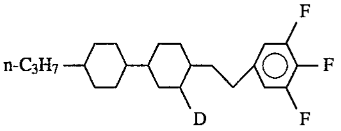
1%

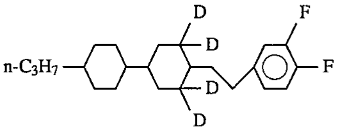
3%

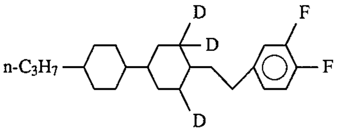
4%

-continued

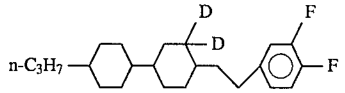
1%

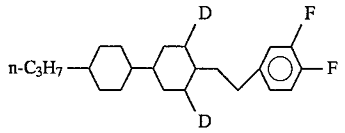
1%

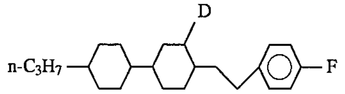
1%

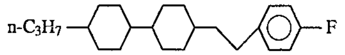
10%

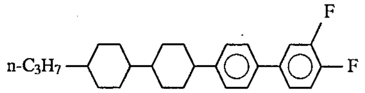
5%

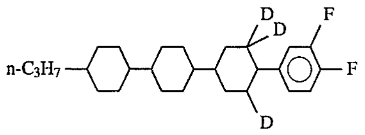
5%

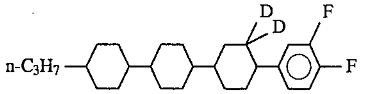
2%

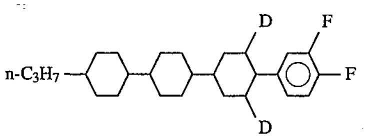
2%

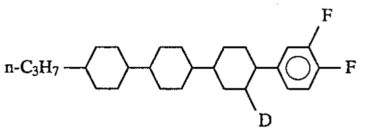
1%

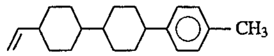
10%

$T_{N\text{-}I}$ Point: 112° C.
$T_{C\text{-}N}$ Point: −70° C.
Threshold Voltage: 1.9 V
$\Delta_\epsilon$: 5.5
$\Delta_n$: 0.086
Response Time: 24 msec Voltage Holding Ratio: 99% (/100° C.)

When composition (M) was preserved at −55° C., no crystallization was observed even after 3 months. A liquid crystal display for TFT driving prepared by using composition (M) exhibited satisfactory driving characteristics even in a low temperature region.

EXAMPLE 46

Liquid crystal composition (N) having the following composition was prepared.

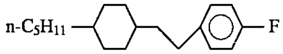
5%

-continued
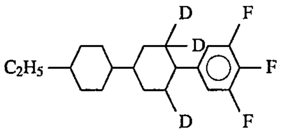
5%
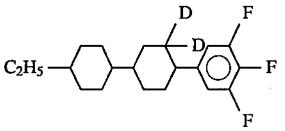
2%
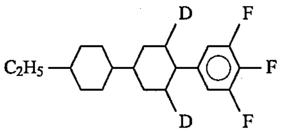
2%
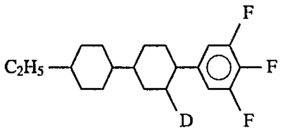
1%
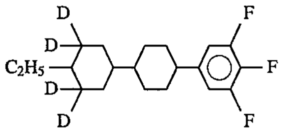
3%
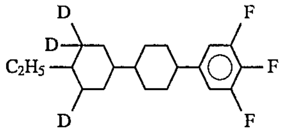
4%
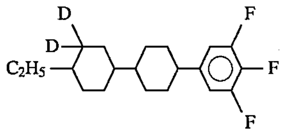
1%
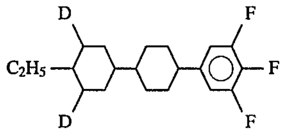
1%
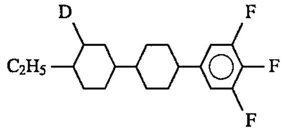
1%
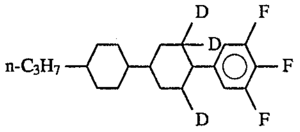
4%
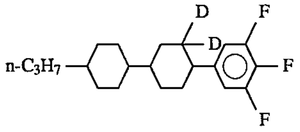
1.6%
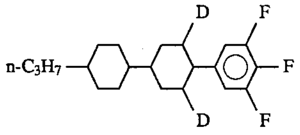
1.6%
-continued
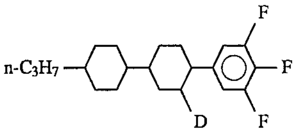
0.8%
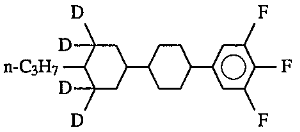
2.4%
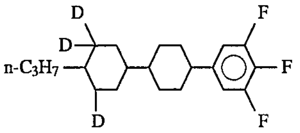
3.2%
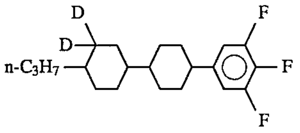
0.8%
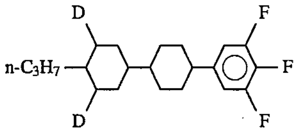
0.8%
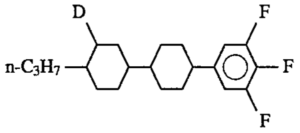
0.8%
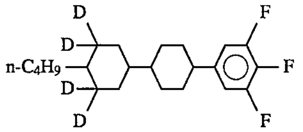
4.5%
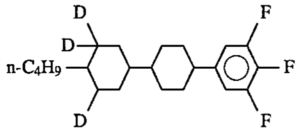
6%
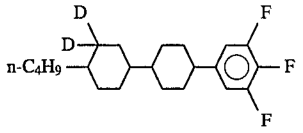
1.5%
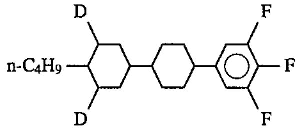
1.5%
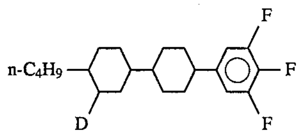
1.5%

-continued

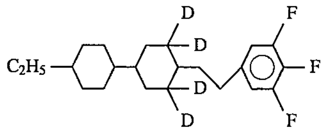

2.55%

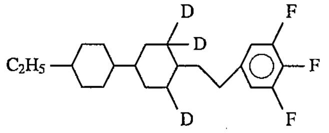

3.4%

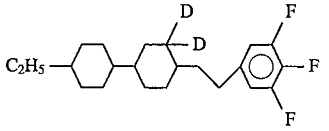

0.85%

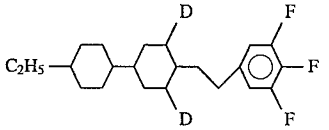

0.85%

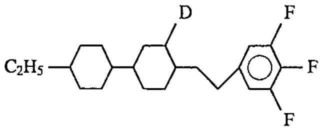

0.85%

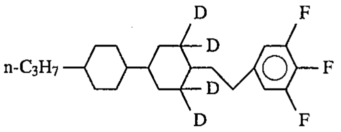

2.55%

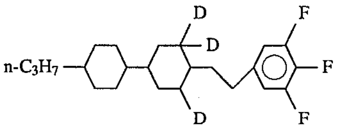

3.4%

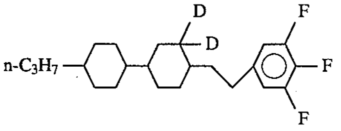

0.85%

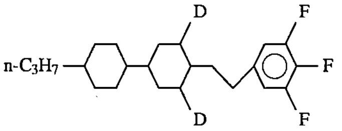

0.85%

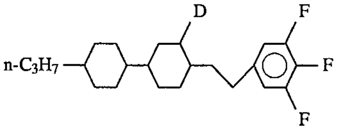

0.85%

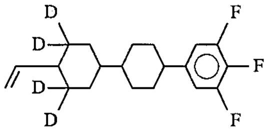

2.55%

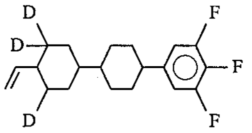

3.4%

-continued

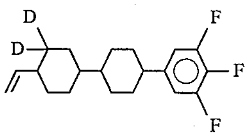

0.85%

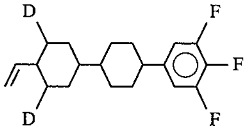

0.85%

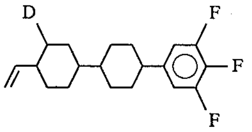

0.85%

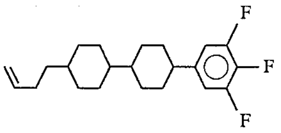

8.5%

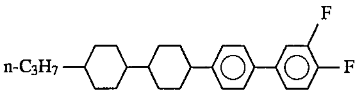

10%

$T_{N-I}$ Point: 86° C.
$T_{C-N}$ Point: −30° C.
Threshold Voltage: 1.10 V
$\Delta_\epsilon$: 9.2
$\Delta_n$: 0.080
Response Time: 33 msec When composition (N) was preserved at −25° C., no crystallization was observed even after 3 months. A liquid crystal display for TFT driving having a cell thickness of 4.5 μm which was prepared by using composition (N) exhibited satisfactory driving characteristics even in a low temperature region.

COMPARATIVE EXAMPLE 15

Liquid crystal composition (n) having the following composition and characteristics was prepared.

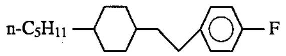

5%

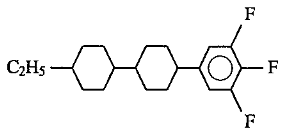

20%

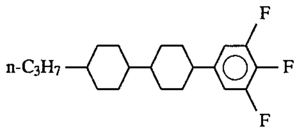

16%

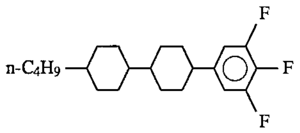

15%

-continued

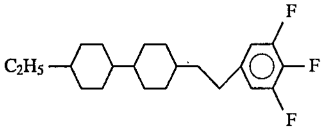

8.5%

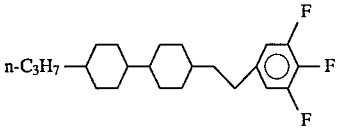

8.5%

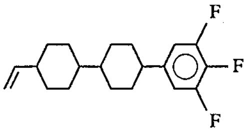

8.5%

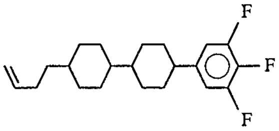

8.5%

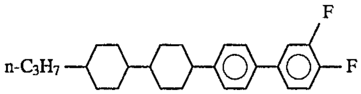

10%

$T_{N-I}$ Point: 87° C.

Threshold Voltage: 1.15 V $\Delta_\epsilon$: 9.1

$\Delta_n$: 0.080

Response Time: 38 msec

When composition (n) was preserved at 0° C., crystallization was observed after 1 day. The above measurement was made using a liquid crystal cell having a cell thickness of 4.5 μm.

EXAMPLE 47

Liquid crystal composition (P) having the following composition and characteristics was prepared.

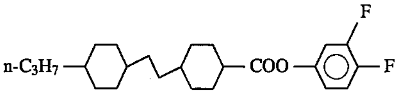

17%

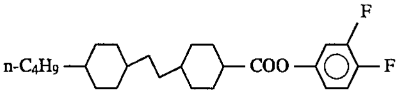

16.5%

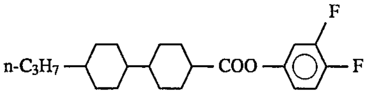

16.5%

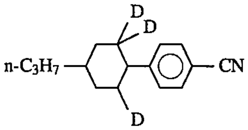

20%

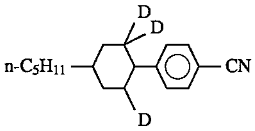

15%

-continued

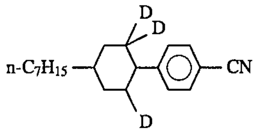

15%

$T_{N-I}$ Point: 84° C.

Threshold Voltage: 1.59 V $\Delta_\epsilon$: 9.9

$\Delta_n$: 0.099

$K_{33}/K_{11}$: 2.4

When composition (P) was preserved at 0° C., crystallization was observed after 14 days.

EXAMPLE 48

Liquid crystal composition (P') having the following composition and characteristics was prepared.

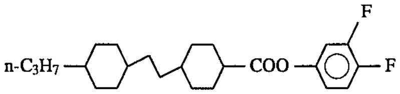

17%

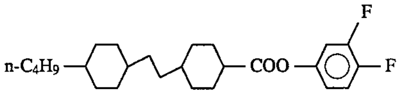

16.5%

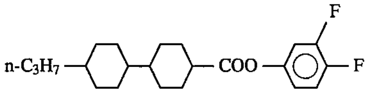

16.5%

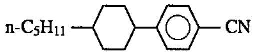

5%

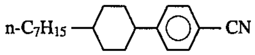

5%

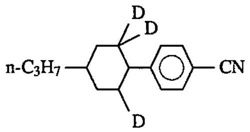

10%

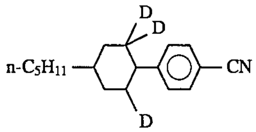

10%

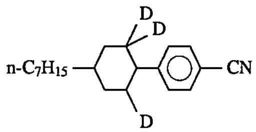

10%

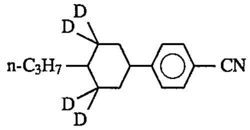

6%

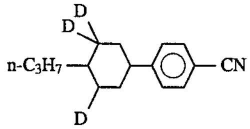

4%

$T_{N-I}$ Point: 84° C.

Threshold Voltage: 1.58 V $\Delta_\epsilon$: 9.9

$\Delta_n$: 0.099

$K_{33}/K_{11}$: 2.4

When composition (P') was preserved at 0° C., no crystallization was observed after 1 month.

COMPARATIVE EXAMPLE 16

Liquid crystal composition (o) having the following composition and characteristics was prepared.

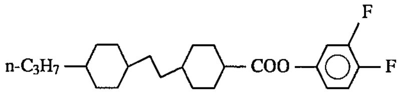

34%

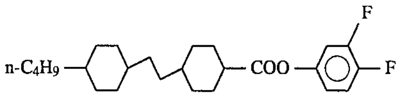

33%

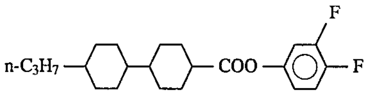

33%

$T_{N-I}$ Point: 139° C.

Threshold Voltage: 2.11 V $\Delta_\epsilon$: 6.0

$\Delta_n$: 0.078

$K_{33}/K_{11}$: 2.5

When composition (o) was preserved at 10° C., crystallization was observed after 1 day.

COMPARATIVE EXAMPLE 17

Liquid crystal composition (p) having the following composition and characteristics was prepared.

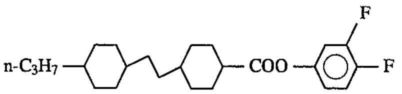

17%

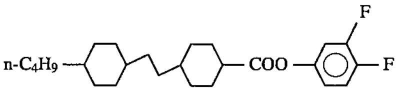

16.5%

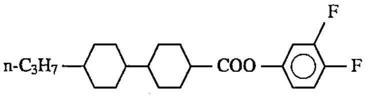

16.5%

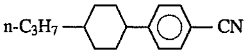

20%

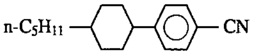

15%

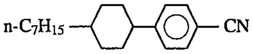

15%

$T_{N-I}$ Point: 84° C.

Threshold Voltage: 1.60 V $\Delta_\epsilon$: 9.9

$\Delta_n$: 0.099

$K_{33}/K_{11}$: 2.3

When composition (p) was preserved at 0° C., crystallization was observed after 1 day.

EXAMPLE 49

Liquid crystal composition (Q) having the following composition was prepared.

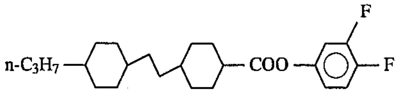

17%

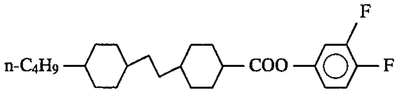

16.5%

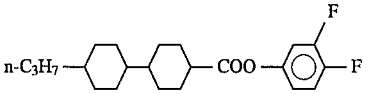

16.5%

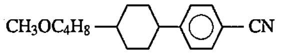

5%

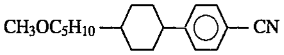

5%

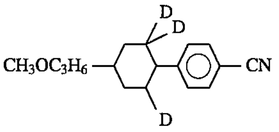

10%

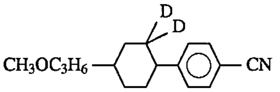

4%

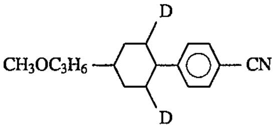

4%

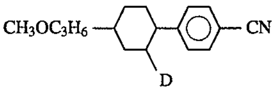

2%

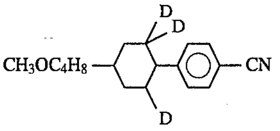

10%

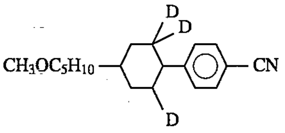

10%

$T_{N-I}$ Point: 82° C.

Threshold Voltage: 1.38 V $\Delta_\epsilon$: 12.5

$\Delta_n$: 0.098

$K_{33}/K_{11}$: 2.3

When composition (Q) was preserved at 0° C., no crystallization of crystals was observed after 1 month.

COMPARATIVE EXAMPLE 18

Liquid crystal composition (q) having the following composition and characteristics was prepared.

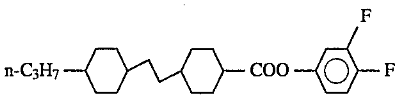
17%

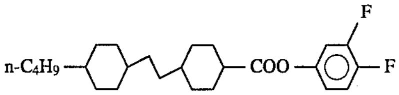
16.5%

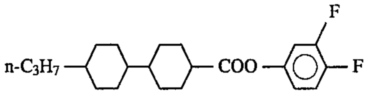
16.5%

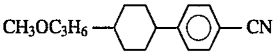
20%

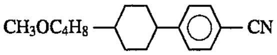
15%

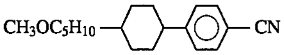
15%

$T_{N-I}$ Point: 82° C.

Threshold Voltage: 1.40 V $\Delta_\epsilon$: 12.5

$\Delta_n$: 0.099

$K_{33}/K_{11}$: 2.2

When composition (q) was preserved at 0° C., crystallization was observed after 1 day.

EXAMPLE 50

Liquid crystal composition (S) having the following composition and characteristics was prepared.

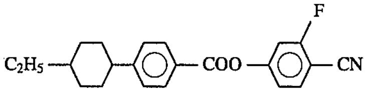
10%

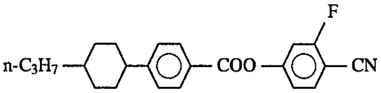
10%

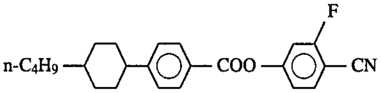
10%

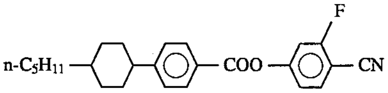
10%

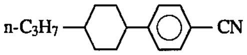
24%

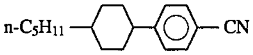
18%

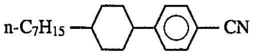
18%

-continued

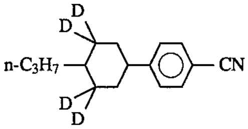
3.6%

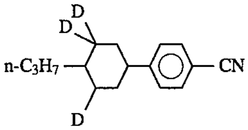
4.8%

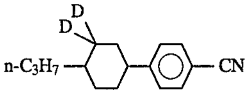
1.2%

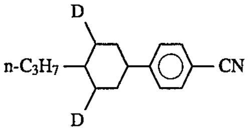
1.2%

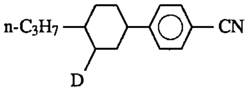
1.2%

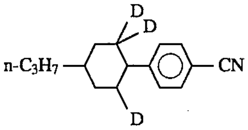
6%

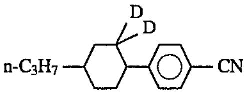
2.4%

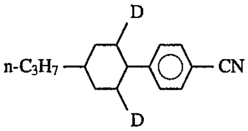
2.4%

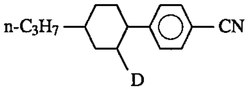
1.2%

$T_{N-I}$ Point: 101° C.

Threshold Voltage: 1.23 V $\Delta_\epsilon$: 23

$\Delta_n$: 0.145 $K_{33}/K_{11}$: 3.7

When composition (S) was preserved at −10° C., no crystallization of crystals was observed even after 1 month.

COMPARATIVE EXAMPLE 19

Liquid crystal composition (r) having the following composition and characteristics was prepared.

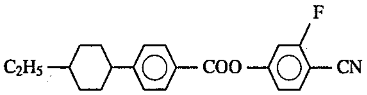
25%

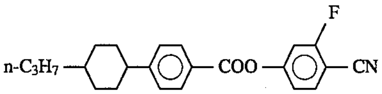
25%

-continued

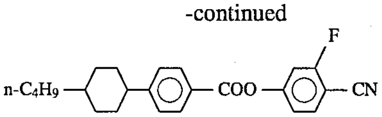

25%

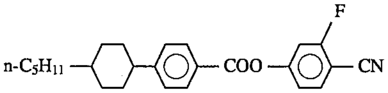

25%

$T_{N-I}$ Point: 191° C.

Threshold Voltage: 1.17 V $\Delta_{\epsilon}$: 36

$\Delta_n$: 0.176

$K_{33}/K_{11}$: 4.6

When composition (r) was preserved at room temperature (20° C.), crystallization was observed on the next day.

COMPARATIVE EXAMPLE 20

Liquid crystal composition (s) having the following composition and characteristics was prepared.

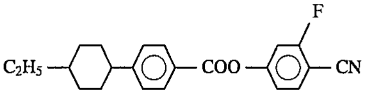

10%

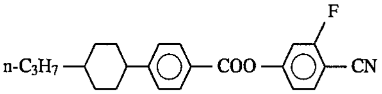

10%

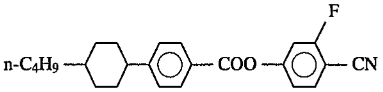

10%

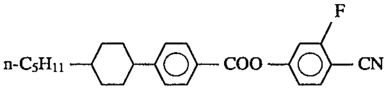

10%

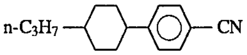

24%

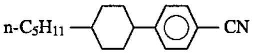

18%

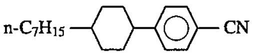

18%

$T_{N-I}$ Point: 103° C.

Threshold Voltage: 1.29 V $\Delta_{\epsilon}$: 22

$\Delta_n$: 0.146 $K_{33}/K_{11}$: 3.6

When composition (s) was preserved at −10° C., crystallization was observed after 3 days.

EXAMPLE 51

Liquid crystal composition (T) having the following composition and characteristics was prepared.

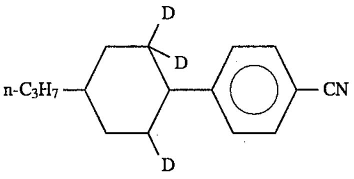

5%

-continued

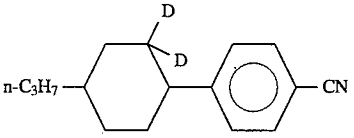

2%

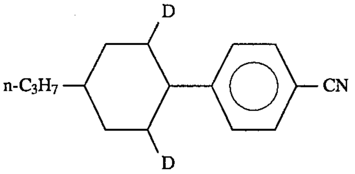

2%

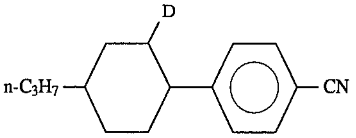

1%

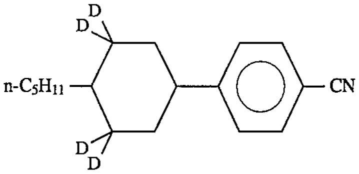

3%

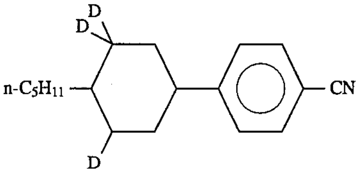

4%

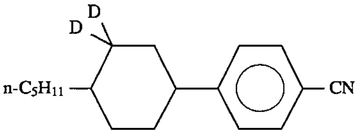

1%

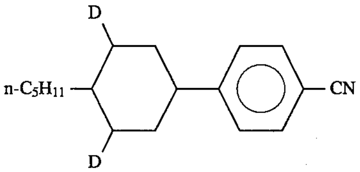

1%

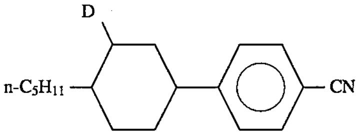

1%

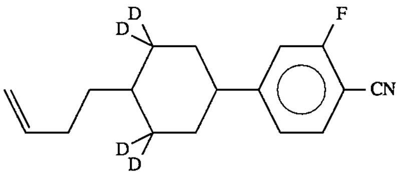

3%

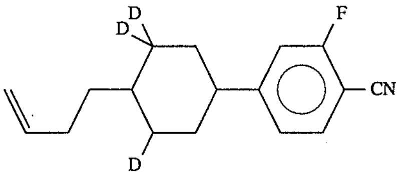

4%

-continued

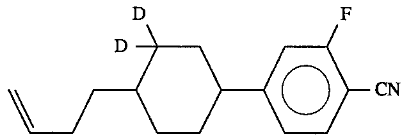

1%

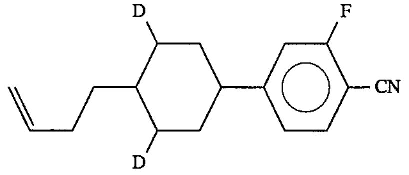

1%

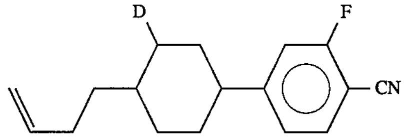

1%

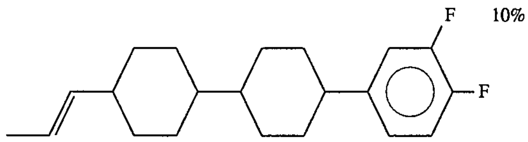

10%

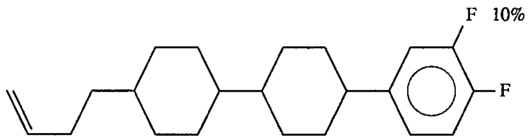

10%

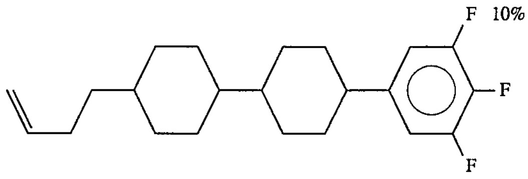

10%

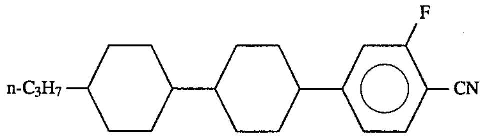

10%

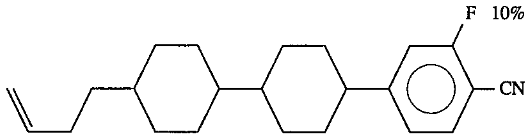

10%

$T_{N\text{-}I}$ Point: 82° C.

Threshold Voltage: 1.10 V $\Delta_\epsilon$: 17

$\Delta_n$: 0.116

$K_{33}/K_{11}$: 2.5

When composition (T) was preserved at −40° C., crystallization of crystals was observed even after 1 month. An STN liquid crystal display having a twisted angle of 260° prepared by using composition (T) showed satisfactory driving characteristics even in a low temperature region.

COMPARATIVE EXAMPLE 21

Liquid crystal composition (t) having the following composition and characteristics was prepared.

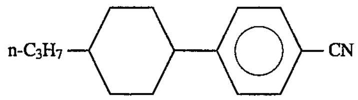

20%

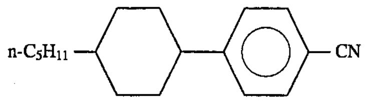

10%

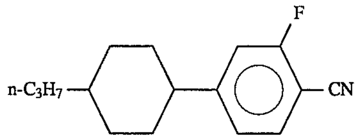

10%

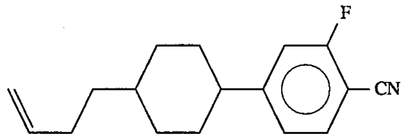

10%

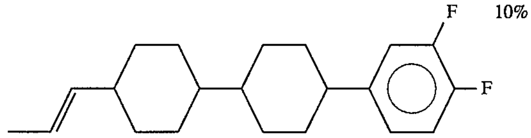

10%

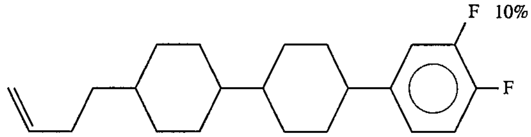

10%

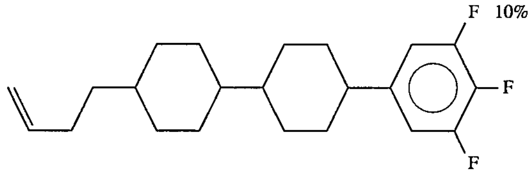

10%

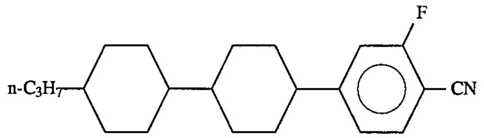

10%

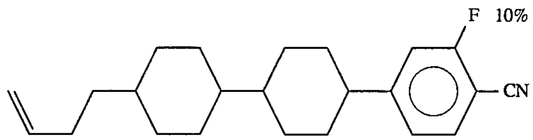

10%

$T_{N\text{-}I}$ Point: 83° C.

Threshold Voltage: 1.12 V $\Delta_\epsilon$: 17

$\Delta_n$: 0.116

$K_{33}/K_{11}$: 2.5

When composition (t) was preserved at −25° C., crystallization was observed after 5 days.

EXAMPLE 52

Liquid crystal composition (U) having the following composition and characteristics was prepared.

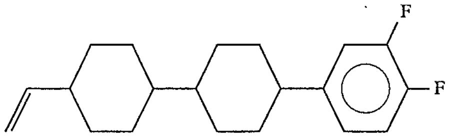

37.5%

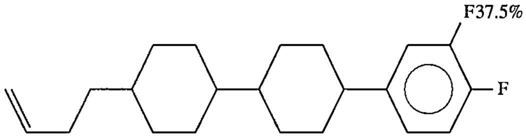

37.5%

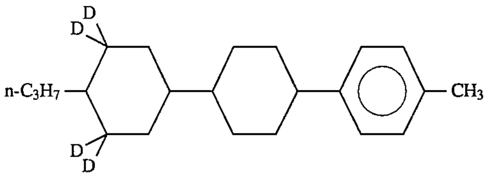

18%

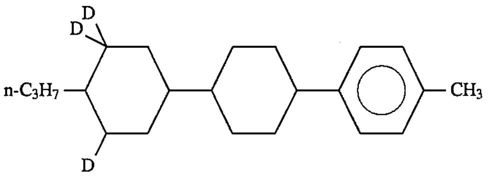

7%

$T_{N-I}$ Point: 132° C.

Threshold Voltage: 2.62 V $\Delta_\epsilon$: 3.9

$\Delta_n$: 0.092

Response Time: 31 msec

When composition (U) was preserved at 10° C., no crystallization of crystals was observed even after 1 month.

COMPARATIVE EXAMPLE 22

Liquid crystal composition (u) having the following composition and characteristics was prepared.

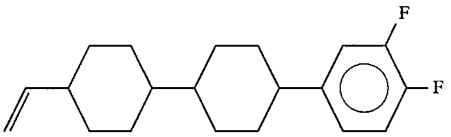

37.5%

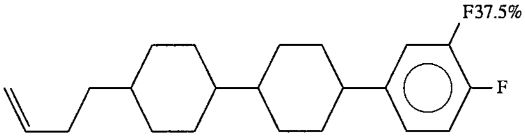

37.5%

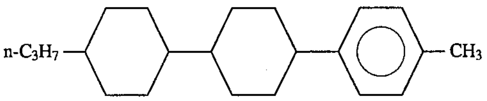

25%

$T_{N-I}$ Point: 133° C.

Threshold Voltage: 2.70 V $\Delta_\epsilon$: 3.7

$\Delta_n$: 0.092

Response Time: 38 msec

When composition (u) was preserved at 10° C., crystallization was observed even after 3 days.

EXAMPLE 53

Liquid crystal composition (V) having the following composition and characteristics was prepared.

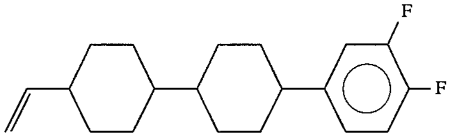

37.5%

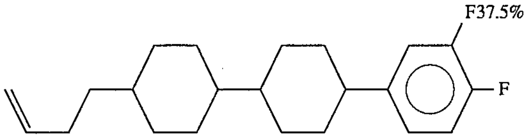

37.5%

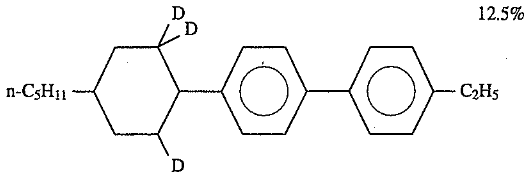

12.5%

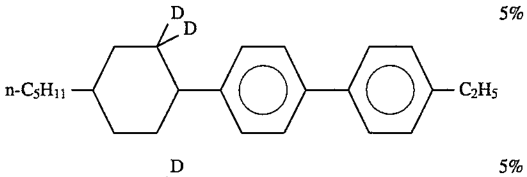

5%

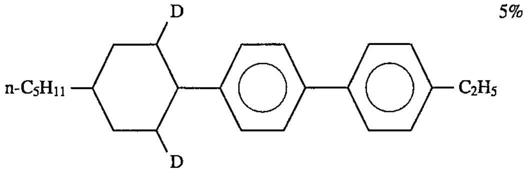

5%

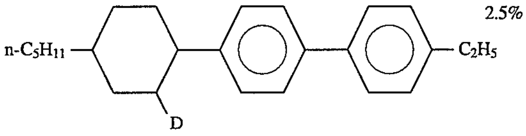

2.5%

$T_{N-I}$ Point: 127° C.

Threshold Voltage: 2.71 V $\Delta_\epsilon$: 3.8

$\Delta_n$: 0.109

Response Time: 37 msec

When composition (V) was preserved at 10° C., no crystallization of crystals was observed even after 1 month.

COMPARATIVE EXAMPLE 23

Liquid crystal composition (v) having the following composition and characteristics was prepared.

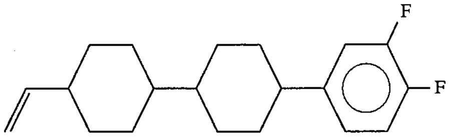

37.5%

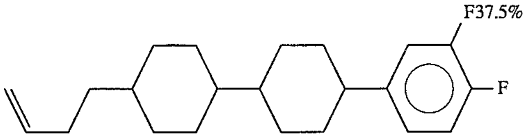

37.5%

-continued

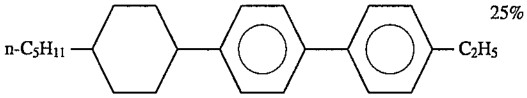

25%

$T_{N\text{-}I}$ Point: 127° C.

Threshold Voltage: 2.73 V $\Delta_\epsilon$: 3.8

$\Delta_n$: 0.109

Response Time: 40 msec

When composition (v) was preserved at 10° C., crystallization was observed even after 5 days.

EXAMPLE 54

Liquid crystal composition (W) having the following composition and characteristics was prepared.

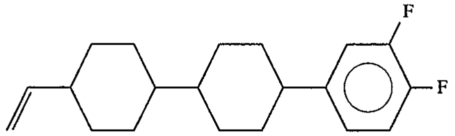

37.5%

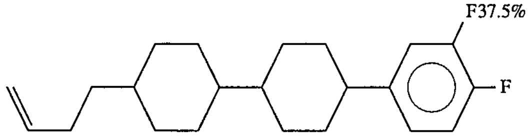

37.5%

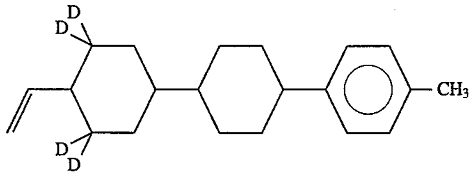

10%

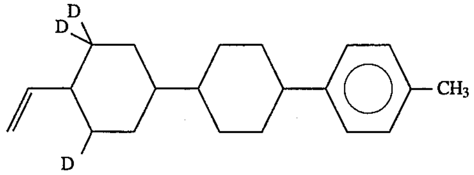

7.5%

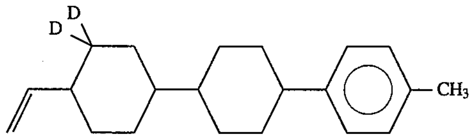

2.5%

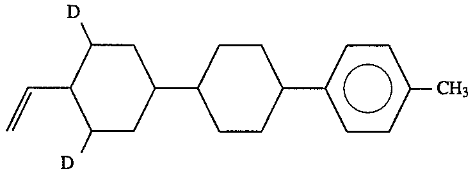

2.5%

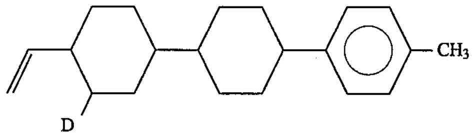

2.5%

$T_{N\text{-}I}$ Point: 128° C.

Threshold Voltage: 2.56 V $\Delta_\epsilon$: 4.0

$\Delta_n$: 0.096

Response Time: 32 msec

When composition (W) was preserved at 10° C., no crystallization of crystals was observed even after 1 month.

COMPARATIVE EXAMPLE 24

Liquid crystal composition (w) having the following composition and characteristics was prepared.

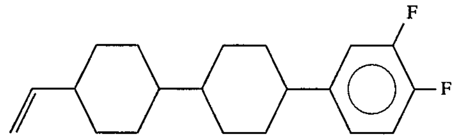

37.5%

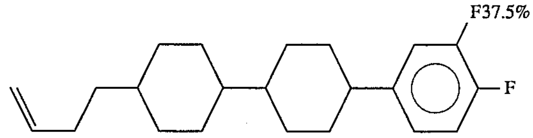

37.5%

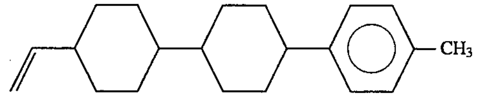

25%

$T_{N\text{-}I}$ Point: 130° C.

Threshold Voltage: 2.64 V $\Delta_\epsilon$: 3.8

$\Delta_n$: 0.095

Response Time: 37 msec

When composition (w) was preserved at 10° C., crystallization of crystals was observed even after 3 days.

While the invention has been described in detail and with reference to specific embodiments thereof, it will be apparent to one skilled in the art that various changes and modifications can be made therein without departing from the spirit and scope thereof.

What is claimed is:

1. A liquid crystal display comprising a liquid crystal composition comprising a compound represented by formula (I):

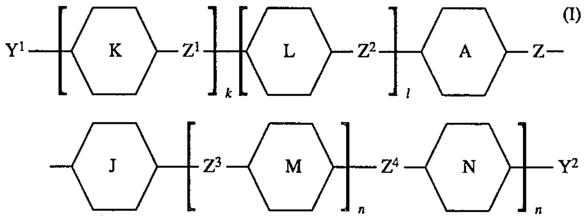

(I)

wherein $Y_1$ and $Y^2$ each independently represent a fluorine atom, a chlorine atom, a cyano group, a cyanato group (OCN), a thiocyanato group (SCN), a trifluoromethoxy group ($OCF_3$), a difluoromethoxy group ($OCF_2H$), a 2,2,2-trifluoroethoxy group ($OCH_2CF_3$), a trifluoromethyl group ($CF_3$), R, —OR, —COOR or —OCOR, wherein R represents an alkyl group having from 1 to 20 carbon atoms, an alkenyl group having from 2 to 20 carbon atoms or an alkoxyalkyl group having from 2 to 20 carbon atoms, provided that at least one of $Y^1$ and $Y^2$ represents R, —OR, —COOR or —OCOR; Z, $Z^1$, $Z^2$, $Z^3$, and $Z^4$ each independently represent a single bond, $—CH_2CH_2—$, —CH═—, —C≡C—, —COO—, —OCO—, $—CH_2O—$, $—OCH_2—$, $—(CH_2)_4—$, $—(CH_2)_3—O—$ or $—O—(CH_2)_3—$; ring A represents a group of formula (II):

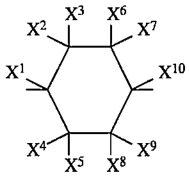

(II)

wherein $X^1$, $X^2$, $X^3$, $X^4$, $X^5$, $X^6$, $X^7$, $X^8$, $X^9$ and $X^{10}$ each independently represent a hydrogen atom (H) or a deuterium atom (D), provided that at least one of them represents a deuterium atom (D); rings K, L, J, M and N each independently represent a trans-1,4-cyclohexylene group, a 1,4-cyclohexenylene group, a trans-1,4- cyclohexylene group substituted with 1 to 4 substituents selected from a fluorine atom and a cyano group, a 1,4-phenylene group, a 1,4-phenylene group substituted with 1 to 4 substituents selected from a fluorine atom, a chlorine atom, a cyano group and a methyl group, a 1,3-dioxane-2,6-diyl group, a pyrimidine-2,5-diyl group, a pyridine-2,5-diyl group, a pyrazine-2,5-diyl group or a group of formula (III):

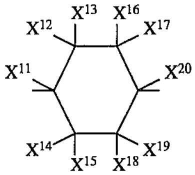

(III)

wherein $X^{11}$, $X^{12}$, $X^{13}$, $X^{14}$, $X^{15}$, $X^{16}$, $X^{17}$, $X^{18}$, $X^{19}$, and $X^{20}$ each independently represent a hydrogen atom (H) or a deuterium atom (D), provided that at least one of them represents a deuterium atom (D); in which the ring of formula (III) may be the same or different with ring A; and k, l, m, and n each independently represent 0 or 1, provided that the sum of k, l, m, and n is 0, 1 or 2.

2. A liquid crystal display as claimed in claim 1, wherein in said compound represented by formula (I), k, l, m and n are each equal to 0.

3. A liquid crystal display as claimed in claim 1, wherein in said compound represented by formula (I), k, l and n are each equal to 0, and m is equal to 1.

4. A liquid crystal display as claimed in claim 1, wherein in said compound represented by formula (I), l, m and n are each equal to 0, and k is equal to 1.

5. A liquid crystal display as claimed in claim 1, wherein in said compound represented by formula (I), k and l are each equal to 0, and m and n are each equal to 1.

6. A liquid crystal display as claimed in claim 1, wherein in said compound represented by formula (I), k and l are each equal to 1, and m and n are each equal to 0.

7. A liquid crystal display as claimed in claim 1, wherein in said compound represented by formula (I), k and m are each equal to 1, and l and n are each equal to 0.

8. A liquid crystal display as claimed in claim 1, wherein said composition as a whole has a dielectric anisotropy ($\Delta\epsilon$) of from +3 to +12 and said composition is for a liquid crystal display of an active matrix driving system.

9. A liquid crystal display as claimed in claim 1, wherein said composition as a whole has a dielectric anisotropy ($\Delta\epsilon$) of not less than +8 and said composition is for a liquid crystal display of TN or STN mode.

* * * * *